US007034691B1

(12) United States Patent
Rapaport et al.

(10) Patent No.: US 7,034,691 B1
(45) Date of Patent: Apr. 25, 2006

(54) ADAPTIVE COMMUNICATION METHODS AND SYSTEMS FOR FACILITATING THE GATHERING, DISTRIBUTION AND DELIVERY OF INFORMATION RELATED TO MEDICAL CARE

(75) Inventors: Jeffrey A. Rapaport, Sunnyvale, CA (US); Seymour A. Rapaport, Los Altos, CA (US); Jeffrey E. Clarke, La Honda, CA (US); Eric R. Rinehart, Virginia Beach, VA (US); Michael U. Bergens, Sunnyvale, CA (US)

(73) Assignee: SolveTech Corporation, Los Altos, CA (US)

( * ) Notice: Subject to any disclaimer, the term of this patent is extended or adjusted under 35 U.S.C. 154(b) by 428 days.

(21) Appl. No.: 10/058,154

(22) Filed: Jan. 25, 2002
(Under 37 CFR 1.47)

(51) Int. Cl.
*G08B 23/00* (2006.01)

(52) U.S. Cl. ............................. 340/573.1; 340/539.1; 600/300

(58) Field of Classification Search ............. 340/573.1, 340/457, 539.1, 3.1; 600/300; 705/9; 379/88.22, 379/37, 38
See application file for complete search history.

(56) References Cited

U.S. PATENT DOCUMENTS

| 5,307,263 | A | * | 4/1994 | Brown ........................ 600/301 |
| 5,325,294 | A | * | 6/1994 | Keene ............................ 705/3 |
| 5,897,493 | A | * | 4/1999 | Brown ........................ 600/300 |
| 5,926,526 | A | * | 7/1999 | Rapaport et al. ......... 379/88.25 |
| 5,954,641 | A | * | 9/1999 | Kehr et al. .................. 600/300 |
| 6,139,494 | A | * | 10/2000 | Cairnes ....................... 600/300 |
| 6,650,238 | B1 | * | 11/2003 | Britton ..................... 340/539.1 |

\* cited by examiner

*Primary Examiner*—Phung T. Nguyen
(74) *Attorney, Agent, or Firm*—MacPherson Kwok Chen & Heid LLP; Gideon Gimlan

(57) ABSTRACT

Automated methods and systems are disclosed for facilitating the timely gathering, monitoring, distribution and delivery of information related to medical care where such may include: (1) finding a communications channel for effectively attempting a message delivery to a specific target person at a specified time; (2) adaptively finding a targeted recipient even if the latter is highly mobile and/or has travel patterns or communications-channel preferences that change over time; (3) verifying that a targeted recipient has actually received an attempted delivery within an applicable time limit; (4) automatically recognizing that an urgent message delivery-attempt was not timely completed and adaptively alerting responsible entities of the in completion; and (5) automatically recognizing that an urgent change or non change of condition has occurred by virtue of information gathered during an automated or manually-conducted Interview where physician expected positive progress prior to Interview and adaptively alerting responsible entities of the changed or unchanged condition based on the urgency of the change or non-change.

31 Claims, 50 Drawing Sheets

3700

Patient Information [3701]

BASIC MEDICAL DATA [3702]

| Name | Minnie Anderson |
|---|---|
| Age | 32 |
| Weight | 150 |
| Height | 5'10" |
| Sex | Female |
| Med-1 | Potassium |
| Med-2 | Hydrochlorothiazide |
| Allergy | Penicillin |

MEDICAL CONDITIONS [3703]

| Conditions | Yes/No | Onset |
|---|---|---|
| Asthma | No | |
| Diabetes | No | |
| Hypertension | Yes | 1999 |

PRIOR OFFICE VISITS [3704]

SURGERIES [3706]

HOSPITALIZATIONS [3705]

Figure 37

Communication Channels [3801]

3800

| [3802] *Order* | [3803] Channel | [3804] Active | [3805] Address | [3806] Avail Mon-Fri | [3807] Avail Weekends |
|---|---|---|---|---|---|
| 1 | WorkPhone | Yes | 555-1212 | 9 to 17 | 9 to 17 |
| 2 | Web | No | manders@home.org | 24 | 9 to 17 |
| 4 | Cell Phone | Yes | 555-1214 | 7to 21 | 9 to 17 |
| 3 | Pager | Yes | 555-1215 | 24 | 9 to 17 |
| 5 | USMail | Yes | 123 Bay St., Cook City,Calif. 92351 | -- | -- |

SCALABLE SYSTEM
4000B

ADAPTIVE COMMUNICATION METHODS AND SYSTEMS FOR FACILITATING THE GATHERING, DISTRIBUTION AND DELIVERY OF INFORMATION RELATED TO MEDICAL CARE

FIELD OF DISCLOSURE

The present disclosure of invention relates to problems encountered in service providing organizations such as may be found in the medical field wherein service-supporting communications are expected to be completed between persons responsible for providing services and/or persons who receive services. More particularly, the disclosure address the medical-services providing field wherein health or medical care-related information is gathered from, and/or exchanged between, and/or sent for delivery to individuals engaged in medical service-related communications. The individuals or entities involved in such communications may comprise one or more of: (a) Patients, (b) Medical Service Providers (e.g. doctors, nurses, etc.), Medical Testing Facilities' Personnel (e.g., lab technicians), and/or automated service-providing agents.

CROSS REFERENCE TO PATENTS

The disclosures of the following U.S. patents are incorporated herein by reference:

(A) U.S. Pat. No. 5,926,526; entitled METHOD AND APPARATUS FOR AUTOMATED PATIENT INFORMATION RETRIEVAL, and filed Dec. 29, 1995 by Seymour A. Rapaport, M. D., Jeffrey A. Rapaport, et al, as U.S. application Ser. No. 08/581/749; and (B) U.S. Pat. No. 6,192,112 B1, entitled MEDICAL INFORMATION SYSTEM INCLUDING A MEDICAL INFORMATION SERVER HAVING AN INTERACTIVE VOICE-RESPONSE INTERFACE, and filed Aug. 5, 1997 as U.S. application Ser. No. 08/906,726 by Seymour A. Rapaport, M. D., Jeffrey A. Rapaport, et al.

CROSS REFERENCE TO RELATED OTHER PUBLICATIONS

The following publications are cited here for purposes of reference:

(A) National Cholesterol Education Program (Journal of the American Medical Association (JAMA), May 16, 2001, pp. 2486–2497.

RESERVATION OF EXTRA-PATENT RIGHTS AND RESOLUTION OF CONFLICTS

After this disclosure is lawfully published, the owner of the present patent application has no objection to the reproduction by others of textual and graphic materials contained herein provided such reproduction is for the limited purpose of understanding the present disclosure of invention and of thereby promoting the useful arts and sciences. The owner does not however disclaim any other rights that may be lawfully associated with the disclosed materials, including but not limited to, copyrights in any computer program listings or art works or other works provided herein, and to trademark or trade dress rights that may be associated with coined terms or art works provided herein and to other otherwise-protectable subject matter included herein or otherwise derivable herefrom.

If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

BACKGROUND

An average patient may not appreciate the extent to which the medical-services providing industry is a communications-intensive enterprise fraught with the potential for missed and miscommunications. Consider as a small scale example, a solo practitioners office. (A medical services-providing organization may have merely one doctor in it, or merely one other kind of medical services-providing person in it, although typically medical SPO's are comprised of more than one person; e.g., a nurse, a receptionist, etc.) Test results may be streaming into the one physician's office at all hours for different patients and from different laboratories or specialists and coming in by way of telephone calls, facsimile machines, email, regular hardcopy mail and/or other communication channels and modalities (e.g., peer-to-peer computer communications). Some of the test results may be important ones that need urgent responding to while most are probably routine ones that merely report results within expected normal ranges. To the untrained eye, it may be hard to differentiate one type of report from the other. As the various reports are coming in through the various communication channels, the affected doctor may be busy running about his or her office ping ponging between the servicing of one patient in one waiting room to another in another room, and/or to talking with other medical service providers (e.g., nurses, radiologists, other doctors, etc.) in the interim all while perhaps being unaware that an important report may have come in and is in need of urgent responding to. Aside from being highly mobile within his/her own office suite, the doctor may at times be situated in his/her car and may be engaged in driving to the hospital for an emergency consultation when a possibly-critical lab result comes in. If the lab result is not truly critical, it would be inappropriate to distract the doctor from his/her driving activities and/or mental concentration on other issues by ringing the doctor's cell phone or pager at that time. One of the many communications problems which face the medical services industry can therefore be characterized as how to efficiently differentiate emergency reports from normal ones and how to locate and inform the appropriate physician of a situation at an appropriate time without overwhelming the doctor with volumes of routine data and distracting the doctor from more pressing matters.

Another of the communications problems facing the medical services industry (even in a small-scale, solo practice) is that patients may be calling in at all hours with questions about their ongoing medical treatment, with concerns about their medical conditions, or with the intent of scheduling a new appointment, or with the desire to reschedule a missed appointment. A worse problem is that some patients may not be trying to contact the doctor's office at all because they believe it is entirely the doctor's responsibility to contact them if something is wrong. Some of the commonly believed myths among lay patients is that, "(A) If I do not hear from the doctor's office that means everything is OK. (B) Even though I am feeling much worse, the doctor has already seen me, diagnosed the situation, and I should not be calling in again to disturb the doctor and complain like a big baby."

Unfortunately the first myth ("If I do not hear from the doctor's office . . . ") is an illogical conclusion that can be amiss for many a reason. The patient who is not hearing from his/her doctor may not realize that the reason is because, as some examples: (1) the battery on their (the patient's) personal cell-phone has run out of energy, or (2) that their home telephone receiver is off the hook or (3) that their answering machine has run into a problem and is not recording or letting messages get through, or (4) that their home facsimile machine (if they have one) is out of paper. It is possible as yet another reason why the patient has not heard from the doctor's office, that (5) a nurse at the doctor's office may have temporarily misplaced the patient's file when she was supposed to call the patient about an abnormal test result and that is why the patient is not being contacted. It is yet further possible that (6) the test results did not even arrive from the laboratory because there is a communications break down between the lab and the doctor's office (e.g., the lab report was lost) or (7) the wrong test was performed and its results came back normal, or (8) the patient's specimen was lost and a test was not even done.

The illogic of the second, above-cited myth ("Even though I'm feeling worse, . . . I should not disturb the doctor . . . ") should also be apparent. If the doctor is not aware of the deteriorating patient condition, how can the doctor knowingly respond to it. Perhaps the patient is experiencing a severe allergic reaction to just-prescribed medicine and needs to be taken to a hospital emergency room immediately? It is not beneficial to either the patient's or the doctor's interests to use a communications system which discourages patients from contacting the doctor's office with their concerns and which does not assure that legitimate ones of such concerns are actually brought to the doctor's attention—as opposed to just sitting on a loose piece of paper by the receptionist's desk. So many things can go wrong, that it is a wonder the medical-care delivery system works at all. Luckily, in terms of statistics, when a particular communications failure occurs, the one missed or miscommunication usually does not have serious consequences. However, once every so-many thousands of cases, such a failure leads to unnecessary catastrophe and exposure of the physician and/or other Medical Service Providers (MSP's) to legal malpractice suits.

The above-given description of a communications-based hazards in a solo practitioner's practice is just a small scale example. Imagine how much more complicated the picture gets when one deals with a multi-physician practice group or a hospital. The chances for missed communications and miscommunications grows astronomically. The laws of probability indicate that such unfortunate events will therefore happen more often. It is well understood that it is important to have timely and effective communications between two or more of a given patient and service-related persons who are involved directly or indirectly in the providing of medically-related services to that given patient. Proper communication between a Medical Service Provider (e.g., doctor) and a Patient, and/or between other service-related persons, may be essential to the delivery of quality medical care. However, conventional practices do not account for many of the things that can go wrong.

Conventionally, in the medical field, attempts to gather, record, convey, and deliver important information may include a variety of different kinds of interviews and different channels for moving the gathered information from the point of collection or creation to the person or persons who most likely (or most urgently) need to receive that information. There may be, for example, a telephonic interview between patient and nurse in which the patient has questions or concerns to relay to the nurse-practitioner about progress following an initial office visit. If some significant development is uncovered by the nurse, and the doctor needs to be informed quickly, then hopefully the oral and/or paper-based results will catch up with the doctor in a hallway before the doctor disappears into a next waiting room and begins examination of a next patient. The telephonically-gathered results may alert the physician to certain unusual items in thus-far-gathered information and/or to unusual patterns, and these may assist or guide the physician in his/her provision of timely patient care. However, in the time-pressured rush of a modern medical practice, the telephonically-originated paper work and/or orally-acquired information may get diverted or delayed and not get to the doctor on time. Or, given that doctors are only human, some items may escape the doctor's attention. There is also the possibility that the patient and/or interviewer left out some important information because a particular question was not understood by the patient or nurse. Such missed opportunities, oversights and/or like problems which may be associated with information gathering, distribution and delivery may lead to inefficient and degraded provision of medical care. Conventional methods and equipment used in the medical field for information gathering and/or information distribution often fail to provide remedies for problems such the ones introduced in the above examples.

A closer study of the situation reveals that there are many opportunities for missed communications and miscommunications due to complications on the patient's side of the equation, and due to complications on the Medical Service Provider's (MSP's) side of the equation. Patients can be highly mobile and hard to locate. Each patient may have available to him or her, at respective locations and times of day, a different assortment of communication tools by way of which the patient may be effectively reached or not, including wired telephone, wireless telephone, telephone answering machine, facsimile machine, wireless portable computer, desktop computer, and so forth. The context of the patient when a delivery attempt is made is also a factor. For example, a patient may be temporarily or permanently hearing-impaired, visually-impaired, distracted, disoriented, or otherwise disposed when a communication delivery-attempt is made by way of a delivery channel that is inappropriate for the patient's current context. Multiply the possible locations at which a given patient may be found with time-of-day, with patient context, and with probable communication tool at hand, and you already have a complicated set of possible permutations. Add to that the possibility that some patients do not answer telephone calls directly but rather screen calls with an answering machine and then call back only if they feel like it and you can see how the risk for failed communications can grow. In the case where an automated answering machine is a link in the attempted-communications chain, you have a situation where the doctor's office may not know if the initial call was recorded at all by the answering machine, or was recorded on the correct or a wrongly-dialed answering machine (some machines do not self-identify), or was listened to by the intended recipient (e.g., the patient), or by another person who inadvertently erased the message from the doctor's office and did not pass the message along. You also have an example of a situation where the doctors office should not be distributing confidential information via that communication channel because it is not clear who will be picking up the dispensed message.

Problems on the Medical Service Provider's side of the equation tend to be equally if not more complicated. A given physician may be highly mobile and hard to locate at certain times. Each doctor may have, at respective locations and times of day, a different assortment of communication tools by way of which they may be reached or not. Like, patients, doctors and/or other medical service providers may have individual contexts whereby they may be temporarily or permanently impaired or involved in particular tasks that inhibit them from effectively receiving or comprehending a given communication when it comes in. Also, the numbers and types of entities that a doctor's office needs to communicate with, and their respective availabilities and contexts, often define a vastly larger set of possibilities than do those parts of the medical-care delivery system that the typical patient communicates with. By way of some examples, the doctor's office may be have different pharmacies calling in to request prescription refills, or to ask questions about a specific patient or to convey and gather other information. Hospitals or external specialists may be calling in with results, inquiries, care suggestions, etc. Visiting nurses may be calling in to report on patient needs. Information may be arriving at the Medical Service Provider's central office at different times of day, by way of different communication channels (e.g., phone, fax, etc.), in different formats (which formats can include hardcopy formats as well as different computer communication formats). This chaotically incoming deluge of data is typically not pre-sorted according to urgency. Loose slips of paper with important information on them may get misplaced because the person handling it (e.g., a clerk without medical training) may not appreciate the information's significance (e.g., an abnormal potassium level) and the need for swift action. Without automated assistance, the conventional approach to medical-services related communications is a prescription for eventual disaster.

Examples of communications between Medical Service Providers and/or a Patient that tend to be important include: 1) reporting normal and abnormal test results; 2) arranging further tests, office visits, and medical procedures as may be appropriate, as well as following-up on these arrangements to make sure the arranged actions are actually carried out; 3) following up on the progress of patients with acute illnesses, 4) providing periodic health maintenance and monitoring services (which may include sending vaccination reminders, medical instructions, as well as periodic gathering and evaluation of patient health information); and 5) following up on Patients who have missed scheduled appointments.

For the Patients' welfare it may be valuable to immediately inform certain Medical Service Providers of: (a) significantly abnormal test results, (b) situations where Patients are not doing well after a prescribed course of therapy, (c) situations where Patients' health status is showing signs of deterioration, and (d) situations where Patients did not follow through on essential referrals, tests, or appointments.

There are situations where patients may want to be immediately informed of developments in their treatments or where patients may want to immediately inform their care-givers of a concern or development. For example, some patients may want to immediately know about their own test results when those results become available, and about the interpretation of such results given the context of the patient's own health status (e.g. for example, what the patient's cholesterol level should normally be within the patient's particular context including that of age, sex, and past heart or other illness). After starting a particular treatment, a patient may desire to have a means for easily communicating concerns regarding their progress to the involved Medical Service Providers, so that, if a follow up is appropriate, such a follow up on the concern will occur. Further, a given Patient's course of health care might be improved by early notification being sent to the appropriate Medical Service Provider of detection of significant deviations from the patient's prior state of health.

The volume of communications involved in trying to attain one or more of the above goals may easily exceed the capacity of conventional medical practices and systems. Medical personnel, facilities and systems are often stressed by trying to maintain conventional levels of communication which generally do not include one or more of the beneficial add-ons mentioned above. Patient's health care may suffer due to the inability of conventional medical systems to consistently and effectively perform one or more of the beneficial medical communication activities outlined above. It is commonly-accepted knowledge in the medical services community that poor communications may often play a significant role in many medical malpractice allegations.

SUMMARY

The present disclosure covers automated and adaptive systems and methods for facilitating medical-service related communications such as those involved in the exemplary problem situations described above.

In accordance with a first aspect of the present disclosure, an MSP-alerting interface is provided for selectively, effectively and efficiently communicating to an MSP (Medical Service Provider) information that the Medical Service Provider is likely to consider as being vital to the quality of medical services being rendered to a specific one or more patients.

In accordance with a second aspect of the present disclosure, an adaptive communications system is provided for adaptively facilitating the effective delivery of medical service information to Patients and/or Medical Service Providers in real-time, non-real-time, automated and/or partly-automated fashions based on probable location, probable-available communication tools and/or probable contexts of the targeted recipient(s). In one embodiment, Medical Service Providers can use such an adaptive communications system to communicate essentially all test results to their Patients on or before a predefined time deadline. Thus Patients can be instructed to contact the Medical Provider if they are not timely informed of all their test results. The carrying out of this instruction can act as a feedback check on the results-delivering performance of the adaptive communications system and as a feedback check on the quality of medical or health care services being provided to the respective patients. Automated follow up on the carrying out of this instruction can also provide future predictors (e.g., attributes) about the data retrieval habits of the targeted patient.

In accordance with a third aspect of the present disclosure, an adaptive communications system is provided for adaptively delivering rescheduling notifications to patients who missed their scheduled appointments, notifying those patients to reschedule the missed appointment. Automated follow upon the carrying out of such rescheduling suggestions can also provide adaptive feedback (e.g., revised patient attributes) on what delivery-attempt strategies are likely to be most successful for a given patient during different times of day and/or by way of different communication channels and/or under other patient-centric contexts.

In accordance with another aspect of the present disclosure, an adaptive communications follow-up system is provided for automatically alerting a responsible Medical Service Provider of a failure by a targeted entity to retrieve or send an important communication within a prespecified time window and/or of a failure by an entity to otherwise act appropriately in relation to one or more delivery-attempts involving such a high-priority communication.

Other aspects of the disclosure will become apparent from the below detailed description.

BRIEF DESCRIPTION OF THE DRAWINGS

The below detailed description section makes reference to the accompanying drawings, in which:

FIG. 37 illustrates a Patient Information screen which may be used by a Medical Service Provider to review Patient Information kept within a System in accordance with the present disclosure;

FIG. 38 illustrates a Communication Channels Preference screen which may be used by a Medical system Provider to review and/or edit a Patient's Communication Channels information as kept within a System in accordance with the present disclosure;

BRIEF DESCRIPTION OF PSEUDO-CODE APPENDICES

Figure 1A:
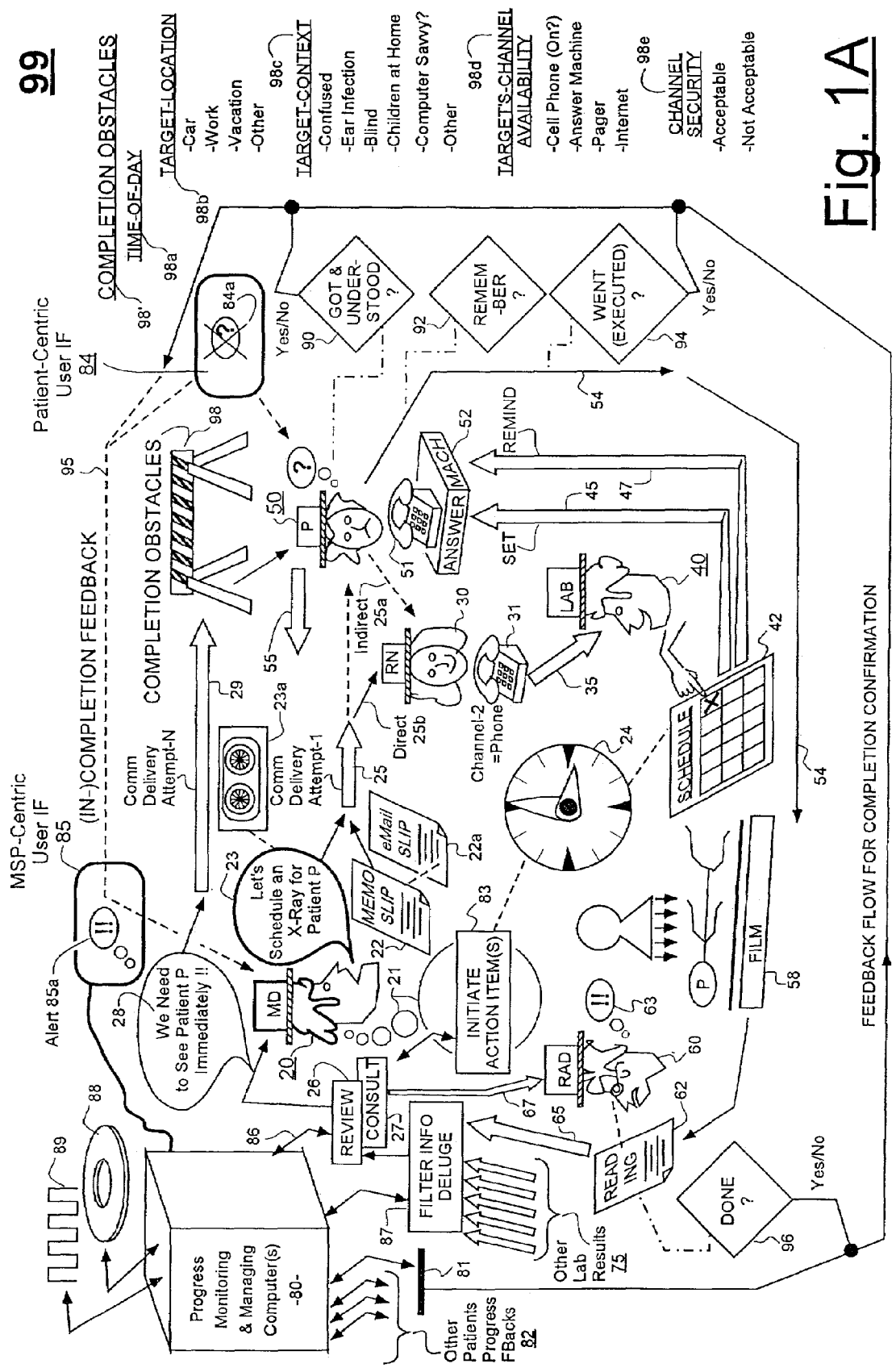
FIG. 1A is a communications flow diagram showing a medical care environment in which progress monitoring and/or managing computers in accordance with the present disclosure are deployed.

The below detailed description section includes pseudo-code appendices in which:

Exhibit 1 is a pseudo code listing example of a Dialog Data Structure for a follow up office visit for asthma in accordance with the present disclosure;

Exhibit 2 is a pseudo code listing example of a Dialog Data Structure for reporting a chemistry battery of tests to a Patient in accordance with the present disclosure; and Exhibit 3 is a pseudo code listing example of a Dialog Data Structure for delivering a result of a *Streptococcus* test to a Patient in accordance with the present disclosure.

Overview of an Adaptive Communications System

An overview is first provided of an adaptive communications system ("System") that is structured in accordance with the present disclosure so as to introduce its possible (I) communication capabilities; (II) user interfaces; and (III) instantiation processes.

I. Communication Capabilities

A System in accordance with the present disclosure may be designed for use in a wide variety of settings, including from that a single Medical Provider facility (e.g., solo practitioner office) to that of a multi-specialty organization; and to that of a general service hospital. Such a System should be able to offer its various communications services either within a restricted, on-premises environment, or over an open channel network such as the World Wide Web where the operations of the System may be coordinated by one or more application service providers.

In one embodiment, the System conducts communicative transactions described herein as "Interviews" by using a variety of communication channels and modalities. The communication channels and/or modalities may include those that rely on one or more of sound-detection (e.g., touch tone), speech-recognition (including speaker identification and/or speech-to-text conversion), conversion of text to speech, compilation of computer files containing data formatted according to Hypertext Markup Language (HTML), Extensible Markup Language (XML), Voice Over Internet Protocol (VOIP), instant messaging, Wireless Application Protocol (WAP), Wireless Hypertext Markup Language (WHTML), and plain or Rich text as well as channels and/or modalities that may operate according to other electronic and/or optical communication protocols. The so-formatted communications may be sent and delivered over a wide variety of devices, including telephones, mobile wireless phones, pagers, computers (including desktop, laptop, palmtop and other mobile forms of automated and programmably instructable machines), as well as other forms of electronic and/or optical data-conveying devices. Many of the markup protocols such as the above-mentioned HTML and XML protocols, may call for the use of browsers (computer programs) that are executed within a corresponding computer, wireless phone, palm-held computer or other information-conveying device for generating user-understandable information. Such devices may be used to exchange user-understandable and/or user-centric information, including information produced by the here-described adaptive communications system, over a network, which may include wireless portions.

Various types of physical layer and primitive layer technologies may be used to achieve information communication between these devices and such base-level technologies may include various networking protocols (such as TCP-IP and Instant Messaging, and User Datagram Protocol (UDP)), data markup languages (such as XML and SOAP), as well as other technologies such as network-content browsers, digital or analog voice-band communicators, text-to-speech converters, and speech-recognition subsystems. It should be noted proprietary protocols may be used as well as industry standard ones.

An adaptive communications system in accordance with the present disclosure may be structured to provide user-centric and/or customized communication delivery. By this we mean that the System should be able to automatically determine how and/or when to deliver specific kinds of information (e.g., an MSP-alerting report), and in so-doing the System should take into consideration one or more of the following factors: (1) the urgency of Interview content (for example, by automatically determining whether there is alerted information in the Interview), (2) the context of the Interview, such as determining what type of people (e.g., medically-trained or not) are to participate-in (who are being referenced to by) the Interview and what their respective, user-centric contexts probably are (e.g., is it appropriate to disturb them now with this type of message delivery-attempt?), (3) the status of the Interview (e.g., the number of prior delivery attempts that appear to have failed), and (4) information gathered from a successful one or more deliveries of the Interview (e.g., responses of the communication recipient or recipients).

The System may be configured to deliver several Interviews to a given Person (or automated agent) in a single, successful contact attempt. These several Interviews may or may not come from different sources (such as different Medical Providers). In an alternate embodiment, each Interview from a correspondingly different Application (e.g., associated with a different hospital or other medical-facility) may be restricted to being delivered to a given Person in a respective single, actual contact.

The System may be configured to attempt to deliver, in response to a single command, separate instances of a single given message to each individual in a predefined group of Persons (or automated agents) using one or an ordered group of Delivery Strategies.

The system may be configured to coordinate information delivery attempts with the predefined delivery goals such as: (a) encouraging precedence for higher priority information, (b) appropriately utilizing communication channels that are most likely to succeed at a given time-of-day for a given recipient through the use of sequenced Delivery Strategies that are target-centric, and (c) using designated Delivery Channels and times-of-delivery attempt(s) that take into consideration delivery resource availability as currently seen by the System, permissions of users to acquire different levels of confidential information via available channels and customizable delivery preferences of users. Delivery strategies can be made responsive to past delivery history.

The System may ensure security through the use of login procedures specific to Roles and privilege limitation specific to a Person's Role(s) in each Application. Logs may be kept of all actions on the System that record the Role, Person Identity, time stamp, and action taken. Messages sent over the Internet or a like untrusted channel should be encrypted. In an embodiment, web pages accessed by users are kept behind the page-holding facility's firewall.

In one embodiment customized phrases are used to allow classification of alerted Patient Interviews for quality assurance purposes.

Recipient Groups may be defined as (1) a collection of Person ID's or (2) by Persons who have particular Attributes values that fall within a given range and/or that equal one or more specific values. The System can then deliver one instantiated Interview to each member that belongs to a specified recipient Group.

The System may utilize a Role-based security architecture. Each Person object may be assigned relations to other objects (such as an Application, an Interview, a Topic, another Person, an Interview Dialog, or the System) by the assignment of a Role Type. The Role Type provides a context in which the Person object interacts with the other object. This Role Type context may be used to determine permissions the given Person object has with the other object.

The System may use Role Types to define permissions and dictate system behavior. Relationships between certain objects may require a specific kind of Role. The Role defines how the objects are related. When a relationship is formed, certain Attributes may be required for a given object to form that relationship. These Attribute values may have to be entered in the proper object as a pre-condition for the relationship to be created and to be valid. In one embodiment, if an Attribute value that is required does not exist, the System will add a default Attribute value for the Entity that is missing a required Attribute.

In one embodiment, Places (meaning the physical or logical location of a given Person or other object) also have Role relationships and Role Attribute requirements.

The System should keep detailed, time stamped logs regarding System activity, including Interview delivery and delivery attempts, content, and information gathering.

Alerts may be automatically set either by the System using predefined rules, or they may be set by manual invocation by a knowledgeable Medical Service Provider (e.g., an R.N. or a physician). Alerts may be used to selectively notify various Medical Providers or Testing Facility Personnel of problems encountered in making urgent delivery attempts and/or of recently-gathered and important Patient information. In one non-preferred embodiment, one or more pre-selected, or all patients may be given the ability to manually invoke an Alert that notifies an appropriate Medical Service Provider that the patient wants to be contacted immediately. Such an Alert may then appear on the MSP's Alert Screen or on another alert-summarizing and reporting mechanism. If the patient is using a computer-network based channel (e.g., the Internet), then each delivered Interview may include a "Reply-Please Message" button or the like which can be activated by the patient to issue an Alert to the doctor's office for an immediate call back. If a telephone-like, voice channel is instead being used, one of the voice-based dialogs may walk the patient through a process that causes the System to issue an Alert to the doctor's office for an immediate call back. In most instances it is not desirable to allow patients to directly Alert their physicians because such an option could overwhelm the doctor with nonessential communications. Instead it is better for manually-invoked Alerts (if any) that are generated by patients to first go through a Medical Assistant for knowledgeable filtering (screening) and possible handling before being sent onto the physician as an actual Alert.

II. Automated Medical Provider to Patient Communications

As indicated above, if information is not selectively filtered, Medical Service Providers may be undesirably drowned in a deluge of routine information and may fail to pick out the one urgent, proverbial needle in the haystack. A adaptive communications system in accordance with the present disclosure preferably reports urgent and already-filtered information by using an Alert Summary Screen or other, channel-appropriate reporting schemes (e.g., voice-only reports) that present important data regarding a given Patient to the responsible Medical Service Provider in a concise manner that is immediately useful to that Medical Service Provider. Such filtered information can include one or more of the following items:

(1) Test results that require substantially immediate Medical Provider review;
(2) Notification Signal(s) identifying Patient(s) who have been treated and are not progressing as would be normally expected;
(3) Notification Signal(s) identifying Patient(s) who have not yet followed through in timely manner on important recommended tests and/or appointments;
(4) Notification Signal(s) identifying Patient(s) who are not following prescribed health maintenance protocols;
(5) Notification Signal(s) identifying Patient(s) whose currently-gathered data-records indicate significant changes in their health status;
(6) Notification Signal(s) identifying Patient(s) who have failed to appear at a scheduled appointment and have not yet rescheduled the missed appointment; and/or
(7) Notification Signal(s) identifying Patient(s) who have not yet retrieved important test result information, for example, information that would have alerted those patients to quickly contact an appropriate Medical Service Provider for follow up.

In accordance with the present disclosure, a result-reporting means may be included in the System for automatically reporting to a subject patient, and preferably in a manner that is consistent with reporting standards of the reporting, medical facility, the normal results of substantially any test that has been ordered for that patient within the medical practice and received by the medical practice. Normal results can therefore be automatically forwarded to Patients independently of the taking of further action by their Medical Service Providers (thereby bypassing a processing of a below-described, Alert Summary Screen or alternate, alert-summarizing and reporting mechanism).

If the Retrieval Deadline date/time of a given Patient, as defined by a corresponding Database rule or a System standard or by the MSP, is exceeded and it is automatically determined by the System that the given patient has not yet retrieved a correspondingly given communication, the Medical Provider who is related to the still-incomplete Interview may be automatically notified of this situation by a Retrieval Alert signal posted on a corresponding System Alert Summary Screen or on a alternate, alert-reporting mechanism.

In addition to predefined, default Interviews, a System in accordance with the present disclosure may include an Interview customizing means for allowing a Medical Provider to define and request delivery of one or more Custom Interviews; where these Custom Interviews may be appended to other Interviews sent by the System.

In accordance with one aspect of the present disclosure, if the System automatically determines that one or more Interviews containing Alert setting(s) have not been successfully communicated to (retrieved by) respective Patients, copies of such undelivered and Alert-containing Interviews are automatically sent to a Quality Assurance body for review and follow up.

Care-related information may be conveyed to and/or gathered from Patients by the generation of one or more Interviews, where each such Interview may include one or more separate Interview Dialogs.

(A) Topic Category: Test Result Reporting

A System in accordance with the present disclosure may include a rule-based, Interview forming means that controls the formation of Interview content based upon predefined rules which are consistent with medical and/or test facility standards.

The System may use such predefined rules to automatically control what content is placed in an Interview so that the Interview content that is specific for (1) the Interview and/or (2) the Patient receiving the Interview Dialog. (For example, the Interview content may be automatically augmented to include lay-person-friendly test-interpretations in an Interview that initially contains just raw test results). In one embodiment, the Interview Dialog content may be automatically varied in response to pre-established, and/or target-centric, Patient Attribute values so as to accommodate context-based preferences of the patient. More generically speaking, Interview Dialog content may be automatically varied in response to content-controlling Attributes of one or more of the Person objects or of other Entities that are logically associated with the Interview.

The System may use predefined categorization rules to automatically identify and categorize on a prioritized basis, Interviews that contain abnormal test results and/or other important medical information. Such categorized Interviews may then be reported on a prioritized and categorized basis to the relevant Medical Service Provider(s) by way of an Alert Summary Screen (and/or an alternate, alert-reporting mechanism) such as that further described below. Such an Alert Summary Screen (or its alternate) may include follow-up selection means which allow the Medical Provider to immediately select and initiate a follow-up Interview in order to try to obtain more detailed information about the underlying facts of the alert-containing, first interview and in order to thereby add the more-detailed information to the System database as may be appropriate.

In one embodiment, Interview-editing means are provided so that the Medical Provider can edit a selected Interview. For example, a Medical Provider may select for-editing, an initially-formed Interview that is to be delivered to a given Patient where the pre-edit Interview includes raw test results information and where the Medical Service Provider wishes to add some clarifying, further information. In accordance with the present disclosure, the System may present pre-formatted information-clarifying Phrases which can be selectively added by the Medical Provider to one or more of the raw test results information items in the results-reporting Interview as may be appropriate so as to make the delivered message more target-friendly.

A System in accordance with the present disclosure may also include an Addendum Phrase means which offers the Medical Provider an opportunity to add Addendum Phrases to an Interview which is to be delivered to a given Patient. Such Addendum Phrases can include routinely-usable, generic text messages such as: "Please call in with your local Pharmacy Phone Number so we can get you a prescription". The latter Addendum Phrase could be checked off by the doctor if a lab-test result with a positive strep-throat culture comes in. If a blood test is performed after an operation where minor blood loss is to be expected and the blood test shows a minor amount of anemia, the doctor could check off, for insertion next to that lab-report item, another Addendum Phrase such as "You do not need to worry about this small deviation from normal values." Thus the Medical Service Provider can quickly add patient-friendly, clarifying text messages to raw, lab-results or other medically-oriented informational transmissions before forwarding these on for attempted delivery to the patient. This can help to reduce the number of times that patients call in with additional questions about their results and can thereby reduce the communications work load of the doctor's office (medical facility).

A System in accordance with the present disclosure may also include a Retrieval-Time Defining means which allows the Medical Provider to manually set a Retrieval Deadline for the Interview or which allows the Medical Service Provider to elect to use a default Retrieval Deadline that has been predefined for the given Interview Dialog.

Once a, targeted-for-specific-patient(s) Interview has been initiated by the Medical Service Provider, the System may begin to make automatic delivery attempts of the initiated Interview to a corresponding one or more Patients and the System may automatically record delivery-attempt and retrieval information pertaining to the System's interactions with each corresponding Patient or lack thereof.

(B) Topic Category: Acute Illness Follow-up

Typically a Patient is prescribed a treatment plan during an office visit. A Medical Provider can anticipate a range of responses that will be indicative of whether the prescribed treatment plan is performing adequately or not. Information regarding the Patient's subsequent health status can be gathered by employing an automated interviewing mechanism containing a particular set of questions and responses. If a given Patient's answer(s) to a particular one or more questions indicates that treatment is not successful, the System should be able to automatically detect this and automatically notify the Medical Provider of the situation Such an automated notification gives the Medical Provider the opportunity to initiate proper counter-actions promptly.

Introduction to Terminology Used Herein

A large number of specially marked, terms and phrases are used herein. Unless explicitly stated herein, words and phrases pertaining to the medical and computer arts have their ordinary meanings respectively as would be understood by ordinary artisans in the respective fields. The first letter in each word of a specially marked term or phrase is capitalized herein. The below alphabetized introductions to the specially marked, terms and phrases are not to be construed as establishing any limiting definitions but rather as introductory remarks which may be further elaborated on in the more detailed descriptions that follow.

Account: When a user successfully logs into a System that conforms with the present disclosure, the user typically then gains access to a set of privileges and also to a set of System Entities, where the accessible Entities may be determined by further items associated with the user such as the user's Role and Attributes. The combination of these privileges and System Entities which the user gains access to when logging on, constitutes that user's Account. System Entities include data objects which the associated user can interact with.

Addendum Phrase: These are phrases stored in a System Entity known as a Topic Entity. An Interview may be augmented with Addendum Phrases by inserting into the Interview, References to the Addendum Phrases of the associated Topic. The Medical Provider in the Provider Screens can add these references to a given Interview.

Advisement: A communication to a user that notifies the user that one or more Interviews or Alert Information messages are part of an attempted delivery and are awaiting acknowledged receipt. In one embodiment, Advisements are constrained so as to hold no confidential medical information.

Agent Interview Instantiation Rules can include rules created for a Health Maintenance Interview Assignment Agent. These terms will be further explained in the detailed sections below.

Alert: An Alert is typically generated automatically by the System when patient-related data is outside of System specified norms. (Examples include abnormal test results or a time deadline for message pickup being violated.) An Alert may be constituted by a deliverable notification sent to given recipient(s) of a corresponding communication where the notification is that of a high-priority circumstance that it is important for one or more of the recipients to be aware of. Amongst the types of Alerts that are usable herein are: Information Alerts, Retrieval Alerts, and Interview Un-sent Alerts. Alerts that have been received and acknowledged are considered inactive and no longer appear on an alerted Person's screen. When Alert information is sent for delivery and retrieval, the System keeps track of it by recording tracking information including status, and logging information (where such logging information can include indications that certain users have logged into respective Interview Dialogs associated with the Alert and/or have logged into the Alert information itself.

Alert (Information Alert): This may be a type of Alert wherein information relating to a Patient's medical condition or circumstance is being communicated; e.g., to a Medical Provider (MSP) so that the MSP can be quickly notified of medically critical information such as the Patient's blood sugar or pulse rate being above a pre-defined threshold.

Alert (Interview Un-sent Alert): This may be a type of Alert wherein a System-supervising person such as a System-administrator is notified that an Interview that was placed on the System was never sent within a pre-defined period of time that had been set for it to be allowed to remain un-sent on the System and that it is therefore being deleted from a Delivery Scheduler maintained within the System.

Alert (others): In one embodiment, the System also has so-called, Blocked Interview Dialog Alerts. These may be constituted by notifications to a supervisory Person such as a Medical Provider or an Administrator that a Interview Dialog is not being delivered because the Target Person has blocked the associated Topic or Application. These may be considered as a type of Interview Un-sent Alert.

Alert (Retrieval Alert): This may be a type of Alert wherein a supervisory individual is notified that the Target of a given Interview has not satisfactorily accessed the Interview within a specified time period. In one embodiment, if the Target subsequently retrieves the Interview for which the Retrieval Alert had been issued, the Alert is withdrawn and canceled.

Alert Deletion Phrases: These may be phrases kept within a Topic and which are selectable by a Medical Provider when such an MSP is deleting an Alerted Interview and the MSP wishes to record the disposition of the alerted situation. Typical Deletion Phrases may include one or more explanations such as: "Patient contacted; situation handled;" "Patient not contacted;" "Patient Refuses Follow Up."

Alert Notes: Alert notes may include textual content included with an Alert when the Alert is delivered. In an embodiment, each Alert note contains information that describes the circumstances underlying the decision to generate the Alert.

Application: Each application entity may be constituted by at least an executable computer program and may further include program-associated data where the latter may include one or more of: Channel Definition References, Prompt References, Greeting Logic definitions, Greeting Phrases, Application Attributes, Place Relationship Role Information, and People Relationship Role Information. The System may use such program-associated data to perform functions of communication, Information delivery, Security Access, and granting Permissions. One or more Applications may be hosted on a given System at any one time. Typical Configurations have plural Applications being simultaneously hosted. For example, a given System may be hosting three Applications that respectively represent: 1) Medical Information Delivery for a first Hospital named ABC, 2) Medical Information Delivery and Appointment Reminders for a second Hospital named DEF, and 3) Emergency Recall for Medical Providers for Hospital GHI.

Application Attributes: These may be constituted by execution control parameters that apply to or are used by a given Application to define things such as the expiration time for the Application's Interviews, to indicate whether or not the Application is active on the System, and to categorize the Application's Interviews priority relative to those of other Applications.

AppServer: A component of the System that can interact with the System Database in order to provide the System's Scheduler Software with a prioritized list of Deliverable Interviews. Typically, the AppServer is used to deliver to Client Servers, requested information from the System Database.

Attribute Data: Data that further characterizes a given Entity. For example, a Person Entity might have a height Attribute, a set of weight Attributes at different dates, and an IsSmoker Attribute. Attributes may be used to represent information. Also, rules (such as Dialog Rules and Interview Instantiation Rules) may use the Attribute values of Entities for controlling a variety of Attribute-dependent functions. By way of example, a patient's age, sex, and/or smoking habits may be used to automatically determine if, and/or in what order certain Interview questions should be presented. A nonsmoker, for example, would not be presented with a question like, "How many packs per week are you now smoking?", whereas for a 50-year old smoker with chronic asthma this might be one of the first questions presented in an Interview and the answer may dictate what further Interview questions are automatically presented. By way of another example, a patient's age, sex, and/or height may be used to calculate the corresponding normal range for an asthma peak flow test. The patient's actual breathing performance may then be compared against the calculated normal range, and an Alert of appropriate level may be automatically issued, and/or additional questions may be automatically posed depending on if, and how far outside of the attribute-dependent, calculated normal range are the actual results of that patient. Some Attributes may be defined as functions of independent variables and the corresponding functional relationships may be stored in an Entity as well as specific Attribute values corresponding to different values of the independent variables. Thus, e.g., a Patient's weights at various times may be stored or otherwise referenced by data kept in a Person Entity.

Attribute Definition: Attribute Definitions contain 1) definition and requirement logic and 2) validation logic. Definition and requirement logic determines whether or not a given Attribute must contain data for a particular role relationship with a given Entity type. Validation logic helps determine the validity of a given Attribute value. For example, a numeric weight value cannot contain a dollar sign ($). In an embodiment, the System can employ rules to determine whether or not to accept a supplied value as valid. For example, a person weight Attribute can use a rule that determines whether or not a weight value is valid based on the person's age. Thus, a 1-year-old child weight value of 100 pounds would be typically deemed automatically as being non-valid.

Attribute Relationship Requirements: An Entity Relationship Role may require the Entity to have certain Attribute values. Thus, e.g., a Person Patient Role Relationship to an Application may require a Name Attribute for the Person. This is an example of an Attribute Relationship Requirement.

Channel: An information delivery means that is typically coupled (pre-fix wise or otherwise) with a Channel Context. Examples of possible communication channels and their context prefixes include: home-phone, work-phone, personal-email, work-email, and emergency-phone.

Channel Address: This usually provides selective addressing information for identifying a given channel. For example, if the Channel is a home-phone, then the Channel Address may be a telephone number (with or without area or country codes). If the Channel is a work-email, then the Channel Address may be a universally-usable or a network-specific email address. In one embodiment such address data is stored with or directly referenced by the Person Entity.

Channel Context: As already explained, this data may be used as an Information delivery classification modifier, such as "home" or "work"

Channel Definitions: These may provide supplemental characterizations for associated Channels and may be represented by parameter data that are usable by the System and that can be referenced by Applications and Delivery Strategies for identifying specific details of the associated communications channel. Examples of such informational parameters may include hours of availability for the given channel and data transmission type (such as voice, text, or HTML) that is usable over the given channel.

Channel Manager: This may be constituted by program logic that processes Deliverable Interview Dialogs received from the Scheduler for delivery. Such processing may include completing necessary fields in the received Dialogs, verifying the validity of all completed fields, and then presenting the validated Dialogs to a specific Channel Type manager for delivery. The Channel Manager may also be constituted by programs for processing Interview Dialog responses and Channel Requests and forwarding these back to the Scheduler for updating the Database.

Chart Note: Per conventional medical terminology, this may be an informational note regarding a Patient and/or a Patient visit where the note has been recorded into the System by a Medical Provider for later access to aid in the care of the Patient.

Channel Request Handler: This subsystem may be constituted by one or more programs in the System that receive Channel requests for more Pending Dialogs to transmit and which pass these requests on to the Interview Chooser, where the latter can then supply these.

Channel Type: A main characterizing attribute of the informational delivery channel means such as telephone, web, email.

Chosen Dialogs: Dialogs that have been chosen for delivery at a given time.

Database: A storage subsystem that holds the information and the procedures typically used by the System to carry out its functions. The Database information may comprise: Delivery Strategy information and logic, Channel Definitions, Entity names and other Attributes including Interview responses and other data, Roles and Role relationships, Alert data and logic, Log-in logic and parameters, and other such data.

Data Maintenance: Routine data management operations such as data archiving, database integrity checks, and database cleaning and purging procedures.

Data Reaper: A portion of the System that is often made responsible for (1) gathering information to determine which Deliverable Interviews should be scheduled, and/or (2) handling data returned from Delivered Interview Dialogs by the Response Handler. The Data Reaper may contain and use the following modules for carrying out Interview Dialog delivery: (1) Interview Chooser, (2) Channel Request Handler, and (3) Response Handler.

Deliverable Dialog: This is a kind of Interview Dialog wherein one or more or all of the following is true: 1) Dialog Status is equal to Pending, 2) the Interview Dialog belongs to an Interview with NeedsReview Property equal to 'False', and 3) the given Interview Dialog has a next delivery time within the Dialog Delivery Schedule of the System taking into account any applicable InterDialog Time Gap.

Deliverable Interview: An Interview that has a Deliverable Interview Dialog.

Deliverable Interviews Manager: This module is responsible for gathering and managing Deliverable Interviews from the Database as requested by the Scheduler. It may also be made responsible for tracking and modifying the state and properties of the Interview as the Interview is processed by the System. The Deliverable Interviews Manager may contain logic that prioritizes Deliverable Interviews for delivery to the Scheduler.

Delivery Strategy: This broadly describes various kinds of data and instructions that the System uses to deliver one or more Pending Interview Dialog(s) to a Target Person. The data and instructions may comprise usable-channel identifiers, appropriate delivery time definitions for each channel, minimum and/or maximum number of attempts per channel, prior communication strategy completion criteria, indications of whether or not Patient restrictions on delivery can be over-ridden, indications of whether or not a telephone hang-up or equivalent action causes cessation of delivery attempts, and specifications for how security is to be handled (such as maximum password entries allowable over a given channel). A Delivery Strategy may inherit into itself, the strategy data or earlier other Delivery Strategies that were being utilized prior to the given Delivery Strategy being used. Delivery Strategies may also contain a progression list specifying an ordered progression of strategies to be tried. Such progression strategies may include mandatory strategies and criteria that must be fulfilled before a subsequent strategy can be executed. Each Interview Dialog in an Interview should contain at least one Delivery Strategy.

Delivery Strategy Group: A specified set of Delivery Strategies that the System may use. Delivery Strategy Groups may be prioritized so that they are used in a sequentially ordered progression by the System, with the more-likely to-succeed Delivery Strategies being attempted first and comparatively less-likely to-succeed Delivery Strategies being attempted later, and perhaps not at all, depending for example on whether the urgency attributes of the communication are below predefined thresholds. Each Delivery Strategy Group may be respectively tuned to a particular kind of delivery mechanism. For example, a high-level emergency Delivery Strategy Group could concentrate on use of cell phones, pagers and/or other recipient-targeting channels that have high likelihood of contacting even a highly mobile recipient. Such high-level emergency Delivery Strategy Groups should have no limits on the channel open-times of their respective communication channels. In contrast, a non-urgent Delivery Strategy Group may take into consideration the temporal bandwidths of the targeted recipient (e.g., the doctor is making hospital rounds now and should not be disturbed for nonurgent matters) and such a non-urgent Delivery Strategy Group may therefore be more apt to use less-intrusive communication channels (e.g., email) because the convenience of the targeted recipient is an overriding factor to immediate retrieval of the message. A non-urgent Delivery Strategy Group may therefore have more reasonable, limited channel open-times, and/or may rely more on less-intrusive delivery mechanisms such as telephone answering machines, email and web channels rather than on pagers, cell phones and the like.

Delivery Strategy Progression Requirement List—For a given Delivery Strategy within a Delivery Strategy Group, such a Progression Requirement List may include a requirement that other Delivery Strategies within the same Group but which are of higher precedence, must have each had a respectively-specified, minimum number of attempts completed before the given Delivery Strategy can be attempted.

Dialog Delivery Schedule: When an Interview is Instantiated; a Delivery Schedule is created for each of its Interview Dialogs. This can be specified in terms of a range of delivery times or a delivery time window for each Dialog relative to the time of formation of the Interview or relative to another relevant sentinel event. A minimal time spacing between successive Interview Dialogs, the InterDialog Time Gap, can also be specified so that the information is delivered or obtained from the Interview Dialogs at appropriate intervals. These factors may interact with delivery Channel parameters of the System and may thereby be used to schedule Dialog deliveries.

Dialog Question and Answer Presentation Rules: Such Rules can utilize Attributes (such as Patient Attributes, Interview Attributes, and System Attributes) to determine which Phrases are presented to a user. In one embodiment, these Attributes can be modified by the System via Interview input, Medical Provider input, and data uploading as well as Patient's responses during an Interview delivery.

Entity: The term "Entity" generally refers to any System object that can have an Attribute. Typically, each given Entity can be made logically-related to other Entities by assigning a Role to the given Entity. Entities can comprise Persons, Places, Applications, Topics, Dialogs, Interviews, and even the object that references the System as a whole.

Entity Role Relationship Requirements—To establish a Role between a Person and another Entity, the System might require the Person to have particular Attribute Values. In an embodiment, if a Person does not have a required Attribute value for establishing a given Role-Relationship to a particular other Entity Type, the Role-Relationship will be rejected by the System. In another embodiment, if a Person does not have a required Attribute value for establishing a given Role Relationship, a default Attribute value will automatically be assigned to the Person so as to enable the establishing of the given Role Relationship. In an embodiment, Entity Role Relationship Requirements are based on Entity Types. In an embodiment, Specific Entities can have specific Entity Role Relationship Requirements.

Entity Type—This data item can identify the type of a respective Entity such as "Person" for a human being or an automated agent, or such as "Application" for a hospital/practice-specific set of interactions, or such as "Interview" for a specific communication between two or more of identified human beings and/or automated agents, or such as "Topic" for a specific set of Rules, Data and/or Logic under which an Interview of that Topic is to be instantiated.

Instantiation: Instantiation of an Interview occurs when the Interview content and controls are made ready for delivery and retrieval. This typically occurs when Interview data is added to a Topic and Topic rules are applied to form the deliverable Interview.

InterDialog Time Gap: Each given Topic Dialog except the last one in an Interview should have associated with it, an InterDialog Time Gap that specifies the minimum time until the next Interview Dialog in the same Interview can be delivered after the given Interview Dialog has been delivered.

Interview: Each Interview should be instantiated within a corresponding Topic so as to contain the data and logic that is to be used during the carrying out of the Interview. An instantiated Interview typically contains Interview Dialogs and a Dialog Delivery Schedule with Priorities corresponding to each Topic Dialog in the Topic, Attributes, Information Alert Data, Retrieval Alert Data, Addendum Phrase references, Delegation Phrase references, Alert Deletion Phrase references, Role Information for the Persons and Places that have a relationship to the Interview, and Channel Delivery Attempt data logs. An instantiated and in-progress Interview may hold data derived during information delivery to a Target, such as Patient's responses. The data in such an in-progress Interview can be used by other Entities that are related to the Interview based on the Role of each of the other Entities relative to the Interview.

Interview Addendum Phrases: When a Medical Service Provider is reviewing or creating an Interview for delivery to a Target Person, the MSP may selectively add Interview Addendum Phrases within the context of the encompassing Topic. The Interview Addendum Phrases selected by the Medical Provider may add further information to be used by the Target in processing the particular Interview.

Interview Chooser: The System may include various forms of Logic for computing the number of Deliverable Interviews that a given Channel Manager can accept in selecting which Interviews to try to deliver. The Channel Manager typically determines which and how many Interviews can be practically sent over each available Channel. The Interview Chooser is responsible for performing the final analysis on the deliverability of an Interview over a set of available Channels.

Interview Delegation Phrases: These phrases may be preselected from within the Topic of a given Interview. Such Interview Delegation Phrases may be used by a Medical Service Provider to indicate to a lower ranked, Medical Assistant his or her desires when delegating responsibility over an alerted Interview to the Medical Assistant.

Interview Dialog: An Instantiation of a corresponding Topic Dialog formed when an Interview is formed from a Topic. It typically includes references to Persons, Attributes, and delivery mechanisms that will be used during the execution of this Dialog. It may also hold information regarding the delivery history and status of the Dialog.

Interview Dialog Status: An Interview Dialog Status may be selected as one from the following nonlimiting list:
1) Pending—the Interview Dialog is awaiting delivery to (retrieval by) a Target Person;
2) Expired—the Interview Dialog has been on the System for a set period of time after which it is no longer eligible for attempted delivery. A Database Cleanup and Archiving Agent can remove such Dialogs from the System.
3) Delivered—the Interview Dialog has been delivered successfully to (retrieved by) a Target Person or, in one embodiment, the Delivered Status may further indicate if and/or when the Interview Dialog has been delivered successfully to all the Target Persons in an associated specified Target Person Group
4) Not Delivered—the Interview Dialog has not been delivered to a Target Person.
5) Blocked—the Interview Dialog has been blocked from delivery by a parameter established at the Topic or Application level
6) Error—the Interview Dialog delivery was not completed because the System encountered an error condition.

In one embodiment, if an Application or Topic is blocked by a Person, i.e., a Person elects to have the System not have him or her as a Target Person for that particular Application or Topic, the Status of the Dialogs of the corresponding Application or Topic are automatically set to "Blocked."

Interview Instantiation Date: This can be the date and time that the System instantiates an Interview and assigns it for delivery to one or more persons.

Interview Instantiation Rules: The System can use these rules to control Interview formation when an Interview is created within the System. These Rules may contain conditions based upon Attribute values for Entities related to the Interview. These Rules may, among other actions: 1) set certain data Attributes for the Interview, 2) set Delivery Schedule for the Interview parameters (such as Priority Values), 3) set Alerts and Alert Notes, 4) set Retrieval Alert deadlines, 5) set Interview routing, 6) set Interview delivery status, and/or 7) abort Interview delivery.

Media Type: This can specify communication protocols and types which may be used when communicating over a given Channel such as HTML version, speech data, or text.

Medical Assistant: This is a Person Entity Role. A Medical Assistant is an individual who assists a Medical Service Provider but does not have primary legal and/or medical responsibility for delivering Patient care. A Medical Provider may designate important Patient care activities including that of carrying out various communications to a Medical Assistant after reviewing the medical data and situation. The MSP typically instructs the Medical Assistant as to how the situation should be handled. In one embodiment, certain types of Patient communication activities may be automatically delegated to a Medical Assistant so that specific review of each instance of such activity by the Medical Provider is not required.

Medical Provider or Medical Service Provider: This is a Person Entity Role. A Medical Provider is a person that has a relatively high level of legal and/or medical-field-recognized responsibility for the Patient's medical care. Medical Providers typically include physicians and those people designated or empowered to have the responsibility to deliver important medical information and/or services to Patients, such as Test Technicians, Specialists, and Medical Assistants.

NeedsReview Property of Interview: If a given Interview has a corresponding NeedsReview Property set to 'True', the System should automatically block delivery of all Dialogs belonging to such Interviews until they are reviewed by an authorized MSP. A Medical Provider using a review mechanism such as the Provider screens and thereby understood to be reviewing the Interview information can be empowered to change the NeedsReview Property to 'False'. The System should automatically record the Person ID and Role and time when the NeedsReview Property is changed so that effective care-review audits can be conducted. Some Dialogs may be automatically Instantiated with their NeedsReview Property='False' so as to default to state that circumvents review. In one embodiment, a specified one or more Medical Assistants may be authorized to also review all or specified types of Interviews and to thereby change the NeedsReview Property to 'False' as may be appropriate.

Person Attribute Group—A group of persons who have one or more Attribute values or range of values in common.

Person Entity: An Entity that is a human being or an automated agent and that can have Role-based relationships to other Entities such as the System, Applications, Interviews, Topics, as well as other Persons. Roles for a Person Entity can include System Administrator, Application Administrator, Medical Provider, Medical Assistant, Patient, Primary Care Provider, and Test Technician.

Person ID Group: A group defined by a set of persons each of which has an unique ID.

Phrase—Phrases may be represented by an ordered list of references to pre-defined Prompts and/or Attributes. Dialogs may use pre-recorded Phrases to define content for Questions and/or Answers. Phrases as well as groups of phrases can be used to define complete sentences or questions.

Place Entity: An Entity that identifies a physical and/or logical location at which medical services are rendered, such as a clinic, an out-patient facility and so forth. Each Place Entity can have Role-based relationships to other Entities such as Applications and Interviews. Roles for this Entity include for example: Medical Facility and Clinic.

Porch: This is a Role-Specific security entryway, whereby a Person may log into an Application with a Role using their Person ID and/or Pass-code and/or other security ensuring measures (e.g., biometric) as may be appropriate. A Person should only be granted access if their Person ID and Pass-code match and the so-authenticated Person has the given Role relationship to the given Application. For example, assume a Person has only one Role relationship to Application A, which is Medical Provider, and a different, singular Role relationship to Application B, which is that of being a Patient. Then this Person should not be enabled to log into the Application-B Medical Provider Porch, but should be able to log into Application-A Medical Provider Porch. The said Person should however, be able to log into Application-B Patient Porch.

Priority: This a System-maintained value that the System can use to determine the precedence of Interview Delivery for each given Dialog. Priorities may include: Application Priorities, Topic Priorities, Topic Dialog Priorities and Person Priorities. In an embodiment, any or any combination of the above Priorities can be automatically modified in response to a Patient's answers to individual Interview Dialog phrases. In certain embodiments, the precedence of an Interview Delivery may be made a function of all the above-mentioned Priorities. In certain embodiments, an Application's Priority is given greater weight than all other priority types.

Provider or Medical Provider: See Medical Service Provider.

Response Handler: This may refer to one or more Programs in the Scheduler that process information received from a delivered Interview Dialog and/or from an Interview whose delivery was attempted but not completed, where the Program(s) pass the received and processed information on to the Database.

Retrieval Deadline: This may refer to the date and/or time or other event-occurrence marker by which an Interview Dialog with a Retrieval Alert set should be accessed by the Target Person to avoid triggering a Retrieval Alert.

Roles: Roles may include those of: System Administrator, Application Administrator, Patient, Medical Provider, Primary Care Provider, Medical Assistant, and Test Technician. Roles may be used to define relationships of Persons with other Entities, such as other Persons, Applications, the System, Topic, and Interview. A given Person may have more than one Role in a given Application. The Roles between a given Person and Application typically define the subset of available Roles for the given Person for Entities belonging to said Application.

Role Based Security: The System may implement a type of Role-Based Security for determining user permissions in the system. Under such a Role-Based Security paradigm, each Person's Role capabilities are generally confined to his or her Roles in the respective Application. Thus, e.g., if a Person is not mapped as a Medical Service Provider to Application A (e.g., Alpha Hospital), then the Person cannot be mapped as a Medical Provider for an Application A Interview. The System Administrator Role may specify a permissive Role for interacting with the System Entity. Persons assigned the Medical Provider Role may be allowed to grant privileges to their account to other users such as to Medical Assistants. The System may use Roles to provide a means for a given Person to have the ability to be associated with one or more Applications. The Role a Person has may dictate which interfaces and resources are available to him or her. Therefore, a given individual may have one login user name and password and use this to access multiple Applications. The individual can then access and utilize select services for each Application based on his or her Role(s) for the given Application.

Scheduler: This may be implemented with logic that selects a group of prioritized Pending Interview Dialogs from the Deliverable Interviews Manager for delivery to Targets. These Pending Dialogs may be referred to herein as the Chosen Dialogs. The Scheduler may combine such Chosen Dialogs with other Dialogs to the same Target Persons in the Database so that several Pending Interview Dialogs may be delivered to the same Target in an Interview Dialog delivery.

System Entity: A System Entity may be comprised of Persons, System Attributes, Channel Types, Prompts, and Channel Definitions. Applications should be referenced to the System.

System Attributes: System Attributes may be comprised of information used by the System such as data maintenance and archiving information and default language specifications for System prompts.

Target: For purposes of an Interview delivery-attempt, the Target is typically the Person to whom a communication is being sent. In at least one embodiment, this could be a Person with a Patient Role or a Medical Provider Role.

Target Group—This can be a group of Persons to whom a same communication is being sent for respective retrieval by each member of the group.

Topic: Each Topic should contain logic that is used for formulating each of its Instantiated Interviews. A Topic can comprise a Dialog Collection where the latter comprises Topic Dialogs which in turn comprise Dialog Delivery Strategies, Alert Logic, Dialog Logic, Phrases, Rules, and/or Attributes, and/or Topic Interview Instantiation/Delivery Rules, List of Persons who have blocked the Topic, Interview Addendum Phrases, Interview Delegation Phrases, Alert Deletion Phrases, and/or Health Maintenance Topic Assignment Criteria. A Topic should be related to one given Application. A Topic may be used to create one or more Interviews. Thus, multiple Interviews may be Instantiated from a given Topic.

Topic Attributes: Topic Attributes may each include a priority value that assigns a relative priority to the associated Topic where the assigned priority is relative to corresponding assigned priorities of other Topics. Each Topic Attributes may further include one or more default Topic prompt specifications, and/or a parameter that determines if the Topic is active on the System or not.

Topic Category: This data structure may identify a category or type of Topic such as Health Maintenance, Acute Illness Follow Up, Specialist Follow Up, Test Follow Up, Custom Interview, or Test-Result(s)-Delivery.

Topic Dialog: Each Topic Dialog may contain delivery strategy sets and/or Topic Dialog logic and/or Phrases which may be used for defining and forming phrases, for adaptive content presentation, for controlling Alert information, and/or for establishing internal variables that direct question and statement delivery phrases. Interview Dialogs may be formed using these rules and data from Topic Dialogs when an Interview is Instantiated from a Topic.

Topic Group: A set of Topics. By organizing Topics into Topic Groups, it is easier to select a particular Topic. In an embodiment, a Topic Group can have a name. This name may be used to give a generalization to the Topics that are in the Topic Group. An Example of a Topic Group might be, the Asthma Follow Up Office Visit topic-group, which, in an embodiment, may include a Topic for follow up for a mild asthma attack, a Topic for follow up for asthmatic bronchitis where an antibiotic was prescribed, a Topic for follow up for asthmatic bronchitis where an antibiotic was not prescribed, and/or a Topic for follow up for severe asthma.

In accordance with the present disclosure, an automated mechanism may be constructed and configured to provide a set of Topics (e.g., Asthma Follow Ups) for a given Application (e.g., Alpha Clinic), where each Topic contains at least one Topic Dialog, and where the Topic Dialog is suitably organized for managing a given medical diagnosis and treatment plan. After a medical diagnosis and treatment plan has been formulated from a corresponding one or more office visits, a Medical Provider or a Medical Assistant can instantiate an Interview based on a particular Topic to be sent to a Patient, where the Interview acts as a monitoring mechanism for assuring that the treatment plan is being carried out and the patient is progressing as expected.

In accordance with the present disclosure, automated means can be provided for formulating, sending, and ultimately delivering to an under-treatment patient, an Interview that will contain one or more Interview Dialogs where the latter can use automatic and interactive logic to interview the Patient regarding his or her status following an office visit. The times and means of contact may be specified in Delivery Strategies as discussed below.

During the automated Interview Dialog, if a Patient response to a given question is determined by the System to be indicative of a problem, the System may automatically set an Information Alert for this Interview Dialog and may thereafter automatically signal the Medical Provider related to the Interview of the situation by way of the Medical Provider's Alert Summary Screen and/or by way of other Alert Reporting mechanisms. In this way, the System can automatically provide a means for the Medical Provider to be directly notified of the problem so that follow up efforts can be initiated rapidly.

During interaction with a delivered Interview Dialog, Patients who are doing as medically expected should be able to indicate this by the answers they provide to the System. The System should be able to automatically record the Interview Dialog question and answer activity and store data representing such activity in its database for possible review by medical personnel if such review is warranted. Interview Dialogs may be structured in accordance with the present disclosure so that the System is able to automatically receive quantitative responses from respective Patients, such as peak flow measurements in asthmatic bronchitis, or pulse rate, or weight, and for the System to use such responses to (1) make comparisons over time for each respective patient, (2) compare the automatically-obtained, quantitative responses with context-based standards, (3) trigger the issuance of Information Alerts where appropriate, and (4) automatically guide the question flow logic in view of already collected information about the patient.

(C) Topic Category: Follow Up for Specialty Referrals, Ancillary Services, and/or Tests Commonly, a Medical Service Provider may want to obtain consultation with a particular kind of specialist regarding a given patient or he/she may want to request ancillary services or order tests for that patient, where the follow-on consultations, services or tests may call for the making of additional arrangements beyond that of scheduling the preliminary office visit. Appointments for such referrals often cannot be made immediately, at the time of the preliminary office visit. In such cases the Patient is typically told that someone will call with an appointment in the future. This open-loop method of operating leaves the door open for a multiplicity of potential problems: (1) The referral request may be misplaced; (2) The insurance clerk may mishandle the request (e.g., the biopsy request of a possible malignant skin lesion may be scheduled for review in two months rather than right away as is typically called for in modern medical practice); (3) The Patient and/or next-in-queue-MSP may not be able to be easily reached by the persons who are trying to schedule the follow up appointment(s) and those persons may simply give up trying; (4) The test lab fails to deliver the requested test results. These are just a few examples of the many opportunities in an open-loop system (a system without a feedback mechanism that assures the desired follow up actually takes place) where scheduling and/or follow up communications may collapse and where the good intentions of the initial Medical Service Provider are thwarted by deficiencies in the communications infrastructure.

A System in accordance with the present disclosure may include means for automatically instantiating a Test, or Consult-Referral Follow-Up Interview which is structured to prevent requests for tests, consultations, and the like from falling through the cracks in a busy medical practice. In one embodiment, such a Test, or Consult-Referral Follow-Up Interview contains at least two Interview Dialogs: A first one that contacts the Patient prior to the appointment to serve as an appointment reminder and a second one that contacts the Patient after the appointment to confirm the appointment or test was completed. If the second Interview Dialog fails to timely confirm that there was adequate follow up, an Information or Retrieval Alert, as is appropriate, is automatically generated by the System.

(D) Topic Category: Health Maintenance

Conventionally, Patients are reminded of home health monitoring interventions during periodic office visits to their Medical Providers. For some chronic conditions these visits may occur every three to six months (provided the patient doesn't miss such appointments). Often Patients' monitoring between visits is poor.

A System in accordance with the current disclosure includes Health Maintenance follow up means which can automatically schedule for the delivery of Interview Dialogs that serve as Health Maintenance reminders, where the scheduling may utilize Rules and Delivery Schedules responsive to one or more Patient Attributes. The timing and/or frequency of scheduled delivery can be determined by prespecified timing rules. In one embodiment this timing of delivery is made responsive to the Patient's age and/or other Attributes, and/or history of prior responses. An example of such Health Maintenance, Interview Scheduling Rules would be a reminder message that is automatically sent to Patients whose Attributes indicate they have emphysema and they are older than 50 and they have had pneumococcus vaccinations more than 5 years ago, where the reminder text includes an advisement to obtain a flu shot and a pneumococcus vaccination. The Delivery Strategy rules for this message could, for example, call for delivery in the month of October and have a Retrieval Alert set for 7 days. Another example of a Health Maintenance, Interview Scheduling Rule could be one that instantiates the automated delivery of a corresponding message to Patients with Diabetes Mellitus with Hemoglobin A1c values more than 8.0 percent where the message requests a home determination of their post-prandial glucose value. The Delivery Strategy for this message could be set for periodic instantiation every two weeks and a Retrieval Alert set for 7 days and an Information Alert set if the glucose value entered by the patient was more than 140 mgm percent.

A System in accordance with the present disclosure may include a Progress follow-up means that automatically, and usually periodically, instantiates one or more Interviews for gathering Patient quantitative data from a respective patient so that the System can use such requested data to automatically monitor the Patient's progress. The lack of a timely response and/or receipt of responses that indicate deteriorating health status, where such indications may be automatically determined from machine-implemented use of pre-defined, Progress follow up rules should trigger alerts. The Progress follow up rules may define when and what kind of Information or Retrieval Alerts should be issued to the Medical Providers who have a relationship with the initial, unanswered or bad-progress-indicating Interview. Typically, at least one Medical Service Provider is designated as the Primary Care Provider (PCP) for a given patient within the bounds of a given Application, and by default, the System should establish an Alert-receiver relationship between the PCP and the Progress follow-up Interviews that are scheduled by the Progress follow-up means so that the designated primary care provider will be alerted by default in the case where no other Medical Service Provider has been delegated responsibility for follow up and where the Progress follow-up Interviews indicate bad progress by the patient or are not answered by the patient within a pre-specified time window.

(E) Topic Category: Follow Up on Patients Who Fail to Keep Scheduled Appointments A System in accordance with the disclosure may also automatically or semi-automatically instantiate one or more Interviews under the Topic Category of Missed Appointments. Typically the task of manually filling in certain customizable message fields is delegated to a particular Medical Assistant who is responsible for keeping track of the Patient that did not keep his or her appointment. Alternatively, Interviews in this Category can be assigned to an automated, follow-up agent by having a Data UpLoader of the System automatically upload a missed-appointment file, where the uploaded file contains information regarding the Patient who was not seen for their appointment. The semi-manually or automatically generated, Missed Appointment Interview requests the Patient to reschedule. In an embodiment, if the Missed Appointment Interview is not retrieved, a Retrieval Alert is set for the Interview, such that the Medical Provider associated with the Interview will see the Alert on the Alert Summary Screen or will learn of the failure by the patient to cooperate via another, alert-reporting mechanism (e.g., a voice-based one). In one embodiment, if a Patient successively fails to keep two or more appointments, an Information Alert is generated to indicate this heightened level of non-cooperation by the patient.

(F) Advisements

Sometimes, the reason that a patient has not responded to a first-sent Interview-request is because an answering-machine or another form of message-intercepting intermediary has accepted the first-sent Interview-request in a manner that leaves the intended Target (the patient) unaware of the fact that the Interview-request came in. For example, someone at home may inadvertently delete pending messages from the answering-machine or cancel the blinking of the pending-new-messages light. A System in accordance with the disclosure may include a Pending-messages Advisement means which automatically generates and tries to deliver an Advisement or notification signal (such as an email or a pager notification signal) which will notify the Patient that he or she has pending messages on the System that have not yet been affirmatively responded to by the patient or by a patient-delegate to whom the patient has delegated the authority to respond on the patient's behalf. (In some cases, an affirmative response may simply call for the recipient to press a touch-tone button, or to click-through to a special web page in order to affirmatively indicate they had gotten and understood the message. In other cases, the Interview delivery-attempt may call for a much more elaborate set of responses.)

In one embodiment, Advisements are sent to all or pre-specified groups of patients only if the unresponsive Patient appears to be not responding to Interview-requests or messages that contain an alert setting or an alert setting above a pre-specified threshold in a spectrum of alert level options. In yet a further embodiment, an Advisement is sent to any one or to a member of a pre-specified group of patients only if the given Patient has messages with a particular alert status.

DETAILED DESCRIPTION

I(a). Exemplary Environment

Referring to FIG. 1A, a flow chart schematic is shown of an exemplary environment 99 in which methods, systems and other aspects of the present disclosure may be practiced. It is assumed in the illustrated example that a physician 20 (also referred to as an MD and shown wearing a hat labeled "MD") has just finished seeing a given patient (P) 50. The MD 20 now wants to have additional tests or procedures performed on patient P. Let us assume the doctor wants X-rays taken of specific areas in the patient and wants the radiologist's reading (62) returned to the doctor for consideration (26) no later than, say, three days.

This is easily said but turns out to involve a fairly complicated set of interactions when studied closely. The MD's mental intentions are represented by thought bubble 21. These thoughts 21 implicitly call for the completion of a series of action items (83) even if the MD does not consciously think about them. We will explore such action items as we follow a trail of interactions developing clockwise around the illustrated clock face 24.

Soon after having the initial thoughts 21, the MD 20 may objectively initiate the implied action items (83) by writing a short note on a slip of paper 22 and/or by verbally expressing the desired course of action with the speaking 23 of a few short words ("Let's schedule an upper GI X-ray for patient P"). The written and/or spoken expressions 22/23 may be directed immediately to another person (e.g., patient P or nurse RN) or the expressions 22/23 may be indirectly routed towards an intended recipient (e.g., nurse RN) by for example slipping the hand-written note 22 onto a to-do pile, or by sending the note as an email message 22a and/or by dictating the spoken words 23 into a voice-recording machine 23a for subsequent retrieval by the intended recipient (e.g., nurse RN).

Just from this short introduction, one can see how things can go astray. What if the hand-written note 22 gets lost in the to-do pile? What if the dictation 23a accidentally gets erased? The very first communication delivery-attempt 25 (shown as a wide-bodied arrow) may fail to complete and the MD's good intentions 21 may evaporate into useless (or even harmful) inaction if things go wrong. Luckily for us, this is a very professional office and our MD 20 habitually knows to employ multiple channels (e.g., tape 23a, email 22a) for his message delivery attempts because he instinctively understands that one or more such attempts may fail. Thus for purposes of moving the example along, we assume that the MD spoke (23) directly to the patient 50 and also scribbled the action plan onto a slip of paper 22 with instructions for the patient 50 to give the memo slip 22 to the physician's medical assistant (RN) 30 and with further indication that the nurse (RN) will take care of scheduling the desired test procedure (e.g., X-ray).

Unfortunately, patient P is not as professionally minded about message delivery strategies as was our MD. A number of things can go wrong with this indirect communication delivery attempt 25a where the intended target is actually nurse 30. The patient 50 may not understand the instructions very well because, for example, the patient generally speaks a different language (e.g., Spanish instead of English) and/or the patient is on medications or under duress and therefore has an impaired ability to understand. Even if the patient initially understands the instructions, he or she may forget by the time they get to the front desk to speak with the RN 30. We assume for sake of moving our example forward that these obstacles do not materialize. The doctor also spoke directly 25b with the nurse 30 and she proficiently got hold of the doctor's memo slip 22 before sending the patient 50 home.

We assume further in this example that the RN 30 decided to use a telephone 31 as her communications channel for trying to see to it that the MD's intentions 21 are converted into actions. After persistently ringing the laboratory scheduler 40 a number of times, the nurse managed to get through and successfully deliver (35) her request for initiating the scheduling of an appointment for patient 50 and for letting the scheduler 40 know exactly what kind of procedure is being requested (e.g., an upper GI X-ray). The lab technician 40 is instructed to attempt to contact (45) the patient 50 and to thereby establish a date and time on the lab's schedule 42 or when the X-ray procedure 58 is to take place.

Regretfully in our example, the lab technician 40 was given only one telephone number for trying to reach patient P via the patient's telephone 51. Upon calling that telephone number, the technician 40 learns that the patient 50 has installed a telephone answering machine 52 to intercept all incoming calls. In attempting to initiate a first interview 45 with the patient 50 for setting the procedure date, the technician 40 may have a large number of obstacles to overcome. First, there is the possibility that the telephone number dialed by the technician 40 is an incorrect one and the technician is leaving messages on a wrong answering machine rather than the one 52 that truly belongs to the patient 50. Second, it is possible that the patient's answering machine 52 is overfilled with messages or otherwise not working and thus is unable to record the technician's initial message. Third, the patient 50 may not realize that there is a recorded message pending on his answering machine 52 because another family member may have already listened to all the messages, deactivated the blinking "message pending" light and forgot to tell the patient 50 about the message and/or worse yet, erased the undelivered message. Finally, even if the patient 50 was told about the message, the patient must remember and actually call back the laboratory technician to thereby complete, what we refer to herein as a "scheduling interview" 45. During the scheduling interview 45, the agreed upon date and time for the procedure should be recorded into the laboratory's calendar 42. And hopefully, patient P will also accurately record the date, time and location for the procedure on his/her personal calendar (not shown).

As the details of the above scheduling procedure (45) began to unfold, we have already begun to appreciate the idea that many obstacles can come into play to block a successful completion of an "Interview", in this case, the scheduling interview 45. Flowchart-diamond 90 illustratively presents two of these potential obstacles. Flowchart-diamond 90 asks whether the original message got through to the targeted recipient (e.g., 50) by way of the chosen delivery channel (e.g., 51/52) and whether the target understood the initial message. Flowchart-diamond 92 addresses the further question of whether the targeted recipient (e.g., 50) remembered about the initiation or completion of the communication attempt 45 so that the targeted recipient (e.g., 50) can take the next expected action. Flowchart-diamond 94 addresses the issue of whether the target actually executes the remembered message and therefore calls back the lab technician 40 to actually complete the scheduling 45 of the procedure and/or to actually go for the procedure 58. If something goes wrong with respect to one or more of these flowchart-diamonds 90–94, the intentions 21 of the initiating MD may not be realized at all or within the time frame (24) originally contemplated by the MD.

We assume that the lab (40/42) is professionally run and that as a consequence, within a few hours or a day before the scheduled procedure 58, the laboratory technician 40 will try (47) to contact the patient 50 again to remind the patient of the scheduled appointment 42 so that the scheduled time slot is not missed. Just as in the case of the schedule-setting interview 45, the attempts to deliver and complete the reminder interview 47 may run into a number of obstacles. These obstacles can include those dealing with getting the reminder interview 47 started by delivering at least an open-loop message to patient P (e.g., an automated recording, "You have an appointment at 3:42 PM . . . ") byway of a communications channel 51/52 that is likely to succeed in actually getting the message to the target 50. A more efficient reminder system will close the loop by asking for acknowledgment by the patient (e.g., an automated recording, "Please press touch tone button 1 if you are coming, 2 if you need to cancel or 0 if you need to speak to an operator"). Let us assume the lab 40/42 relies on an open-loop reminder system which merely leaves a manually-generated voice message on the patient's telephone answering machine 52. However, at the time the technician 40 tries (47) to remind the patient 50 about the appointment, the patient is in his car driving to work. The patient does not check in with his answering machine 52 and completely forgets about the appointment that had been earlier scheduled during interview 45. Once again, the intentions 21 of the initiating MD 20 may not be realized at all or within the time frame (24) originally contemplated by the MD because of a communications problem. If the technician 40 had known to call the patient 50 on the patient's cell phone (an alternate channel) at that time, perhaps the reminder attempt 47 would have been more successful.

We assume in this example that the reminder interview 47 completed successfully. The patient 50 not only got and understood (90) the contents of the reminder interview, the patient also remembered them (92) and actually went for the appointment (94) at the scheduled time. Path 54 represents the patient's actions in correctly responding to the reminder interview 47 and/or the scheduling interview 45. Once on path 54, patient P actually completes his or her part of the scheduling cycle and timely appears for the intended procedure 58. We further assume that nothing goes wrong at the laboratory. The film is properly developed and delivered to a radiologist 60. The radiologist timely sees the film and provides a reading report 62. (As in the case of our doctor's (20) initiating request 22/23, the radiologist's report 62 may be dictated and transcribed by a typist before being ready for delivery to the MD 20.) In this particular case, the radiologist 60 notices (63) something suspicious in the X-ray and the radiologist attempts (65) to expeditiously notify the MD 20 that the reading is done (that state being represented by diamond 96) and that there is something suspicious (63) in the reading 62 which the doctor 20 should review (26) quickly and perhaps act upon (28) immediately. If and upon receiving and reviewing (26) the reading 62, the MD 20 might wish to first consult (27) with the radiologist 60 before deciding what to do next (28).

It should be apparent from our above discussion that as the events involving the radiologist 60 unfold, all of the communication delivery problems discussed so far can again come into play as attempts (65) are made to deliver the reading contents 62 to the doctor's office. Among the areas of concern are those of assuring that the doctor got and understood the message (90), remembered (92) among his or her many other pressing tasks about the message and did something (94) about it, such as reviewing 26 the reading and/or consulting 27 with the radiologist. There are further complications here, however. The doctor's office may be deluged with many other lab results 75 coming in at the same time by way of the same or a wide assortment of different communications (e.g., telephone, facsimile, e-mail, etc.). Within this volume of incoming and diversified data, the doctor 20 may fail to spot the alert item 63 in the incoming X-ray reading 62. Luckily for most patients, their lab results are usually negative. That makes the doctor's problem of spotting a worrisome result all the harder because it is like trying to catch a chance needle out of an emptying barrel of hay. It would be beneficial to have a system and method (e.g., 87) for automatically filtering through the deluge of incoming lab results 75 and for automatically spotting and alerting the MD 20 as to a received and unusual test result (e.g., 62/65).

In one embodiment in accordance with the present disclosure, an automated results-filtering mechanism 87 is provided which detects normal test results and directs such, detected-as-normal test results directly to corresponding Patients (50) and/or to a Medical Assistant (30) (where the latter could relay the results to the corresponding Patients) thereby bypassing the MD (20) and freeing him/her from having to scan through a deluge (75) of incoming, normal test results. The MD-circumventing system also helps to reduce the number of Patients calling in inquiring about their results because in most cases, the test results will have been automatically forwarded (delivered) to the Patient without physician or other human intervention as may be allowed under the machine-defined rules for intervention less processing by operations occurring under the System's and/or Application's (e.g., Service Providing Organization's or subdivisions thereof, SPO's for short) and/or Topic's auspices. On the other hand, if the automated results-filtering mechanism 87 detects an abnormal or otherwise note-worthy test result (abnormal or otherwise note-worthy for the specific Patient) it may send an Alert to the MD (20) indicating that this particular result (e.g., 62) appears to need review by the MD. In such a case, the note-worthy result may be held up and not automatically sent to the Patient at least until the MD (20) has had a chance to first review (26) the result and optionally act (e.g., 26) upon it.

Also in an embodiment, an Alerts Summarizing mechanism (86, see also FIG. 10A) is provided which summarizes alerted situations and allows the MD (20) to conveniently check-in on the summarized alerts around the clock and by using different kinds of communication channels as may be appropriate for the circumstances the MD (20) finds him or herself in (e.g., on the golf course and can still check in via cell phone, wireless PDA, etc.). The Alerts Summarizing mechanism (86) also allows the MD to zoom-in (visually and/or otherwise) on details of the alerted situation, where the latter, up-to-date details may be stored in a Database (88) maintained by one or more progress-monitoring/tracking and/or progress-managing computers 80 which are provided in accordance with the present disclosure. Upon zooming in on details of a particular, alerted situation (e.g., 62), the MD may ask the System (80/88) to initiate a set of action items (83) such as sending various communications to the involved Patient (50) and/or to involved, other medical service providers (30, 40, 60) at various time points and in coordinated fashion so as to establish a pattern of situation-following up actions (e.g., scheduling more tests, more office visits, prescribing new or modified dispensing of medications, etc.). Once the MD asks the System (80/88) to initiate such a set of action items (83), the MD can rely on the System to follow through and use intelligent delivery-strategies for getting the desired communications through to their respective recipients (e.g., 30, 40, 60) in timely fashion, and if one or more, communication delivery-attempts does not succeed, the MD can rely on the System to recognize the in-completion of task (95) and alert (85*a*) the MD and/or other care-concerned persons (e.g., 30) of the failure to complete the expected action item on the action items task list (83). The so-alerted persons can then be asked by the System to follow up on the in-completion(s) and the System can track those follow ups to make sure they are completed.

Returning to our specific example of a note-worthy X-ray reading (62) being detected by the filtering system 87, being alerted to the MD and being reviewed (26) by the MD, it should be apparent from the foregoing that, if upon such notice and review of the troublesome reading the MD 20 wishes to consult 27 with the radiologist 60, the problems of scheduling and establishing a Consultation Interview 67 can be equal to those of a patient 50 trying to get in touch with a busy doctor. Like the primary care physician (MD) 20, the radiologist 60 will typically be a busy person who is handling many readings and consulting with many other primary care physicians at once. Accordingly, the scheduling and completion of a consultation interview 67 may itself be a complicated matter. Note now that we have primarily been following the progress of just a single patient (81) and the management of just a single test procedure (58) from the time of the primary care physician's initiation 22/23 of the detailed chain of events to the point where the process comes full circle (if there are no vital communication or execution breakdowns) and the MD 20 gets notice of and reviews 26 the requested test results. It should be remembered in all this that the MD 20 probably has many other patients (82) and each may have their own complicated progressions of medical treatment steps and follow-ups. The question then becomes how to manage such a complex system of attempted communications and action-item completions in a user-friendly and efficient manner.

Note incidentally from FIG. 1A, that after the MD 20 decides on a next course of action 28 (e.g., "We need to see patient P immediately!!"), a new round 29 of communication delivery attempts and completions begin. Ultimately, the doctor's new intention (21) may be to have the patient to call back (55) quickly and schedule a next visit with the doctor as soon as possible. There are many possible obstacles 98 to completion of such a transaction. A number of these have been alluded to above. Such communication obstacles are further reviewed in the sidebar 98' of FIG. 1A. The time-of-day (98*a*) at which a communication delivery attempt (e.g., 45, 55, 67) is made may play an important role in the likelihood of successful completion. At different times of the day and/or week, the targeted recipient (e.g., 50) may likely be physically located in many places 98*b* other than the home. For example, the target may be driving a car in heavy traffic, or may be busy at work, or may be in an airplane on the way to a one-week vacation in a different time zone. These are just of few examples of the situational permutations that may occur when a communication delivery attempt (e.g., 29) is made and the likelihood of successful completion may be altered due to target-centric attributes (e.g., effective time of day for target, location of target, mood of target, etc.). There are also questions 98*c* regarding what kind of communication channels are likely to be readily available to the target given the target's physical location and time of day. Does the targeted recipient have a cell phone that is turned on? Does the targeted recipient regularly check with his/her answering machine (52)? Does the targeted recipient have a telephone pager or immediate access to the Internet? Also, there are questions regarding the recipient-centric context (98*c*) in which the target will be receiving the attempted interview delivery. Is the target confused due to medications or other factors? Will the target be able to hear a voice-based communication attempt if the target is temporarily deaf (e.g., due to an ear infection)? Does this particular recipient suffer from blindness? Are there little children at home who cannot be trusted to pass a message on to an adult patient or guardian? Does the patient (50) know how to operate a computer such that it would be wise to send a copy of the message-pending notification by way of e-mail? These and many other factors may affect the delivery strategies that are used to try to get a communication delivery (e.g., 29) effectively delivered to the intended target (e.g., 50) such that it will be actually received, understood (90), remembered (92) and properly acted upon (94). At 98*e*, it is also indicated that the contents of the attempted communication (29) may have to be tempered depending on whether the selected communication channel is secure or not and whether the patient/target has agreed to having confidential information being sent over such a communication channel.

As should already be apparent from FIG. 1A, the present disclosure contemplates the use of one or more progress-monitoring/tracking and/or progress-managing computers 80. Such computers or like kinds of programmably-instructable machines can automatically keep track of details such as: (a) what specific communication channels are more suitable for a given target at a given delivery-attempt time, (b) whether communication delivery-attempts were timely completed or not, and (3) what to do if a vital completion deadline is missed or an alerted result (62/63) is received. Such computers (instructable machines) can automatically and adaptively instantiate action item lists (83) and follow their progress so as to assure that a care-giver's intentions (21) are timely fulfilled, or if not, that a responsible person is alerted and/or that follow up action (e.g., 28) is taken.

Computer deploy-able interfaces such as 81/82 and 85 may be respectively used to provide a feedback system 95 that checks for timely completion of instantiated action items 83 and/or to provide timely alerts about important completion milestones (e.g., 96—reading done) and/or important, missed ones of completion milestones (e.g., patient did not call back 55 in response to delivery-attempt 29). This may be contrasted with conventional medical practices wherein there is rarely any sort of feedback mechanism provided for tracking progress and checking on the many possible obstacles 98 that could interfere with, and finding ways to adaptively improve the likelihood of completion of the action items 83 which the primary care physician 20 thought (21) that he/she was initiating at the beginning of the cycle. More specifically, and in accordance with the present disclosure, automated machines and/or methods (80) are provided for collecting information 81/82 from the various communication channels and notifying appropriate personnel of completion of high-alert action items (e.g., 63) and/or of in-completion (e.g., 90) of certain actions within an expected time frame (24) so that the notified individuals can take corrective action. Doctor-centric (or more broadly, Medical Service Provider-centric) user-interfaces (e.g., 85) are contemplated in which non-vital information is filtered out so that the medical-service giver can focus on only alerted data 85*a* (e.g., an abnormal potassium level in a just-run, blood test). Patient-centric (or more broadly, non-Medical Person-centric) user-interfaces (e.g., 84) are contemplated in which clarifying information 84*a* (e.g., addendums) is added to help a non-medical recipient (e.g., 50) better understand the status of medical care being given directly to him/her or to a relative (or other such person) under his/her care. For example, a patient 50 may wish to know, "Did my blood test results come back, and if so what do all the numbers mean?" The clarifying information 84*a* may say something to the effect of, "Don't worry, for your age, sex, weight, etc. all numbers are within normally expected ranges and you do not have to come back and see the doctor again." Or it may say, "For your age, sex, weight, etc. the cholesterol numbers are bit high. Click here to schedule a follow up appointment."

In counterpart to the non-Medical Person-centric user-interfaced reports 84*a*, the disclosed feedback filtering means 87 can automatically intercept "normal" ones of the reports 75 for each of the patients 82, automatically insert the appropriate clarifying information with personal adaptations for the age, weight, etc. of the respective patient, and automatically begin a result-reporting Interview with the patient 50, thereby bypassing the busy Medical Service Providers (20, 30) while assuring that the patient will be adequately informed of progress in his/her medical care. The disclosed feedback filtering means 87 can automatically intercept "abnormal" ones (e.g., 62/63) of the reports 65/75 generated for all the patients 82, and can automatically issue an Alert 85*a* to the responsible care-giver (20) via the MSP-centric reporting interface 85. Means are provided for helping the doctor to clarify to a targeted patient what the abnormal results mean and for helping the doctor's office to effectively communicate (29) with the targeted patient in view of that patient's personal situation (e.g., context attributes 98*a*, 98*b*, . . . 98*e*).

The illustrated block diagram in FIG. 1A of the computer-automated system 80–87 is intended to broadly convey a machine-implemented carrying out of one or more aspects of the present disclosure. As those skilled in the computer arts know, there are many possible methods for interconnecting components of a computer system in order to realize the represented results. The schematically illustrated set of one or more, progress-monitoring and/or managing computers 80 may each include a central processing unit (CPU) or other data processing means (e.g., plural processors), and a system memory for storing immediately-executable instructions and immediately-accessible data for use by the CPU or by other processors. The system memory may take the form of DRAM (dynamic random access memory) and cache SRAM (static random access memory). Other forms of high-speed memory may be further or alternatively used. Various system and network buses and/or links may be used to operatively interconnect components of the computer system 80–87. The computerized system may include non-volatile mass storage means 88 such as a magnetic hard disk drive, a floppy drive, a CD-ROM drive, a re-writeable optical drive, or the like that is operatively coupled or couplable to the system for transferring instruction and/or data signals 89. Instructions for execution by the CPU's or other programmable processors may be introduced into the system by way of computer-readable media (88) such as a floppy diskette or a CD-ROM optical platter or other like, instructing devices adapted for operatively coupling to, and providing instruction signals and/or data signals for operative use by the CPU or by an equivalent instructable machine. The computer-readable media (88) may define a manufacture for coupling to, and causing the system to perform machine-implemented operations in accordance with the present disclosure. Instruction and/or data signals are not limited to those conveyed by nonvolatile media (88). The computer system may include input/output (I/O) means for providing interfacing with peripheral devices such as displays, keyboards, mice, and so forth. The I/O means may provide interfacing to communications networks such as an Ethernet network, a SCSI network, a telephone network, a cable system, a wireless link system or the like. Instructions for execution by the computer(s) and/or data structures for use by the computer(s) may be introduced into system by way of corresponding instruction and/or data signals 89 that are transferred over the communications network(s) or otherwise introduced into the system. The communications network(s)—represented among other things by 88—may therefore define means for coupling to, and the machine system 80–89 to perform one or more operations in accordance with the present disclosure. The instructing signals and/or data signals that are transferred through the communications network(s) for causing the system to perform said operations may be manufactured and structured in accordance with the present disclosure.

I(b). Hardware Architecture

Figure 1B:
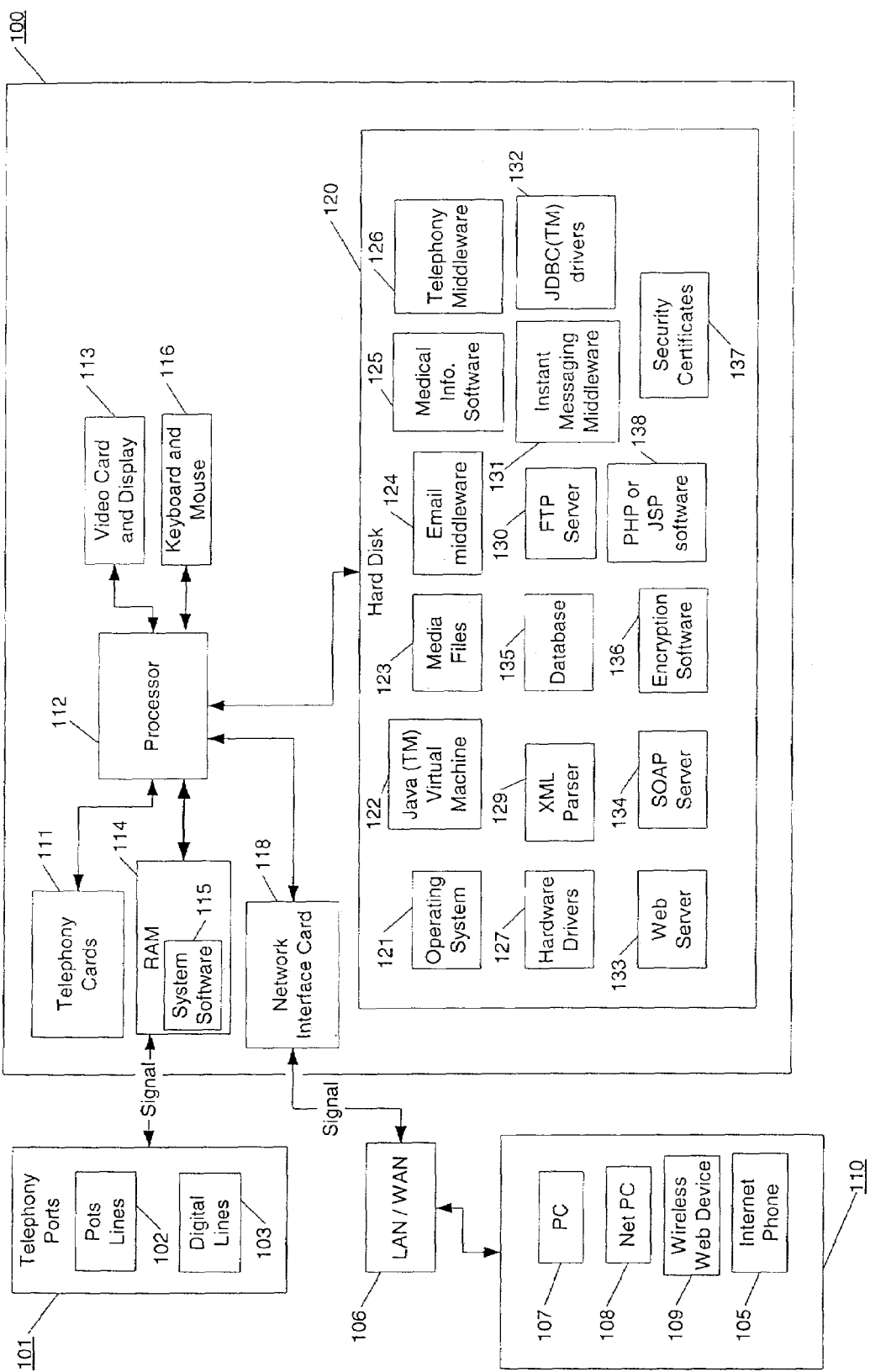
FIG. 1B is a block diagram of a server computer that may be configured in accordance with the present disclosure to provide automated and adaptive communication of medical services related information.

FIG. 1B illustrates a simplified block diagram of a server 100 that may be used in a System in accordance with the disclosure. Interactions of the Server 100 with various input and output devices are also illustrated. Server 100 may include an instructable data processor 112 which can be coupled to a hard disk 120, a keyboard, mouse 116, and/or another form of user interface (e.g., voice input, not shown) as well as to a video card and display 113, a network interface card 118, telephony cards and circuits 111, and random access memory (RAM) 114, where the latter alone or in combination with the hard disk may contain system software 115 which provides instruction signals for instructing the data processor 112 and/or other instructable data processing means (not shown) to carry out machine-implemented operations in accordance with the present disclosure. It is to be understood that the instruction signals within computer 100 may loaded into the computer through any of a variety of means including, but not limited to, installation from a removable data-conveying means such a sa CD or DVD disk and/or the downloading from a network (118) of instructing signals that are adapted to cause the computer 100 to carry out machine-implemented operations in accordance with the present disclosure. It is to be understood that the present disclosure contemplates not only the conveying of such instructing signals by way of various media, but also the conveying of data-structure signals that represent one or more data-structures described herein and which are useful for carrying out machine-implemented operations in accordance with the present disclosure.

In one embodiment, the disk 120 stores data defining one or more of: an operating system 121, a Java™ virtual machine 122, media files 123, e-mail middleware 124, medical information software 125, telephony middleware 126, hardware drivers 127, an XML parser 129, an FTP server 130, instant messaging middleware 131, JDBC (Java Database Connectivity)™ drivers 132, a web server 133, a SOAP (Simple Object Access Protocol) server 134, a Database 135, encryption software 136, security certificates 137, and PHP (Personal Home Page) or Java Server Pages 138. In an alternate embodiment, one or more of the medical information server programs and data may be stored at a remote location and accessed via a network by the server 100.

Users of the System may access the Server 100 via telephony ports 101 where the latter may operate with POTS lines 102 and/or Digital Lines 103. Additionally or alternatively, users may access the Server 100 by way of LAN or WAN 106 means. The LAN/WAN 106 interface may interact with input/output devices 110 where the latter may comprise PC's (personal computers) 107, Net PC's 108, Wireless Web Devices 109, and/or Internet Phones 105.

In an embodiment, Operating System 121 is Red Hat® Linux 7.1, Voice Boards 111 is VoiceTronicx® V4PCI, Telephony Middleware 126 are VPB device drivers from VoiceTronicx®, and VPBapi, an open source program interface for Linux OS to control the card, email Middleware 124. In an embodiment the instant messaging middleware is JXTA and Jabber™; Java™ 122 is JDK 1.3.1™ from Sun Microsystems ©, JDBC™ Drivers and JDBC™ 2.1; XML parser 129 is Apache Xerces 1.4.3; the web server 133 is Apache HTTP server; PHP 138 is open source PHP software; and email middleware is JavaMail™ API. JSP or Java Server Pages 138 may be implemented using an Apache Tomcat Server.

In an embodiment, client applications, Medical Provider, and Patient screens are built with Visual Basic runtime code, which parses XML Files and presents and sends data via the SOAP exchange. Medical Providers can be connected to the System by the Internet. In an embodiment, Medical Providers and other users of the System may be connected by an intranet behind a firewall and other users connected by the Internet. Encryption software such as Java Cryptography Extension™ and Java Secure Socket Extension™ may be used to help insure confidentiality of transmissions outside of the firewall.

Figure 2:
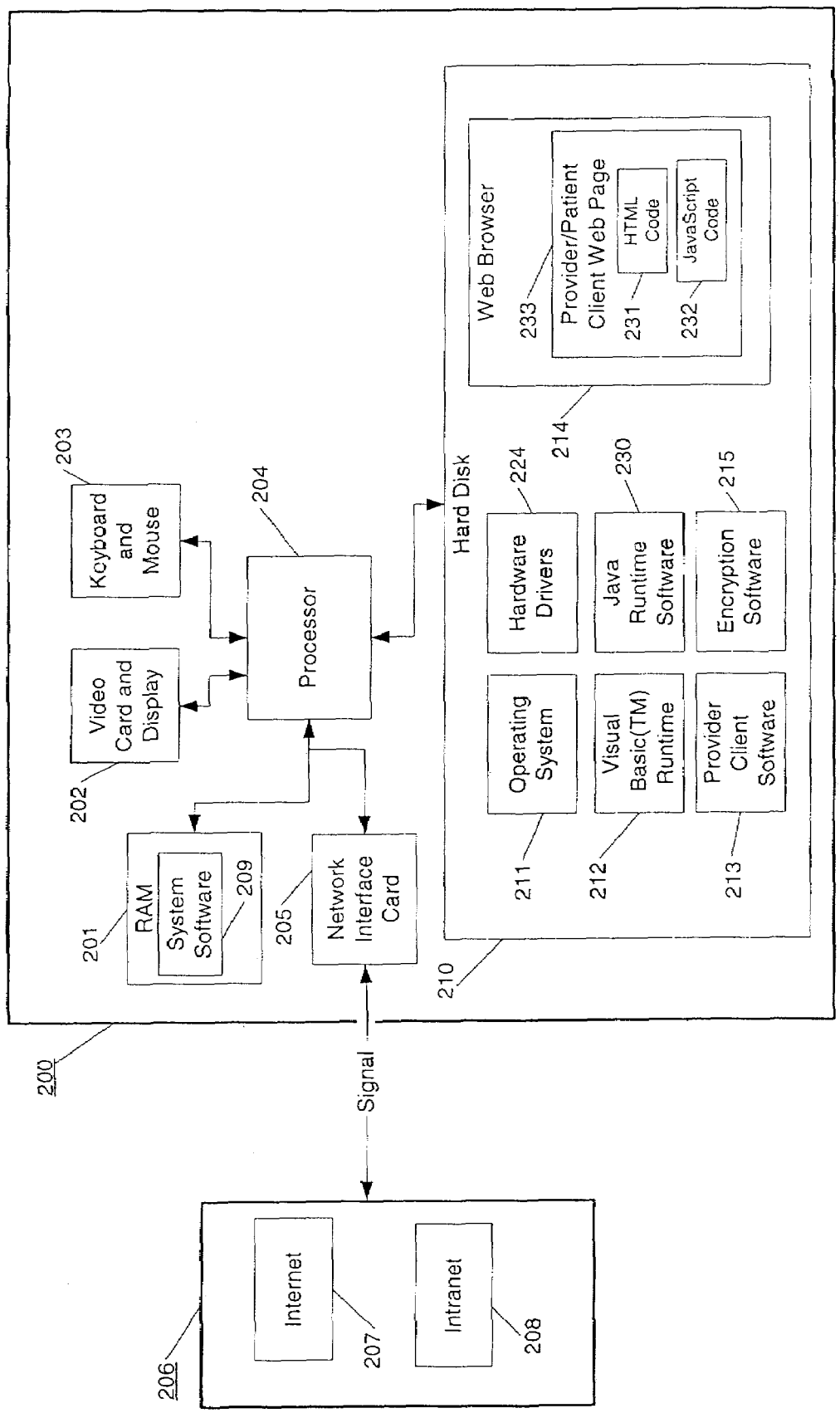
FIG. 2 is a block diagram of a client computer that may be configured in accordance with the present disclosure to provide automated and adaptive communication of medical services related information.

A System client computer system may be operatively coupled to the Server computer 100 through the use of a web browser such as Microsoft's Internet Explorer™. FIG. 2 illustrates a client computer 200 such as may be used by a Medical Provider, a Patient, or another user of the System and its connection to a corresponding Intranet or the Internet. The client computer 200 comprises a processor 204 coupled to one or more of a hard disk 210, keyboard and mouse 203, video card and display 202, network interface card 205, and random access memory (RAM) 201 where the latter may contain additional System software 209.

Disk 210 in an embodiment includes an operating system 211, hardware drivers 224, encryption software 215, Visual Basic™ runtime software 212, Java runtime software 230, web browser 214, and Medical Provider client software 213. The web browser 214 may include means for displaying and/or editing a Provider-specific or Patient-specific web page (233) using appropriate means such as HTML code 231 and/or JavaScript code 232 and/or other information presenting, editing and/or defining data structures.

The illustrated Client Server 200 may interact with the System Server computer 100 through an I/O unit 206 that comprises an Internet interface 207 and/or an intranet interface 208.

II. System Entities and Their Attributes (A) System 301

Figure 3A:
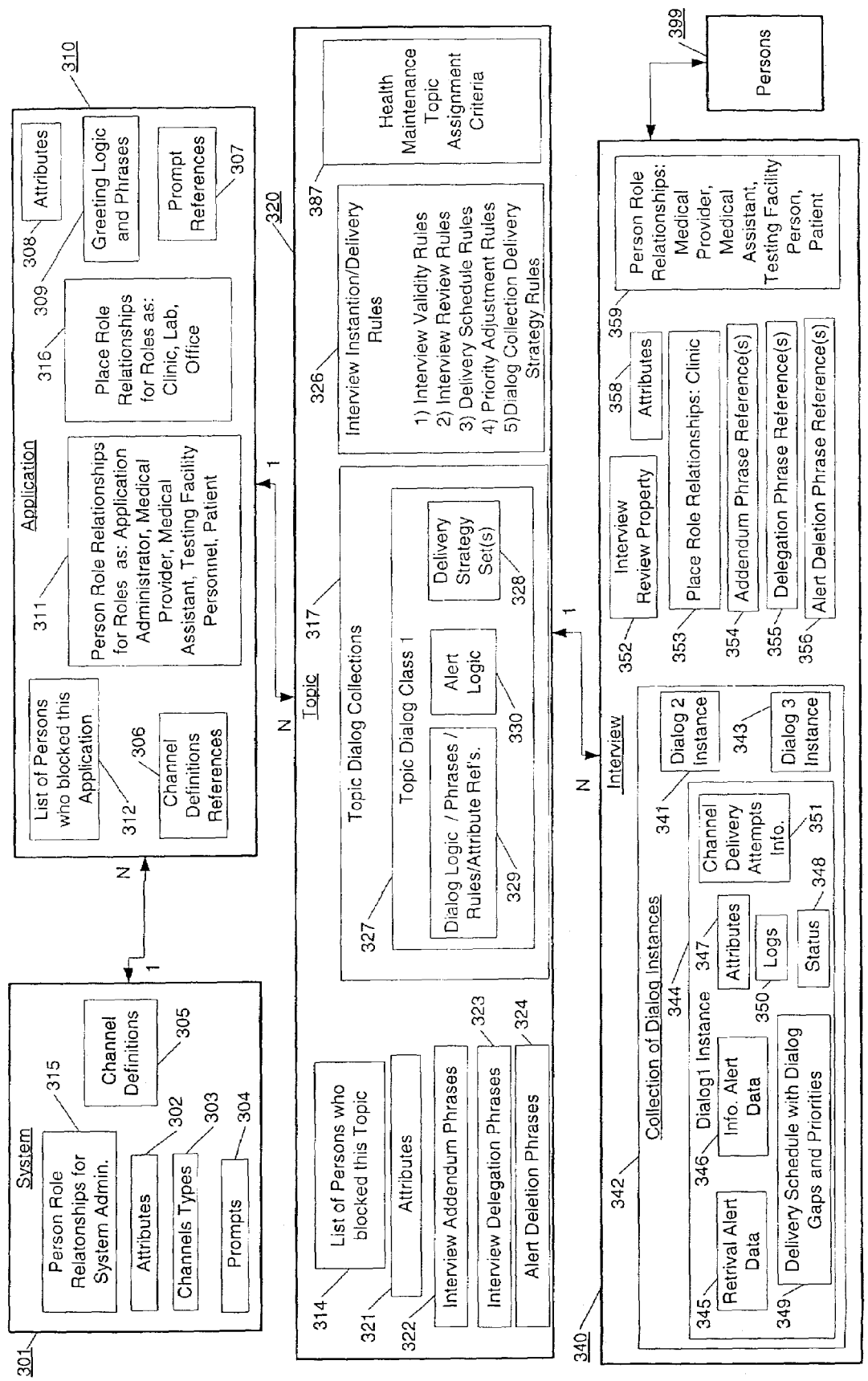
FIG. 3A illustrates a first portion of an object data architecture that may be used in an adaptive communications system that is structured in accordance with the present disclosure.
Figure 3B:
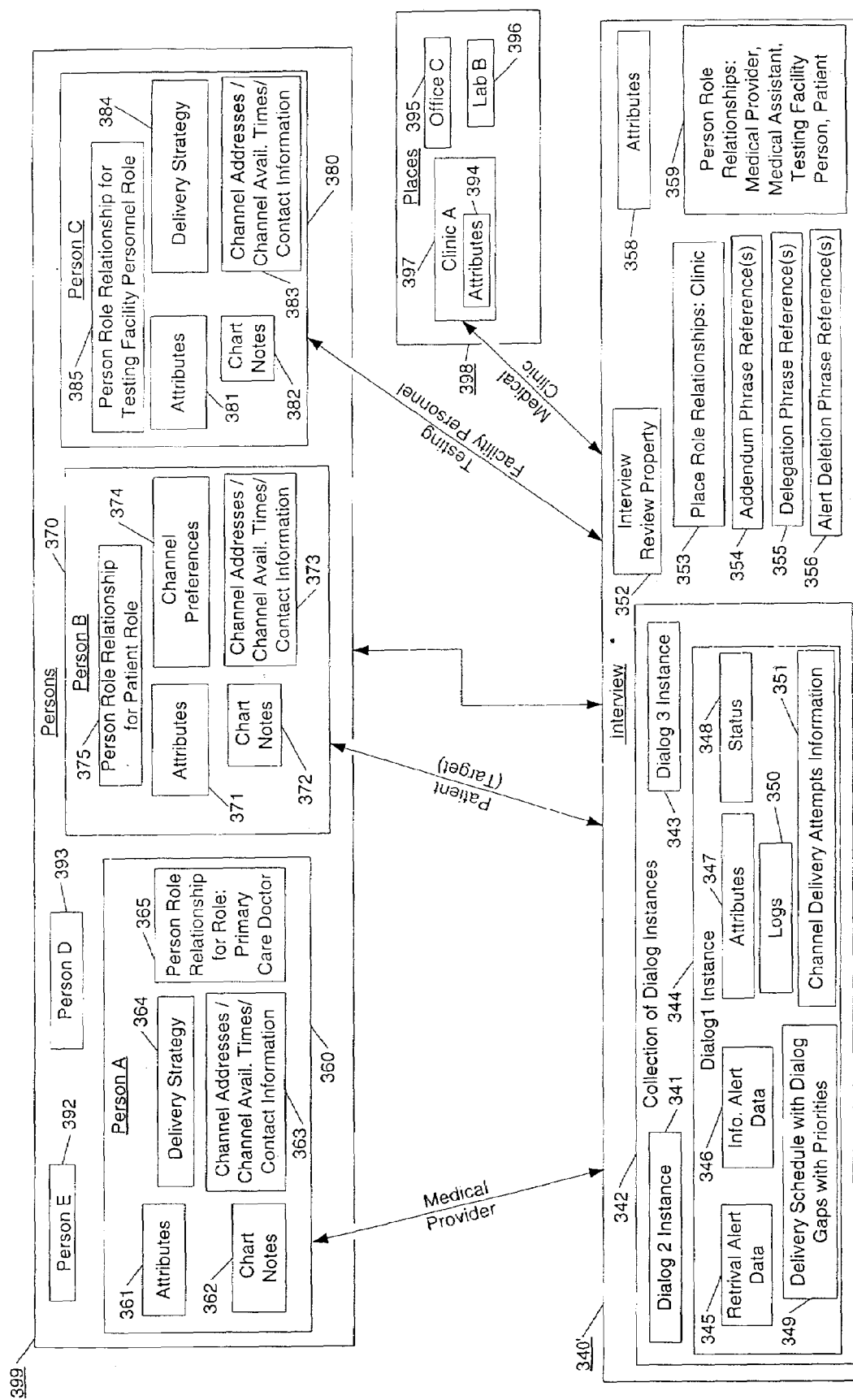
FIG. 3B overlaps with FIG. 3A and illustrates a second portion of the object data architecture.

FIG. 3A and FIG. 3B illustrate an object data architecture that may be used for the System. Block 301 represents the System Entity. The System Entity comprises System Attributes 302, Channel Types 303, System Prompts 304, Person Role Information for the System Administrator 315, and System Channel Definitions 305.

System Attributes 302 may comprise information that is utilized by the System such as the following: (1) database maintenance schedule information, which gives information regarding frequency and circumstances for updating the Database; (2) location of archived files, which gives the location(s) for the System to store archived files; (3) archive frequency, which specifies the System frequency of data archiving; and (4) default language for prompts if there is no other language specified for prompts in the Person, Interview, Topic, or Application Entity Attributes, any of which override this System Attribute with precedence in the stated order. If no language preference is specified in any of these Entities, the default language used by the System is English.

Channel Types structure 303 contains data definitions of Channel Types. Channel Types can include delivery means types (such as telephone, e-mail, web, wireless phone, and WAP (wireless application protocol) devices.

System Channel Definitions 305 are definitions of communication Channels that the System may use to deliver Interviews. Each Channel Definition contained in System Channel Definitions 305 may comprise:

1) Time ranges which determine the availability of the Channel,
2) An indication of whether or not the Channel will handle inbound or outbound initiated requests,
3) An indication of whether the Channel has the capability to send notification or Advisement signals that indicate Interview status,
4) An indication of which Media Type the Channel will support (such as html version, speech data, text, etc.),
5) An indication of the maximum number of attempts allowed to utilize this Channel over a given period of time,
6) An indication of the maximum number of security errors allowed over a given period of time, and
7) An indication of the maximum number of disconnects (e.g., hang-ups) allowed before cessation of delivery attempts.

Some Channel Definitions may contain more data, such as minimum time allowed between busy attempts. In an embodiment, a Channel Definition can support multiple Media Types.

System Prompts structure 304 contains Prompts, which may comprise Prompt definitions and Prompt content. Each Prompt has content in at least one Media Type (such as text, sound file, html) and one language (such as English, Spanish, Japanese).

The System Person Role Relationships for the System Administrator, 315 may identify one or more people who have a Role of System Administrator to the System and Attributes for these Person(s) such as name and contact addresses.

(B) Application 310

The instantiation relationship between the illustrated System Entity 301 and the illustrated instantiation 310 of an Application Entity can be one-to-many (1-to-N). There is at least one Application Entity 310 related to the System Entity 301. Each instantiated Application may have different information stored in its respective data structures. This information may comprise: Attributes 308, Prompt References 307, Channel Definitions References 306, Place Role Relationships 316, Person Role Relationships 311, Greeting Logic and Phrases 309, and/or a List of Persons Who Are Blocked from participating in communications under this Application 312. As a concrete example, consider one Application as being Medical Group-A and a second Application as being Medical Group-B. At some point in time, doctor X and nurse Y leave Medical Group-A and shift their practices to Medical Group-B. At a later date, patient Z, who regularly saw doctor X asks that all his medical records be moved to Medical Group-B. In such a case, the List of Persons Who Are Blocked (312) of the Application for Medical Group-A might be modified to include Persons X, Y and Z.

Application Attributes 308 may comprise Attributes that the Application utilizes, such as indications of the maximum time an Interview of the Application may remain on the System before it is archived, whether or not the Application is active on the System, the priority setting for processing of the Application relative to other Applications, and the default language preference for the Prompts used in the Application. If there is a language preference specified in the Person, Interview, or Topic Entity Attributes these override this Application Attribute in the stated order of precedence.

Application Prompt References 307 may contain references to respective subsets of the System Prompts 304. As a concrete example, Medical Group-A may prefer to use one style of Prompts while Medical Group-B prefers to use another.

Application Channel Definitions References 306 may contain references to respective subsets of the System Channel Definitions 305 of the respective Application.

Person Role Relationship 311 may include identity and other control information for the following Roles: Application Administrator, Medical Service Provider, Medical Assistant, Testing Facility Personnel, and Patient. Information for these Roles should include the names of Persons. Privileges and limitations of Persons related to the Application may be defined in terms of their Roles. As a concrete example, Medical Group-A may allow Medical Assistants to review and dismiss alert reports while Medical Group-B allows only persons of the MSP (doctor) Role or higher (Application Administrator) to review and dismiss alert reports.

Place Role Relationship 316 may comprise geographically-related information for Places related to the Application such as the following: Medical Clinics used by the Application, X-ray Facilities used by the Application, Chemistry Laboratory Facilities used by the Application, Physical Therapy Facilities used by the Application, and Offices used by the Application. Information for these Places may include their names, street or other mappable locations, telephone numbers, web addresses, and normal hours of operation.

The List of Persons 312 Who Are Blocked from this Application 312 may reference Persons who have indicated they do not want to interact with this Application. The System can use this information 312 to block Topics and Interviews of this Application from communicating with these blocked Persons.

Greeting Logic and Phrases structure 309 may include information that announces to Target Persons the name of the Application. Also this structure 309 may contain log-in logic and security and authentication protocols used by the Application. (E.g., "This email from Medical Group-A is encrypted using the PGP standard.")

(C) Topic 320

There can be one or more Topic Entities (320) related to each Application (a 1-to-N instantiation relationship). As a concrete example, assume that Medical Group-B provides services relating to eye, ear, nose and throat. One Topic may contain Interviews relating to eye cataracts. Another Topic under the same Application may contain Interviews relating to thyroid problems. The illustrated Topic Entity 320 relates logically to the illustrated Application Entity 310. Topic Entity 320 may be comprised of Topic Attributes 321, Interview Addendum Phrases 322, Interview Delegation Phrases 323, Alert Deletion Phrases 324, Dialog Collections 317, Health Maintenance Topic Assignment Criteria 387, Interview Instantiation and Delivery Rules 326, and/or a List of Persons Who Are Blocked from this Topic 314. As a concrete example: Mr. Jones decides to have his thyroid treated at a different Medical Group but continues to use the current Medical Group-B for treating his eye cataract. Mr. Jones would therefore not be blocked from the Application, but rather just from the thyroid Topic.

The Interview Instantiation and Delivery Rules 326 of the given Application may be comprised of one or more of the following:

1) Interview Validity Rules: These are Rules that set forth requirements for the creation of a corresponding, Topic-related Interview under Application policies and may include restrictions on allowed Roles, Entity Attributes, and other data objects that may be associated with the planned Interview and on what valid values such other objects may be required to posses before the Interview is allowed to be Instantiated. In an embodiment, if certain valid data is not present for a required Entity Attribute, Application-provided default values may be used instead for such necessary data.

2) Interview Review Rules: Each Interview may have a property called NeedsReview, which has a value such as 'True' or 'False'. Interviews with NeedsReview set as True are generally blocked from being delivered to their Target(s) until the NeedsReview property is changed to 'False' while being processed under one of the Provider Screens or other Provider review mechanisms allowed by the given Application so that the modified state indicates that a Medical Service Provider or other System-authorized Person has probably reviewed the Interview before allowing it to go out. Some Interviews, such as those for normal test result delivery to Patients, may have their NeedsReview Property automatically set to False upon Instantiation, so they do not need be reviewed by a Medical Provider prior to being routed for Patient delivery. Other kinds of Interviews may have their respective NeedsReview property automatically set to 'True' upon Instantiation. Examples of such latter Interviews can include those reporting tests with abnormal results, where under the policies of the Application, such results require Medical Provider Review prior to being sent to Patients.

3) Delivery Schedule Adjustment Rules: Each Topic can have a set of Topic Dialogs (329). Interview Dialogs may be formulated from one or a composite collection of such Topic Dialogs. Each Topic Dialog may have designated time ranges that are to be used to create a Delivery Schedule for its corresponding Interview Dialog. Certain Topic Dialogs may also have logic that specifies InterDialog Time Gaps. An InterDialog Time Gap can work to prevent confusing overlappings of Interview Dialog Deliveries and can insure that a proper minimum time gap exists between respective Interview Dialog deliveries. If a given Topic has only one Topic Dialog, then it does not need to have an InterDialog Time Gap. Typically, the last Topic Dialog listed in a Topic Dialog Collection has no InterDialog Time Gap assigned to it.

4) Priority Adjustment Rules: The Topic may have priority Adjustment Rules that affect the Delivery priority of each Interview's Dialog. These rules may be used to adjust priorities in response to the Topic's priority, the priority of the associated Application, and Attribute values. Interview Dialog Target Responses may influence the Delivery priority of subsequent Dialogs based on System rules. In an embodiment, such rules may require any Interview Dialog with a potential for including a Retrieval or Information Alert that might be sent via a means that does not routinely notify the Target of the receipt of a message (such as in an email account) to also be sent by a different Channel (e.g., telephone) that actively notifies a Target of an incoming message on the first channel. Thus, at least two different channels may be called upon to notify a Target of an incoming message that may contain a high-priority Alert.

5) Dialog Collection Delivery Strategy Rules: The System tries to deliver Interview Dialogs in a precedence order according to their pre-assigned Priorities. Typically, an Interview Dialog chosen for delivery on the basis of its Priority will have to contend with other Pending Interview Dialogs that are targeted for delivery to the same Target Person and as such the newly added Interview may be packed or bundled with the other Pending Interview Dialogs as available System capacity allows. These other Pending Interview Dialogs may therefore be delivered at the same time as the newly added one. Logic and rules that pertain to this are discussed below under Methods of Interview Formation, Scheduling, and Delivery.

Dialog Collection structure 317 holds classes of Topic Dialogs belonging to the Topic. One of these is a first Topic Dialog Class (Dialog-1) 327. Topic Dialog-1 (327) may contain its respective Topic Dialog-1 Logic, Phrases, Rules, and Attribute References 329 and Topic Dialog-1 Delivery Strategy Set(s) 328, and Alert Logic 330. These Topic Dialog-1 Logic, Phrases, Rules, and Attribute References 329 may comprise:

(A) A selected subset of Phrases from the Application Prompt References 307 and selected Entity Attribute references that may be used individually or compiled to automatically and/or manually form statements, answers, and/or questions contained in specific instantiations of this Topic Dialog.

(B) Rules and logic to formulate phrases and present questions, statements, and/or answers. These Rules may use Attribute values from the Entities related to the Interview Dialog-1 344 (such as Attributes from Medical Provider, Lab Tech, Clinic, and Target Patient) as well as Attributes from the Interview Dialog-1 itself to control how specific instantiations of Interview Dialogs are generated. In an embodiment, some boiler-plate questions in a form Interview Dialog may be replaced by declarative statements.

Rules may be used to automatically generate new Dialog content that is responsive to the Target answer choices. Such Rules may determine when and how questions, answers, and/or informational phrases will be presented in the Interview Dialog after certain Target responses are received.

An Interview Dialog can have prompts that adapt automatically to Entity Attributes and Rules. This serves to customize information content as well as the behavior of the Interview Dialog. This can result in a very tailored communication that is appropriate to the Target's indicated situation. Also, an Interview Dialog may use the Topic Dialog's Rules to offer prompts and phrases that are specific to the Target's language. A Target Person's Language Preference Attribute may be used to determine which language prompts to use. If a Person doesn't have this Attribute specified under the Person's Attributes (for example, 361 or 371 of FIG. 3B), then the Topic or Application Attribute, 'Default Language Preference,' may be automatically used in the stated order of precedence. If these are vacant, then a System language preference may be used; if this is vacant, English may be used as the System default language.

Alert Logic structure 330 holds Alert generation logic for the corresponding Topic Dialog Class. Such Alert Logic 330 may automatically determine, e.g., which Target responses automatically generate Information Alerts, which Persons are to be targeted to receive these Alerts, and the corresponding Alert Notes that will be contained in the automatically formulated Alert messages. Alert Logic structure 330 may also include logic for automatically generating Retrieval Alerts and their associated information. Rules for sending information to the proper persons if a formulated Interview Dialog is automatically blocked for some reason or if a "Not Timely Delivered" status appears for a given Interview Dialog, may also be included in the Alert Logic structure 330. Rules for automatically canceling Retrieval Alerts when, after a delivery deadline passes the Target Person nonetheless retrieves the Interview Dialog may also be included in the Alert Logic structure 330.

Topic Dialog-1 Delivery Strategy Set(s) 328 should contain at least one Delivery Strategy rule for the given Topic Dialog Class. Each Delivery Strategy rule may include one or more of:

1) A reference to a reference contained in Channels Definitions References 306,
2) An indication of the minimum and maximum number of attempts to be tried
3) Requirements regarding which other Strategies must be completed before this Strategy can be used,
4) An indication of whether or not the Strategy can be cancelled due to a delivery-obstacle event such as a hang-up or equivalent, and
5) An indication of whether or not Patient's preferences regarding the Channel are being taken into account when using this Delivery Strategy.

The illustrated Topic Attributes structure 321 may include: (1) An indication of whether or not the Topic is active in the system and/or (2) a Priority Value, which determines the importance of information spawned from this Topic relative to other Topics.

Interview Addendum Phrases structure 322 holds a set of Phrases a Medical Provider may choose from, to add to an Interview that is being formulated for subsequent transmission to a Patient so as to convey patient-friendly, added information to that Patient. As a concrete example, an Addendum Phrase may state, "Although this result is slightly out of normal range, it is expected for your situation and should not be of concern."

Interview Delegation Phrases structure 323 are a set of Phrases a Medical Provider may choose from to indicate desired action(s) by a delagee upon delegating the alerted Interview to another Person such as a Medical Assistant.

Alert Deletion Phrases structure 324 are a set of Phrases that a Medical Provider may choose from to indicate for creating a recorded audit trail how an alerted Interview situation was followed up on when deleting that Alert from the Medical Provider's Alert Summary Screen (and/or other alerting mechanism).

The List of Persons Who Are Blocked from this Topic structure 314 identifies Persons who have indicated they do not want to interact with this Topic. The System may use this information to automatically block Interviews of this Topic from being sent to these Persons.

The Health Maintenance Topic Assignment Criteria structure 387 may contain criteria used to automatically and/or semi-manually develop Health Maintenance Interviews such as, e.g., the Person's age Attribute, the Person's sex Attribute, and/or various other parameters determining the frequency and nature of periodic health examinations and/or interventions (e.g., vaccinations) that are to be undertaken like Pap Smears, mammograms, or prostate specific antigen tests. The Health Maintenance Topic Assignment Criteria structure 387 may also contain criteria for automatically generating messages that make recommendations for flu shots. Structure 387 may also contain parameters for determining the frequency and nature of periodic health maintenance disease specific inquiries, recommendations, and the like.

(D)Interviews 340

Interviews are individual Instantiations under a respective Topic and thus there may be 1-to-N Interviews instantiated under a given Topic. An Interview typically holds data specific to a planned communication with a Target Person (e.g., a Patient). An Interview data structure 340 may be comprised of one or more of: Interview Attributes 358, an Interview Review Property 352, Place Role Relationships: (e.g., from-Clinic) 353, Person Role Relationships: (e.g., from-Medical Provider, Medical Assistant, Testing Facility Person, Patient) 359, Addendum Phrase Reference(s) 354, Delegation Phrase Reference(s) 355, Alert Deletion Phrase Reference(s) 356, and Collection of Interview Dialogs 342.

Interview Attributes structure 358 may comprise: (1) values of variables that may pertain to more than one Interview Dialog and may apply to responses obtained in the Interview, and/or (2) values of variables for tracking results of delivery of the Dialogs and the sequence of question presentations that are to occur during the Interview.

As already explained, each Interview can have a Review Property structure 352 called NeedsReview, which is set to "True" if the Interview must be reviewed by a Medical Provider before being sent to a Patient, and which is set to "False" if this is not the case. The value of this Interview property is held in structure 352.

Place Role Relationships for Roles: (e.g. from-Clinic) 353 is a data structure that holds Attribute information such as names and locations of Places such as one identifying the Medical Clinic associated with the Interview.

Person Role Relationships: (e.g., from-Medical Provider, Medical Assistant, Testing Facility Person, Patient) 359 is a data structure that holds Attribute information relative to the Persons and Roles involved in the particular Interview which may include such information as the following for the each Role Person who is a generator or recipient of the Interview delivery attempt:

Patient: Birth date, Age, Height, Presence of illnesses such as hypertension, diabetes, Medication allergies, etc.

Medical Service Provider: Name, Clinics he or she works at, Alert limits for high laboratory values of potassium, Alert limits for peak flow values during asthma office visit follow ups, etc.

Medical Assistant: Name, Clinic worked at, Medical Provider(s) works with, etc.

Testing Facility Person: Name, Name of Testing Facility, references to panic levels for specific laboratory test results, etc.

The Interview Addendum Phrases 354 is a data structure that holds references to the phrases of Topic Interview Addendum Phrases 322 used by the Medical Provider to add information for the Patient in processing the particular Interview before it is sent for delivery to the Patient.

Interview Delegation Phrases 355 is a data structure that holds references to the phrases of Topic Interview Delegation Phrases 323 used by a Medical Provider in delegating the particular Interview if it is alerted and then delegated to a Medical Assistant or the like.

Alert Deletion Phrases 356 is a data structure that holds references to the phrases of Topic Alert Deletion Phrases 324 that may be used by a Medical Provider in creating a recorded audit trail and upon deleting the particular Interview from the System if it was alerted for follow up action.

Collection of Interview Dialogs 342 (for Interview 340) is a data structure that can comprise instantiations of plural Interview Dialog Classes such as: Interview Dialog-1 344, Interview Dialog-2 341, and Interview Dialog-3 343. The illustrated Interview Dialog1 Instance (344) comprises Retrieval Alert Data 345, Information Alert Data 346, Attributes 347, Status 348, and Delivery Schedule with Dialog Gaps with Priorities 349, Logs 350, and Channel Delivery Attempts Information 351.

The Dialog Delivery Schedule with Dialog Gaps and Priorities 349 is a data structure that holds specific information relating to this instantiated Interview's Dialog Delivery Strategies including delivery attempt times and/or priority and/or contact results. It may also contain information that is used to determine the order and timing of the Interview Dialog deliveries that involve this Interview Dialog. In one embodiment, the Interview Dialog Delivery Schedule with Dialog Gaps and Priorities 349 is a data structure that may contain information regarding 1) A Time Range when the instantiated Interview Dialog can be Sent in reference to the time the Interview was Instantiated, and/or 2) The relevant minimum time spacing between Dialogs of an Interview (also known as the InterDialog Time Gap).

Information provided here may affect not only the delivery of this Interview Dialog but also other Interview Dialogs of the same Interview. In an embodiment, the Dialog Delivery rules may be made responsive to information obtained in previously sent Interview Dialogs of the Topic Interview.

Retrieval Alert Data 345 is a data structure that comprises the date and time of formation of each Retrieval Alert associated with the instantiated Interview Dialog, if any, together with the Alert Note and the Person to whom the Alert is sent. Data regarding disposition of the Alert such as time of delegation or deletion and the Persons involved in these actions may also be held here. Data regarding cancellation of the Alert, for example, by the Patient subsequently retrieving an Interview that triggered a Retrieval Alert, may also be held here. Information specifying review of handling of Retrieval Alert data by quality assurance groups may further be held in the Retrieval Alert Data structure 345.

Information Alert Data 346 is a data structure that comprises the date and time of formation of each Information Alert associated with the instantiated Interview Dialog, if any, together with the Alert Note and the Person to whom the Alert was sent. Data regarding disposition of the Alert such as time of delegation or deletion and the Persons involved in these actions may also be held here. Information specifying review of handling of Information Alert data by quality assurance groups may also be held here.

Interview Dialog1 Instance Attributes 347 is a data structure that may comprise one or more of: (1) values of variables representing responses obtained in the Interview, (2) values representing test results delivered in the Interview, (3) values representing test results obtained in the Interview, and (4) values representing tracking results that are generated by the System as it tracks an attempted delivery and/or completion of the instantiated Interview Dialogs and/or the sequence of question presentations developed during the Interview.

Status 348 is a data structure that represents the status of the Interview Dialog. The Interview Dialog Status may be defined as being at least one of the following:

(1) Pending,—by which is meant that the Interview Dialog is pending delivery to the Target Person;

(2) Expired,—by which is meant that the Interview Dialog has expired or exceed its designated time period to be on the System. A Database Clean Up and Archiving Agent may be used to automatically remove such Dialogs from the System;

(3) Delivered,—by which is meant that the Interview Dialog has been delivered to its Target Person;

(4) Not Delivered,—by which is meant that the instantiated Interview Dialog has not been delivered to its Target Person. An Interview Dialog may be placed in the Not Delivered status by an action from a Person which effectively blocks the corresponding Application or Topic from being deliverable to the designated Target (e.g., patient Z has asked that all his thyroid-related records be transferred to Medical Group-C); and (5) Error—i.e., the Interview Dialog delivery was not completed because the System encountered a communications link or other error condition.

Logs structure 350 may hold information regarding successful accesses or attempts by various Persons to access a correspondingly-instantiated Interview Dialog or information held within it. Logs structure 350 may include identifying data which identifies one or more Persons accessing or changing data in the Interview Dialog and time stamps of such actions. It may also comprise delivery information regarding how the Interview Dialog was transmitted, how the Interview Dialog was accessed and/or subsequently modified to thereby generate Interview Dialog Alert information, the times of Alert setting, and/or the times and Persons who accessed Alerts, and other information pertaining to the use and access of the Interview Dialog or information contained therein.

Channel Delivery Attempts Information 351 is a data structure that which can hold information detailing prior attempts at delivery for the given Interview Dialog including the type of channel used, the time of each attempt, and the results of the various attempts (e.g., successful, on time, or not).

(E) Persons 399 and Places 398

The Persons data structure 399 shown briefly in FIG. 3A and then again in more detail in FIG. 3B can logically link each of the 1-N Interviews 340 with one or more Persons under respective Roles such as the illustrated Person-A of FIG. 3B (360, having the Role of MSP relative to Interview 340'), Person-B (370, having the Roles of Patient and Target relative to Interview 340'), and Person-C (380, having the Role of Test Lab Technician relative to Interview 340'). Other Persons within Persons Set 399 may have no logical link and role relative to a given one or more Interviews such as the exemplary one Interview 340' shown in FIG. 3B. Thus, Person-E (392), and Person-D (393) of FIG. 3B are shown as having no link and role with respect to Interview 340'. Persons who are associated with the overall System and/or an Application under the System may be so-associated in defined Roles such as System Administrator, Application Administrator, Medical Service Provider, Medical Assistant, Testing Facility Personnel, and Patient. A Person may have more than one Role in a System or under any one or more Applications in the System and may have plural Roles in more than one Application in the System. Information which may be held in Person blocks such as 360, 370, and 380 is explained in more detail below.

Places 398 in FIG. 3B is a data structure that represents Places such as Clinic-A (397), Lab-B (396), and Office-C (395). Data held regarding Clinic-A in block 397, for example, will be explained in more detail below.

The illustrated Interview 340' of FIG. 3B is shown to be logically associated with Person-A (360) who happens to be in the Role of Medical Provider relative to the Interview 340'; with Person-B (370) who happens to be the Patient and the communication's primary Target Person in the context of Interview 340'; with Person-C (380) who happens to be a Testing Facility Person; and with Place-C (397) which for this example happens to be a Medical Clinic. Components of Interview 340' are denoted similarly to those of 340 of FIG. 3A as described above.

The Person-A data structure 360 may comprise Chart Notes 362; Person-A Attributes 361; Person-A Delivery Strategy 364; Person-A Channel Addresses and Channel Available Times and/or other Contact Information 363; and/or a Person Role Relationship 365 which in the illustrated example is the Role of Primary Care Doctor.

The illustrated Person-A Attributes structure 361 (Medical Provider) includes the Medical Provider's name, clinic associations, specialty, specific personal limits at which to be notified for laboratory test abnormalities such as minimum alert levels for elevated potassium, parameters determining if he or she desires to be notified of Patient peak flow values in asthma office visit follow ups, and other information. It may also include a default language preference for Prompts and screens viewed (or otherwise retrieved) by the Medical Provider while using the System; this preference over-rides language preferences expressed in similar Attributes for these areas at the Application, Topic or System level. The Person-A Attributes structure 361 may also hold information on how various Alerts are to be processed upon deletion from Person-A's account.

The illustrated Person-A Chart Notes 362 may comprise Chart Notes made by Person-A which are relevant to this Interview 340'.

The illustrated Person-A Delivery Strategy structure 364 may include preferences for parameters for follow up Interviews such as time-from-sending of first Interview Dialog for follow up for an office visit for a mild asthma attack, channel preferences, and similar information.

Channel Addresses and Channel Availability Times and Other Contact Information 363 is a data structure that can be comprised of the Channel definitions and their respective times of availability and preferences for contacting the given Person (Medical Provider), logic defining those alerted situations for which the given Person (Medical Provider) desires to be reached on any of these Channels and logic defining how alerted situations are to be handled if he or she is not available, names and contact means for back up responsible Persons (e.g., other Medical Providers), and names and privileges of yet other Persons (e.g., medical personnel) who have permission to access his or her account.

The illustrated Person Role Relationship for Role as Primary Care Doctor structure 365 comprises information as to whether or not Person-A can fulfill the Interview-assigned Role of a Primary Care Doctor and whether or not Person-A is the primary care doctor in terms of Interview 340' and in relation to the Interview-designated Patient, Person-B (370).

The illustrated block 370 of Person-B (Patient) represents the Target of the included Interview 340'. This Person-B (Patient) block can be comprised of: Person-B Attributes 371; Person-B Channel Preferences 374; Person-B Channel Addresses, Channel Availability Times and other Contact Information 373; Person-B Chart Notes 372; and the Interview-designated Person Role Relationship 375 which is that for the Role of Patient.

The illustrated Person-B Attributes 371 of the designated Patient should include the Patient's name; date of birth; medical parameters such as height; weight at specified dates; allergies to medications; current medications being taken; genetically related information regarding predisposition to or protection from specific illnesses; genetically related information relating to deviation from usual drug metabolism pathway parameters; and other genetic information influencing medical parameters; and whether or not the patient has specific chronic medical conditions such as asthma, diabetes, or hypertension, and/or family history of specific illnesses. The Person-B Attributes may also include a default language preference for Prompts and screens (and/or other reports) viewed (and/or otherwise appreciatively obtained) by the Person-B while using the System; this preference over-rides language preferences expressed in similar Attributes for these areas at the Application, Topic, or System level.

The Person-B Channel Preferences structure 374 may include indications of the Channel types and respective delivery-attempt times which are preferred by Person-B (the Patient) for contacts.

The Person-B Channel Addresses and Channel Available Times and other Contact Information structure 373 may include the addresses of the Person's Channels and the respective, expected times of availability of these Channels.

The illustrated Person-B Role Relationship for the Interview (375) shows that Role as being one of Patient and this data structure 375 may comprise the name of the Patient's Primary Care Physician, insurance information and limits on insurance coverage, and information such as whether or not a referral visit is necessary before the Patient sees a specialist.

The Person-B Chart Notes 372 may include all active Chart Notes pertaining to Person-B made by Medical Provider, Person-A. In an embodiment, the Chart Notes 372 include all Chart Notes for this Person-B Patient as made by Medical Providers within the System other than the Medical Provider who Instantiated this Interview 340'. Further in an embodiment, the Chart Notes 372 may include Chart Notes for this Person-B (Patient) as made by Medical Providers other than the Medical Provider who is Person B's primary care provider.

Block 380 for Person-C is that of a Testing Facility worker and it accordingly comprises Person-C Attributes 381, Person-C Delivery Strategy 384, Person-C Chart Notes 382, Person-C Channel Addresses, Channel Availability Times, and other Contact Information 383, and Person Role Relationship 385 which in this case is the Interview-assigned Role of Testing Facility Person.

The Person-C Attributes 381 may comprise a Testing Facility name, clinic associations, limits for test values beyond which Alerts are sent to a Provider, retrieval deadlines for these Alerts, normal ranges for test results, and standard sets of tests. Person-C Attributes also includes a default language preference for Prompts and screens (or other data reporting means) viewed or otherwise appreciatively obtained by Person-C while using the System; this preference over-rides language preferences expressed in similar Attributes for these areas in other Entities of the System.

The Person-C Chart Notes 382 may be comprised of Chart Notes of the Testing Facility Person that relates to this Interview and/or the of the associated Medical Service Provider(s). The Person Role Relationship for the Role of Testing Facility Person (385) may comprise information such as the testing facility Name, testing facility limits for panic values for certain tests, and testing facility paradigms for contacting Medical Providers in the event of a panic value for a test.

The Person-C Delivery Strategies 384 may indicate Channels, times, and other information relating to how Person-C is able to receive and/or deliver information relating to this Interview 340'.

The Person-C Channel Addresses, Channel Available Times, and other Contact Information structure 383 may indicate addresses and times for the Channels available to Person-C for communications used for this Interview.

Within the Places structure 398, Clinic-A 397 is a Medical Clinic associated with Interview 340' and it has a corresponding Clinic-A Attributes structure 394. These attributes 394 may include characteristic of the clinic such as name, contact addresses, and location and rules the Clinic has relating to the information communicated in Interview 340'. The latter rules may comprise rules relating to quality assurance matters, normal or abnormal limits for tests, and privileges for handling alerted Interviews.

III. Method of Interview Formation, Scheduling and Delivery

Figure 4:
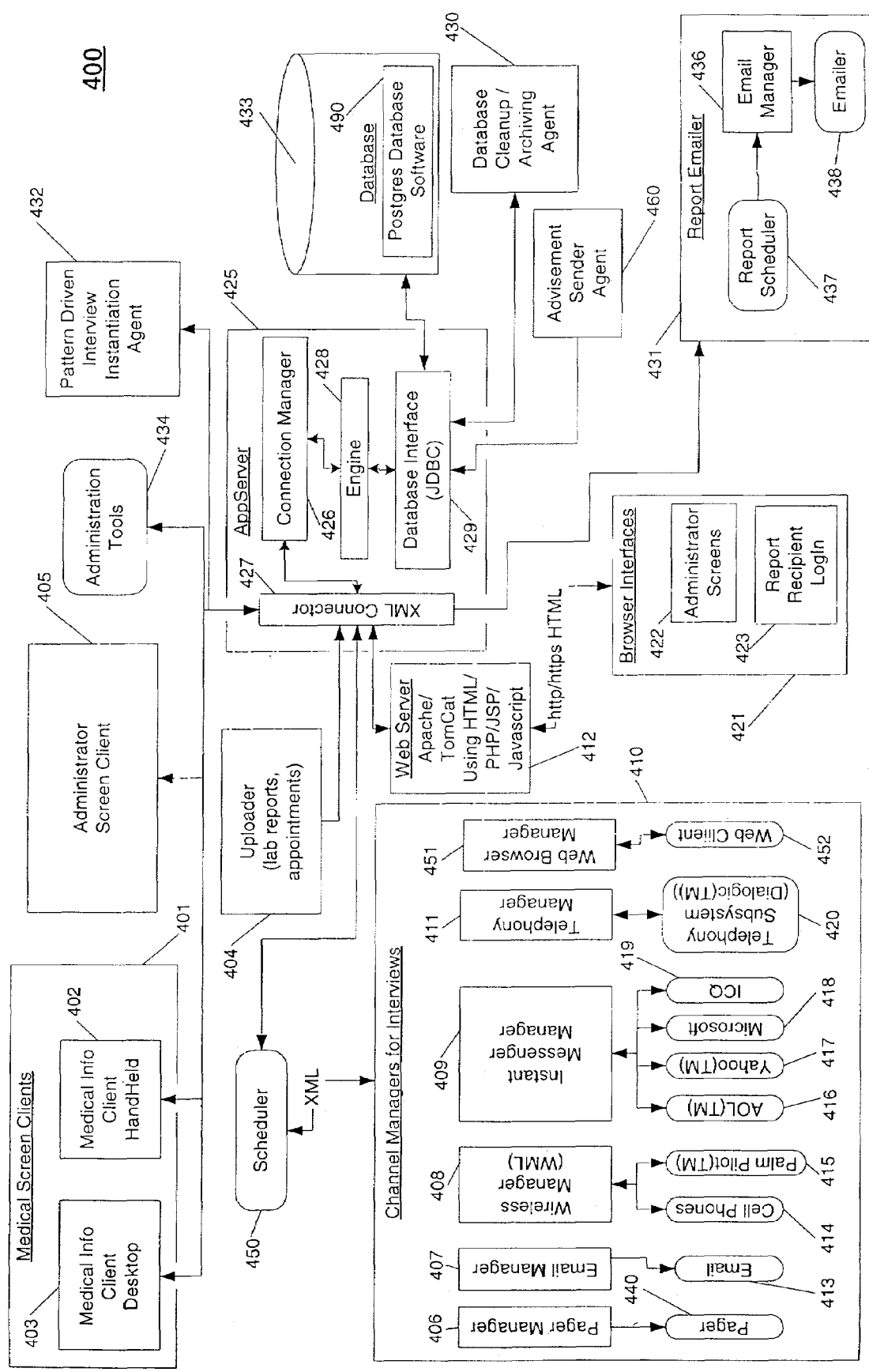
FIG. 4 is a block diagram of software components that may be used in accordance with the present disclosure for Interview formation and delivery.
Figure 5:
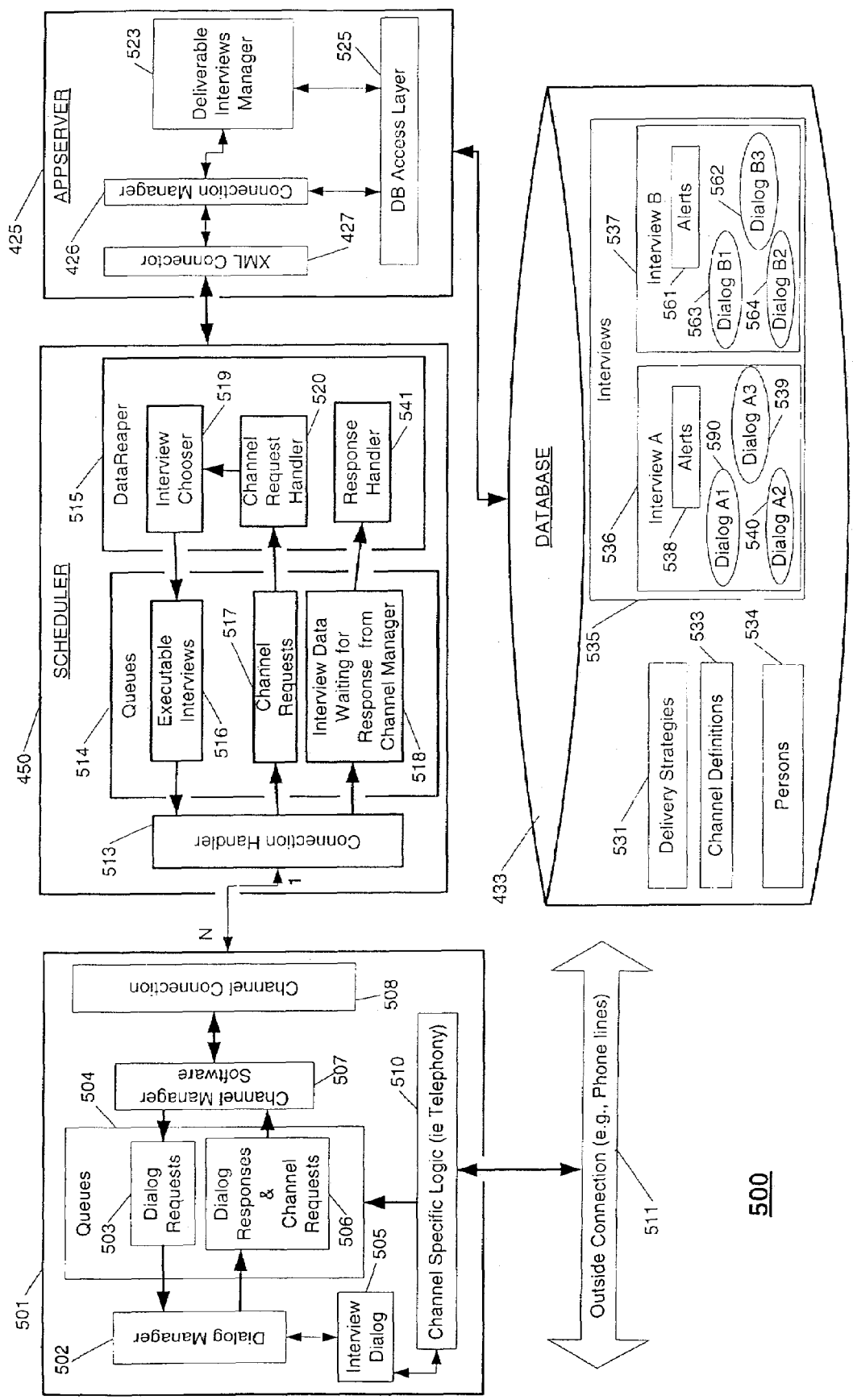
FIG. 5 is a detailed block diagram of software components that may be used in accordance with the present disclosure for Interview formation and delivery.

FIG. 4 and FIG. 5 illustrate a method of Instantiating, scheduling and delivering Interview Dialogs in an embodiment according to the disclosure.

(A) Structural Components:

FIG. 4 illustrates the interactions and relationships that may take place in accordance with the present disclosure between a System Database 433, a System Engine and Interface Programs of an AppServer 425, a Scheduler 450, Channel Managers 410, Medical Provider Screens 401, Administrator screen 405, a Pattern-Driven Interviews Instantiating Agent 432 (which is also at times referred to more under a more specific role herein as a Health Maintenance Interview Assignment Agent), an Interview UpLoader 404, Administration Tools 434, Report Emailer 431, an Administrator Browser Interface and Report Browser Interface 421, and a Database Cleanup/Archiving Agent 430. Also illustrated is a Web Server 412 that can interface between the Administrator Browser Interfaces and the XML Connector 427, and the Advisement Sender Agent 460.

A Database 433 in one embodiment, uses Postgres 4.1™ Database Software to aid in interacting with other components of the System. The Postgres 4.1™ Database Software is available from PostgreSQL, Inc., P.O. Box 1648 Wolfville, Nova Scotia, Canada.

The Medical Provider Screen Clients 401 may comprise Medical Information Desktop Clients 403 and Medical Information Handheld Clients 402.

The Administrator Browser Interfaces 421 may include one or more Administrator Screens 422 and/or one or more Report Recipient Login Screens 423.

The AppServer 425 may be constituted by an XML Connector 427 through which XML-compatible (Extensible Markup Language protocol compliant) Interviews may be uploaded to the AppServer 425 for use by the Connection Manager 426 which conveys data from the XML Connector to and from the Engine 428, and the Database Interface 429. The Database Interface 429 is an interface through which the Engine interfaces with the Database 433 and/or the Database Cleanup and Archiving Agent 430.

The Report Emailer 431 may be comprised of a Report Scheduler 437, an Email Manager 436, and an Emailer, 438. In an embodiment, reports can also be sent as web or intranet files or by way of other report content delivery means as may be appropriate.

Channel Managers 410 for managing Interview Communications may be comprised of specific Channel-type managers and corresponding clients including but not limited to: a Pager Manager 406 and Pager 440, an Email Manager 407 and Email-er 413, a Wireless Manager 408 and Cell Phones 414 and/or wireless Personal Digital Assistants (PDA's e.g. Palm Pilots™) 415, an Instant Messenger Manager 409 and AOL™ 416, Yahoo™ 417, Microsoft Internet Explorer™ 418, ICQ 419 or like Instant Messaging Search Engines, a Telephony Manager 411 and Telephony Subsystem such as a Voice Tronicx™ or Dialogic™ System 420 (where the latter may be respectively obtained from VoiceTronix, 63 Reynell Street, Kilkenny 5009, Australia and Dialogic Corporation, 1515 Route Ten, Parsippany, N.J. 07054, USA), and a Web Browser 451 and Web Client 452.

FIG. 5 illustrates some further detailed structures which may be provided in the Scheduler 450, AppServer 425, Database 433 and a more detailed view of a Channel Manager 501. The illustrated Channel Manager 501 is one of the many Channel Managers noted in 410 that can interact with Scheduler 450. Channel Manager 501 comprises a Channel Connection 508 that interacts with a Connection Handler 513 of the Scheduler and Channel Manager Software 507. Queues 504 may be comprised of an Interview Dialog Requests Queue 503 and/or Interview Dialog Responses and Channel Requests 506. Both these queues may interact with the Channel Manager Software 507 and the Dialog Manager 502. The Dialog Manager can responsively supply a completed Interview Dialog 505 to the illustrated Channel Specific Logic 510 for transmission to the Target. Logic 510 may be used to establish a connection to a corresponding transmission client 511 (e.g., which handles phone lines or other corresponding communications channels).

The Scheduler 450 may be comprised of Queues 514 that interact with the Connection Handler 513 and the DataReaper 515. Queues 514 may hold Executable Interviews 516, Channel Requests 517, and Interview Data Waiting for Response from a Channel Manager 518. The DataReaper 515 may be comprised of an Interview Chooser 519, a Channel Request Handler 520, and a Response Handler 541. Executable Interviews 516 may be supplied from the Interview Chooser 519. Channel Requests 517 may be delivered to the Interview Choose 519 via the Channel Request Handler 520. The Interview Dialog Data Waiting for Response data structure of the Channel Manager 518 should be combined with the corresponding Interview Dialog response data when an Interview is completed and forwarded to the Response Handler 541 and thence via the AppServer 425 to the database 433 for retrievable storage in the database.

The Scheduler 450 can interact with the AppServer 425 via the illustrated XML Connector 427. These couplings allow the Scheduler 450 to interact with the illustrated Database Access Layer 525 through the Connection Manager 426.

A Deliverable Interviews Manager 523 may be included in the Engine 428 part of the AppServer 425 as well as web support and client protocols. These may also interact with the Database Access Layer 525.

As is illustrated, various components of the AppServer 425 can therefore interact with the Database 433. The Database 433 can hold data structures representing Delivery Strategies 531, Channel Definitions 533, Persons 534 and/or Interviews 535. The exemplary set of Interviews 535 may contain a first Interview-A (536) and a second Interview-B (537) among others. As seen, Interview-A, may contain corresponding Alert Data 538 and a first Interview Dialog-A1 (590), a second Interview Dialog-A2 (540), and a third Interview Dialog A3 (539). Interview B may similarly contain respective Alert Data 561 and a first Interview Dialog-B1 (563), a second Interview Dialog-B2 (564), and a third Interview Dialog-B3 (562).

(B) Interview Instantiation and Activation:

Referring to FIG. 4, Interviews may be loaded into the System, or instantiated, via at least three ways:
 [1]. Direct upload via UpLoader 404;
 [2]. By way of actions of the Pattern-Driven Interviews Instantiating Agent (i.e. when acting as a Health Maintenance Interview Assignment Agent) 432; and
 [3]. By way of actions undertaken when using the Medical Provider and/or Medical Assistant Screens 401.

These are discussed in turn below:

[1]. When Direct upload via the UpLoader 404 is used, the UpLoader processes data by: (A) reading a file or (B) inputting data via a data-input stream. In one embodiment, the UpLoader input data should be in XML format, wherein there can be separate tags assigned for each UpLoader Command. The UpLoader Commands may comprise one or more of the following:
 i. Instantiate Interviews for a given Application,
 ii. Add Persons to the System,
 iii. Add Places to the System,
 iv. Establish or Modify a relationship between a Person and an Entity,
 v. Establish or Modify a relationships between a Place and an Entity,
 vi. Establish or Modify Attributes for an Entity,
 vii. Delete an Entity,
 viii. Add an Entity,
 ix. Add an Application,
 x. Add a Topic to an Application.

In one embodiment, more than one UpLoader can exist for a given System. Each such UpLoader should be able to support any subset of the above-described UpLoader Commands. Moreover, in the one embodiment, more than one UpLoader Command can exist in an Upload Data Stream or an Upload File. For example, an Upload File might include the following Upload Commands: to add a plurality of People, one Upload Command to Create an Interview, and ten Upload Commands to change Attribute Values for various Entities in the System.

Examples of XML pseudo-code of upload commands follow.

(a) Upload Command: Instantiate Interview:

An example of an Instantiate Interview Command is shown immediately below. Note that if there is an error, all sub-parts (e.g., Persons to be added) are not added:

<InstantiateInterview AppID="San Jose Medical Info Server"Topic="Test Result

```
Delivery-Cholesterol ">
    <Attributes>
        <Attribute LDLVal = "165"/>
        <Attribute HDLVal = "40"/>
        <Attribute TotalCholVal = "194"/>
        <Attribute AccessionNumber ="45454"/>
    <Attributes>
    <AddPersToInterview Role="Patient">
        <Attribute FirstName="Jay" />
        <Attribute LastName ="Thompson" >
        <Attribute ID="23222" />
        <Attribute DOB="12/22/93"/>
        <Attribute PersSex="Female" />
        <CommunicationChannel ID="HomePhone" Address=
"408-721-8222"/>
    </Add PersToInterview>
    <AddPersToInterview Role="Medical Provider" Default Phone =
"406768-5645">
        <Attribute FirstName="Mark" />
        <Attribute LastName ="Jillians" />
        <Attribute ID="299933" />
    </AddPersToInterview>
    <AddPersToInterview Role="Lab Tech">
        <Attribute FirstName="Sam" />
        <Attribute LastName ="Houston" />
        <Attribute ID="293983" />
    </AddPersToInterview>
    <AddPlaceToInterview Role="Clinic">
        <Attribute Name="Main Clinic" />
        <Attribute ID="23" />
    </AddPlaceToInterview>
</InstantiateInterview>
```

The above example of the Instantiate Interview XML pseudo-code loads an Interview for delivering lipid test results for the Application named San Jose Medical Information Server. The values of the components of the lipid test are loaded in the first section; the Patient data Attributes including patient name (Jay Thompson) is next loaded, followed by the Medical Service Provider Attribute information for Dr. Mark Jillians, the laboratory Attributes information under the name of Sam Houston, and then the medical clinic Attributes information.

Suppose that upon an uploading of this data to the Instantiate the Interview object from the Topic "Test Result Delivery-Cholesterol", the System automatically compares the uploaded test result values with the normal ranges in the System associated with the Lab Tech named Sam Houston and finds the LDL level outside of the corresponding normal range. As a consequence, the NeedsReview Property of the resulting Interview is set to "True," and a synopsis of the Interview is sent to the Medical Service Provider's Alert Summary Screen. An example of such an Alert Summary Screen (for a different doctor) is illustrated in FIG. 10. Also a Retrieval Alert is set for the Interview with a default Retrieval Deadline, and a default Priority is given to the Interview Dialog responsive to the LDL test result being abnormal. The Delivery Strategy Schedule for the Interview is also set by the Topic rules. As a result, Dr. Mark Jillians should be alerted that an abnormal LDL test result has been received. If Dr. Jillians does not timely retrieve this alert, another responsible person will be notified of the past-due alert.

The logic used for the UpLoader to Instantiate Interviews for a particular Application can use the following to process the Upload Command:

i. Read Upload Command Data into memory; if no more input exists, exit process ii. Locate Topic from which to Instantiate the Interview iii. Load Interview including Dialog Attributes into memory iv. If the Topic Upload Rules (Interview Instantiation Rules) don't allow Instantiating the Interview, abort the Interview Instantiation and go to Step i.

v. Use the Topic Rules to a) Set Alerts, if any.

b) Set Priorities for each Interview Dialog for the Interview c) Set the Delivery Schedule for each Interview Dialog for the Interview d) Set the NeedsReview Property of the Interview.

e) Create relationships with Persons to the Interview

In an embodiment, Topics that are uploaded this way include appointment reminders and test result deliveries.

(b) Uploading Persons into the System:

The process to upload Persons into the System may be comprised of the following steps:

i. Read input record into memory; if no more input exists, exit process ii. Read Attributes for Person iii. Create Person Entity with the read Attributes An example of the commands to do this is:

```
<AddPers Role="Patient">
    <Attribute FirstName="Bill" />
    <Attribute LastName ="Ton" />
    <Attribute ID="23982" />
    <Attribute DOB="12/22/50" />
    <Attribute PersSex="Male" />
    <Attribute PersLastFluVac="10/11/00"/>
    <Attribute PersDiabMellitus = "Yes"/>
    <Attribute PersLastEyeExam="5/9/00" />
    <Attribute PersMedAllergy1= "Penicillin"/>
</AddPers>
```

The-above XML pseudo-code loads a Person with a Patient Role into the System. The Person Attributes including first name, last name, ID number, date of birth, sex, date of last flu shot, whether or not the Patient has Diabetes, the date of the Person's last opthalmological examination, and a medication allergy should be loaded successively into the System in the order given.

(c) Uploading Places into the System

The process to upload Places into the System may be comprised of:
  i. Read input record into memory; if no more input exists, exit process
  ii. Read Attributes for Place
  iii. Create Place Entity with the read Attributes An example of the commands to do this is:

```
<AddPlace Role="Clinic">
    <Attribute Name="Clinic B" />
    <Attribute Address1="2347 Oakville Dr." />
    <Attribute Address2="San Jose" />
    <Attribute Address3="CA" />
    <Attribute Phone ="330 678-9800" />
</AddPlace>
```

This XML pseudo-code loads a Place, Clinic B, with a Place Role of Clinic into the System. The Place Attributes loaded include name, address, and phone number.

(d) Modify Relationship Between a Person and an Entity:

These modifications comprise changes in the relationships between Persons and Entities including the creation or deletion of relationships between Persons and Entities.

A process to modify the relationship between a Person and Entity may be comprised of the following steps:
  i. Read input record into memory; if no more input exists, exit process
  ii. Locate Person Entity and the Target Entity for the relationship
  iii. Load at Target Entity's Attribute Relationship Requirements for Roles
  iv. If the Person Entity does not have the Attribute Relationship Requirements, and there are defaults values for all of the said Attribute Relationships that are lacking, then add the Attributes to the Person Entity with the default values
  v. If the Person Entity has all the required Attributes for the Roles, create the relationship.
  vi. Goto Step (i)
  In an embodiment, if Attributes are lacking in the Entity for completing the process of modifying a relationship between a Person and another Entity, but however, there are default values for all of the said necessary Attribute Relationships that are lacking in that Entity, then these default values are instead used to complete the modification process.

An example of commands which may be used to do this are as follows:

```
<ChangeTopic TopicID="567" Topic="Office Visit: Severe Asthma">
    <Topic.Person.Provider.Attributes Provider = "Dr. Lon Jones">
        <Topic.Provider.Attribute.FUSevereAsthma.FirstContact = "1 day"/>
        <Topic.Provider.Attribute.FUSevereAsthma.AlertLimitPeakFlowPerCent="65"/>
        <Topic.Provider.Attribute.FUSevereAsthma.Dialog1Dialog2TimeGap="1 day"/>
    </Topic.Person.Provider.Attributes>
</ChangeTopic>
```

The above XML pseudo-code sets Dr. Lon Jones' Attributes for the Topic named: Follow Up of an Office Visit for Severe Asthma. For this Topic the exemplary process sets the time for the first follow up contact with the Patient, after the office visit, to being one day after the visit. The exemplary process further sets an Information Alert to be triggered if the Patient's reported peak flow is less than 65% of the normal value for that patient, and sets the time interval between the first and second Interview Dialogs to one day.

(e) Modify Relationship Between a Place and an Entity:

These modifications comprise changes in the relationships between Places and other Entities including the creation or deletion of relationships between Places and other Entities.

An example of such a process to modify the relationship between a Place and another Entity may be comprised of the following steps:
  i. Read input record into memory, if no more input exists, exit process
  ii. Locate Place Entity and the Target Entity for the relationship;
  iii. Load at Target, the Entity's Attribute Relationship Requirements for Roles;
  iv. If the Place Entity does not have the Attribute Relationship Requirements, and there are defaults values for all of the said Attribute Relationships that are lacking, then fill the missing Attributes to the Place Entity with the default values;
  v. If the Place Entity has all the required Attributes for the Role, create the relationship.
  vi. Go to Step (i)
  In an embodiment, if Attributes are lacking in the Entity for completing the process of modifying a relationship between a Place and another Entity, but however, there are default values for all of the said necessary Attribute Relationships that are lacking in that Entity, then these default values are used instead to complete the modification process.

Examples of commands for carrying out such a modification between Place and another Entity are as follows:

```
<ChangeApplication AppID="667" Place= "Ely Chemistry Lab" Application="Test Result Delivery">
    <Application.Topic>
        <Application.Topic.Haptoglobin = "Not Available"/>
    </Application.Topic>
</ChangeApplication>
```

The above XML pseudo-code removes the Topic Haptoglobin from the Application "Test Result Delivery" for Ely Chemistry Lab.

Another example of commands for carrying out such a modification between Place and another Entity are as follows:

```
<ChangeTopic TopicID="5643" Place= "Ely Chemistry Lab" Topic= "Test Result Delivery: Chemistry Screening Battery">
    <Topic.LDL.Range>
        <Attribute.LDLMaxNormal ="100"/>
    </Topic.LDL.Range>
    <Topic.Potassium.Range>
        <Attribute.PotassiumMaxNormal = "6.5" />
    <Topic.Potassium.Range>
</ChangeTopic>
```

The above, exemplary XML pseudo-code sets the maximum normal value for LDL cholesterol to "100" and the maximum normal value for a blood Potassium test to "6.5" in the Chemistry Screening Battery Test Result Delivery Topic for Ely Chemistry Lab.

In an embodiment, if the Place or Person Entity do not have the Attribute Relationship Requirements for the required Role for the Entity under consideration and default values are not available, then the respective relationship modification between the Place or Person and the Entity is aborted and the user is informed of the missing, but needed data.

(f) Uploading Attribute Changes to Entities:

The following process is an example of steps that may be taken for carrying out an Uploading of Attribute Changes to respective Entities:

For each record:
  i. Read input record into memory; if no more input exists, exit process
  ii. Locate Entity, and replace and/or add Attributes for the record-identified Entity

[2]. Pattern-Driven Interviews Instantiating Agent 432

The Pattern-Driven Interviews Instantiating Agent 432 of FIG. 4 may function among other things as a Health Maintenance Interview Assigning Agent which automatically generates, Instantiated Health Maintenance Interviews. Provided within the System Database and/or the Interviews Instantiating Agent 432 itself there may be a set of one or more Agent Interview Instantiation Rules. An Agent Interview Instantiation Rule may be comprised of data and/or logic defining:
  i. Set(s) of Application/Person Role(s)
  ii. Person Attribute(s) Qualifying Ranges
  iii. Person Sex Values (Male Only, Female Only, Male or Female)
  iv. Frequency Fire Criteria
    a. Age of Person Qualifier Range
    b. Calendar Date Qualifier Range
  v. Last Fired Time.
  vi. Next Fire Time
  vii. Next Fire Time Determination Logic
  viii. Interview Instantiation Rules In one embodiment, the Pattern-Driven Interviews Instantiating Agent 432 automatically and periodically loads each Agent Interview Instantiation Rule into memory and if the Pattern-Driven Interviews Instantiating Agent 432 finds that the Next Fire Time is less than the current time, and the Pattern-Driven Interviews Instantiating Agent 432 then performs the following steps:
  a. For each of the Application(s) listed in Part (i) of the Agent Interview Instantiation Rule, create a set of Patients where the Relationship Role exists.
  b. From the set, remove Patients who do not have each proper value for the Patient Attribute, including, if applicable, Sex Attribute, that falls within each Person Attribute Qualifying Range.
  c. From the set, remove Patients who are not within the Age of Person Qualifier range
  d. From the set, remove Patients who are not within the Calendar Date Qualifier range
  e. For each Person in the set
    i. Instantiate an Interview if Topic Rules allow.
    ii. Use the Topic Rules to
      1. Set Alerts, if any.
      2. Set Priorities for each Interview Dialog for the Interview
      3. Set the Delivery Schedule for each Interview Dialog for the Interview
      4. Set the NeedsReview Property of the Interview to "False."
      5. Create relationships with Persons to the Interview including Primary Care Provider
      6. Use the Interview Instantiation rules, if they exist, to modify Interview Attributes
  f. Use Next Fire Time Determination Logic to set the Next Fire Time value for the Agent Interview Instantiation Rule.
  g. Increment the Last Fired Date to now

[3]. Medical Provider and Medical Assistant Screens 401.

A Medical Service Provider or Medical Assistant who has access to the System screens and/or to other user-interfaces, (i.e. voice-based user-interfaces of the System) can perform one or more of the following actions: 1) Instantiate an Interview with a Target Person or a Target Group and thereafter change the NeedsReview property of the instantiated Interview, and 2) Upon reviewing such an Interview, change the NeedsReview property of an Interview whose NeedsReview property is "True". Examples of screens that may be used to accomplish the above in one given embodiment are illustrated in FIGS. 10A, 11, 12, 13, 14, 15, and 16.

Figure 10A:
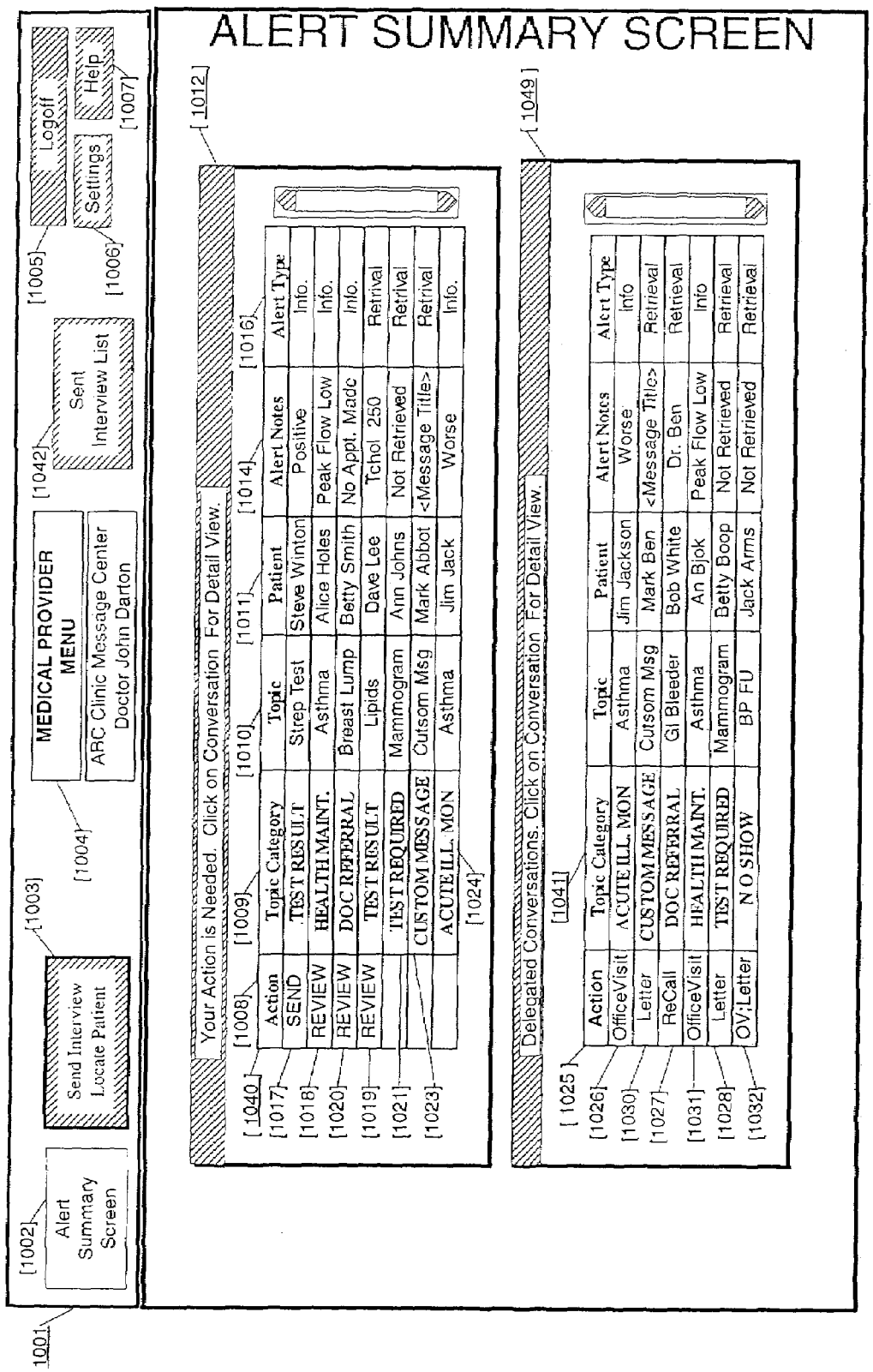
FIG. 10A illustrates an alerted action-items summarizing mechanism (e.g., an Alert Summary Screen) that may be used by a Medical Service Provider to learn of, and/or take responsive action on, action-items that are alerted by the System as calling for relatively quick attention thereto.
Figure 11:
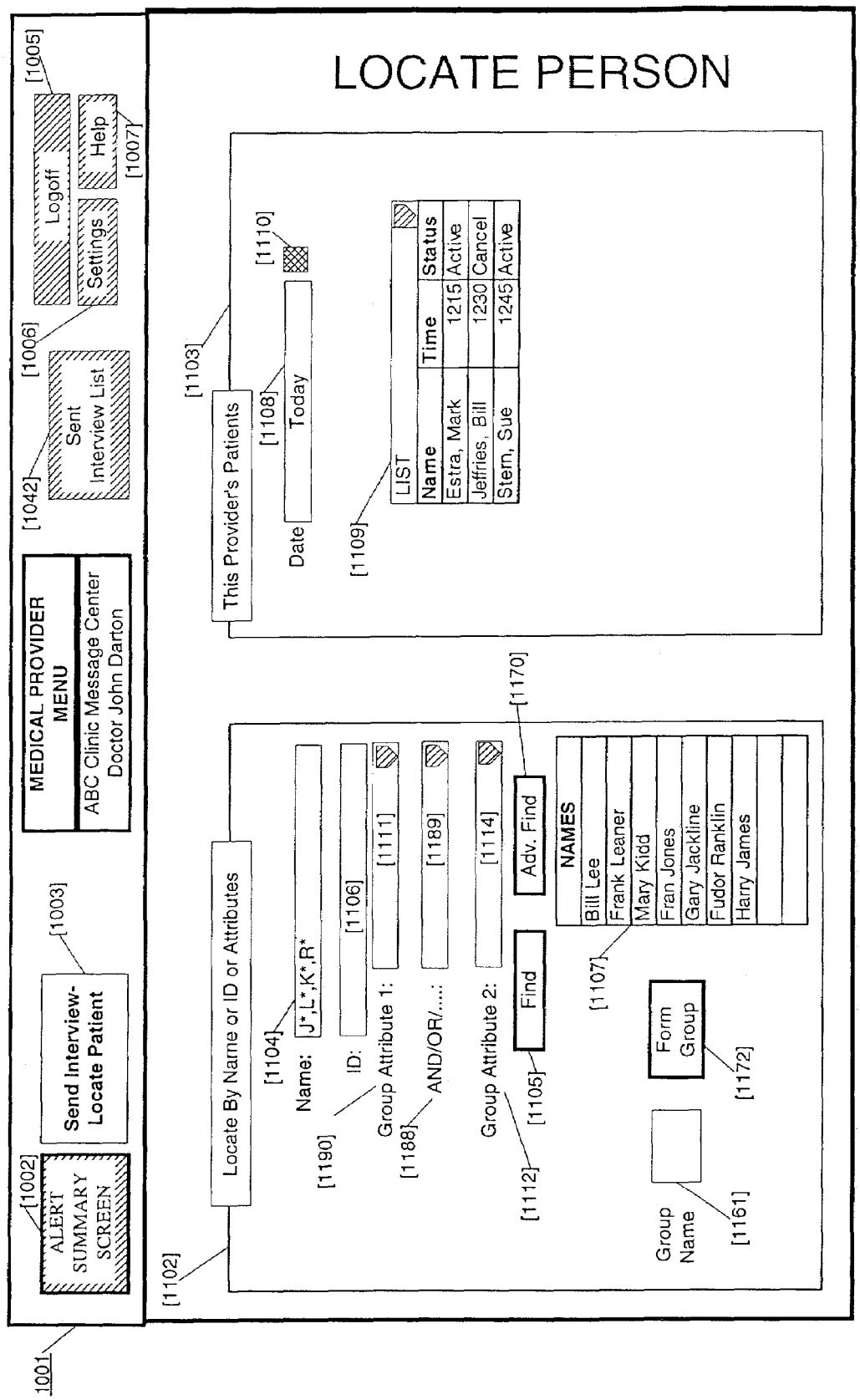
FIG. 11 illustrates a Person-Finding screen which may be used by a Medical Service Provider, Medical Assistant or another authorized person to locate and/or access information in the System about Patients or other persons and/or to define Patient Groups.
Figure 12:
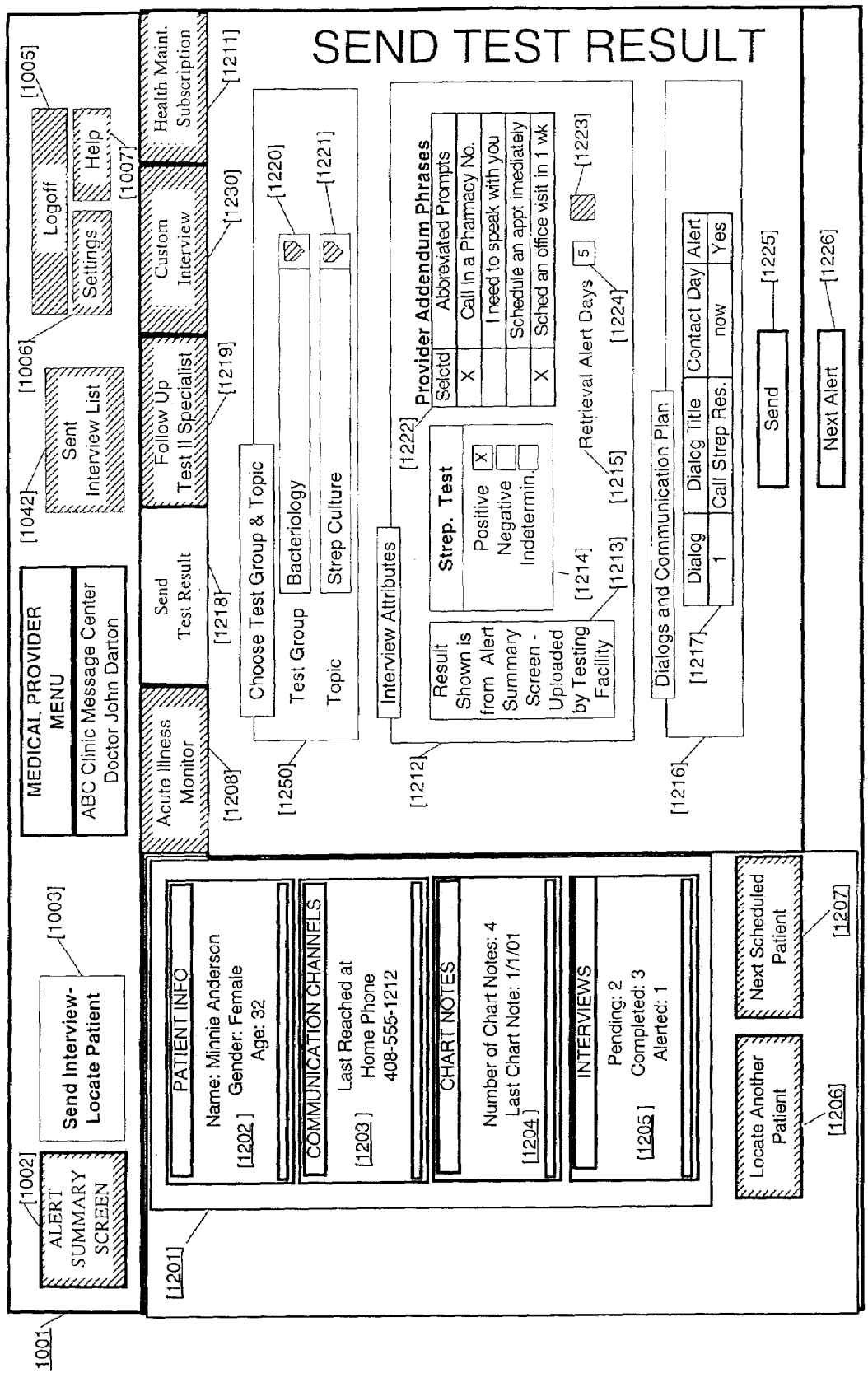
FIG. 12 illustrates an Interview formulation screen which may be used by a Medical Service Provider to formulate a Test-Results Reporting Dialog that is to delivered to a Patient in accordance with the present disclosure.

A process for carrying out such an instantiating and modifying of an Interview may comprise the following steps:
  a) An authorized user such as a Medical Service Provider or Medical Assistant selects the Target Person or Target Group, byway of a Target-locating screen such as shown in FIG. 11.
  b) The user then selects the Topic Category of the Interview from the tab buttons (e.g., 1208, 1218, 1219, 1230, or 1211 of the selection options shown in FIG. 12) on the user interface. Topic Categories may include Acute Illness Monitor, Specialist Follow Up, Test Follow Up, and/or Health Maintenance. Screens may be provided for Custom Interviews as well and also for reporting Test Results. (Incidentally, if a reference number is enclosed in square brackets in an illustrated screen, that means the reference number is not part of the screen-displayed information.)
  c) The user selects a Topic Group: For example, "Test Group: Bacteriology" in 1220 in FIG. 12 or "Diagnosis: Asthma" in 1304 in FIG. 13.
  d) Using a pop-down menu or another appropriate selection mechanism, the user selects a particular Topic in that group, such as in 1221 ("Strep Culture") in FIG. 12 or in 1305 "Asthmatic Bronchitis-antibiotics" in FIG. 13.
  e) Depending on the Topic the user sets a time value, which helps determine when the first Interview Dialog of the Interview is to be sent, such as shown at 1407 in FIG. 14. The user may also choose a time to trigger a Retrieval Alert or accept a default time, such as shown in box 1224 in FIG. 12.
  f) The user may add additional phrases as desired, such as shown in the X-able selection box 1222 in FIG. 12.
  g) If permitted by the applicable Rules, the Interview's NeedsReview Property may be automatically set to 'False' after the user presses the "Send" button, such as shown in the mouse-clickable box 1225 in FIG. 12. In such a case, the formulated Interview will be instantiated for sending without need for further review. The latter, review-free-sending can be contrasted with row 1017 (Action=SEND) of FIG. 10A which shows how there may still be a true NeedsReview Property in a partially, or even fully, formulated Interview concerning *new information about test results recently received from a laboratory indicating that the Patient (Winton) appears to have a case of Strep Throat. The Primary Care Provider (PCP) has not yet looked at the details of this, uploaded-from-LAB Interview; which is why the ACTION requested (1008) is SEND rather than REVIEW. In the example, the System or Application Rules require the PCP to be first informed of this new situation even if the UpLoaded Interview (the details that will appear when "clicking-through" row 1017), even if the underlying Interview is already fully formulated; which is why the NeedsReview Property for the underlying Interview is forced to be True at least until the PCP indicates he/she has received the report and approved the SEND-ing (1008) of the underlying Interview (as modified or not by the PCP) to the affected Patient and/or other Targeted Persons.

The instantiated Interview (of FIG. 12) with NeedsReview property set to "False" is then sent from the Screens Client unit 401 via the XML connector 427. The XML data is transferred from XML Connector 427 to the Engine 428. The data is then transferred to Database 433.

The Database stores such user-formulated, Instantiated Interviews with their associated Target Person or Target Group along with their Delivery Schedules. In one embodiment, the System can only deliver Interviews to their designated Target(s) if the NeedsReview property is equal to "False" (or an equivalent indicator). If the NeedsReview property is instead "True", an MSP or other responsible person is alerted to perform the required Review before the formulated Interview is permitted to become deliverable.

For a Test Result reporting-Interview, the NeedsReview property can be changed to bypass the need for a Review as described herein or by the Medical Provider accessing the corresponding Interview such as in box 1012 of FIG. 10A and thereafter changing the NeedsReview property. For example, a Medical Provider upon clicking (e.g., once-clicking, double-clicking or other wise activating by special keying or other input) on an abnormal laboratory result Alert noted in box 1012 (i.e., such as the one shown in row 1017) of FIG. 10A may be presented with a screen such as illustrated in FIG. 12. The Medical Provider may next select Addendum Phrases in 1222. When the Medical Provider then presses the "Send" button 1225, the selected Addendum Phrases 1222 references are added to the Interview, and the Interview NeedsReview property is automatically set to "False" because the System deduces from the MSP's actions that he/she has finished reviewing the Interview.

Typically, Interviews for reporting to Patients their corresponding results when the results are within the medical and/or testing facilities' normal range relative to the corresponding Patient's Attributes are initially Instantiated with their NeedsReview property set to "False", and are therefore able to be delivered to their Target without calling for intervening Medical Provider review. The MSP is thereby relieved of having to review most of the incoming, and typically normal, test results and can focus his/her attention on those of the received test results that the System determines as showing one or more abnormal results.

(C) Advisement Instantiation and Activation

Advisements serve to notify Patients that there are Pending Interviews that they should access. In an embodiment, Advisements are a specialized form of an Interview.

In an embodiment according to FIG. 4, the Advisement Sender Agent 460 contains Advisement Send Rules, which are used to send Advisements. The following are examples of Advisement Send Rules:

1) If Target Person has at least one Deliverable Interview with a Retrieval Alert and has not retrieved this Interview within an Application Attribute set number of days before this Retrieval Alert is to be triggered, the Target Person is sent an Advisement of such an upcoming Retrieval deadline.
2) If the Target Person still has pending an amount equal or greater than an Application-established Attribute number of Retrieval Alerts, the Target Person is sent an Advisement about having such an excessive number of still-pending Retrieval Alerts.
3) If a user of the System activates a System function for sending an Advisement to a Target Person, then that Target Person is sent a corresponding Advisement.

In one embodiment, Advisements are sent to the Target at least via an email or pager notification or the like to thereby bypass the answering-machine problems noted above.

(D) Selection and Loading of Pending Dialogs

In one embodiment, all Interviews are stored in the Database 433. Each such Interview has at least one Interview Dialog. An Interview Dialog uses logic and data from its corresponding Topic Dialog for formulating the Dialog content and delivery methods.

Each Topic Dialog may contain one or more of:
(1) Delivery Strategy Sets;
(2) Dialog Logic and Phrases, that:
  a. Define Phrases (i.e., for example, statements, questions, and answers in the Dialog);
  b. Define question, statement, and answer formation and logic
  c. Define adaptive content presentation;
  d. Define rules for Information Alert formation; and/or
  e. Define internal variables used for directing question or statement delivery.

Each Interview Dialog should contain specific questions, statements, and answer choices for provision in a correspondingly-formulated Dialog as well as Information Alert Data and delivery attempt and history information pertaining to that Dialog.

An Interview Dialog typically presents, in a single contact session, its questions and/or answers to the Target and collects corresponding answers or requests from the Target during the session. Each Interview Dialog is associated with a corresponding Delivery Schedule and a Delivery Strategy.

During Instantiation of an Interview, a Dialog Delivery Schedule is created for each Interview Dialog. This Delivery Schedule can be specified as a Time Period whose counting commences immediately after the Interview is set to the Deliverable State. The Interview Dialog delivery time range may have one or both of an upper and lower value. These values may be used to create the Delivery Schedule of the Interview Dialog.

When an Interview is Instantiated for a given Topic, exactly one Interview Dialog should be created for each Topic Dialog for the given Topic. These Interview Dialogs should be ordered in precedence of Delivery Times, with earliest being scheduled first for delivery.

Each Topic Dialog may have an InterDialog Time Gap that specifies the minimum time before a next Interview Dialog can be delivered after the given Interview Dialog has been delivered. The InterDialog gap serves to prevent overlapping of Interview Dialog Deliveries, and also to make sure a proper minimum time exists between Interview Dialog Deliveries as may be appropriate. If a given Topic has only one Topic Dialog, then it does not need to have a corresponding InterDialog Time Gap Value. Also, in one embodiment, the last Topic Dialog in a Topic Dialog Collection has no InterDialog Time Gap.

The Delivery Scheduler may use the InterDialog Time Gap in conjunction with the Dialog's Delivery Schedule to determine if the Interview Dialog is currently deliverable. In an embodiment, Interview Dialog delivery times are made automatically responsive to Interview Dialog Responses. More specifically, in an embodiment, the delivery-attempt time to initiate the attempted delivery of a first, new Interview Dialog is determined using an Attribute, such as a Person Attribute which stores the last time the Patient came into the office for an office visit, or stores other sentinel medical events. In this way, the Interview can be delivered on a patient-centric time schedule.

In an embodiment, the Dialog Time Gap and Delivery times for Interview Dialogs may be specified as fuzzy specifications—that is, e.g., a minimum time gap specified as one day (e.g., next day) may be interpreted by the System as meaning the next morning at, say 8 AM, instead of strictly twenty four hours after the setting of the Interview NeedsReview Property to "False." This would permit, e.g., Interview Dialog delivery attempts during optimal times both for morning and evening of the following day.

In an embodiment, Dialog Time Gaps can be set as fixed periods, which are stored in the Topic. In an embodiment, Dialog Time Gaps can be made automatically responsive to Patient responses of prior Dialogs in a given Interview so that Dialog Time Gaps automatically adapt to patient-centric factors.

The Deliverable Interviews Manager 523 of FIG. 5 automatically scans the Database 433 for Deliverable Interviews. Deliverable Interviews are defined in that embodiment as Interviews that have a Deliverable Interview Dialog. A Deliverable Interview Dialog is defined in that embodiment as an Interview Dialog wherein: 1) the Interview Dialog Status equals "Pending", 2) the Interview Dialog belongs to an Interview which has an Interview NeedsReview Property set equal to "False," and 3) the Interview Dialog to be delivered has a next delivery-attempt time within the Interview Dialog Delivery Schedule, taking into account Dialog Time Gaps.

The Deliverable Interviews Manager 523 orders such Deliverable Interviews by their respective Pending Interview Dialog Priority values. The Priority value of a given Deliverable Interview may be determined automatically as a function of the Priority value of its Application, the Dialog's Priority value, and the Target Person's Priority value. In an embodiment different weights are assigned to each of these types of Priority values on a Topic by Topic basis, Person by Person basis, Application by Application basis and so on.

The Deliverable Interviews Manager 523 can further and adaptively adjust the Priority of a Deliverable Interview Dialog in a Deliverable Interview in response to Entity Attributes and the time period the Interview Dialog has been pending on the System. This method increases the chances for Deliverable Interview Dialogs from Deliverable Interviews that may have low Priority, where such relatively low Priority values may otherwise make it less likely that the Interview will be delivered in the face of competition from higher Priority Interviews. Long-pending Interviews tend to have their Priority value increased before they are removed from the System due to being too old.

In an embodiment, the Interview Dialog Priority is determined by a function responsive to the Priority of the Person that initiated the Interview. In the same or another embodiment, the Administrator may manually set or reset the Interview Dialog Priority. In one particular embodiment, the Priority of the Target Person is weighted greater than the Interview Dialog Priority and the Application Priority. In another embodiment, the Application Priority is weighted greater than the Person and Interview Dialog Priority values. In an alternate embodiment, the Interview Dialog Priority is weighted greater than the Application Priority and Person Priority.

The Deliverable Interviews Manager 523 may also be made responsible for removing from the Deliverable Interview Dialog queue any Deliverable Interview Dialogs that have been on the System for a period of time past a predetermined expiration time. In an embodiment, when a Deliverable Interview is removed from the System, a Deliverable Interview Unsent Alert is automatically sent to a corresponding Quality Assurance Body and/or a corresponding Medical Service Provider associated with the unDelivered Interview. In an embodiment, the sending or not of this Interview Unsent Alert is made programmably responsive to the content of the Deliverable Interview.

Upon request and/or after a chosen time period the Deliverable Interviews Manager selects by Priority, Deliverable Interviews Dialogs and passes them to the Scheduler. The chosen time period may depend on the System's delivery capacities and the number of Deliverable Interviews then pending in the System. This chosen time period should be selected to avoid prolonged storage of undelivered Deliverable Interviews in the System. The priority-wise, selected Deliverable Interviews and their Interview Dialogs are transferred from the Deliverable Interviews Manager 523 to the Scheduler 450 for subsequent processing.

(E) The Scheduler 450

A. Selecting Interviews (Interview Dialogs) to Deliver

The Scheduler 450 interacts through the Channel Manager 501 with one or more communication Channels. The Interview Chooser 519 of the Scheduler computes the number of Interview Dialogs that each Channel Manager can process over a given time period. This number of Interview Dialogs may be determined so that the request will retrieve a suitable number of Interview Dialogs to allow timely re-access for new Interview Dialogs by each Channel Manager. The methods the Scheduler uses to determine the number of Interview Dialogs to be sent by way of each channel are discussed below. The Interview Chooser 519 then requests the number of Interview Dialogs from the set (ordered by Priority) of Deliverable Interviews Dialogs in Deliverable Interviews held in the Deliverable Interviews Manager 523.

(a) Selecting the Appropriate Delivery Strategy:

Each Deliverable Interview has a corresponding Target Person. For each Target Person the System finds a corresponding set of preferred Channels and preferred delivery-attempt times. Then the appropriate set of Delivery Strategies for the current Instance of each Deliverable Interviews Dialog is formulated.

Delivery Strategies may be comprised of a set of data structures including those defining a Channel Type, suitable delivery times, relative Priority—i.e., the order of use of different Channels, whether or not to abort the use of the Channel if there is a hang-up or an equivalent disconnect action, and whether or not to override pre-specified Target restrictions on use of the given Channel.

A Delivery-Strategy selecting algorithm may be used to determine which Delivery Strategy to use from a provided set of available Interview Dialog Delivery Strategies. This algorithm can include matching the Target Person's Channel preferences to find suitable channel candidates for making delivery attempts. The Delivery-Strategy selecting algorithm may be comprised of the following steps:
 (i) Determining if the Target person has blocked this Dialog, Topic, and/or Application. If the Topic is blocked, the status of all Interview Dialogs for the Interview is set to blocked and the Interview Dialog is automatically removed from the list of Deliverable Interview Dialogs. The System stores the information that the Interview Dialog was blocked as the reason that the status of all these Interview Dialogs was set to Not Delivered. In an embodiment, if the Interview Dialog is blocked, then a Blocked Dialog Alert is sent to a corresponding Quality Assurance Body and/or to the corresponding Medical Provider. In an embodiment, the determination of whether or not to send a Blocked Alert is specified in a Topic Setting.
 (ii) Determining if the Delivery Strategy Channel has been exhausted for this Interview Dialog—that is, have there been more than a pre-determined maximum number of failed contact attempts using this Channel. If the maximum allowed number of failed contact attempts has been reached or exceeded, then this Delivery Strategy Channel is removed from further use by the Scheduler for the given Interview.
 (iii) A search is made to find matches for the Target's preferred Channels with their corresponding Delivery Time Preferences and the Dialog's Delivery Strategies, where the present time falls within said Delivery Time Preferences.
 (iv) If a match is found, the System checks to see if the Required Strategy Completions for the given Delivery Channel has been satisfied for the Interview Dialog. If not, this Delivery Strategy Channel is not considered further by the Scheduler for the given Interview. For a given Delivery Strategy, the Required Strategy Completions specify the Delivery Strategies that must have been completed prior to the given Delivery Strategy being considered to be used for delivering the Interview Dialog. In one embodiment, in order for a Strategy to be considered completed, it must have been utilized a minimum number of attempt times for a given Interview Dialog. If a given Interview Dialog Strategy has no Required Strategy Completions, then the Interview Dialog Strategy can be used for delivery of the Interview Dialog.
 (v) The current number of attempts to deliver the Interview Dialog should be less than the Delivery Strategy's maximum number of allowed attempts.
 (vi) If all the above requirements and matches are satisfied, the Delivery Strategy is placed in a list of eligible Delivery Strategies for this Interview Dialog. This list is ordered in terms of Priority of eligible Delivery Strategies.

If there are no eligible strategies after the above testing, then this algorithm is repeated but modified to disregard the Target Person's preferred Channel open times.

If there exists at least one eligible strategy, this is added to the list of Delivery Strategies that can be used for this Interview Dialog communication attempt. Those of the selected Interview Dialogs that become associated with eligible Delivery Strategies are now marked as "Chosen Interview Dialogs" in the list of prioritized Pending Interview Dialogs. For each Target, the Interview Dialog in the list of the Chosen Interview Dialogs that has the highest Priority is called the Primary Interview Dialog.

(b) "Packing" or Collecting Other Pending Interview Dialogs for Delivery to a Target with a Chosen Interview Dialog If a Target Person has several Deliverable Interviews, each containing a deliverable Interview Dialog, it is advantageous to deliver more than one Interview Dialog in a single, successful contact. This decreases interruptions of the Target Person and increases the efficiency of the System.

In an embodiment, this is done as follows by the Scheduler 450:
 (i) Collect all Target Persons associated with the chosen Interview Dialogs.
 (ii) "Pack" the Interview Dialogs associated with each Target Person—that is,
   (a) Combine all Deliverable Interview Dialogs for each Target Person with a Primary Interview Dialog with the limitation that each communication pack contains Interviews only for a single Application. In an embodiment, each said communication pack may contain Interviews for more than one Application.
   (b) For each of these Pending Interview Dialogs the Scheduler verifies that the Interview Dialog delivery can occur on the same Channel as the Primary Interview Dialog.
   (c) For each Pending Interview Dialog the System also verifies that the Interview Dialog delivery can occur at the same time as the Primary Interview Dialog.
   (d) If the above are true, then the System adds this Interview Dialog to the list of Interview Dialog(s) to be delivered to the Target in Priority order.
 (iii) "Prune" this packed list of Interview Dialog(s) to be delivered to Targets to an acceptable maximum number if the latter number is exceeded. In different embodiments, there are different ways for the System to compute this maximum number, For example:
   (a) In one embodiment, the Application specifies a maximum number of Interview Dialogs acceptable for delivery per Channel Type. The list of packed Interview Dialogs is then trimmed back to this maximum number by removing from the list, those Interview Dialogs with the lowest Priorities.
   (b) The Channel may compute the total number of Interview Dialogs to be delivered based on an acceptable total overall time for delivery of a set of Interview Dialogs. In an embodiment, the maximum allowable time is specified by the Application per Channel Type. Each Interview Dialog specifies a metric related to the average number of questions that the Interview Dialog would present before being completed. An estimated completion time for the set of packed Interview Dialogs can then be calculated using the average number of questions per Interview Dialog. Interview Dialogs will be pruned off the packed list in reverse priority order until the estimated, total conversation time for the planned contact-pack is less than the maximum allowed by the Application.
 (iv) The remaining Interview Dialogs selected are then marked by the System as scheduled Interview Dialogs and thereby removed from the class of chosen Interview Dialogs.

(v) The Interview Dialogs not selected for attempted-delivery are cleared from the delivery-processing elements of the System so they may be considered for processing again later.

(vi) For each Interview Dialog selected for delivery, the System retrieves all the corresponding Interview Dialog information, Person identifiers, and Attributes from the Database and completes the data requirements for generating a deliverable communications package therefrom.

(vii) Each deliverable Interview Dialog is then 1) added to the "Waiting for Response" queue of "Executable Interview Dialogs" 516 and 2) forwarded to the appropriate Channel Manager in 501 via the Connection Handler 513.

(viii) The Connection Handler 513 also loads the Interview Dialog into queue block 518, namely, the Interview Data Waiting for Response from Channel Manager.

In an embodiment, a Topic parameter may be used to selectively bypass the process of packing other undelivered Target Interview Dialogs with a chosen Interview Dialog. This packing-bypass option can be advantageous if it is desired in certain situations (e.g., a medical epidemic) for the System to contact as many Targets as possible as fast as possible. In another embodiment an Application parameter may be used to selectively bypass the process of packing other undelivered Target Interview Dialogs with a chosen Interview Dialog.

(c) Channel Manager 501

The Channel Manager 501 receives requests to deliver Interview Dialogs from the Scheduler 450. The Channel Manager retrieves the corresponding Interview Dialogs and passes them to an Interview Dialog request queue 503.

When a free port is or becomes available for an appropriate Channel, the Dialog Manager takes the next Interview Dialogs Pack available for delivery from the Interview Dialog request queue 503 and passes it (505) to the corresponding, channel-specific logic 510 for further handling. In the process, the System should check to see that the Channel request is valid and that the to-be-transmitted Interview Dialog information is complete. If any of the required information is missing, the Interview Dialog should be removed from the Interview Dialogs Pack and the Interview Dialog should be rejected with a message being sent to the responsible entity indicating what data is still missing.

If System determines that the Interview Dialogs Pack under consideration has no (further) Interview Dialogs, then the Interview Dialogs Pack is removed from memory. Once the delivery-supporting information is complete and validated for each Interview Dialog in the Interview Dialogs Pack, and the Interview Dialogs Pack has at least one Interview Dialog, the Channel Specific Logic 510 assigns the Interview Dialogs Pack to a port and calls the corresponding delivery actualizing routine as is indicated for the Outside Connection 511. The Interview Dialog Pack is then passed to a Channel Client Manager and Client such as Pager Manager 406 and Pager 440 or Web Browser Manager 451 and Web Client 452 for subsequent handling.

(d) Executing an Interview Dialog:

When an Interview Dialog is delivered and processed, the System retrieves the Attributes from the Entities associated with the Interview needed to process the under-delivery Interview Dialog in response to a processing request returned from the Dialog Manager 502.

Part of the under-delivery processing can include use of a Topic Dialog. A Topic Dialog may be comprised of a set of rules described in an appropriate programming language. These rules may be used to specify:

(i) How the Phrases used in the Interview Dialog are built and combined with one another. Phrases may be formed from a combination of predefined prompts and certain information obtained dynamically from the Target and/or from other sources during the Interview Dialog delivery process.

(ii) When and how to ask the questions in the delivery of the Interview Dialog.

(iii) Adaptive prompting—i.e., what prompts are to be selectively presented, removed, or modified in the Interview Dialog in response to Attributes related to the Interview Dialog and/or in response to data returned by the Target Person. As the Interview Dialog progresses, it may receive various kinds of information from user responses, and such should be stored in the Database for later processing.

(e) Return of Results from Interaction Between the Interview Dialog and the Target:

When the Interview Dialog Delivery Attempt terminates, whether successful or not, the information derived from the attempted execution of the Interview Dialog is packed together into a response message by the Dialog Manager 502 and passed to an Interview Dialog Response Queue in 506 for ultimate return to the Database 433. Such returned information may be comprised of one or more of:

(a) The status of the Interview Dialog and other delivery parameters—e.g., whether it completed successfully or with errors, identification of the point of any disconnect during the Interview Dialog, and specification of the number of access attempts;

(b) New Attribute values;

(c) Any Alert information generated during the Interview Dialog delivery process;

(d) Whether this Interview Dialog needs to be rescheduled for later re-execution; and (e) The time and duration of the Interview Dialog.

The Channel Manager 501 picks up this response message and sends it back to the Scheduler 450 via the Channel Connection 508 when the corresponding Channel becomes available. In the Scheduler 450, the corresponding data for the post-execution Interview Dialog is found in the "Waiting for Response" queue 518 and both the response and the corresponding Interview Dialog delivery information are sent for subsequent processing by the response handler 541.

The response handler 541 may carry out the following operations:

(i) Updates (a) Updating of status: The result section of the Interview Dialog's response should contain delivery-status data (i.e., if delivery was successful or not), delivery time, whether or not there was a hang up, whether the Channel was busy, number of security errors, whether a person answered, and whether a Retrieval Alert is required.

(b) Addition of result information to a Delivery History Record. This information is entered into the delivery attempt record, but is more detailed and may be used to calculate the number of attempts, security errors, hang ups, etc. over a relevant time period.

(c) Updating the delivery attempt record by determining and recording:

1) Whether the strategy is finished, where the latter may be true:

A) if the Interview Dialog is successfully delivered

B) if the number of delivery attempts is greater or equal to the specified maximum attempts to be tried (Unless this is overridden)

C) if the strategy was aborted

2) Whether or not this strategy should be aborted due to a hang up.

(d) Update the Delivery Schedule if a Retrieval Alert is required to be set (i.e., would be required if the time expires.)

Note that the determination of whether or not a Retrieval Alert is to be set is handled by logic in the Topic Dialog, since such determinations depend on the data included in the Interview Dialog. For example, normal test results do not require Retrieval Alerts.

(ii) Update Attributes (a) A comparison should also be made between the "before" and "after" values of Attributes associated with the Interview Dialog and any modified values should be automatically updated in the Database and any new Attributes created during the Interview Dialog should be added to the Database with optional time and date stamping of the changes.

(iii) Process Retrieval Alerts (a) If the Interview Dialog was not delivered successfully, the response handler 541 should check to see if any Retrieval Alerts need to be set.

(b) A check should also be made to see if the Retrieval Deadline Date of this Interview Dialog has been reached. If so, a check should be automatically made with the Delivery Schedule to see whether a Retrieval Alert is to be set for this Interview Dialog.

(c) If a Retrieval Alert is set, the Delivery Schedule should indicate the Person Roles for the sender and Target, and the response handler can then use this information to build a corresponding Retrieval Alert object and to send this information to the Database.

(iv) Process Information Alerts

Information Alert data included in the response message should be automatically sent to the corresponding response handler. This information can include identification of the sender and receiver Role Persons. The response handler using the Database can then build a corresponding Alert object for the data for each Information Alert and can send these to the Database.

(v) If Applicable, Update the Interview Dialog Status

The response handler informs the AppServer to update Interview Dialog Status to Delivered, Not Delivered, or Expired. If appropriate, the Interview Dialog may be rescheduled for subsequent re-execution.

(vi) Reschedule (i) If the Interview Dialog delivery was successful, the next Interview Dialog in the Interview is scheduled, taking into account the minimum required time gap between this last Interview Dialog and the next Interview Dialog.

(ii) If the Interview Dialog delivery failed, the Interview Dialog should be automatically rescheduled.

(iii) The System should compute the next available time for every eligible Delivery Strategy and should use the earliest time for the reschedule time.

(iv) For each Delivery Strategy, the system should obtain the current Channel status and decide if there have been too many attempts on this Channel by comparing the history and calculating the number of hang ups, security errors, attempts, and/or persons answered who were not the Patient. The system should then compare these numbers to the maximum allowed for each of these parameters for a relevant time period. If any of these values have exceeded their maximum during this time period, the Channel should be considered ineligible for further use by the given, Interview-delivery attempt. This ineligibility may extend for only a specified "time out period."

(v) If the Channel is still eligible, calculate the next available time f or the Channel.

(vi) Compare this time to the soonest available time so far. If it is sooner, then it becomes the best choice or "soonest available time for a Channel."

(vii) If there is a "soonest time", reschedule this Interview Dialog using the soonest time as the next available time for the rescheduling.

(viii) If a good next available time is not found, the AppServer should reschedule the Interview Dialog once it gets past the time out period specified when the Channel exceeded the allowable number of hang ups, security errors, attempts, or wrong person answering previously.

(f) Selection of Interview Dialogs for Inbound Requests:

A Patient can request retrieval and execution of his or her Interview Dialogs on an inbound Channel—e.g., by calling into the System to receive messages. This request is routed through a Channel Client such as 420 or 452 and the associated Channel Manager such as 411 or 451 respectively. In an embodiment, Email 413 and an Email Manager 407 is used for this purpose.

The Channel Manager 501 forwards the patient-originated request on to the Channel Connection Handler 513 of the Scheduler 450. The Channel Connection Handler 513 places this request on the Channel Request Queue 517 where it is forwarded to the Channel Request Handler 520 of the DataReaper 515.

The Channel Request Handler processes these Channel requests by determining which Person is requesting Interview Dialogs and on which Channel. The Channel Request Handler then issues a request to the AppServer 425 for all the Pending Interview Dialogs for this Person where these Interview Dialogs have a Delivery Strategy able to be used that supports this inbound Channel. When these Interview Dialogs are returned they are sent to the Interview Chooser 519 with the appropriate Channel selected. The Interview Chooser then sends these Interview Dialogs to the Person as described above for outbound Interview Dialogs, in order of priority.

The Steps for a Patient telephoning into the System to obtain his or her Interviews may be comprised of the following steps:

i. Patient Calls into a Telephone Port which is assigned to a given Application ii. Patient enters ID and pass code iii. Patient has a System parameter set number of tries to validate. If the Patient fails validation in this number of tries, the System informs the Patient that he or she has exceeded the allowed entry attempts and ends the call; if validation is successful, the System proceeds to the next step.

iv. Channel Manager Locates Deliverable Interviews for the Patient for this Application; if there are no Deliverable Interviews, a prompt states: "No interviews available at this time," and the call is ended. If there is at least one Deliverable Interview, then the System proceeds to the next step.

v. Present Each Interview, with highest priority Interview first.

vi. End Call.

In an embodiment, requests are Application specific, and the inbound channel entrance would specify the Application. In an alternate Embodiment, the inbound requests are not Application specific, and all or a prespecified subset of all Interview Dialogs related to the in-calling Patient would be presented.

(IV) Architecture Scalability

In an embodiment each of the components can be replicated to provide for scalable growth of the System. For instance, multiple Schedulers, Channel Managers, Application Servers, Databases and Web Servers can all be replicated as needed for performance, scalability and reliability.

(V) Interview Delivery to Target Persons

The following examples of pseudo-code illustrate delivery of Interviews to Target Persons in an embodiment according to this disclosure. The below examples illustrate the triggering of Information and Retrieval Alerts, use of Patient Attributes to influence information delivery and means of delivery, use of Medical Provider and Place Attributes to influence information delivery and means of delivery, and the influences of different delivery strategies in different media.

(A) Acute Illness Monitor for an Office Visit for Asthmatic Bronchitis

Figure 13:
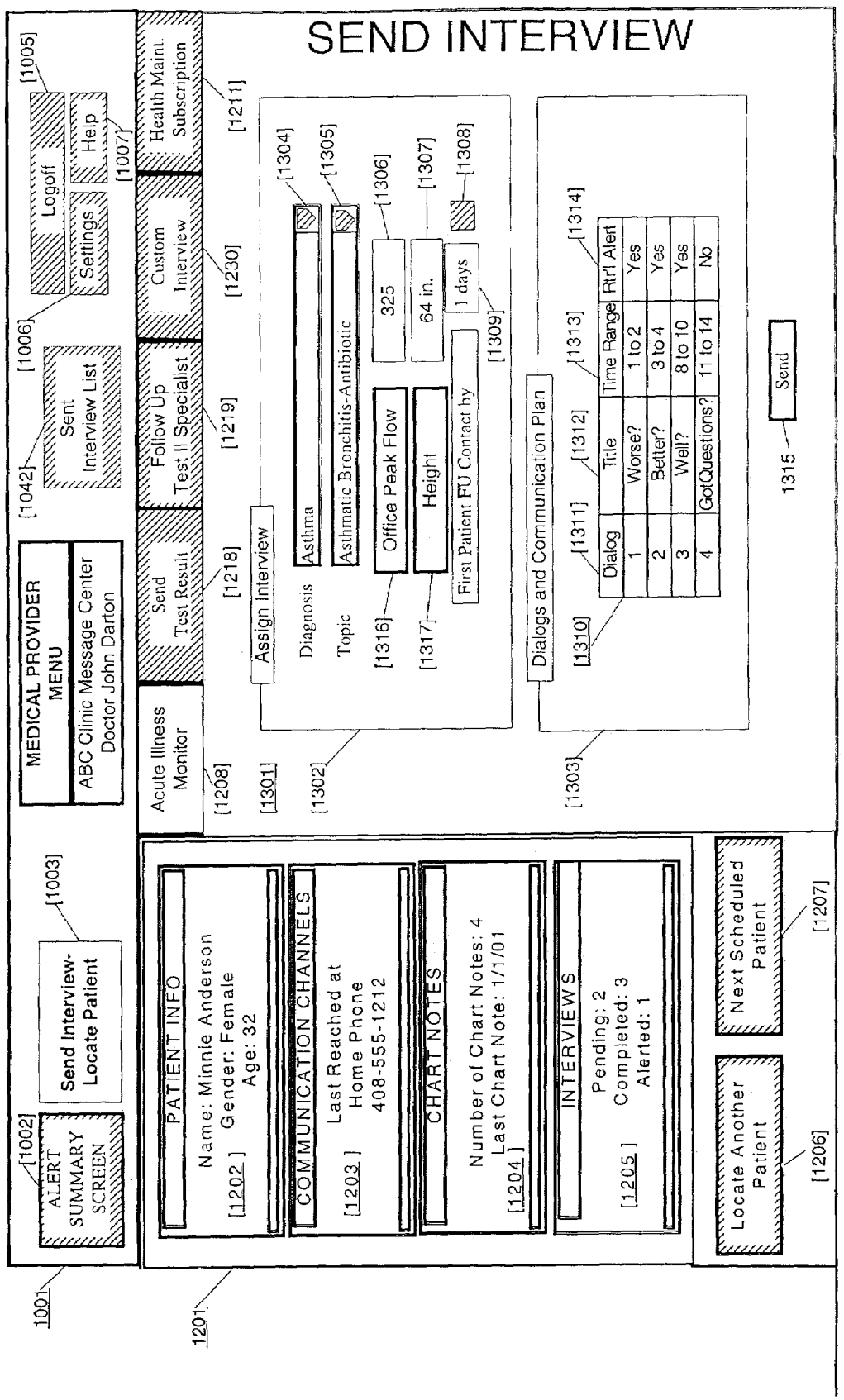
FIG. 13 illustrates another Interview formulation screen which may be used by a Medical Service Provider to formulate an Acute Illness Monitoring Interview that is to delivered to a Patient in accordance with the present disclosure.

In an embodiment, after the Medical Provider sees a Patient with acute asthmatic bronchitis and prescribes a treatment regimen, the Medical Provider informs the Medical Assistant of the diagnosis and treatment regimen and requests an Acute Illness Monitor process be initiated on the System. The Medical Provider also informs the Medical Assistant of the peak flow value measured during the office visit. The Medical Assistant enters the System and brings up the an Interview formulating screen such as shown in FIG. 13. The Medical Assistant chooses "Asthma" for the diagnosis in text box 1304 and selects from the various Topics for Interviews available for this diagnosis in text box 1305 "Asthmatic Bronchitis-Antibiotic." Patient variables needed for formulating this Interview are automatically requested in response to these choices and the Medical Assistant next enters the office peak flow value in text box 1306 and the Patient's height in text box 1307. (If the Patient's height Attribute is already in the System it is inserted automatically into box 1307.) The default value for the time of first Patient contact for this Interview is inserted in text box 1309; and if desired, the Medical Assistant may edit these entries. If information regarding the Patient's height or office peak flow are not available at the time of Interview formulation or if data validity checks of these fields fail, these fields are left blank and the System's code adjusts prompts to carry out an automatically-modified follow up Interview which does not use questions that rely on the missing data.

The illustrated Interview of FIG. 13 comprises four Dialogs. Delivery Strategies will be discussed in detail below, but for clarity pertinent aspects will be mentioned here. By default in this Interview the first Interview Dialog will be sent within 24 hours (1309). This delivery instruction will be matched against the Patient's delivery channels and preferences, if there is no Interview Dialog or Topic or Application delivery instruction for this Interview Dialog to over-ride these. If, e.g., the Dialog Delivery Strategy calls for contact only between 6 to 24 hours after the office visit, and the Patient's preferences indicate a telephone or pager channel with available hours in this time range, the Interview Dialog may be delivered this way. Also the Interview Dialog will be posted on a web site available to the Patient and through an XML interface after 6 hours. Note that retrieval of the Interview Dialog by either of these means will cancel the remaining unretrieved versions of this Interview Dialog designated for delivery by other channels. Thus the Interview formulation is structured to urge the use of multiple channels and to thereby overcome delivery obstacles that may arise on any one given channel.

In an embodiment, if an Interview Dialog that is under formulation (e.g., FIG. 13) has the potential of triggering an Information or Retrieval Alert, transmission of the Interview Dialog by a channel whose message delivery operations may not directly notify the Target of the pending message (e.g., such as an email account which must be accessed by booting up a computer as opposed to a direct telephone call which must be answered by the Target) is automatically accompanied by transmission by another channel whose message delivery operation scan better assure that the Target will actually be notified of the pending message (i.e., such as leaving a flashing message on the Target's cell phone voice mail account or directly ringing the Target at his home telephone).

(i) First Interview Dialog of Interview for Follow Up for an Office Visit for Acute Asthmatic Bronchitis:

Exhibit 1 (appended hereto) comprises a listing of pseudo code that is usable in an embodiment of the current disclosure for delivering Interview Dialogs for an Acute Illness Follow Up Monitor Interview for a Patient with acute asthmatic bronchitis who was placed on antibiotics. Lines 1 through 201 of Exhibit 1 represent the first Topic Dialog of this Interview. (Note: due to printing vagrancies, line numbers given here for code lines in the appended Exhibits are merely approximate rather than precise designations of the specific code portions.)

Lines 1–3 import the class libraries, packages and base classes required for the program. Line 4 declares the class for this Topic Dialog as an extension of the class DialogBase. Lines 6 through 20 define constants used in the Topic Dialog code.

Lines 22 to 28 declare variables:

(a) Variable doctor_uses_pf1 reflects a Person Attribute for the Medical Provider indicating if the Medical Provider uses peak flow rule1, defined below, to monitor Patient's home peak flow measurements in the first Interview Dialog;

(b) Variable doctor_uses_pf2 reflects a Person Attribute for the Medical Provider indicating if the Medical Provider uses peak flow rule2, defined below, to monitor Patient's home peak flow measurements in the first Interview Dialog;

(c) Variable in OfficePF is the value of the Patient's peak flow reading obtained in the office;

(d) Variable retrig is an internal counter used to track the number of requests to ascertain if the Patient has a peak flow value ready to enter the System;

(e) Variable age is the age of the Patient in years;

(f) Variable height is the height of the Patient in inches;

(g) Variable sex is the sex of the Patient.

Lines 38 to 44 assigns values to these variables from the Medical Assistant's input, the program, and/or Attribute values stored in the System. Lines 50 to 80 register the Dialog's Attributes and Prompts, and Roles with the delivery scheduler program. Lines 88 to 104 present a statement greeting the Patient and then a statement saying, "This is a message from" '(Medical Provider's name is communicated here)' and retrieves a response.

The new Phrase ( ) function, line 88, gets the necessary Prompt(s) in the proper format for the Channel. If it is web, this is a text format; if it is a telephony Channel, then the Prompt(s) is a recorded voice file. In an embodiment the recorded voice file is in .vox format which is 8 Khz ulaw. In an alternate embodiment, text prompts can be played over the telephony Channel using text-to-speech. If the response indicates the Patient has not been reached (or, in an embodiment, can not be readily reached by, for example, coming to the phone), the communication ends and the System records that there was no response.

Note that prior to this point other portions of the System have done verification and identification of the Patient.

Line 111 processing depends on the value of the variable "retrig." This is initialized to zero at the start of the Dialog, but is incremented in line 129. The code lines 112 to 123 presents and processes the first query to the Patient: "Are you feeling worse than you were when you were seen in the office?" Line 114 defines a variable "worse" to hold this answer, which is stored in line 115. Lines 116 to 117 cause an Information Alert with Alert Note "worse" to be sent to the Medical Provider's Alert Summary Screen if the Patient answers that his or her condition has worsened.

Lines 118 to 120 cause an Information Alert with Alert Note "No Response" to be sent to the Medical Provider's Alert Summary Screen if there is no response from the Patient to the question. Lines 124 to 154 present and process the Dialog's second question to the Patient. Line 125 defines a variable ready to hold the Patient's response to the question presented by "PROMPT_ID_READY_PF1." This asks the Patient: "Are you ready to report a recent peak flow meter measurement?" If the Patient's response to this second question is not "Yes," line 127 causes lines 128 to 154 to be executed.

Line 129 increments the retrig variable by one. Lines 130 to 152 represent a switch statement dependent on the value of retrig. If retrig is "1", case 1, lines 132 to 138 are executed. Line 135 informs the Patient that the System will call back in 30 minutes. Line 136 instructs the Delivery Scheduler to call again in 30 minutes. Line 137 "break" causes the execution of the code to skip to line 153 "return" and the session ends.

The System then under the influence of line 136 "callAgainMinutes(30)" calls the Patient after 30 minutes. The initial processing, introduction and greetings (lines 1 to 110) are presented again. Since retrig has been incremented to "1," lines 113 to 122 are skipped.

Lines 124 to 127 again present and process a query to the Patient: "Are you ready to report a recent peak flow meter measurement?" If the Patient does not answer "Yes," line 127 results in incrementing the retrig variable by one (line 129) to "2" and the switch statement in line 130 causes lines 139 to 144 to be executed. The Patient's answer to the second query is saved and the Patient is informed the System will recall in 30 minutes. Line 144 breaks out of the switch to 153 and the system ends the contact.

The System then recalls the Patient after 30 minutes. The initial processing, introduction and greetings (lines 1 to 110) are presented again. Since retrig has been incremented to "2," lines 113 to 122 are skipped.

Lines 124 to 127 again present and process a query to the Patient: "Are you ready to report a recent peak flow meter measurement?" If the Patient does not answer "Yes," line 127 results in incrementing the retrig variable by one (line 129) to "3" and the switch statement in line 130 causes lines 146 to 151 to be executed. Line 148 causes an Information Alert with Alert Note "No PF1" to appear on the Medical Provider's Alert Summary Screen. Then line 150 breaks out of the switch statements to 153 and the system ends the contact.

In an embodiment, the System may continue with an Interview Dialog even if the Patient inputs no peak flow value. If the Patient answers positively to the second Interview Dialog question presented and processed in lines 125 to lines 126, the criterion of line 127 is not fulfilled and the code execution proceeds to the third question in lines 155 to line 157. Line 156 defines a variable pf to store the value of the peak flow entered by the Patient in line 157.

If the current peak flow is less than the office observed peak flow and the relevant Medical Provider Attribute indicates this rule is to be used here, line 160 causes an Information Alert to appear on the Medical Provider's Alert Summary Screen with Alert Note "Peak Flow below in-Office Peak Flow Value."

Line 158 uses peak flow rule1 in lines 176 to 181 to test if the peak flow value entered by the Patient is less than the peak flow measured during the office visit. If this is the case, line 160 causes an Information Alert with Alert Note "Peak Flow below in-Office Peak Flow" to be sent to the Medical Provider's Alert Summary Screen. If this is not the case, then next, in line 162, the Patient entered peak flow, pf, is tested against peak flow rule 2 in lines 184 to 200, if the relevant Medical Provider Attribute indicates this rule is to be used here.

Peak flow rule 2 compares the Patient entered peak flow with the normal value predicted using a formula depending on the Patient's sex, age, and height as indicated in lines 187 to 195. If this comparison shows the current Patient peak flow, pf, is less than 50% of the calculated normal value, line 164 causes an Information Alert with Alert Note "Peak Flow less than 50% predicted Peak Flow" to be sent to the Medical Provider's Alert Summary Screen.

In an embodiment, tables of normal values of peak flow as a function of sex, height, and age are provided and used for reference values. If neither peak flow rule triggers an alert, then lines 169 to 170 are executed which impart a message such as: "We are pleased that you are doing satisfactorily after your office visit and will contact you for another follow up in two days." and end the contact session.

If either lines 160 or 164 are executed and an Information Alert regarding a seriously low peak flow value engendered, lines 169 to 170 are skipped and lines 173 and 174 are executed. These produce a message to the Patient advising a prompt re-evaluation of his or her medical condition, such as, "Your peak flow indicates a low value. Your status should be rechecked promptly. Please come to the office now or go to a currently open urgent care center now." An Information Alert is sent to the Medical Provider's Alert Summary Screen with an Alert Note reflecting this, and record make of the Patient's acknowledgement of this message. The Interview Dialog then ends.

(ii) Second and Subsequent Dialogs:

If the first Interview Dialog does not result in an Alert, a second Interview Dialog is sent to the Patient in accordance to the Delivery Schedule Rules for this Interview; typically this would be about 48 hours after the first Interview Dialog. In an embodiment, these rules are made adaptively responsive to information received during the first Interview Dialog including the success or not of various contact means in making contact with the Target.

The second Interview Dialog is roughly analogous to the first. The first question, however, asks if the Patient is doing better and automatically sends an Information Alert to the responsible MSP if the Patient indicates "No." A current peak flow reading is requested in a way analogous to Interview Dialog 1 above and assessed as above.

Upon completion of the second Interview Dialog Delivery Schedule Rules determine the contact time and means for sending the third Interview Dialog. Typically, this would be sent about seven days later. This Interview Dialog is also roughly analogous to the first Interview Dialog. The first question, however, asks if the Patient now feels normal. Assessment of current peak flow is again performed. In an embodiment, the current peak flow could be automatically compared with the Patient's "normal" and actions taken on the basis of this comparison. The Interview Dialog typically ends with a statement regarding proper monitoring and care of asthma.

In an embodiment, a fourth Interview Dialog is automatically scheduled for and sent one to two weeks later to recheck the Patient's status and ask if the Patient has questions or desires to speak with the Medical Service Provider.

(B) First Dialog of Interview for Test Result Delivery of a Comprehensive Chemical Screening Battery Test Panel Exhibit 2 (appended hereto) comprises a listing of pseudo code in an embodiment of the current disclosure for carrying out an Interview Dialog that delivers results of a comprehensive screening chemistry test panel to a Patient. Lines 1 through 733 represent the single Interview Dialog of this Interview. (Note: due to printing vagrancies, line numbers given here for code lines in the appended Exhibits are merely approximate rather than precise designations of the specific code portions.)

Lines 2 and 3 import the class libraries, packages and base classes required for the program. Constants in the program needed for the delivery message are next defined and assigned indexes. These may include:
  i. Definitions of constants used in comparing test result values to normal values in lines 7–10,
  ii. Constants for Patient Attributes such as age and sex (lines 13–14) that interact with the program to determine, among other things, normal test value ranges, advisory messages to users regarding medical situations, or, in an embodiment, differential diagnoses to be consider in relation to certain test results, and
  iii. The component constants and indexes (lines 17 to 43) used with tables formed by the program to hold and report test results to a user.

The System first forms a table to record all component test results and associated test Attributes; the fields of this table are named in the test field constant names in lines 17 to 25. This table is used to formulate two types of test information delivery to the Patient:
  i) A "verbose" form, which, e.g., would be suitable for a visual (e.g., web page) presentation, and
  ii) A "terse" form, which, e.g., would be suitable for a voice (e.g., telephony) presentation.

The various Delivery Channels used in the Delivery Strategies associated with this Topic contain logic that selects, for example, one of these forms of presentation.

In other embodiments, other formulations of this table and the test data are made into other delivery formats. The verbose form presents a table to the Patient that is formed utilizing constants named and indexed in lines 27 to 35 and the constants in lines 42 and 43. The terse form utilizes constants named and indexed in lines 37 to 43. The headers for the columns of the internal System table used to hold the test results are named in lines 50 to 58. These hold the titles of descriptive information for each test and are:
  i. the test name,
  ii. the specific test result for the Patient,
  iii. the low normal or minimum normal value for the test,
  iv. the high normal or maximum normal value for the test,
  v. the units for the reported test value,
  vi. a "reference normal," which is a comment or a reference link to a comment for normal result information for the test in question,
  vii. a "reference low," which is a comment or a reference link to a comment for information relating to a low result for the test,
  viii. a "reference high," which is a comment or a reference link to a comment for information relating to a high result for the test, and
  ix. a "reference indeterminate," which is a comment or a reference link to a comment for information relating to an indeterminate result for the test in question, such as "This test could not be competed due to technical difficulties."

Each row of this table represents a different test. Indexes are assigned to the names of the tests in lines 64 to 79; Attribute names for each test corresponding to each of the table's column headers are subsequently defined as illustrated in lines 84 to 267.

Lines 272 through 278 hold a standard explanation regarding the tests that make up the chemical test panel; this helps test interpretation in reporting the results to the Patient. The next lines hold two tables of explanation statements relating to abnormally high individual test results (lines 288 to 346) and abnormally low individual test results (lines 353 to 409).

For each test ("test name") the Patient's test results are held in testRows[TEST_INDEX_(test name)][TEST_FIELD_RESULT]. The System's internal table listing the Patient's test results has column header names as noted in lines 17 to 25 and are loaded into the table in lines 450 to 453. Each row of the table represents a different test in the chemistry screening panel. Each row has an entry for the Attribute Field Names in the column headers. Thus the values of a row would correspond, in order, to the test name of that row, the Patient's test result, the low value for the normal range of the test, the high value for the normal range of the test, the units used for the test and a reference. These values for each test are loaded into the table by lines 456 to 469.

Patient Attribute values such as age and sex are loaded in lines 471 and 472 and allow for the System to compute normal ranges appropriate for the Patient in question when these ranges are functions of such Attributes.

To insure that the elements that are needed for Interview Dialog delivery are present prior to initiating the delivery, these elements are registered with the Dialog Manager. This includes: the table headers (lines 486 to 488); information needed to compute normal ranges for tests such as the Patient's age and sex (lines 492 to 493); and the required Roles (lines 501 and 502).

Lines 514 to 515 present a statement to the Patient such as: "These are the results of your recent Chemical Screening Panel tests." If there is no acknowledgement of receipt by the Patient of the message, line 518 records this. This information may be used to send a Retrieval Alert to the Medical Provider. In this case line 519 ends the delivery attempt.

Lines 527 to 545 use the compare method to classify if each individual test result is lower or higher than normal, and associate the corresponding abnormal low or high test explanation to the result. If there are abnormal results, lines 548 and 549 sets the variable "have Abnormal Tests" to "true." Line 551 forms an instance of the code of class Dialog Table to hold the table of test results.

Line 552 determines if the Delivery Strategy calls for a verbose data presentation, in which case the following lines are executed: Lines 554 to 561 add the header names to the columns of this table, which include the name of the test, the Patient's test result, the low normal for the test, the high normal for the test, how the Patient's test result compared to the normal range, the units of the test, and a corresponding reference phase suitable for the high, low, or normal test result. For each test result Lines 565 to 587 adds the corresponding data in rows to this table and thus completes the data presentation. The reference phrase for this table is obtained with the aid of lines 630 to 647.

If the Delivery Strategy calls for a terse data presentation, this is performed using lines 591 to 627. If all the test results are normal, the Patient is so informed by lines 595 to 596, and the session is ended. If there are abnormal results, lines 593 to 594 present the message: "All your tests were normal with the exception of the following tests:" Lines 598 to 626 then present only the abnormal test results in terse form. If, in the group of test results presented, a given test is not normal, line 605 causes the name of the test, its result, and units to be presented and lines 622 to 626 append an appropriate brief explanation for either high or low results for the abnormal test result.

Lines 658 to 731 illustrate a method to test if a test result is within normal range for the test when the limits of the normal range depend on the Patient Attributes of age and sex. Arrays in lines 685 through 689 and lines 695 through 699 include arrays that on a given row give, in succession, the lower age limit, the upper age limit, the lower limit of normal for this age range, and the upper limit of normal for this age range for alkaline phosphatase, the test under consideration. Lines 685 to 689 apply to males and lines 695 to 699 apply to females. Lines 706 through 713 select the proper table and comparison values. Lines 717 and 718 find the appropriate age range and lines 720 to 726 classify the test result value as to whether it is lower than normal, higher than normal, or normal. If the result is not classifiable this way, line 730 returns an indeterminate classification.

(C) First Dialog of Interview for Test Result Delivery for a *Streptococcus* Culture Exhibit 3 (appended hereto) comprises a listing of pseudo code in an embodiment of the current disclosure that may be used for a Topic Dialog that delivers results of a *streptococcus* test to a Patient. Lines 1 through 96 represent the single Topic Dialog of this Interview. (Note: due to printing vagrancies, line numbers given here for code lines in the appended Exhibits are merely approximate rather than precise designations of the specific code portions.) Lines 1 to 5 import the appropriate packages, classes and libraries for the program. Constants needed for the message delivery are next defined in lines 10 to 27; these include explanation strings in lines 14 to 24 for the various possible test results. Variables for the Topic Dialog are defined in lines 26 and 27 and are assigned values in lines 38 to 40. Attributes and Roles are registered for the Dialog Manager in lines 43 to 59.

Line 71 presents an introductory announcement to the Patient, which is followed by information of the results of the test given by lines 73 to 84. One of the three possible results, "POSITIVE," "NEGATIVE," or "INDETERMINATE," is assigned together with a corresponding explanation statement. Lines 86 to 90 are activated if the Interview Dialog delivery is not acknowledged or successful and cause the Dialog delivery to cease. In an embodiment, a Retrieval Alert may be automatically sent to the Medical Provider in this event. This last action may be made adaptively dependent on the result of the test. Lines 92 to 94 allow further information to be delivered such as a link to a web page or document that discusses material relevant to *Streptococcus* infections.

(VI) Role Relationships in Applications and Interviews

Figure 6:
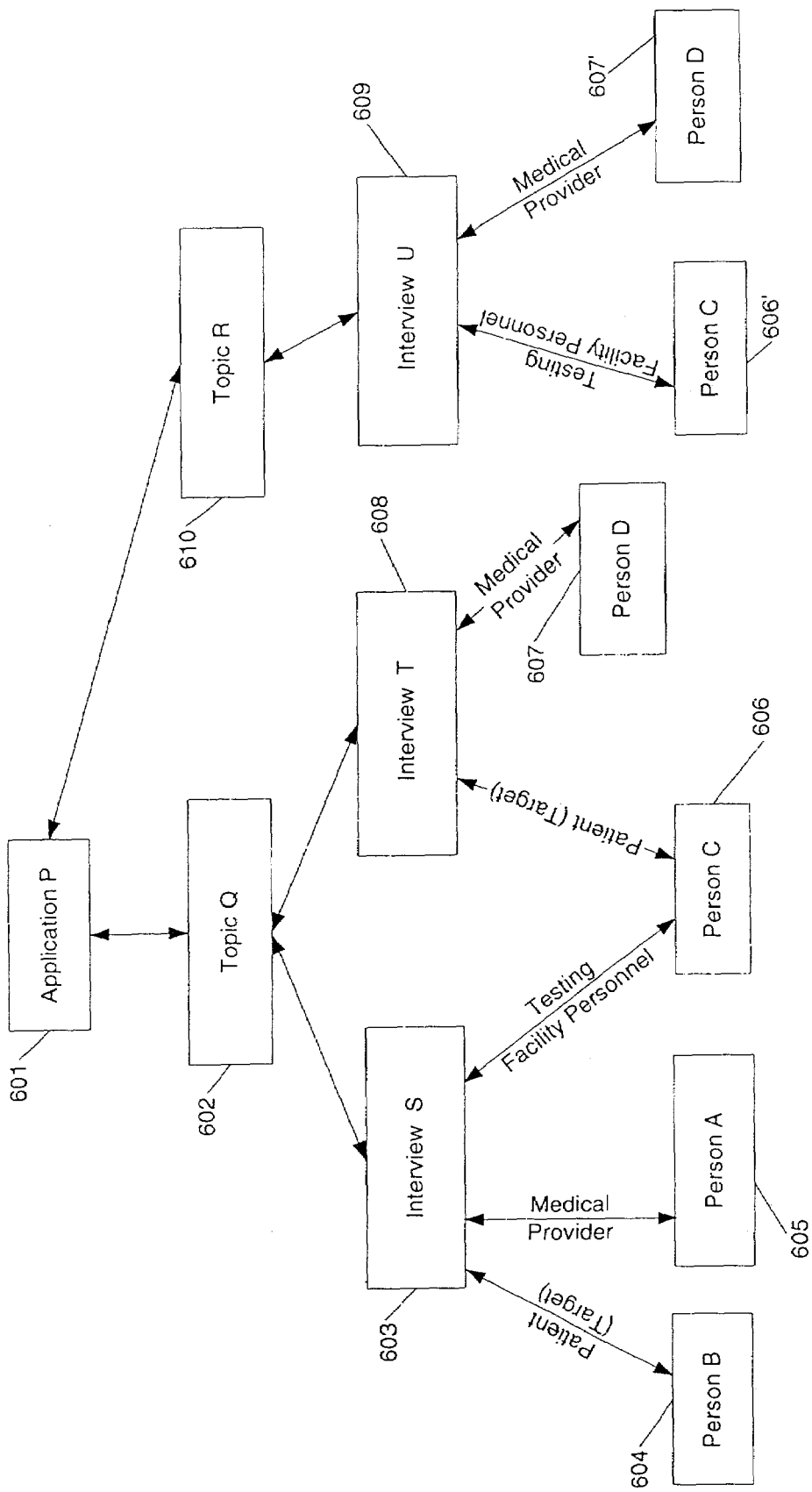
FIG. 6 illustrates different relationships that may exist between Person objects and Interview objects executing in an Application Program that is structured in accordance with the present disclosure.

FIG. 6 illustrates some of the different logical relationships that may be developed within the System between respective Entities, including Persons having respective Roles and Interviews that may be formulated under a given Application and according to the present disclosure. An Application named P (601) is shown to have at least a first Topic Q (602) and a second Topic R (610). The first Topic Q is shown to have developed under it at least a first Interview S (603) and a second Interview T (608). Similarly; the second Topic R has a third Interview U (609). Person B (604) is logically related within the System to Interview S as a Patient. Person A (605) is related to Interview S as a Medical Service Provider. Person C (606') is shown related to Interview S as a Testing Facility Person. The same Person C (606) is shown to be also related to Interview T as a Patient. Person D (607) is related to Interview T as a Medical Service Provider. Person C (606) is shown to be logically related within the System is related to Interview U as a Testing Facility Person. The same Person D (607') is related to Interview U as a Medical Provider. This illustrates that a person such as Person C may interact with more than one Interview in a Topic such as Interview S and Interview T and may interact with more than one Topic in an Application such as Topic Q and Topic R. It also illustrates that a person may have different roles in different Interviews of the same Topic.

Figure 7:
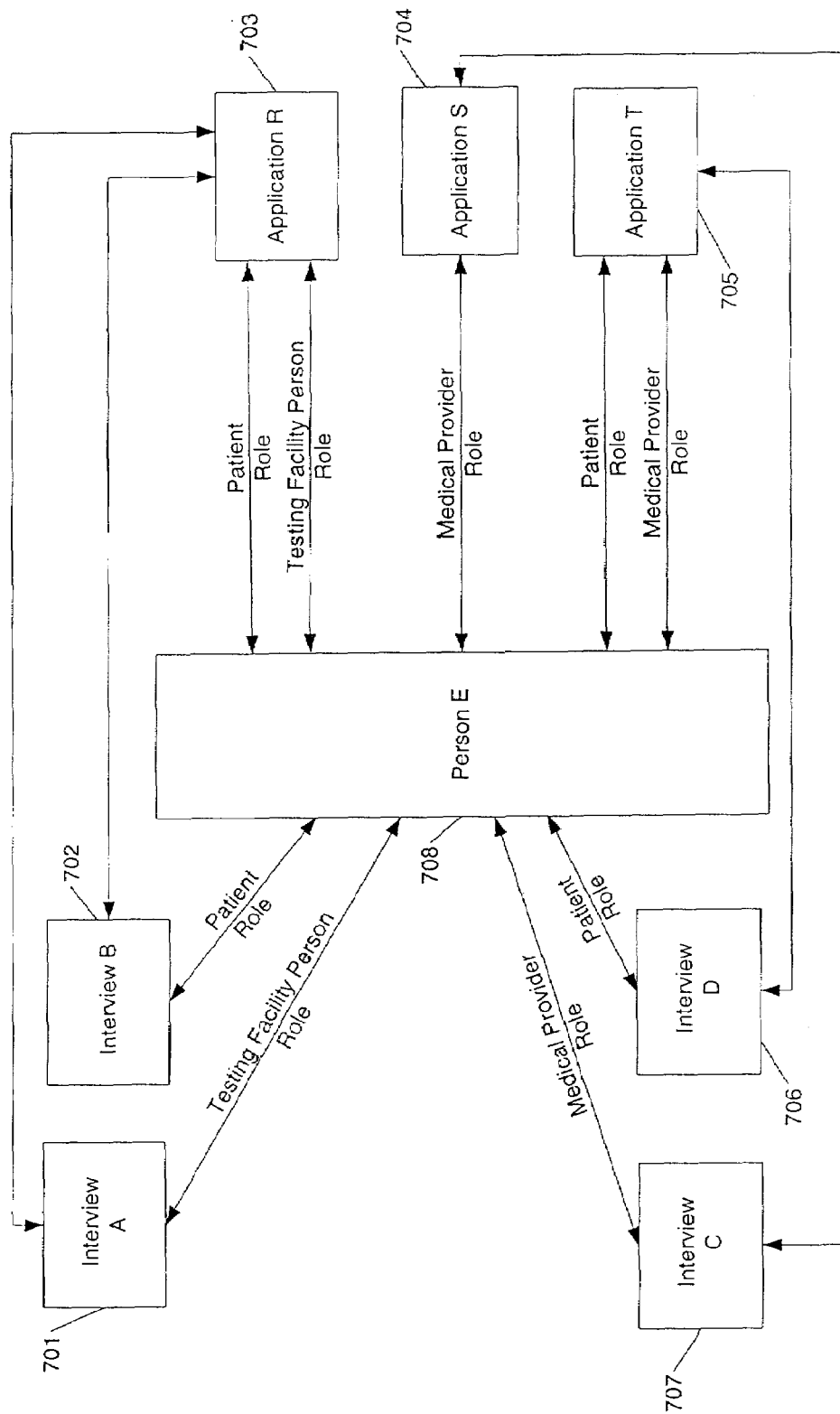
FIG. 7 illustrates different relationships that may exist between a Person object and several Interview objects and several Applications that are structured in accordance with the present disclosure.

FIG. 7 further illustrates how different relationships between Roles, Persons, Applications, and Interviews may develop in an embodiment of the present disclosure. In the illustrated example, Person E (708) interacts with an Interview A (701) as a Testing Facility Person and with an Interview B (702) as a Patient of Application R (703). The same Person E (708) interacts with Application S (704) as a Medical Provider. Person E (708) interacts with Interview C (707) in a Medical Provider Role and with Interview D (706) in a Patient Role. Interview D (706) and Interview C (707) are respective Interviews of Application T (705) and Application S (704) respectively. This illustrates that the same Person E (708) can have different Roles in different Interviews such as Interview A (701) and Interview B (702) within the context of a same Application R (703) and that these Roles do not have to be the same as the Roles of this same Person in other Applications such as Application S (704) and Application T (705) where again the same Person may have different Roles in different Interviews.

(VII) Login Screens

Figure 8A:
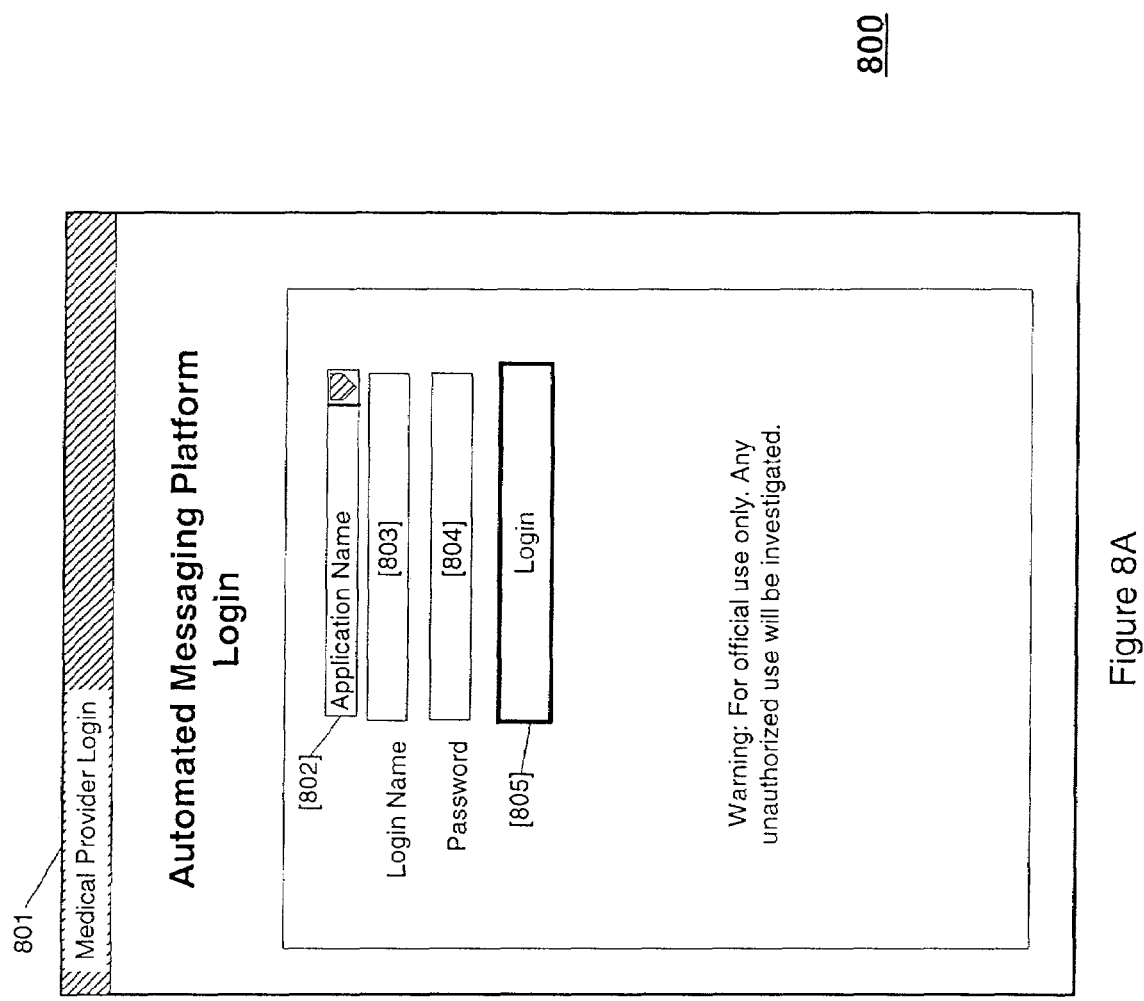
FIG. 8A illustrates a login screen that may be used by a Medical Service Provider in accordance with the present disclosure.

FIG. 8A illustrates a Medical Service Provider Login-Screen 800 that may be displayed in accordance with the present disclosure. The illustrated title bar, 801, indicates the general function of the displayed screen window. A drop-down text box 802 allows the Person who is trying to log-in to choose an appropriate Application name (e.g., Good Samaritan Hospital) from those allowable on the specific System. To log-in the Person may next enter an appropriate User log-in name in text-entry box 803 and a corresponding password in text-entry-accepting box 804. To continue logging-in, the Person may next activate the login button 805 with a mouse click or other appropriate means. If the Person who is trying to log-in has the Role of a Patient rather than an MSP for the respective Application, the System may display a fairly-similar screen to that (800) illustrated in FIG. 8A except that the title bar 801 would instead state "Patient Login" or an equivalent function identifier. If the logging-in Patient or Medical Service Provider is recognized per their log-in name (803) as having a corresponding such Role only on one Application in the System, then the name of that one Application will automatically appear as an unvariable default choice in text box 802.

Figure 8B:
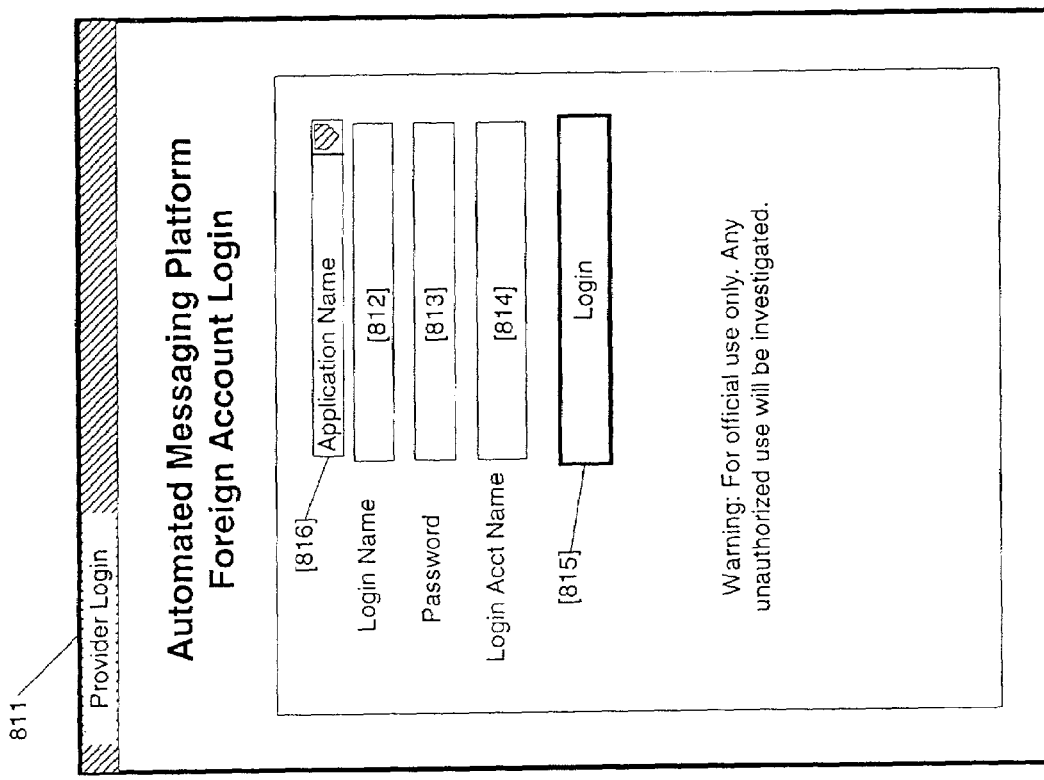
FIG. 8B illustrates another login screen that may be used by a Medical Service Provider to log-in into a foreign account in accordance with the present disclosure.

FIG. 8B illustrates a Medical Provider Login Screen 810 for use by a Medical Service Provider when logging into a foreign account—i.e., an account for which another Medical Service Provider is responsible. This foreign account screen 810 may be accessed from a log-in selection menu (not shown) in the System. The guest Medical Provider enters his or her login name in text box 812 and password in text box 813. The identification of the account that the guest Medical Provider desires to login to is entered in text box 814. The Application that the guest Medical Provider desires to use may be selected in drop down text box 816. The Medical Provider may then complete the log in procedure by activating the login button 815. In an embodiment, the Login Account Name may be for identifying a specific Application and/or may be a Medical Provider's code name that allows access to all Applications of the Medical Provider for whom the guest Medical Provider is to cover.

Figure 9A:
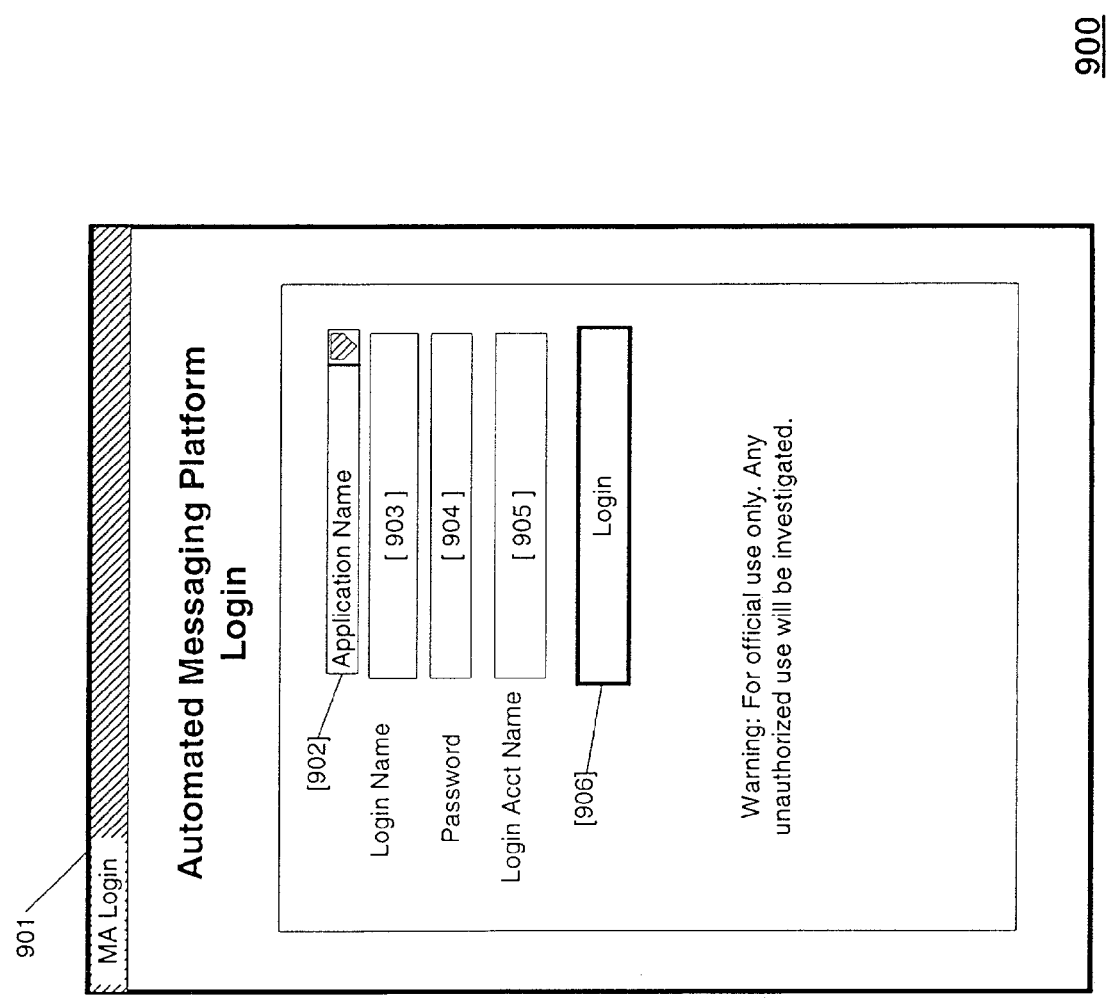
FIG. 9A illustrates yet another login screen that may be used by a Medical Assistant to log-in into one or more authorized accounts in accordance with the present disclosure.

FIG. 9A illustrates a Medical Assistant Login Screen 900 that may be displayed in accordance with the present disclosure. This screen or window 900 may be accessed from a menu in the System. Title bar 901 indicates the title of the screen. The Medical Assistant may input the name of the desired Application in text box 902 or may select it from a drop down list. The Medical Assistant may further input his or her login name in text box 903, the password in text box 904 and the appropriate login account name in text box 905. The Medical Assistant then selects the login button 906 to enter this information into the System and, if the input has been done correctly, the Medical Assistant will be deemed by the System to be logged onto the specified Application (902) and Account (905).

Figure 9B:
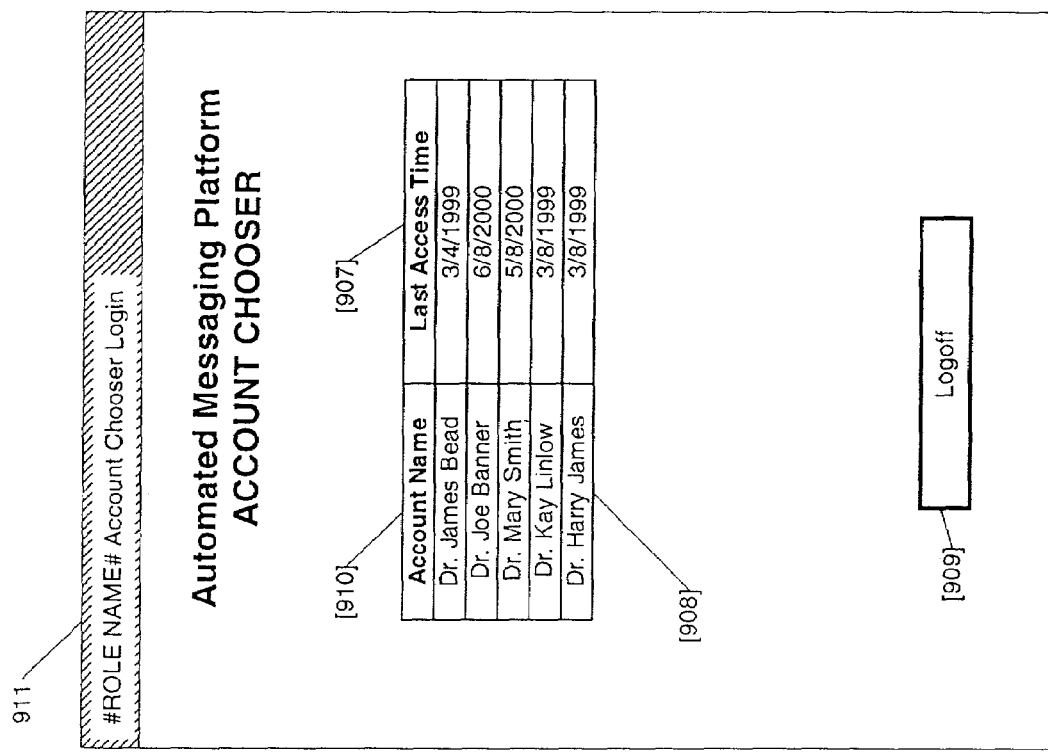
FIG. 9B illustrates an account selection screen that may be used by a Medical Assistant to choose which accounts he or she will use during a login session.

In an embodiment, the System allows the Medical Assistant to log into any of several accounts that he or she has permission to use in a single login interaction. In this situation the Medical Assistant may leave text box 905 (Login Account Name) blank when activating the login button 906. This causes the screen (or window) 912 illustrated in FIG. 9B to appear. Table 908 holds the Account Names 910 for which the Medical Assistant has been granted access permission. Column 907 holds the corresponding date of the last Medical Assistant access to the corresponding Account on the same row. By clicking on (or otherwise activating) the Account Name which is desired for access, the Medical Assistant is entered into that Account. This allows the Medical Assistant to access any of the Accounts for which he or she has permission to access with a single log in procedure. Button 909, when activated, logs the Medical Assistant off the System.

(VIII) Medical Provider, Medical Assistant, Administrator and Patient Screens (A) Screens For Sending Interviews:

FIGS. 10A, 11, 12, 13, 14, 15, and 16 illustrate various screens that may be used by Medical Service Providers and/or Medical Assistants in an embodiment of this disclosure to formulate Interviews that are to be respectively transmitted (delivery-attempted) to Patients. FIG. 10A illustrates a Medical Provider's Alert Summary Screen 1000 in one embodiment. This screen 1000 can summarize all or a highest priority subset of the currently active and critical (i.e., alerted) situations in his or her practice as they are currently known to the System and/or it can summarize action item requests regarding other items for which the MSP and/or his/her delegees are responsible or may wish to be kept advised of. The active and critical situations (or action items requested) may relate to corresponding test results, health maintenance issues, specialty and ancillary facility referrals for tests or consultations, Custom Messages to Patients, follow up for acute and chronic medical conditions, Patients who were not able to be contacted after missing a scheduled appointment, and so forth.

In the upper main part of the illustrated screen 1000 is a first box 1012 that lists alerted Interviews that have been deemed by the System as those most urgently calling for the Medical Service Provider's attention. In the lower box 1049 there is a display of alerted Interviews that have been delegated by the Medical Provider to a Medical Assistant to act on. Typically, alerted Interviews are placed in box 1049 only after having been "reviewed by" and then delegated under System-enforced policies by the responsible Medical Provider to the Medical Assistant. In one embodiment, the MSP is empowered to see or otherwise access and modify the information of both of the primary-responsibility alerts box 1012 and the delegated-responsibility alerts box 1049 and to zoom into the details of any item provided therein. On the other hand, the MA can only zoom into and/or modify (as authorized) the details of items provided in her/his delegated-responsibility alerts box 1049, although the MA can still see the summarized alert reports of the MSP's primary-responsibility alerts box 1012. In an alternate embodiment, the MA is not allowed to even see or otherwise access the information of the MSP's primary-responsibility alerts box 1012; and if there are plural MA's under a given Application, the MA might be restricted to only seeing or otherwise accessing delegated alerts that were specifically delegated to her/him.

In an embodiment, selected cases or classes of alerted Interviews can be directly placed in the delegated-responsibility alerts box 1049 according to pre-established criteria. In an embodiment, a Medical Assistant may access the Interviews listed in box 1012 in the same way as a Medical Provider can, but cannot remove the alerted Interview from box 1012. In an embodiment, a Medical Assistant may access the Interviews listed in box 1012 in the same way as a Medical Provider can and the MA can remove the alerted Interview from box 1012 and shift it into box 1049, but cannot alter any Alert property of the Interview. In an alternate embodiment, a Medical Assistant may be empowered to alter any or prespecified Alert properties of one or more types of Interviews.

The header bar 1001 in FIG. 10A holds a button 1002 that is highlighted (or otherwise distinguished over other header bar buttons) to indicate the screen being viewed is the Alert Summary Screen. Button 1003, "Send Interview-Locate Patient" may be activated by the user to go to another screen (FIG. 11) which may be used to identify (locate) a Patient to whom the subject Interview is to be delivered. Title section 1004 indicates this is the "Medical Provider Menu" and gives the name of the medical facility and the Medical Provider that corresponds to the password used to enter the System. Button 1005 allows for logging off the System and Button 1007 is for accessing System help files. Activating button 1006 takes the Medical Provider to a "Settings Screen" (e.g., FIG. 26) where System parameters may be adjusted. Button 1042 allows the Medical Provider to view a screen (e.g., FIG. 25) showing previous Interviews sent. In an embodiment, the Medical Provider can access Interviews sent by all Medical Providers to a given Patient in the System.

The urgent-action-called-for box, 1012 has a title bar that indicates to the Medical Provider that his or her immediate action is being called for, for the Interviews listed in each row. The table 1040 may have the following columns:

(I) "Action" column 1008, that lists the requested activity for the Medical Provider to do relative to the alerted Interview. This is uploaded to table 1040 from the source of the Alert with the Alert Note and information of the Interview. Column 1008 may list a "SEND" activity as in the exemplary case of Interview 1017 indicating that the Medical Provider is being alerted to immediately send an Interview regarding the alerted subject matter of the corresponding Interview (e.g., a positive strep culture or a high Potassium level). Column 1008 may also list a "REVIEW" activity being called for as in the exemplary case of Interview 1018. This indicates that the Medical Service Provider is being called upon by the System to review (as soon as practical) an alerted Interview that has been sent and to decide on its disposition. By clicking on or otherwise activating a row within Table 1040, the provider can bring up a display showing details of the Interview in the row of interest—e.g., by clicking on row 1017, the MSP can bring up a screen such as shown in FIG. 12 that provides further information about the exemplary strep throat results of interest.

(II) "Topic Category" column 1009 is a column that lists the category or type of the alerted Interview. The category or type designations may be selected from the following, nonlimiting set::
 (a) TEST RESULT, such as in Interviews 1017 and 1019, which could be an alerted test result Interview being sent to the Medical Provider from a Testing Facility or, as in Interview 1019, an alerted Interview regarding a test result that was sent to a Patient and was not timely retrieved;
 (b) HEALTH MAINTENANCE, as in Interview 1018, which, e.g., could be either a Retrieval Alert if a Patient did not timely retrieve a periodic health maintenance Interview or an Information Alert if information requested from the Patient during a follow up session was outside specified limits;
 (c) DOC OR SPECIALIST REFERRAL, as in Interview 1020, which is a follow up Interview related to a referral to a specialist or ancillary service. This could represent an Information Alert, if the Patient indicated a problem in the follow up Interview, or a Retrieval Alert.
 (d) TEST REQUIRED, as in Interview 1021, which is a follow up Interview related to a requested test. This could represent a Retrieval Alert if the Patient did not retrieve the Interview or an Information Alert if the Patient did not have the desired test performed within a specified period;
 (e) CUSTOM MESSAGE, as in Interview 1023, which is a customized follow up Interview that could result in a Retrieval Alert if the Patient did not retrieve it or, in an embodiment, an Information Alert depending on the Patient's response;
 (f) ACUTE ILLNESS MONITOR, as in Interview 1024, which is a follow up Interview to monitor a Patient's progress for an acute illness. This could be a Retrieval Alert if not picked up by a Patient or an Information Alert which was automatically produced due to the Patient's response; and
 (g) NO SHOW, as in Interview 1032, which is a Retrieval Alert for an Interview sent to a Patient who failed to appear at a scheduled appointment.

(III) "Topic" column 1010 is a column which gives specific information regarding the subject matter of the Interview, such as "Asthma" for the Acute Illness Monitor in Interview 1024.

(IV) "Patient" column 1011 is a column which gives the name or other identification of the Patient who is related as such to the Interview.

(V) "Alert Notes" column 1014 is a column which gives information regarding the situation that resulted in the Alert being raised and may be a phrase that is pre-stored in the System and is attached to the event that engenders the Alert; and, (VI) "Alert Type" column 1016 is a column which indicates if a Retrieval Alert or an Information Alert is associated with the Interview.

Respective information regarding individual alerted Interviews is given in respective rows of table 1040: Thus the information of row 1017 may be read as representing a "TEST RESULT" Interview from a testing facility to a Medical Provider regarding a positive strep test result. It is an Information Alert and indicates that the Medical Provider should immediately send an Interview regarding this worrisome result to the Patient. In an embodiment, the Testing Facility automatically obtains a Retrieval Alert if the Medical Service Provider does not access this alerted information within a specified time. Row 1018 represents an Information Alert for "HEALTH MAINTENANCE" for Asthma indicating a Patient has an alarmingly low peak flow reading. The Medical Provider is requested to review this.

Row 1020 represents an Information Alert the Medical Provider is asked to review regarding a specialist referral for a breast lump and indicates that the Patient did not keep the appointment within the requested time frame. Row 1019 represents a Retrieval Alert for the Medical Provider's review regarding lipid tests in which the total cholesterol was 250. Row 1021 represents an Interview with a Retrieval Alert for a "REQUIRED TEST," a mammogram. The Interview was not retrieved timely within the System's delivery parameters. Column 1008 is empty for the case of row 1021, this indicating that the Medical Provider has previously reviewed this Alert and decided to keep it as being an active item in his active Alert box 1012 rather than moving it elsewhere or disposing of it. Likewise, the Interview of row 1023 is a Custom Message regarding "<Message Title>", an input placed in the System when the Medical Provider composed the Custom Message, that has generated a Retrieval Alert; and the Interview of row 1024 is an "ACUTE ILLNESS MONITOR" for Asthma with an Information Alert engendered when the Patient indicated he was worsening. By appropriately selecting on the given row of table 1040, the Medical Provider's displayed screen may be automatically switched to another one that gives further detail about that Alert as will be illustrated subsequently.

In an embodiment, the Interviews displayed in box 1012 are automatically ordered according to prioritizing rules. For example, Interviews not yet accessed by a Medical Provider are listed first in a shaded area; Interviews requiring the action "SEND" precede those requiring "REVIEW;" certain categories of Alerts can have display-order precedence over others.

Table 1041 of box 1049 holds alerted Interviews that have been delegated by the Medical Provider to a Medical Assistant to follow up on. The title bar 1025 contains column headings that are typically identical to those above in table 1040. The Action column in 1025, however, now indicates actions requested of the Assistant by the Medical Service Provider when the Interview was delegated to the Assistant. This is discussed in more detail below.

In an embodiment the Medical Provider can choose to automatically have all Alerts of a specific Topic or Topic Category be placed directly in delegation box 1049; thus, e.g., all Alerted Health Maintenance Interviews could be placed directly in box 1049. In an embodiment, such Interviews could be color coded or otherwise tagged to indicate that they were automatically placed in box 1049 without prior Medical Provider review.

In an embodiment, the Medical Assistant may access alerted Interviews in box 1012 to view these Interviews in more detail, but may not transfer them to box 1049. In another embodiment, the Medical Assistant may have the same capabilities as a Medical Provider regarding one or more selected Topics or Topic Categories in box 1049. These abilities may be controlled by relationships established in the System relating to the login identifier used to enter the System.

For purpose of example, box 1041 is shown to hold the following delegated alerted Interviews: Interview 1026 which has an Information Alert indicating the Patient who is being followed after an office visit for asthma is doing worse. The Medical Provider has requested the Medical Assistant to have the Patient set up another office visit. Interview 1030 involves a Custom Message Interview Retrieval Alert and the Medical Provider has requested the Assistant to send a letter to the Patient regarding this. Interview 1027 is for a Patient with gastrointestinal bleeding that was referred to a specialist; this Patient did not retrieve this Interview Dialog and the Medical Provider desires that the patient be called again.

Further in box 1041, Interview 1031 has an Information Alert regarding a low peak flow value noted in a Health Maintenance follow up Interview; the Medical Provider desires that an office visit be scheduled for the Patient. Interview 1028 has a Retrieval Alert and is a follow up for a requested mammogram. It is requested that a letter be sent to the Patient regarding this. Interview 1032 is for a Retrieval Alert for a Patient that did not keep an appointment regarding his hypertension; the Medical Provider desires a letter be sent and an office visit scheduled.

While FIG. 10A shows alert summarization and reporting occurring by way of a System screen 1000, it is within the contemplation of the present disclosure to report summarizations and/or details of a Medical Service Provider's Alerts by voice-only and/or hybrid communication means. In one embodiment, the physician dials into the System with a conventional telephone, cell phone, 3G-phone or like means. The System authenticates the physician's right to access his account using touch-tone password entry and/or voice-recognition and/or other security measures as may be appropriate. The System then establishes a voice-based Interview with the in-calling physician (or another qualified Person whom the physician has entrusted, e.g., his/her MA) and walks the caller through a voice based Dialog such as the following: System: "Welcome to the Alerts Summarizing Report for Dr. Jones. Press or speak "1" to hear a summary of the 3 alerts currently pending for Dr. Jones. Press or speak "2" to hear a summary of the 5 alerts currently pending and delegated out by Dr. Jones. Press or speak "4" to access a different Menu. Press or speak "9" to hang up. Press or speak "0" to speak with the System operator." In this example, simply by logging in by phone, the physician can learn how many alerts are currently pending. This tersely-summarized information may be enough for the MSP to understand that nothing new has happened and the MSP may therefore simply hang up.

Suppose the MSP (or MA or other trusted Person responds by asking for the Physician's Alerts summary, e.g., by speaking the number "one" into the phone. The System may then walk the caller through a second voice based Dialog such as the following: System: "Welcome to the Pending Alerts Summary for Dr. Jones. At any time, Press or speak "1" to hear details of the summarized alert. Press or speak "2" to hear a summary of the next alert. Press or speak "3" to hear a summary of the previous alert. Press or speak "4" to access a different Menu. Press or speak "8" to establish a conference call with the Patient. Press or speak "9" to hang up. Press or speak "0" to speak with the System operator." In this example, we assume the caller quickly says the number "one". The System may then respond as follows (using row 1017 of FIG. 10A as the basis for this example): "The highest priority Alert is a Positive Strep Throat Culture that just arrived for Patient Steve Winton. Antibiotic treatment is indicated for following up on this Test Result. Press or speak "1" to Supply details for the suggested follow up. Press or speak "2" to hear a summary of the next alert. Press or speak "3" to hear a summary of the previous alert. Press or speak "4" to access a different Menu. Press or speak "8" to establish a conference call with the Patient. Press or speak "9" to hang up. Press or speak "0" to speak with the System operator." If the caller says "one", the System may then walk the caller through a voice based version of FIG. 12 to thereby instantiate a Test Follow up Interview for the infected Patient.

If the caller instead speaks, or touch tones the "8" key, the System may automatically try to establish a conference call with the affected Patient, using the delivery strategies stored in the System for optimizing the chances that the conference call will successfully complete. If the System nonetheless fails to establish the conference call with the MSP in timely manner, the System should inform the MSP of the failure and allow the MSP to choose other options. In one embodiment, while the MSP is waiting for automatic establishment of a conference call with first Patient, the System allows the MSP to hear other summarized alert reports, and interrupts the MSP with a call-waiting signal if the requested conference call is established. Conference calls may established in a variety of ways including but not limited to conferencing through the medical facility's main office, conferencing through the System's telephone facilities and forming a conference bridge connection through the telephone company's equipment. In each case, for security reasons, the connection to the calling-in physician should be temporarily suspended until the call-waiting signal is given so that the MSP can securely call-in into the System at the same time via a different channel for confidential information regarding a different, e.g. next Patient on the physician's alerts list.

While the above describes a voice-only, alerts-handling transaction with the System. Other alerts-handling transactions may include combined use of visual and audible information via third-generation wireless devices (3G devices), via wireless Personal Digital Assistants (e.g., PDA's such as the Palm Pilot™) and other such means. Other alerts-handling transactions may include use of visual-only terse communication such as through a data-displaying pager or non-3G cell phone. The System should be made flexible so that MSP's and other care-concerned Persons can easily and with regularity check in on the status of their System-generated alerts as may be appropriate for the circumstances the MSP/other finds him or herself in (e.g., driving a car, attending a conference, etc.). While it may be preferable to have the MSP or other care-concerned Person unilaterally dial into the System, it is also possible to have embodiments where, for high-priority alerts as so defined within the System, the System actively contacts the MSP/other care-concerned Person to initiate the alerts-handling transaction. One example is where a Testing Lab has sent in an alerted Test Results report and has not heard back from the doctor within a System defined time limit. Note that due to the different kinds of communication channels the System can handle (e.g., both Internet email and voice-based telephone), a unified and internally-coordinated communications solution can be provided for getting the necessary information to the appropriate Target by whatever communication channel is appropriate under the circumstances, and that once the Target has been successfully communicated with via one communication channel, the System can (through its internal coordination as between channel managers) make sure the same Target is not annoyed with further, repeated transmissions of the same information via different communication channels.

The above description of screen and voice-based presentation of Alert summaries can be expanded to include voice and/or other biometric based authentication of user rights and voice-based navigation through System information and actions. For example, when a physician momentarily drops into his office chair during a busy, often interrupted, day, an already-on terminal of the System can automatically detect his/her presence (e.g., by sound and/or motion detection), and if there are pressing alerts awaiting handling by the physician, the smart terminal may query with a voice question such as, "Is that you, Dr. Miller?". The physician will understand this to mean that the smart terminal has some pressing matters to inform him/her of but is awaiting authentication by way of a voice and/or otherwise-based password. The physician may simply need to say something like, "Yes its me, what's up Alice?" where automated voice-signature recognition verifies that is indeed Dr. Miller (the physician for whom pressing alerts are pending). Alternatively or additionally, the physician may be required to scan in his/her fingerprint or retinal pattern into a System security device. Once authentication completes successfully, the smart terminal may provide voice-based information by saying something like, "Dr. Miller, you have 3 new alerts today. Do you want me to tell you about them or show them?". The physician may then reply, "Yes Alice, please tell me," or "Yes Alice, please show me," or "No thanks Alice". In response, the smart terminal may respectively provide a voice-based summary as was already explained for the telephone example above, or display the Alerts Summary such as in the form of FIG. 10A. The smart terminal may further allow the physician to navigate by voice-command through different screen presentations and/or voice presentations, to select items within the presentations by voice-command, to formulate and send Interviews by voice-command and/or to locate Patients within the System by voice-command and retrieve information about them or launch a System-mediated telephone and/or other communication with the located Patient.

Figure 10B:
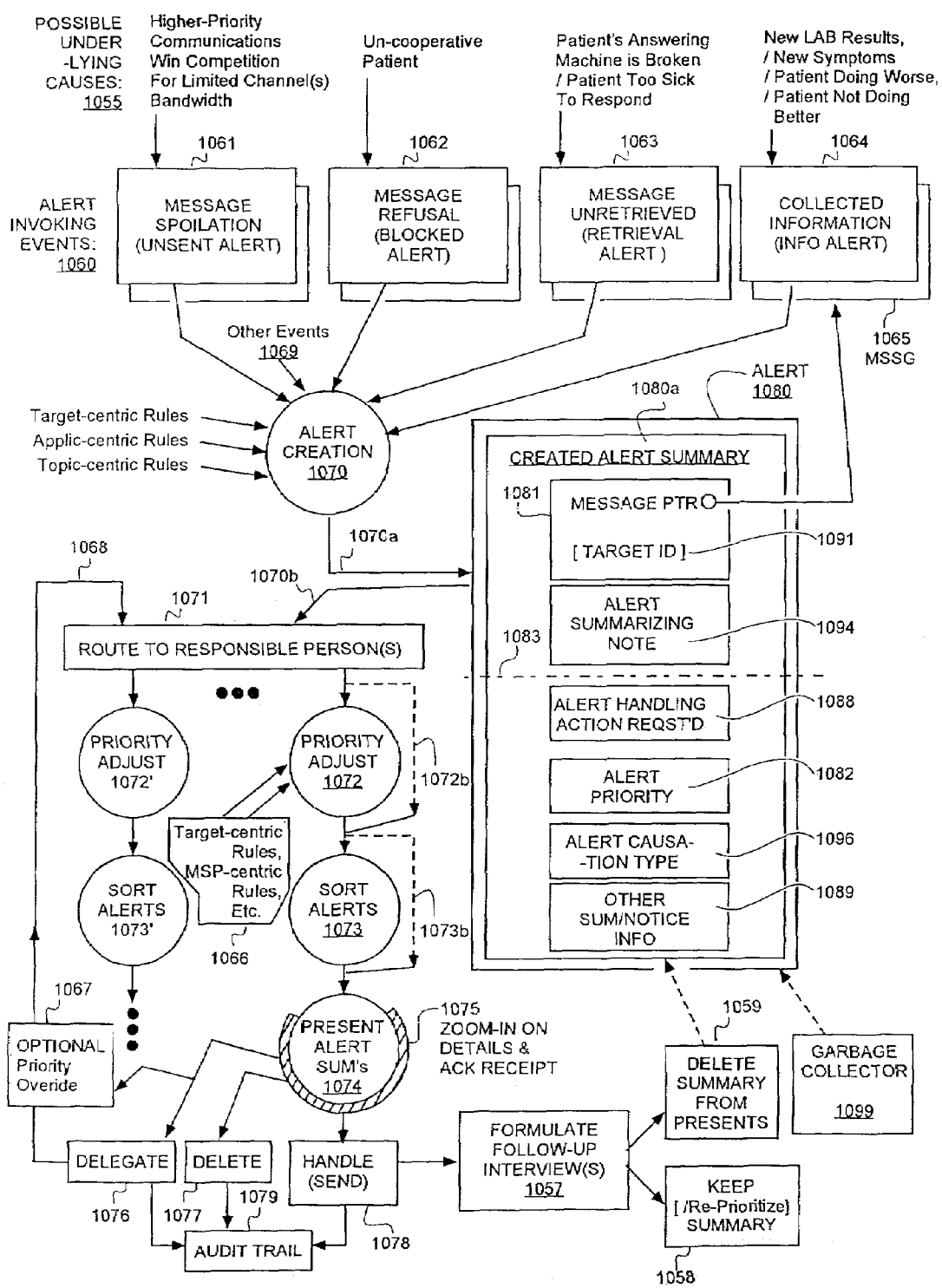
FIG. 10B is a block diagram of an Alerts generating and handling signal flow within a System provided in accordance with the present disclosure.

Referring briefly to FIG. 10B, a signal and action flow diagram is presented to show how, in one embodiment, action-item summaries (e.g., SEND 1017, REVIEW 1018) and/or other progress/notification summaries (e.g., blank ACTION in row 1023) may be generated and managed. Each Application (e.g., Service Providing Organization, SPO for short) can define within the System, one or more abbreviations (Alert-summarizing Notes, e.g. column 1014 in FIG. 10A, item 1094 in FIG. 10B) for respective action-item summaries and/or other progress/notification summaries as may be appropriate under that Application. A non-limiting example of such Alert-summarizing Notes as may be defined within a general medicine clinic is as follows: "Strep+" (to represent a positive strep throat culture, e.g. like in row 1017); "AsthmaWorse" (to represent a change in a known medical condition, e.g. like in row 1024); "ChestPain" (to represent a reported symptom by a Patient); "Can'tBreathe" (to represent another reported symptom by a Patient); "AllergyWorse" (to represent another change in a medical condition that is already known to the System to be present in the corresponding Patient); "Arrhythmia" (to represent a diagnosis reported by a medically-trained person for the corresponding Patient); "Temperature" (to represent a self-reported condition assessment by the corresponding Patient or a friend/guardian); "Coma" (to represent a serious condition assessment provided by a friend/guardian of the corresponding Patient); "NotGotBetter" or "Progress=0" (to represent a lack of positive progress with a medical condition that is already known to the System to be present in the corresponding Patient); and "Progress<0" or "GotWorse" (to represent negative progress).

Each Application (e.g., representing an SPO or an arbitrary association of one or more persons) can establish for itself (or inherit a default value from the System for) a base, Alert priority (1082) for each kind of Alert-summarizing Note. For example, a clinic that services older patients may assign a base priority of 80 (on a scale of 0–99) to "ChestPain" and to "Cough" whereas a clinic that services children may assign a base priority of 30 to "Cough". The System may then automatically increase or decrease the actual priority value of a given alert, relative to its initial base value, in response to priority adjusting rules that take into account one or more factors such as: Action requested (1088), Patient attributes, MSP attributes, Topic attributes, and so forth (see input factors box 1066). In terms of a more specific example, assume the Alert-summarizing Note (1094) of a given alert is "ChestPain" and the Application's base value for this 80. One of the attached, priority adjusting Rules (1072) might indicate: IF Patient attributes=ChronicAnxietyDisorder AND Age<25 AND Sex=Female, THEN multiply current value of Priority by 0.50 (in essence a 50% reduction). Another attached, priority adjusting Rule (1072) might indicate: IF Patient attributes=ChronicHeartProblem AND Age>45 AND Sex=Male, THEN multiply current value of Priority by 1.3 (in essence an increase). Multiple ones of such adjustment rules may come into play for any given Patient and/or the Service-Providing person (e.g., physician) to whom the Alert is being routed. Thus FIG. 10B shows separate priority adjustment operations (1072, 1072', etc.) for each respective recipient to whom the Alert is routed.

Priority adjustment operations (1072, 1072', etc.) are optional and not necessary for providing Alert Summaries such as shown in FIG. 10A. Thus an alternate bypass path 1072b is shown in FIG. 10B in dashed form. Sorting of Alerts is also optional and not necessary for providing Alert Summaries. Thus an alternate bypass path 1073b is shown in FIG. 10B in dashed form about Alert Summaries Sorting operation 1073. The optionally prioritized, and optionally sorted Summaries are then presented to the Alerted Person (e.g., the physician) in step 1074. Screen 1000 of FIG. 10A is an example of such a presentation. The above-described, voice-based presentations are other examples. The extent of what Alert Summaries are presented in a given type of Alert Summarizing Presentation (e.g., screen 1000 or voice—latter not shown) can vary and can be based on priority thresholds, recipient preferences, communication channel limitations, and so forth. Alert Summaries may be color-coded, associated with bell or other sounds and otherwise embellished on to help the recipient appreciate the importance or other aspects of different kinds of summarized notifications/alerts.

In one embodiment, next step 1075 represents the Alerted Person (e.g., the physician) clicking-in, or otherwise zooming in details of the summarized Alert and thereby acknowledging receipt of the underlying details. It will be seen shortly that, upon zooming in, the Alerted Person may have action options such as Delegating (1076) responsibility for responding to the Alert to another person (see FIG. 17, described below); Deleting the Alert (1077, see also FIG. 18, described below); and/or Handling the Alerted situation themselves (1078, see also FIG. 19, described below) where the latter can include the option of nonetheless keeping the Alert Summary in the Alert-summarizing Presentations (1058, see also item 1706 of FIG. 19 as described below); or the latter can include the option of letting the System automatically delete the Alert Summary from the Alert-summarizing Presentations (1059). Because various response and action screens have not yet been detailed, other aspects of FIG. 10B will be discussed further below.

FIG. 11 illustrates a screen 1100 which may be displayed according to the disclosure to allow Medical Providers to identify and/or locate Patients. Button 1003 is highlighted (or otherwise distinguished) to indicate that the user is viewing this screen. Section 1102 may be used to locate a Patient using the Patient's name or ID number and comprises a first text box 1104 for receiving a name or a search query to be entered by the Medical Provider. (In the illustrated example, the user has entered a query for names having a starting letter of J* or L* or K* or R* where star (*) is a string wild card.) Text box 1106 alternatively allows the Patient's ID or a search query therefor to be entered. Upon entering information in 1104 and/or 1106 and activating the Find button 1105 a list of names from the list of all Patients in the System responsive to the inputted data appears in area 1107. If the Medical Provider then selects an appropriate one or more names from these, a corresponding one or more Send Interview screens may be responsively displayed with System-available parts of the corresponding Patient specific information filled in it. (See for example FIG. 13 discussed below.)

In addition, or as an alternative to searching for Patients according to name and/or ID, various Patient Attributes such as age, weight, height, sex, chronic diseases, etc. may be used to selectively find and list Patients with corresponding attributes and/or to assign such found Patients to Interview Groups so that corresponding Interviews may be formulated for and sent to members of the formed Groups. In one embodiment, data-entry region 1111 has a first pull-down menu for allowing one-click selection of a first Patient/Group Attribute (such as, Has Diabetes). Alternatively, the user may type in, or copy in the identification of the first Patient/Group Attribute (1190) into entry-region 1111. Similarly, data entry region 1114 has a second pull-down menu for allowing one-click selection of a second Patient/Group Attribute (such as, Has Hypertension). Alternatively, the user may type in, or copy in the identification of the second Patient/Group Attribute (1112) into entry-region 1114. The third entry region 1189 has a third pull-down menu for allowing one-click selection of a logical relationship (e.g., AND, OR, BUT-NOT, EXCLUSIVE OR, etc.) that is to exist in the found group of Patients between their first and second Attributes (1190, 1112). If the third entry region 1189 is left blank, the System may default to using only the first Patient/Group Attribute (1190) as the (or part of the) search criteria. Activation of the Advanced Find button 1170 can bring up a more complicated, searching tool which allows the user to script a search that uses more than just the few search categories provided by boxes 1104, 1106, 1111, 1189 and/or 1114. In one such, Advanced Find screen (not shown), pull-down menus for available attributes and possible relationships between them are provided to aid the user in formulating a search (e.g., Find all Patients whose age>50 AND whose last major physical examination was more than 3 years ago AND whose primary-care clinic is ABC clinic BUT-NOT including those who received major physical reminders within the last 2 months).

When a satisfactory set of search results is obtained in area 1107 (the user may manually pare down the list or add to it), that Group of Patients may be assigned a Group Name by entering such a name in entry area 1161 and then activating the Form Group button 1172. The so named and formed Group may be called up later for other uses besides sending a personalized, Group Interview to its individual members. The user may also manually select one or more members from a found group to send custom Interviews to.

In an embodiment, the list from which Patients are selected in response to the query posted in box 1102 may by default be comprised of all the Patients in all the System Applications or only those Patients for whom the Place Attribute location is the clinic at which said Patients obtain medical care or by alternative default, only another prespecified subset of Patients known to the System.

Figure 14:
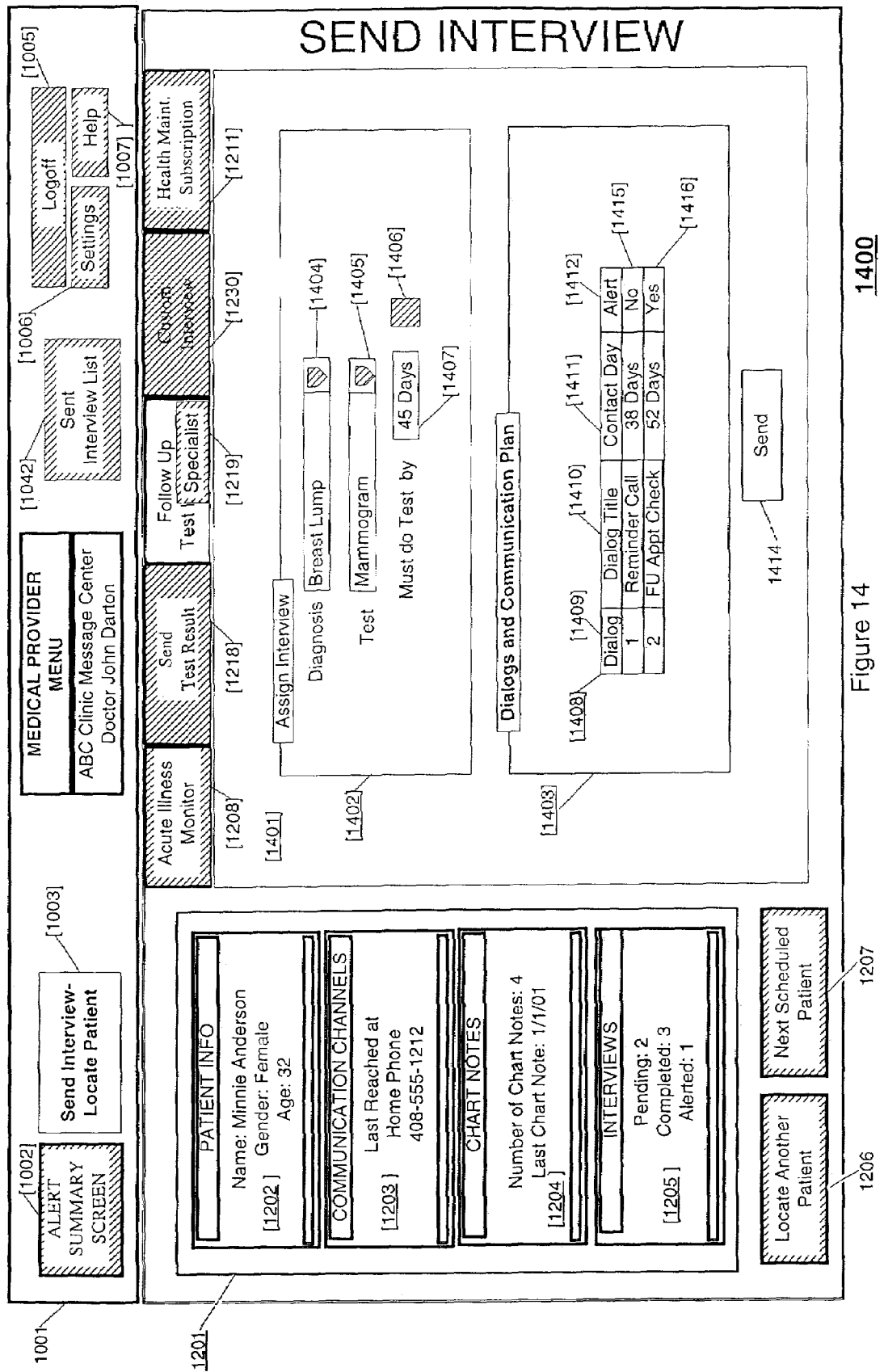
FIG. 14 illustrates another Interview formulation screen which may be used by a Medical Service Provider to formulate a Test Follow-Up Interview whose Dialogs are to be delivered per a schedule to a Patient in accordance with the present disclosure.

An alternate form of locating may be performed using the search tool of section 1103 (This Provider's Patients). When using Section 1103 of FIG. 11 the Medical Provider may enter a date in text box 1108 or choose an appropriate date using a calendar-revealing icon 1110 to show a list of Patients seen by him or her in list box 1109 on that date. Selecting the appropriate Patient from this list causes a Send Interview screen such as illustrated in FIG. 14 to appear with appropriate information as is available in the System for that Patient.

In an embodiment, FIG. 11 may also hold a group selector from which a Medical Provider may query for and/or select a group type such as, e.g., all Patients in his practice with diabetes and on a given medication, or all members of a specific work section. In response, the MSP will be presented with a list of such Patients. From this list the Medical Provider can choose to send a Custom Message to the entire group or a selected subset of the group or pick a specific Patient to whom to send an individualized Interview. The list may also be the appointment schedule for the Medical Provider for that or a selected other day. In an embodiment, Medical Providers are able to form customized groups for sending Interviews to or for other uses. In an embodiment, Section 1102 also provides other query formation boxes such as for example, a text box that contains the birth date, Social Security number, or another identifier for Patients.

In an embodiment, the Medical Provider selects a date in box 1108 and the System's program generates a conforming list of Persons by using the following logic (or an equivalent):

Select Persons where
1) The Person has a relationship Role of "Patient" to a given Application, and
2) The Person has an Interview with: (A) the Attribute of Primary Care Doctor equal to the Medical Provider and (B) an appointment reminder Interview with the appointment being for one or more selected day(s).

In an embodiment, the MSP's Patients list 1109 may be programmably configured to display all Patients in the System with appointment reminder Interviews for one or more date(s) where the Medical Provider has the Role of the Patient's Primary Care Doctor.

In an embodiment, the MSP's Patients list 1109 may be programmably configured to display all Patients with appointment reminder Interviews for one or more date(s) where the Medical Provider has the Role of the Patient's Primary Care Doctor and the Patients' appointments are for a specified section of a Medical Facility, such as Surgical Clinic.

In an embodiment, the MSP's Patients list 1109 may be programmably configured to display all Patients with appointment reminder Interviews for one or more date(s) where the Medical Provider selecting the Patient has had the Role of Medical Provider for the Patient.

FIG. 12 illustrates a screen in an embodiment in accordance with the present disclosure that enables a Medical Provider to formulate a Test Result Interview for sending to a Patient. In accordance with the medical facility's standards (as stored in the System Database), normal and certain other test results may be automatically sent to the Patient through pre-defined protocols without Medical Provider intervention. Other tests, however, are automatically uploaded as Information Alerts originated by the Testing Facility and listed on the Medical Service Provider's Alert Summary Screen, 1000 (FIG. 10A) for Review and possible modification or substitution by the MSP before being forwarded on to the affected Patient. If the Medical Provider selects the corresponding Interview in Box 1012, e.g. Interview 1017, he or she is presented with a screen such as 1200 of FIG. 12. Alternatively, the Medical Provider may learn of a test result from outside of the System—e.g., by a telephone message, and may desire to report it to the Patient through use of the System. In this situation, the Medical Provider enters the System and locates the Patient using an identifying Screen such 1100 as in FIG. 11. Upon selecting the Patient through the identifying screen, the Medical Provider may be adaptively or by default, presented either with the Screen in FIG. 12 or a similar one with one of the other function tabs 1208, 1218, 1219, 1230 or 1211 highlighted. (See, e.g., also FIGS. 13, 14, 15, and 16 described below.) Upon clicking the "Send Test Result" tab 1218 in one of the alternate screens, the screen of FIG. 12 will be presented.

The Patient Details Section 1201 of the Screen in FIG. 12 comprises means for the Medical Provider to obtain further information regarding the Patient identified by 1202. This further information can include Communication Channels 1203, Chart Notes 1204, and prior Interviews 1205 related to the Patient. Each of these buttons provides a preview of pertinent summary information: Thus, the Patient Personal Info box 1202 can indicate the Patient's name, sex, age; etc. Communication Channels box 1203 can similarly pre-display the address or telephone number at which the Patient was last successfully reached. Chart Notes box 1204 can pre-display the number of Chart Notes on the System for the Patient and the date the last one was placed. Interviews box 1205 can pre-display the number of pending, recently completed, and alerted Interviews. By clicking on the appropriate one of these buttons the Medical Provider may learn further details about each of these areas as illustrated, e.g., in FIGS. 36, 37, and 38. Thus clicking on 1202 can expose a table listing Patient attributes such as medication allergies, presence or absence of specific diseases, current medications, etc.

To the right of the Patient Details Section 1201, the Screen 1200 shows a set of five tabs corresponding to the types of Interviews whose formulation and/or delivery the Medical Provider may desire to initiate: Acute Illness Monitor 1208, Send Test Result 1218, Follow Up Test/Specialist 1219, Custom Interview 1230, and Health Maintenance Subscription 1211. If the tab appropriate to what the Medical Provider desires to do is not highlighted, the Medical Provider may select it to bring up the needed screen.

The screen illustrated in FIG. 12 may be used to send a test result to a Patient. This Screen 1200 comprises three sections: Choose Test Group and Topic 1250; Interview Attributes 1212; and Dialogs and Communication Plan 1216. The Choose Test Group and Topic section 1250 comprises a drop down text box 1220 that can provide a list of groups of tests and another drop down text box 1221 that can provide a list of tests for the test group chosen in 220. Interview Attributes 1212 can provide a displaying of a table such as is illustrated at 1214 with a title bar illustrating the name of the test and a grid showing the test result value(s), and can further provide a displaying of a table such as is illustrated at 1222 of "Provider Addendum Phrases," which are phrases the Medical Provider may choose to add on to the System's standard Interview for the indicated test result to the Patient. In box 1224 the Medical Provider may choose the number of days after which a Retrieval Alert is triggered. Calendar 1223 may be used in conjunction with this. If the Medical Provider accesses this screen from selecting the Test Result on FIG. 10A, fields 1220, 1221, and 1214 are automatically filled in with the appropriate information when this screen comes up and are partly grayed out to indicate the default provision of such information. Also a default value for the Retrieval Alert may be presented in box 1224. The Medical Provider, in this case, may need to only decide on whether or not to add one or more phrases from the Addendum Phrases section 1222 and whether to alter the default value in 1224. The MSP may then click button 1225 to initiate the attempted delivery of the so-supplemented Interview. If the Medical Provider learns of the test result from outside of the System, the Medical Provider may select the proper information for 1220 and 1221, which will result in the appropriate test result box 1214 appearing. The Medical Provider may then enter the result in 1214 and add appropriate information from 1222 and 1224 as above if desired. If upon the Medical Provider entering the result in 1214, the System senses that this information is also present on the Alert Summary Screen of FIG. 10A, a warning box such as shown at 1213 appears with a message so informing the Medical Provider. Otherwise, warning box 1213 is not visible on this screen.

Dialogs and Communication Planning section 1216 holds box 1217 indicating parameters regarding the Dialog and Delivery of the Test Result Interview. There is only one Interview Dialog involved in this Test Result Delivery Interview entitled "Call Strep Result." The Contact Day is the day the Interview delivery is initiated by the Medical Provider and it has a Retrieval Alert set. When the Medical Provider selects button 1225 to send the Interview, the System indicates this action and the corresponding Interview with Action "SEND" is removed from table 1040. The Medical Provider may then select button 1226 to move to a screen showing the next Alert in table 1040; if this is another Test Result with Action "SEND," the screen in FIG. 12 re-appears this time filled in with the appropriate data for the next action item. If the next action item is a message to "REVIEW," another appropriate screen as detailed further below appears. If instead, the Medical Provider selects button 1207, data regarding the "Next Schedule Patient" from the List in 1109 is loaded into the fields in section 1201 and, if information for this Patient is present on FIG. 10A, the appropriate screen for "SEND" or "REVIEW" is presented with this information entered. Alternatively, the Medical Provider may select button 1206 to return to the screen in FIG. 11 to locate another Patient or select 1002 to return to the Alert Summary Screen, or 1042 to go to a screen that lists previous Interviews sent. Alternatively, the Medical Provider may select button 1005 to log off the System.

FIG. 13 illustrates a screen 1300 which allows a Medical Provider to formulate and initiate the attempted delivery of an Acute Illness Monitor Interview to a Patient suffering from asthmatic bronchitis. Most of the elements of the screen 1300 which are outside of the acute illness monitoring section 1301 have been previously described. It is seen that the Acute Illness Monitor tab 1208 has been highlighted or otherwise distinguished to indicate that an acute illness monitoring function has been selected. Activation of tab 1208 may be used to bring up the display structures shown in section 1301 including the illustrated Assign Interview section 1302, the Dialogs and Communication Planning section 1303, and the Send button 1315 which allows one or both of the Medical Service Provider and Medical Assistant to initiate the attempted delivery of the formulated communication.

The Assign Interview section 1302 may include a pull down text box 1304 from which the Medical Assistant or Medical Provider can pick the Diagnosis relevant to the office visit. The pre-listed Diagnoses could include "Cellulitis," "Otitis Media," "Low Back Pain," etc. Each of the pre-listed diagnoses has associated with it several possible Topics and/or Communication Plans for follow up. Thus the diagnosis of Asthma could have the following Topics pre-associated with it within the System:

(a) Asthmatic Bronchitis-Antibiotic, (b) Asthma-Prednisone started, (c) Asthma-bronchodilator added, (d) Asthma-Steriod Inhaler started, (e) Asthma-Critical Peak Flow, (f) Asthma-mild exacerbation. The pull down text box 1305 may list these and thereby allow the Medical Service Provider to quickly select a suitable follow up Communication Plan. In one embodiment, the MSP is also given the option of typing in queries for System-held Diagnoses and Topics and/or of typing in specific Diagnoses and Topics directly.

The Communication Plan 1303 chosen may call for added information in its paradigm. Some of this additional information may be stored in the System already as Attributes for the Patient. The selection of a particular Communication Plan may cause the System to automatically search for the associated Attribute information and fill it in. If the additionally called-for information is not available within the System, then title bars such as 1316 "Office Peak Flow" and 1317 "Height" and corresponding input boxes, such as 1306 and 1307 are displayed in highlighted or other fashion for indicating to the MSP or Medical Assistant that they should input this information manually. Box 1309 shows a default time for first Patient follow up contact for the Topic selected; the Medical Provider may edit this. An invoke-able calendar function 1308 may be used to aid in this selection of the follow up date.

The Dialogs and Communication Plan 1303 holds an outline of the Topic structure chosen in 1305. The table 1310 has column headings that respectively identify their information as representing: the Interview Dialog Number 1311, the Title of the corresponding Dialog 1312, the Time Range 1313 in which the System will try to deliver a given Dialog, and an indication 1314 of whether a Retrieval Alert is set for the given Interview Dialog. The Time Ranges in 1313 may be made adaptively responsive to the information given in box 1309 for the time of first Patient contact via System rules. Thus, FIG. 13 indicates in the example of table 1310 that the Topic "Asthmatic Bronchitis-Antibiotic" specified in 1305 has four System-automated and sequential Dialogs: The first is titled "Worse?" and will be delivered between 1 and 2 days after the office visit; the second is "Better?" and will have delivery attempts made between the third and fourth day after the office visit; the third is "Well?" and is to be delivered at 8 to 10 days after the office visit; and, the last is "Got Questions?" and is to be delivered 11 to 14 days after the office visit. All these exemplary Dialogs, except the last, have Retrieval Alerts set by the System, meaning that the MSP or another responsible person will be alerted if the Patient fails to affirmatively retrieve and respond to the attempted delivery of the Dialog. In an embodiment, the Medical Service Provider may choose not to have Retrieval Alerts by entering "NO" in the appropriate part of column 1314. Additionally or alternatively, in one embodiment, the MSP may click-on or otherwise activate one of the Retrieval Alert control boxes in column 1314 to bring up a detailed dialog box that allows the MSP to, at any appropriate time, change the Retrieval Alert control state for the correspondingly-planned Dialog (e.g., 1–4) to YES, NO or another, System-allowed state, for example: YES-but use only CATEGORY-1 Alert Generating Rules.

FIG. 14 illustrates a Test follow-up screen 1400 that may be used in an embodiment to send a follow up Interview regarding a special test ordered for the Patient. This allows the Medical Service Provider to ascertain if there were any problems with the Patient actually having the test properly scheduled and/or it allows the Medical Service Provider to confirm that the Patient did actually have the test carried out. Most of the elements of the screen 1400 outside of the Interview Test follow-up section 1401 have been previously described. A highlighting or other featuring of the Follow Up Test tab 1219 in the illustrated screen indicates that the Medical Provider has selected the Follow Up Test function. An activation of the featured tab 1219 results in section 1401 being displayed as shown to provide a corresponding Assign Interview section 1402, a Dialogs and Communication Planning section 1403, and a Send button 1414 for the user to use to initiate the attempted delivery of the planned communication.

The Assign Interview section 1402 provides a drop down menu box 1404 for allowing the Medical Provider to select a diagnosis with a single mouse click or like activation. In the same or another embodiment this drop down menu 1404 may hierarchically present two or more categories of tests under which selection of the suspect Diagnosis is set forth. Below the Diagnosis specifying box 1404 there is another drop down menu box 1405 that provides for one-click selection of specialized tests. The displayed options in box 1405 may be made adaptively responsive to the input of or selection made in the Diagnosis box 1404. Thus, if the selected/input Diagnosis "Breast Lump" was indicated in box 1404, the drop-down choices presented through box 1405 could be made to adaptively include "Mammogram," "Ultra-Sound Study," or "Fine Needle Biopsy." The Medical Assistant or Medical Provider may select the appropriate test for box 1405. In one embodiment this action automatically results in a default number of days appearing in box 1407, where the latter indicates the time limit for test completion by the Patient. The Medical Provider can edit this number. An invoke-able Calendar function 1406 may be used to aid in the date selection process.

The Dialogs and Communication Planning section 1403 can generate a scheduling table such as shown at 1408 that lists the Dialogs to be used in the selected communication plan. Column 1409 holds the Interview Dialog Number, 1410 the Interview Dialog Title, 1411 the Contact Day or day after the Interview is initiated that the System will deliver the Dialog, and 1412 Alert Status which indicates whether or not a Retrieval Alert is set for the Dialog. The Contact Times displayed in column 1411 may be made responsive to the input in 1407 by rules and logic contained in the System. Table 1408 holds two Dialogs for the indicated follow up: Interview Dialog 1 which is an appointment reminder call and which is to be sent at 38 days after the initiation of the Test Follow Up Interview and does not have a Retrieval Alert; and, Interview Dialog 2 which is a check on completion of the Follow Up Test that is to be sent at 52 days and does have a Retrieval Alert.

Specialist referral follow up Interviews can be carried out in a manner similar to that of FIG. 14. A drop down menu box similar to 1404 may be used to identify the diagnosis. A drop down menu box below it may be used for listing various referral sources or specialists from which an appropriate choice can be made.

Figure 15:
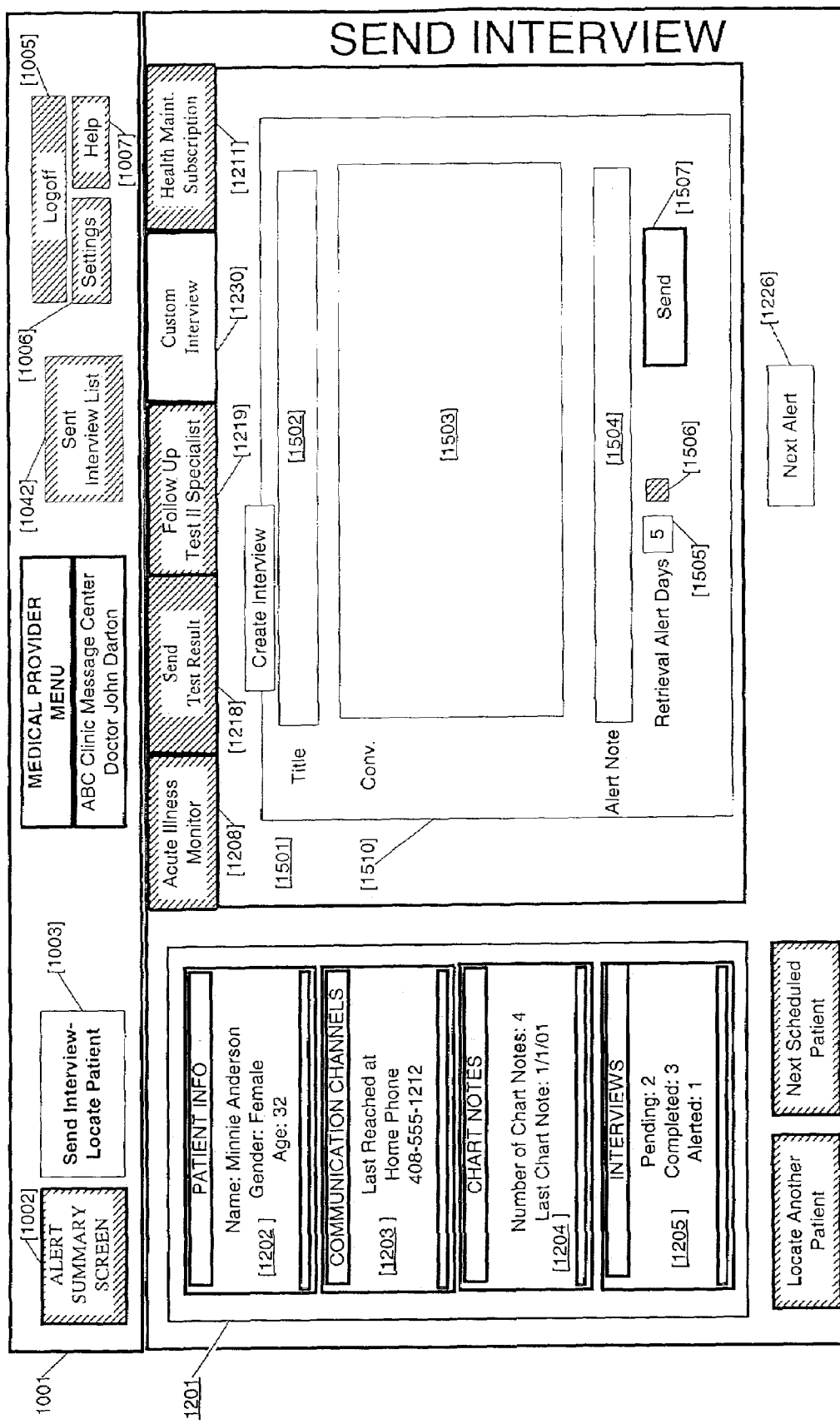
FIG. 15 illustrates another Interview formulation screen which may be used by a Medical Service Provider to formulate a Custom Interview that is to delivered to a Patient in accordance with the present disclosure.

FIG. 15 illustrates a Create Interview screen 1500 which may be used by a Medical Service Provider to formulate a Custom Interview for delivery to a given one or more Patients. Most of the elements of the screen outside of the Custom-formulation section 1501 have been previously described. The featuring of the Custom Interview tab 1230 in the screen 1500 shows that the Medical Provider has elected to formulate a Custom Interview. Activation of the Custom Interview tab 1230 produces the illustrated section 1501. This Custom-formulation section 1501 contains a Create Interview section 1510. Area 1502 allows the Medical Provider to enter a Title for the Custom Interview. Text entry area 1503 allows the Medical Provider to enter the custom Interview text therein. Alert notification area 1504 may be used for entering an Alert Note, if any is to be entered. The Interview Alert Note can be used in the System, for example, by being displayed in table 1040 column 1014 if this Custom Interview is alerted. Box 1505 allows the Medical Provider to enter a number of days for activating a Retrieval Alert or a "0" if the MSP desires to have no Retrieval Alert. A calendar invocation function 1506 may be used to aid in choosing the Retrieval Alert time. Button 1507 allows the user to initiate the delivery of the Custom-formulated Interview. In an embodiment, text-to-speech conversion software is included in the System for automatically converting the text entered in area 1503 to a voice file whose content is suitable for voice-based (e.g., telephony) delivery to the Targeted recipient by way of a voice-based communication channel.

Figure 16:
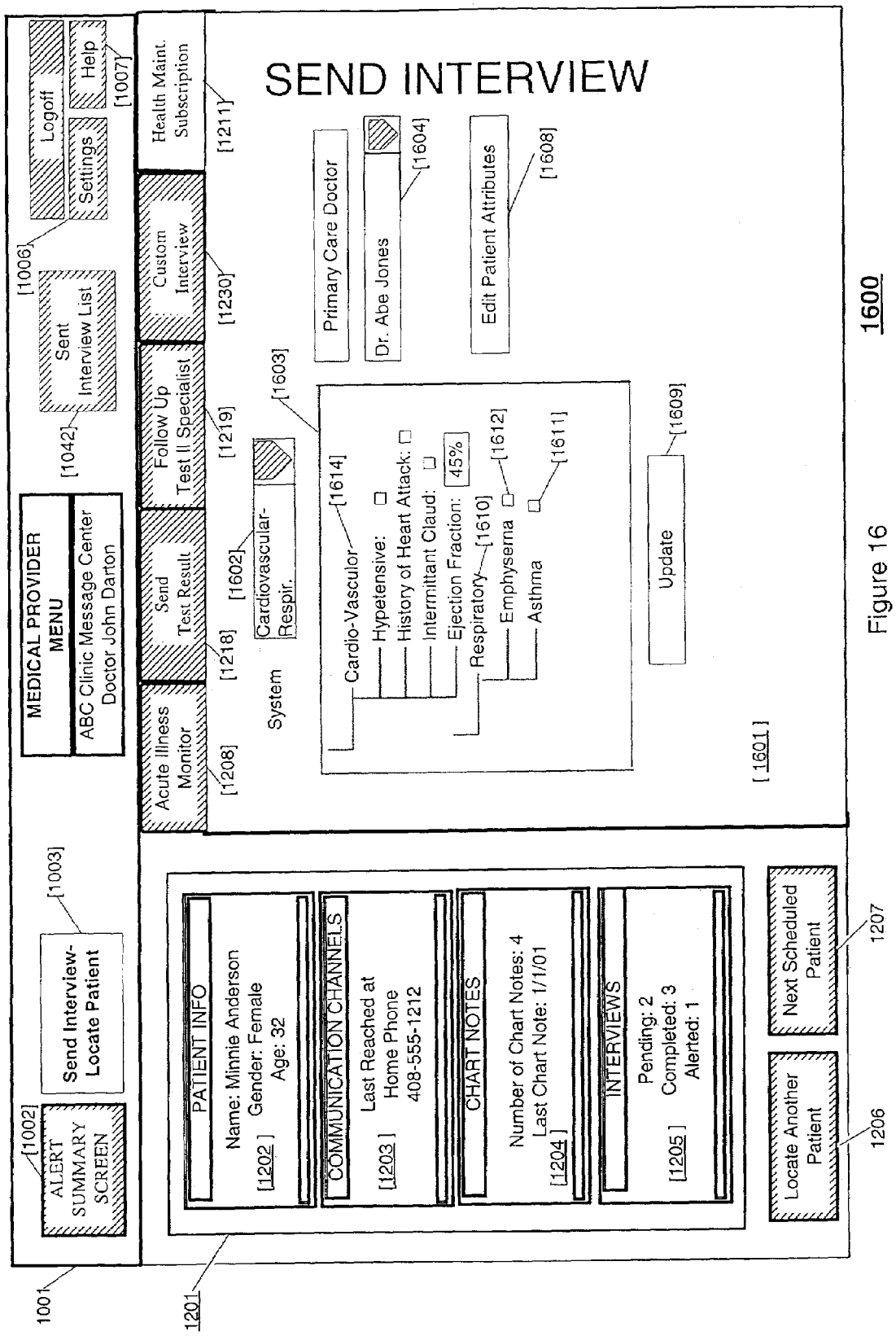
FIG. 16 illustrates another Interview formulation screen which may be used by a Medical Service Provider to formulate a Health Maintenance Interview that is to delivered to a Patient in accordance with the present disclosure.

FIG. 16 illustrates a Health Maintenance Interview formulating screen 1600 which may be used by a Medical Provider for formulating a Health Maintenance Interview and initiating delivery of it to a Patient. Most of the elements of the screen 1600 outside of the Health Maintenance Interview formulation section 1601 have been previously described. The featured Health Maintenance Subscription Interview tab 1211 indicates that the Medical Service Provider has selected the Health Maintenance Subscription Interview formulating function. Activation of tab 1211 results in the displaying of the illustrated screen 1600. Interview formulating section 1601 includes a drop down box 1602 that may be used to identify body organs, systems and/or disease groups. Upon a selection of one of these (whether by a one-click selection from a pop-down menu, or a typed-in choice) related medical conditions and parameters suitable for determining follow up are typically presented automatically by the System in box 1603 as is shown for example by the cardiovascular parameters illustrated in FIG. 16. More generally speaking, the pertinent Patient's Attributes held in the System and which are appropriate for use in determining the Health Maintenance Follow Up paradigm to be used for the instant Patient can be made to automatically appear in pre-checked and/or checkable form as is shown in box 1603. Thus the exemplary box 1603 illustrates the Topics and parameters that may be used for formulating a Health Maintenance Interview paradigm relating to the indicated Cardiovascular system (1614) and Respiratory system (1610). The Medical Service Provider can select or deselect those conditions or descriptors in box 1603 that the MSP believes to correspond to the particular Patient's medical state by modifying the displayed Patient's Attributes. The System's logic may use the MSP-provided information to automatically select an appropriate, Health Maintenance follow up Interview Plan for the Patient. The System has pre-defined sets of Dialogs customized to many of the conditions or descriptors that the MSP might select and these can be built upon as may be appropriate for the practice over time. Note that the follow up Interview Plan can be adaptively individualized in an automatic way for the specific Patient using the Patient Attributes including prior diagnoses, current status and medical history and the System's logic. Thus, for example, a hypertensive follow up plan for the Health Maintenance of a Patient with diabetes might include the automatic displaying of an alert to the Medical Provider at a diastolic pressures greater than 80 had been observed. On the other hand for a Patient without diabetes only if this measurement was greater than 90 would a similar alert be automatically displayed to the Medical Provider. Thus automatic alerting may be made adaptive to the Attributes of specific Patients.

The illustrated drop down box 1604 allows the Patient's primary care physician to be identified with one click from a list of clinic-recognized Medical Service Providers. Alternatively, it may be typed in or copied into data-entry box 1604 from other sources. The primary care physician (PCP) identified in box 1604 is typically the one whom the System automatically advises of when test results have been obtained from Testing Facilities and is typically the one to whom the System automatically sends Alerts for this Patient and the PCP is also typically the one who is made primarily responsible by the System for communicating with and following up with the Patient. In an embodiment, any Medical Service Provider who is using the Health Maintenance Interview formulating screen 1600 is given permission to view all systems and conditions that may apply to a Patient by selecting or making a choice via box 1602. In an alternate embodiment, the System(s) specifying box 1602 may be made adaptively limited to certain specialties which the System associates with the Medical Service Provider who is using the Health Maintenance Interview formulating screen 1600.

In an embodiment, the Health Maintenance Interview formulating screen 1600 may be used for simultaneously formulating Interviews for a Group of Patients. For example, the Medical Provider may specify as part of the identifying criteria for formulating a Group Interview for plural Patients that such Patients be all over 50 years old with Emphysema where the Database shows that they have not had a pneumococcus vaccination. These criteria can be established for example by using one or more of the Group-forming resources of box 1102 in FIG. 11 and such or other resources can be used to search the Database of the System and to thereby define a Group that satisfies the established criteria. Delivery of the so-formulated Group Interview can then be simultaneously initiated for each member of this group.

In an embodiment, Edit Button 1608 provides the Medical Provider with a means of editing a Patient's Attributes as listed in box 1603. Update Button 1609 allows indicated changes (indicated by highlighting or otherwise) to be recorded in the System's Database.

In an embodiment, the System allows for delegation to Medical Assistants of the routine sending of Acute Illness Monitor Interviews, Required Test Interviews, Required Specialty Referral Interviews, No Show Follow Up Interviews, and Health Maintenance Interviews in response to directions passed through the System from the Medical Provider. With such delegation for the handling of routine matters, the Medical Service Provider would have his or her attention focused mainly on: (1) formulating and sending Alerted Test Result Interviews (in response to data uploaded into box 1012 of FIG. 10A by a given Testing Facility); (2) formulating and sending Custom Messages such as shown in FIG. 15, and (3) Reviewing Alerted Interviews such as those that will now be described with reference to FIG. 17-*etc*.

(B) Screens For Reviewing Interviews

Screens for reviewing Interviews may be typically accessed by selecting in the Alert Summary Screen 1000 illustrated in FIG. 10A the Interview to be reviewed. Interviews may also be reviewed by selecting the Interview of interest from a list of Sent Interviews (1042) provided by the System.

Figure 17:
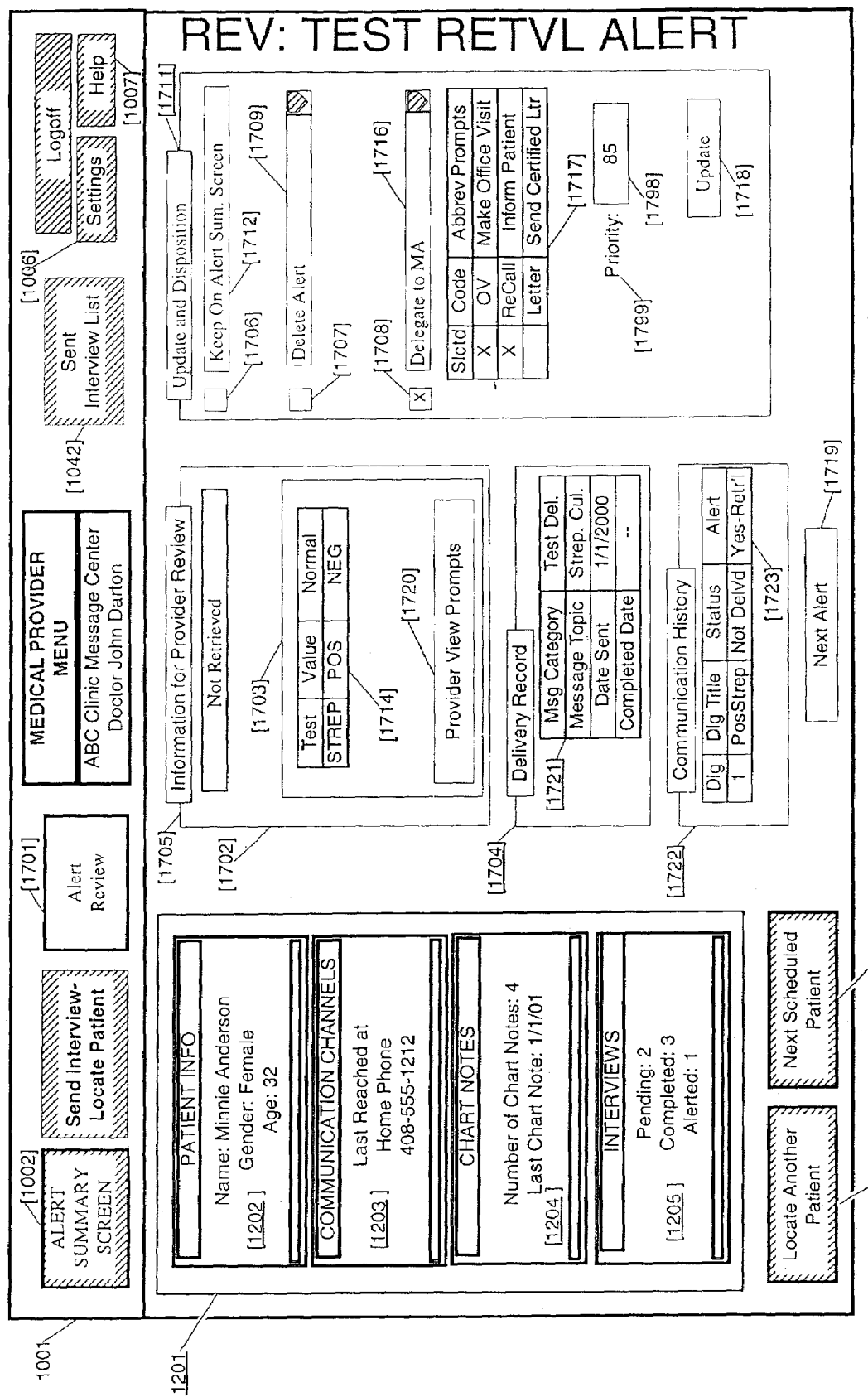
FIG. 17 illustrates an Interview Reviewing screen which may be used by a Medical Service Provider used to review the status of a Test-Result Delivering Interview whose in-completion triggered a Retrieval Alert in accordance with the present disclosure.

FIG. 17 illustrates, for one embodiment, a corresponding screen 1700 which may be used to review a Retrieval Alert. In the illustrated example, the Patient has apparently failed to retrieve and/or respond to an initially sent Interview warning of a positive Streptococcus throat culture result. The illustrated, Review: Test Retrieval Alert screen 1700 may be presented when the Medical Service Provider selects a corresponding summary row in table 1040 in FIG. 10A (See for example row 1019). Most of the elements of the illustrated Test Retrieval Alert screen 1700, particularly in the header bar and on the left hand portion of the screen (1201) have already been described above and thus do not need to be detailed again.

Button 1701 is highlighted to indicate that the current screen 1700 is for Review of an Alert. Section 1702 illustrates a method for summarily providing the pertinent Information for Medical Provider Review. This may include specific information such as identifying the purpose of the boxed, summary Information in field 1705, providing a summary in boxed area 1703 of the Interview that had been sent but apparently not retrieved, and/or such as displayed in boxed area 1720 any associated Medical Provider prompts—such as the Addendum phrases chosen in box 1222 of FIG. 12. The Delivery Record set forth in the example of box 1704 indicates that the current Interview which is under review was not "completed" because for example it was not retrieved within the time limits of the Retrieval Alert. Table 1714 summaries the Interview and indicates the Test was Strep and had a value Positive and that the normal value is Negative. Section 1704 displays a Delivery Record for the Interview under review. This can be done by means of a message tracking table such as shown at 1721, which gives further information regarding the Interview. This arrayed information may include the Interview Category, which in the example is Test Delivery, the Interview Topic, which in the example is Strep. Culture, the date the Interview was sent, and the date the Interview was completed, which in the example is blank since the Patient did not retrieve it. Below this is a Communication History summarizing section 1722 which can provide the communication history for this Interview in an arrayed format such as shown in table 1723. This table furnishes information regarding the Dialog(s) in the Interview. It indicates that there was only one Interview Dialog entitled PosStrep and that its Status is 'Not Delivered' since it has not been retrieved and that it has a Retrieval Alert that has been activated.

Update and Disposition section 1711 illustrates a means for updating the status of the Interview and its further disposition. Illustrated are three fields and their corresponding check boxes: The Keep-on-Alert section 1712 with checkbox 1706 indicates, if checked, that the Interview and Alert will be kept on the Alert Summary Screen. The Delete-Alert section 1709 with checkbox 1707 indicates, if checked, the Alert is to be deleted from the System's menus. The Delegate to MA section 1716 with checkbox 1708 may be used for delegating the alerted Interview to a Medical Assistant. A pull-down menu section within section 1716 may be used to select one of various delegation phrases for display in the main delegation area of section 1716.

Figure 18:
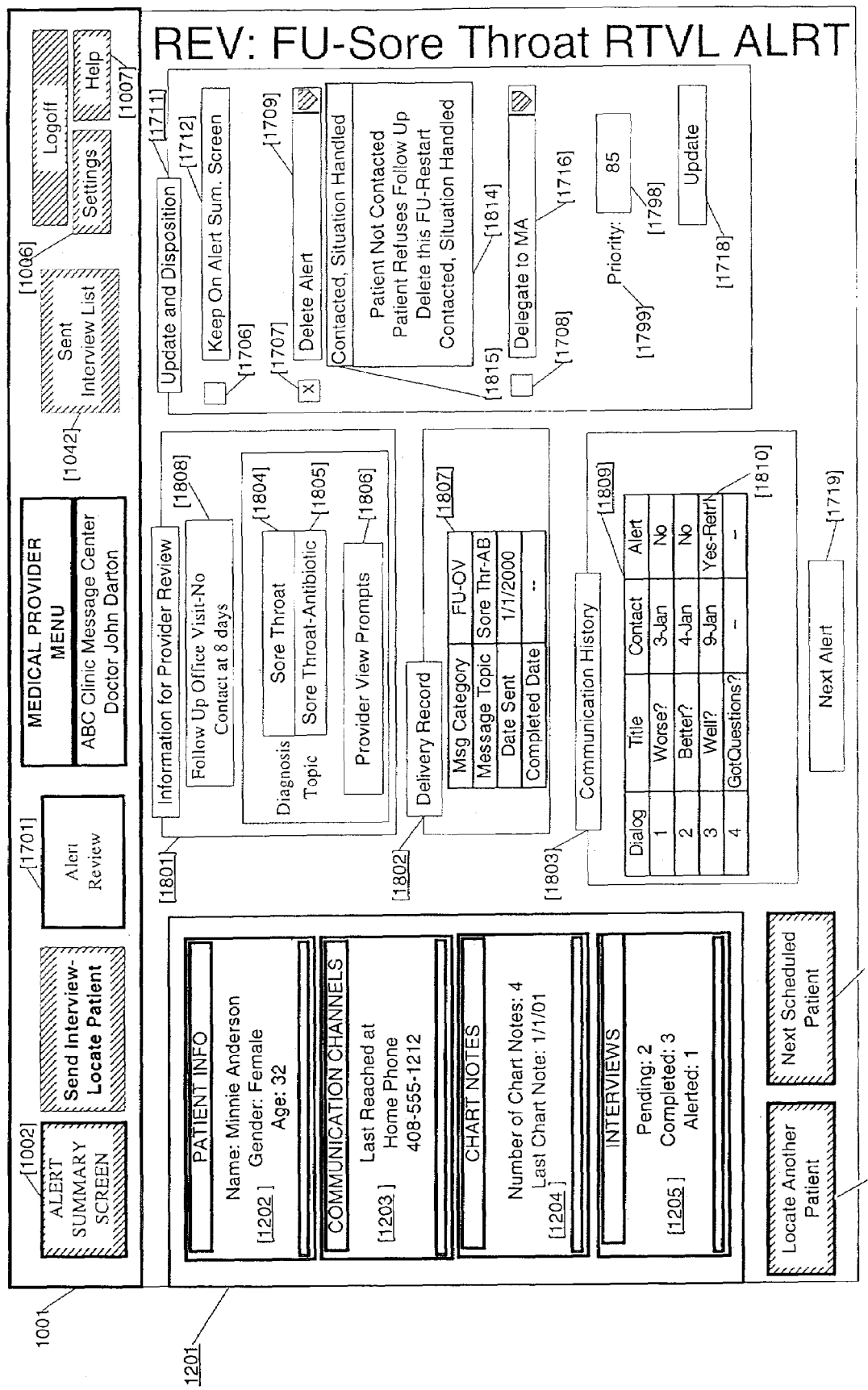
FIG. 18 illustrates another Interview Reviewing screen which may be used by a Medical Service Provider used to review the status of an Office Visit Follow Up for Sore Throat Interview whose in-completion triggered a Retrieval Alert in accordance with the present disclosure.

If checkbox 1707 is checked, indicating the Alert is to be deleted an audit-trail creating, drop down box such as the one (1814) shown in FIG. 18 appears indicating phrases relating to the disposition of the to-be deleted Alert. As a consequence of such delete-and-audit actions, the Alert is automatically removed from its corresponding row in table 1040 of FIG. 10A. In an embodiment, there is logic that automatically routes deleted Alerts for further review by a Quality Assurance Body in accordance with the medical facility's quality assurance standards and the indicated disposition of the Alert.

If in FIG. 17, the Delegate-to MA checkbox 1708 is checked, a table such as shown at 1717 appears listing actions the Medical Provider can check to indicate what the Medical Assistant should do regarding the delegated handling of the Alert. Thus in the example of FIG. 17 the Medical Service Provider has requested through appropriate checkings that the Alert be handled by the Medical Assistant and that the Medical Assistant contact the Patient, inform the Patient of the results, and have the Patient set up an office visit. By checking box 1708 the Medical Service Provider causes the System to responsively move the Alerted Interview from the primary responsibility table 1040 to the delegated responsibility table 1041. Through the illustrated checking of FIG. 17, the MSP further causes the System to responsively set for the corresponding row (not shown) and in the Action column of the Alert in table 1041 the corresponding Action codes "Recall" and "OV" (not shown explicitly, but see row 1032). When delegating an Alert to a Medical Assistant, the MSP may be provided with the option of altering the priority of the delegated Alert so that it will be displayed higher or lower on the MA's prioritized list of delegated Alerts. In one embodiment, the initial, System-calculated priority (1799) for the delegated Alert is displayed in editable region 1798. The priority value can be a positive integer on a scale of, for example, 1–100. So in the illustrated example, the System has initially calculated the priority to be 85 for this particular Alert item (Strep Throat Positive 1714). However, the MSP may supercede this initial value by entering a higher or lower value (or otherwise changing the initial value). The change takes place in response to the MSP activating the Update Button 1718 as explained below. In one embodiment, the System maintains separate priority ratings for a same Alert respectively for the MSP and his/her MA and these, machine-calculated original values, can be independently changed by the MSP if he/she desires to do so and is al lowed to by Application policies. In such a case, the illustrated single box-label 1799 ("Priority") and single, data display/overwrite region 1798 may be replaced by a plurality of such priority display and/or edit mechanisms; e.g., one box label that says "Dr.'s Priority" and has an accompanying first data display/overwrite region such as 1798, and a second box label that says "RN's Priority" and has an accompanying, second data display/overwrite region.

The Update Button 1718 allows updating of the System Database relative to the newly inputted information. The illustrated Next-Alert Button 1719 allows the Medical Provider to proceed directly to a screen appropriate for reviewing the next Alert in table 1040.

FIG. 18 illustrates for one embodiment a Follow up Review screen 1800 which may be used to review a Retrieval Alert of an Interview for following up a sore throat office visit. This screen is presented when the Medical Provider selects a corresponding summary row in table 1040 in FIG. 10A. Most of the elements of the screen in the header bar and on the left hand portion (1201) have been described above. Elements 1701, 17191711, 1706, 1707, 1708, 1712, 1709, 1716, 1798, 1799 and 1718 have also been described above.

Section 1801 holds information for the Medical Provider to review regarding the Alert. The Alert Note gives the basis for the Alert in the highlighted region 1808. The diagnosis applicable to the Interview is listed in box 1804 and the Topic is listed inbox 1805. The Medical Provider or the Testing Facility may have previously placed this information in the System Database. (See, e.g., FIG. 13.) Medical Provider View Prompts are presented in 1806; this area holds information for the Medical Provider generated on the basis of the test results. In an embodiment, typical entries here could hold differential diagnoses for abnormal results on a comprehensive screening battery or suggestions for further tests based on the results found. This information may be formulated on the basis of the test results found for the Patient. In an embodiment, these results may be used in conjunction with Patient Attributes that are recorded in the System Database to further aid in the diagnosis and treatment of the Patient.

Section 1802 holds information regarding the Delivery Record of the Interview, which is presented in table 1807. This indicates that the Interview Category is "FU-OV" or "Follow Up for Office Visit," the Interview Topic is "Sore Throat-Antibiotic," the Date Sent is "1/1/2000," and that the Completed Date is blank.

Section 1803 holds information relating to the Communication History of the Interview. This is detailed in table 1809. Table 1809 shows each of the Dialogs of the Interview and has columns that show the Dialog Number, Dialog Title, Contact Date, and Alert Status. This last column indicates if the Dialog had an Alert and the type, Retrieval or Information. Thus Interview Dialog-1 entitled "Worse?" was retrieved on 3-Jan and engendered no Alert; Interview Dialog-2, "Better?" was retrieved on 4-Jan and resulted in no Alert, but Interview Dialog-3, "Well?," which was sent on 9-Jan resulted in a Retrieval Alert. There is no contact information for Interview Dialog-4, "GotQuestions?," since no attempt has yet been made by the System to deliver it.

In the Update and Disposition section 1711, the Medical Provider has checked box 1707 indicating a desire to delete this Alert. This results in a drop down box 1814 being presented from which the phrase "Contacted, Situation Handled" as shown in 1815 has been selected to indicate how the Alert was taken care of. These actions result in this Alert being removed from table 1040 in FIG. 10A. These actions are logged by the System into an audit-trail log.

In an embodiment, deleted alerts are automatically routed for review by a quality assurance organization. The specific routing of such information for quality assurance review can be made adaptively responsive to the Alert Deletion Phrase used or the Alert Note or the Alert Type.

Figure 19:
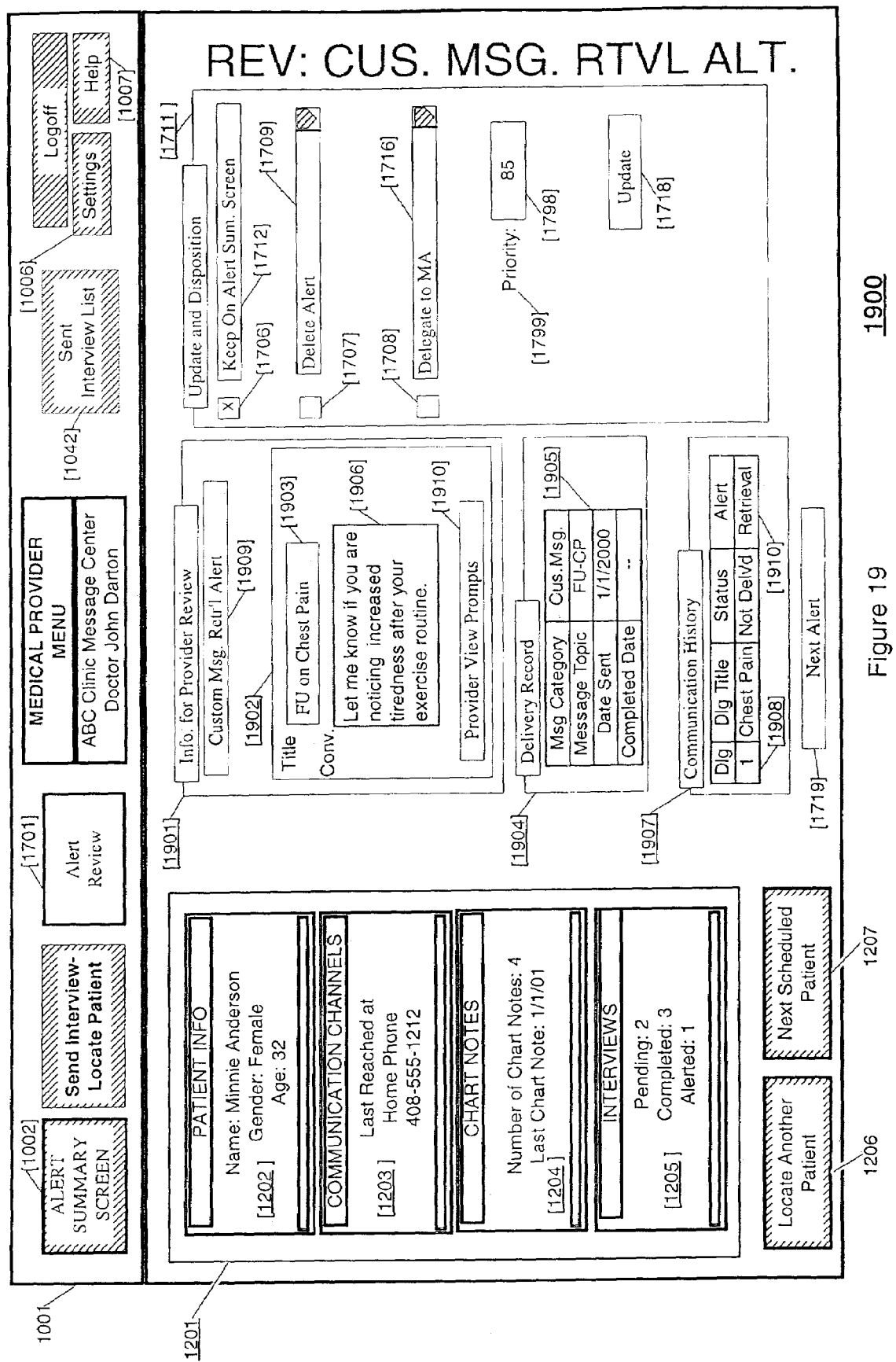
FIG. 19 illustrates another Interview Reviewing screen which may be used by a Medical Service Provider used to review the status of a Custom Message Interview whose in-completion triggered a Retrieval Alert in accordance with the present disclosure.

FIG. 19 illustrates for one embodiment, a Retrieval Alert screen 1900 for reviewing a Retrieval Alert that automatically issued in response to untimely completion of a Custom Interview. This screen 1900 is presented when the Medical Provider selects a corresponding summary row in table 1040 in FIG. 10A. Most of the elements of the screen in the header bar and on the left hand portion (1201) have been described above. Elements 1701, 1719, 1711, 1706, 1707, 1708, 1712, 1709, 1716, 1798, 1799 and 1718 have also been described above.

Section 1901 holds information for the Medical Provider to review regarding the Alert. The highlighted region 1909 indicates this is a Retrieval Alert for a Custom Message. Section 1902 holds information regarding the Custom Message: Box 1903 holds the title of the Interview and Box 1906 holds the text of the message. This information was placed into the System's Database when the Medical Provider created the Interview, e.g., in FIG. 15. If there are any, Medical Service Provider-generated, View Prompts are illustrated in area 1910. Section 1904 shows the Delivery Record of the Interview in table 1905. This indicates the Interview Category is "Custom Message," the Interview Topic is "Follow Up Chest Pain," the Date Sent is "1/1/2000," and that the completion date is blank. Section 1907 gives the Communication History of the Interview in table 1908. This indicates that there is only one Interview Dialog with title "Chest Pain" and Status "Not Delivered;" this Interview Dialog has had a Retrieval Alert triggered. The Update and Disposition section 1711 indicates that the Medical Service Provider has checked box 1706 to keep this Alert in table 1040 of FIG. 10A.

Figure 20:
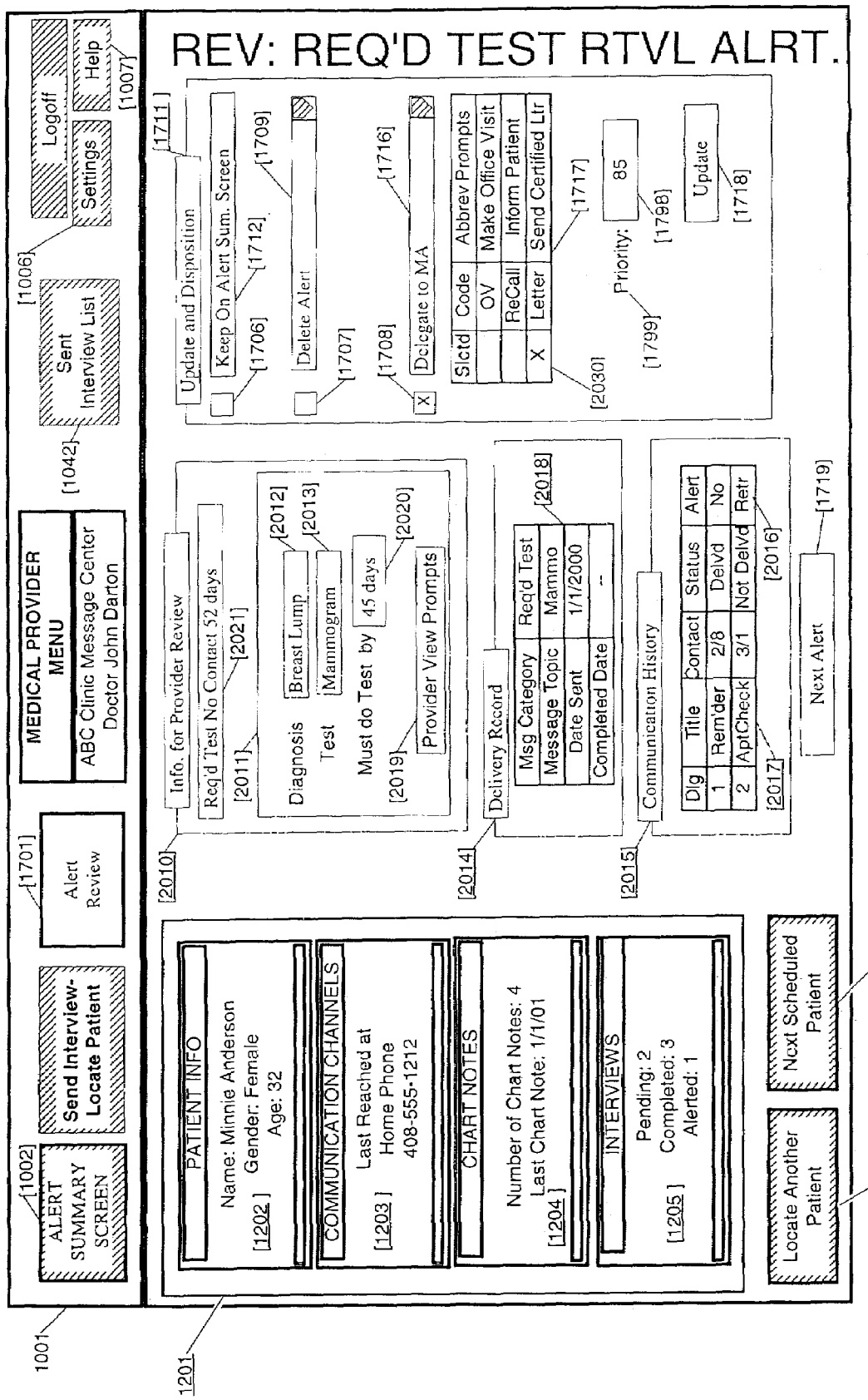
FIG. 20 illustrates another Interview Reviewing screen which may be used by a Medical Service Provider used to review the status of a Required Test Interview whose in-completion triggered a Retrieval Alert in accordance with the present disclosure.

FIG. 20 illustrates for one embodiment, a Test Follow Up screen 2000 which may be used to review a Retrieval Alert for a Required Test Follow Up. This screen is presented when the Medical Provider selects the corresponding summary row in table 1040 in FIG. 10A. Most of the elements of the screen in the header bar and on the left hand portion (1201) have been described above. Elements 1701, 1719, 1711, 1706, 1707, 1708, 1712, 1709, 1716, 1717, 1798, 1799 and 1718 have also been described above.

Section 2010 holds Alert information for the Medical Provider to review. The highlighted region 2021 indicates this is a Retrieval Alert for a required test and that there was no contact with the Patient after 52 days from the time attempted delivery of the Interview was initiated. Section 2011 holds information regarding the Interview: The Diagnosis is 2012 "Breast Lump;" the Test ordered is "Mammogram" 2013, and the Medical Provider felt the test needed to be done within 45 days from the time the Interview was initiated as is indicated in the Must-Do-by box 2020. Section 2019 displays the Medical Provider View Prompts, if any.

Section 2014 has Delivery Record information in table 2018. This indicates the Interview Category is "Required Test," the Interview Topic is "Mammogram," the Date Sent, "1/1/2000," and that the Completion Date is blank.

Section 2015 illustrates the Communication History in Table 2017. The columns in this table show the Dialog Number, the Dialog Title, Contact Date, Dialog Status, and the Alert Status. There are two Dialogs: Interview Dialog-1 is a Reminder Interview that was delivered on 8-February and had no Alert. Interview Dialog-2 is a check that the appointment for the mammogram was kept and was attempted to be delivered on 1-March; it has a Retrieval Alert triggered for it, meaning the MSP's office has not been able to verify that the scheduled test was carried out.

The Update and Disposition section 1711 indicates the Medical Provider has checked box 1708. This last action caused table 1717 to be presented, and the Medical Provider checked box 2030 instructing the Medical Assistant to send a certified letter regarding the need for this test.

Figure 21:
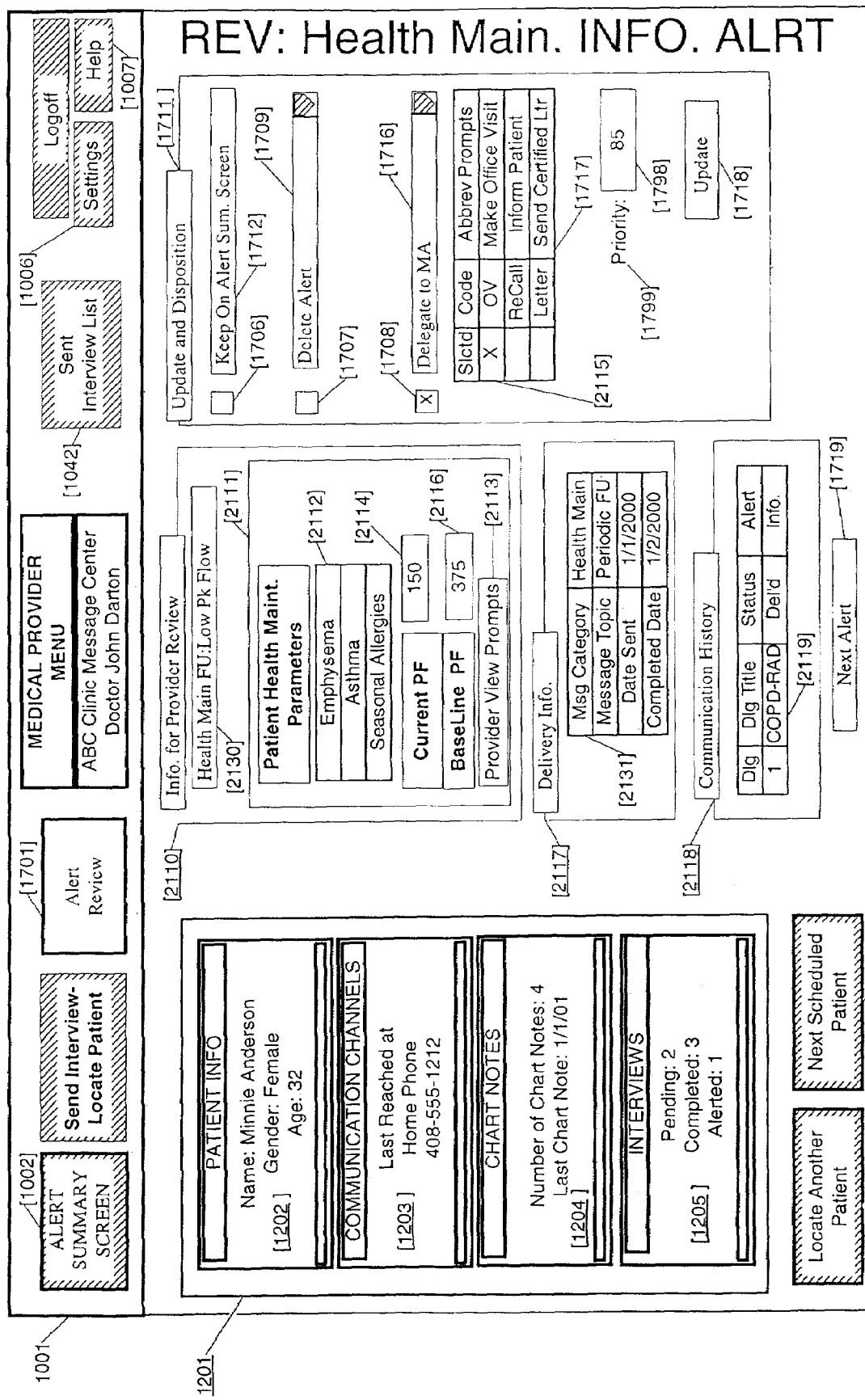
FIG. 21 illustrates another Interview Reviewing screen which may be used by a Medical Service Provider used to review the status of a Health Maintenance Interview whose collected information triggered an Information Alert in accordance with the present disclosure.

FIG. 21 illustrates for one embodiment, an Information Alert screen 2100 which may be used to review an Information Alert for a Health Maintenance Follow Up. This screen is presented when the Medical Provider selects the corresponding summary row in table 1040 in FIG. 10A. Most of the elements of the screen in the header bar and on the left hand portion (1201) have been described above. Elements 1701, 1719, 1711, 1706, 1707, 1708, 1712, 1709, 1716, 1717, 1798, 1799 and 1718 have also been described above.

Section 2110 holds information for the Medical Provider to review regarding the Alert. The highlighted region 2130 indicates this is an Alert for a Health Maintenance Follow Up and that a low value for Peak Flow has been obtained from the Patient. Section 2111 holds information regarding the health status of the Patient relative to the Health Maintenance Follow Up Interview scheme. This data is retrieved from Patient Attributes stored in the System that determined this Health Maintenance Follow up paradigm. Here it is noted that the Patient has emphysema, asthma, and seasonal allergies and in 2116 that her baseline peak flow is 375 and in 2114 that the reported peak flow that lead to the alert is 150. Section 2113 shows any Medical Provider view prompts.

Section 2117 indicates the Delivery Status of the Interview in table 2131. This shows that the Interview Category is "Health Maintenance," the Interview Topic is "Periodic Follow Up," the Date the Interview Dialog was sent was "1/1/2000," and the Date the Interview Dialog was completed was "1/2/2000." Section 2118 illustrates the Communication History of the Interview in table 2119. This table indicates that there was only one Interview Dialog with title "COPD-RAD," (an abbreviation for: Chronic Obstructive Pulmonary Disease and Reactive Airway Disease), and that the delivery status is "delivered" and that the Communication has resulted in an Information Alert, meaning that during the delivered Interview, the System automatically determined that information provided by the Patient needed alerted attention by the Medical Service Provider and that the System therefore automatically generated a corresponding Alert which was posted to the MSP's alerts table (see for example row 1018 of FIG. 1A).

Section 1711 of FIG. 21 indicates that the Medical Provider has checked box 1708 causing table 1717 to be presented. The Medical Provider has indicated a desire to have the Medical Assistant set up an office visit for the Patient by the check-off indicator activated in box 2115.

Figure 22:
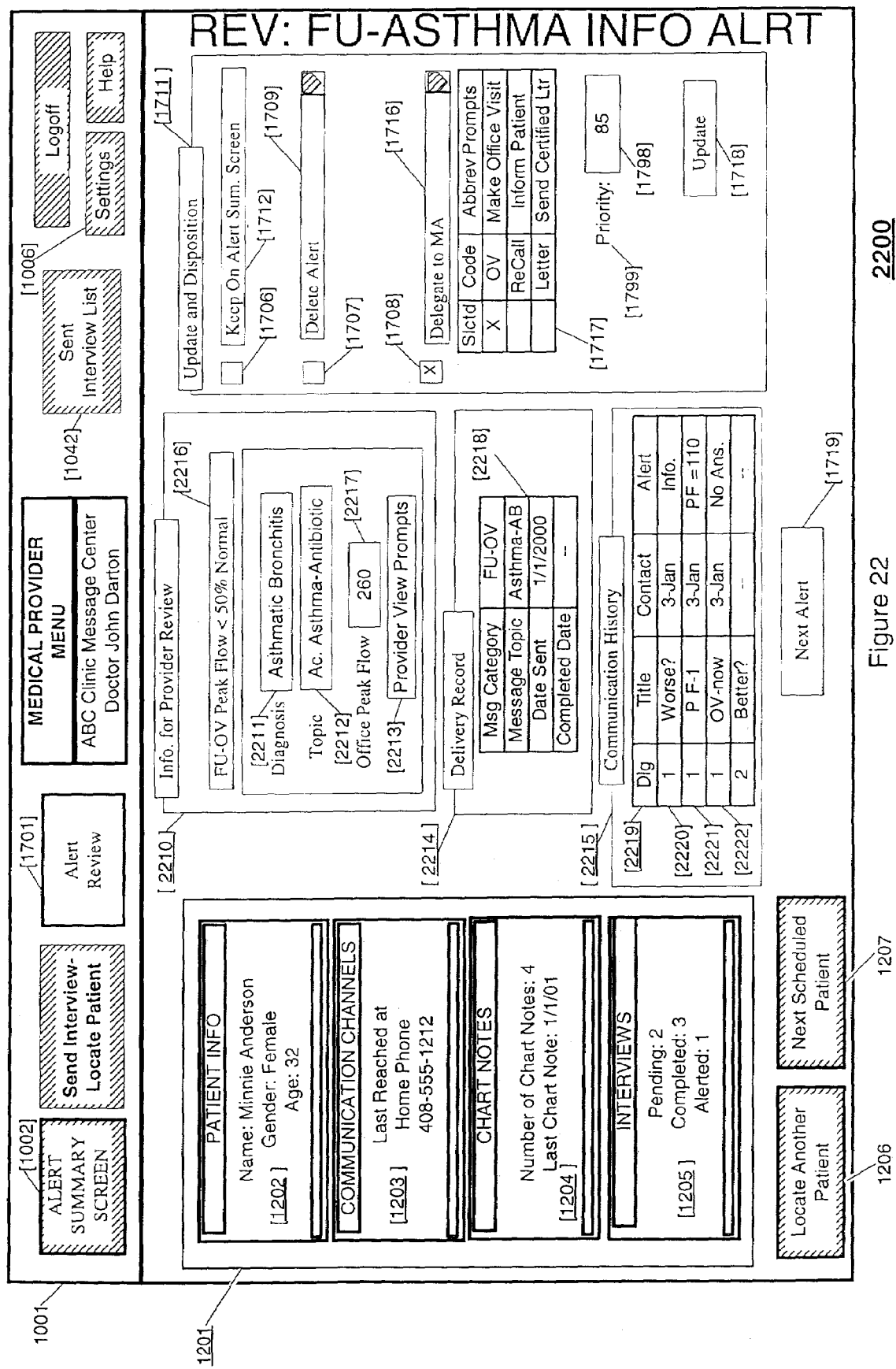
FIG. 22 illustrates another Interview Reviewing screen which may be used by a Medical Service Provider used to review the status of an Office Visit for Asthma Follow-Up Interview whose collected information triggered an Information Alert in accordance with the present disclosure.

FIG. 22 illustrates another Follow up Review screen 2200 which may be used in an embodiment to review an Information Alert that was automatically generated by the System during an Interview for following up an acute asthmatic bronchitis office visit. This screen is presented when the Medical Provider selects the corresponding summary row in table 1040 in FIG. 10A. Most of the elements of the screen in the header bar and on the left hand portion (1201) have been described above. Elements 1701, 1719, 1711, 1706, 1707, 1708, 1712, 1709, 1716, 1798, 1799 and 1718 have also been described above.

Section 2210 holds information for the Medical Provider to review regarding the Alert. Several Alerts have been triggered by this example of an alert-generating and under-review Interview. The System can present one or more of the corresponding Alert Notes in the highlighted region 2216. The diagnosis applicable to the Interview, "Asthmatic Bronchitis," is listed in box 2211 and the Topic, "Acute Asthma-Antibiotic," is listed in box 2212. The Medical Provider or the Medical Assistant may have previously placed this information in the System Database. Also shown in box 2217 is the Peak Flow value observed during the office visit. Medical Provider View Prompts, if any, are given in box 2213.

Section 2214 holds information regarding the Delivery Record in table 2218. This shows that the Interview Category is "Follow Up Office Visit," the Interview Topic is "Asthma-Antibiotic," the Date Sent was "1/1/2000" and that there is no completion date.

Section 2215 illustrates the Communication History of the Interview in table 2219. The column headings of this table are: Dialog Number, Title (of Dialog or Question in the Dialog), Contact Date, and Alert. Four entries are shown in the table. The first is for the question of Interview Dialog-1 entitled "Worse?" The Contact Date was "3-January" and the Patient's response resulted in an Information Alert. The second entry is for the Peak Flow reading requested in Interview Dialog-1 of the Interview; the Contact Date is again "3-January." The value inputted into the System is 110 and this resulted in the automatic generation of yet another Information Alert since the reported value is significantly low and below 50% of normal for the Patient. The third entry is for the acknowledgment to the next Interview Dialog phrase requesting the Patient go immediately to the office or an emergency room. The Contact Date is again "3-January." No response was obtained from the Patient to acknowledge receipt of this instruction, so this is also automatically alerted. The next entry row in table 2219 is the first question of the second Dialog, "Better?" and the table indicates that this message was not delivered. The Medical Provider has made an entry in box 1708 in section 1711 of FIG. 22. This instructs the Medical Assistant to arrange an office visit for the Patient and moves the Alerted Interview to table 1041 in FIG. 10A.

Figure 23:
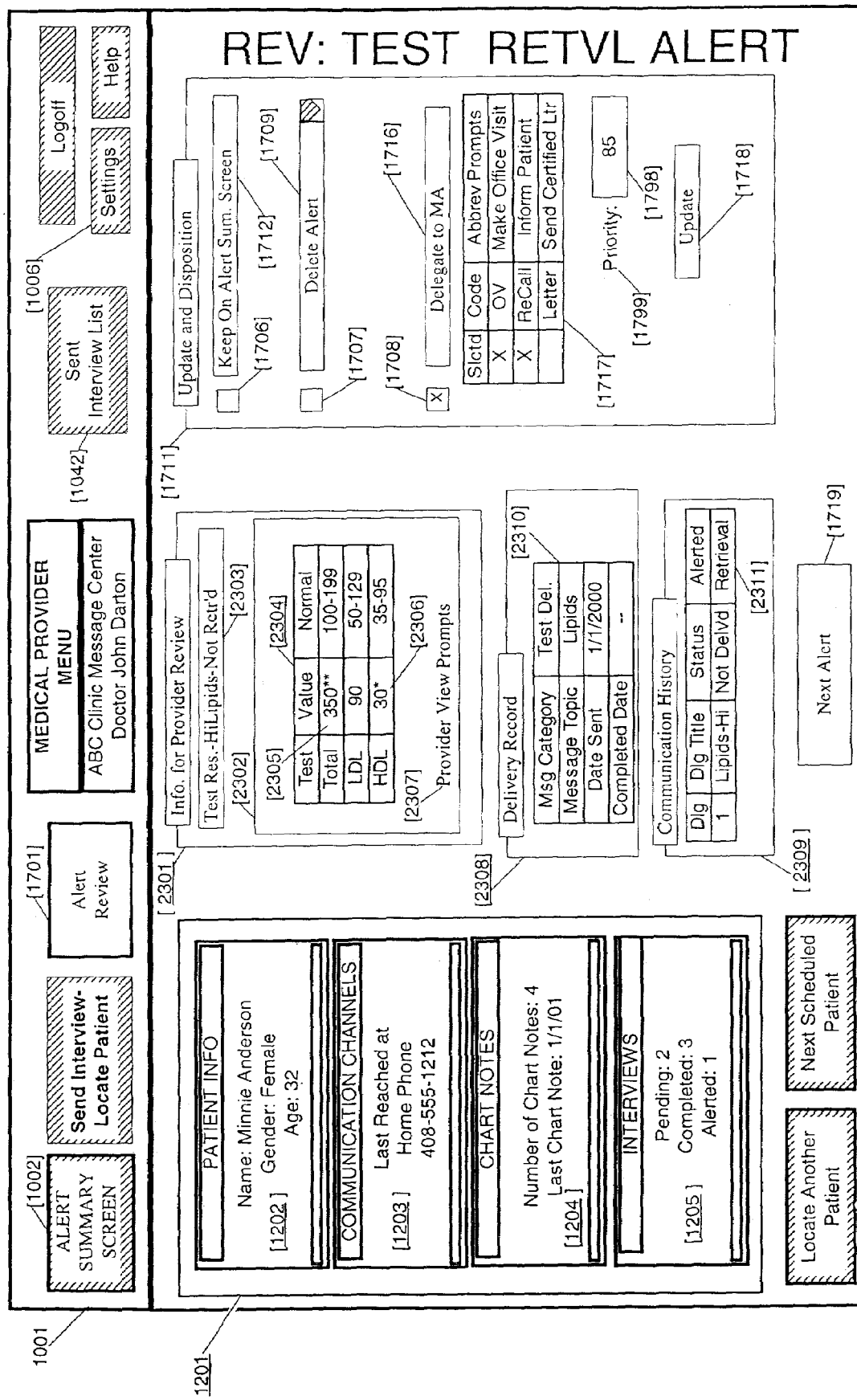
FIG. 23 illustrates another Interview Reviewing screen which may be used by a Medical Service Provider used to review the status of a Test-Result Delivering Interview whose in-completion triggered a Retrieval Alert in accordance with the present disclosure.

FIG. 23 illustrates another Test Result Retrieval Alert screen 2300 which may be used in an embodiment of the current disclosure to review a Test Result Retrieval Alert for an Interview delivering lipid test results to a Patient. This screen is presented when the Medical Provider selects the corresponding summary row in table 1040 in FIG. 10A. Most of the elements of the screen (2300) in the header bar and on the left hand portion (1201) have been described above. Elements 1701, 1719, 1711, 1706, 1707, 1708, 1712, 1709, 1716, 1798, 1799 and 1718 have also been described above.

Section 2301 holds information for the Medical Provider to review regarding the Alert. The highlighted area 2303 indicates the basis for the Alert from the Alert Note. Here it is indicated that this is a Retrieval Alert for a Test Result that showed elevated lipids. Section 2302 holds table 2304 that contains the name of the test, the values observed, and the normal range for the values. Cell 2305 is highlighted (e.g., by double asterisks) and indicates an abnormally high value for the Patient's Total Cholesterol; cell 2306 is highlighted differently and indicates a lower than normal HDL level, which is of relatively less concern. In an embodiment, displayed or other (e.g., voice-based) presentations of test results can be made adaptively responsive to rules defined within the System and some of these presentations may be visually and/or otherwise (e.g., auditory alarm bell sound) accentuated automatically to reflect the seriousness of the result.

Area 2307 holds Medical Provider View Prompts, if any. Section 2308 illustrates delivery information for the Interview in Table 2310. This shows the Interview Category is "Test Delivery," the Interview Topic is "Lipids," the Date Sent was "1/1/2000," and that the completion date is blank. Section 2309 holds information on the Communication History of the Interview in Table 2311. This table indicates that there is only one Interview Dialog with title "Lipids-High" and Status "Not Delivered." This Interview Dialog has had a Retrieval Alert triggered as indicated in the highlighted cell 2311.

The Medical Provider has indicated in FIG. 23 at section 1711 by checking box 1708 that this Retrieval Alert is to be delegated to the Medical Assistant. The Medical Provider has checked boxes in the table 1717 instructing the Medical Assistant to inform the Patient of the test results and have the Patient set up an office visit.

Figure 24:
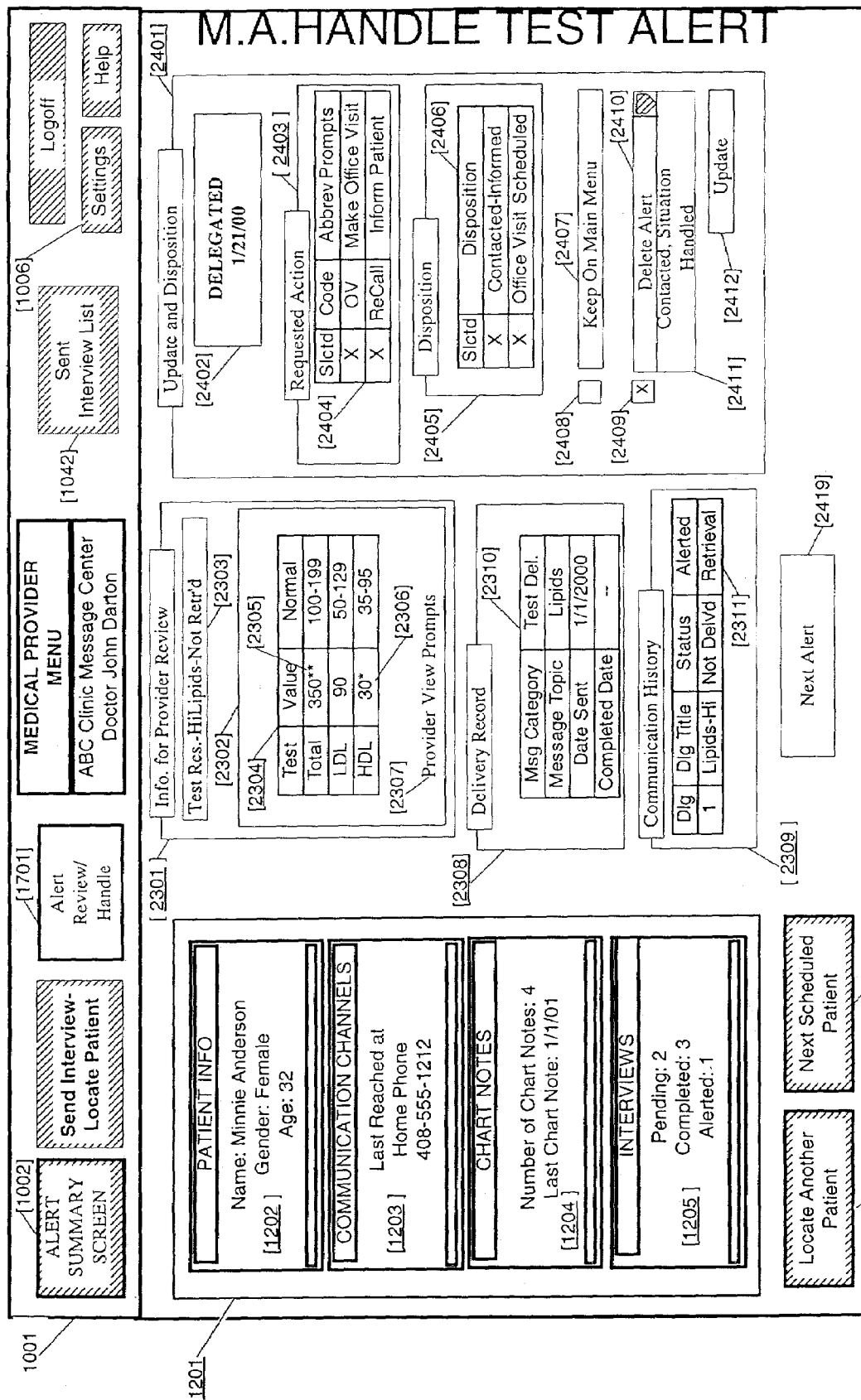
FIG. 24 illustrates a Delegated Alert Follow-Up screen which may be used by a Medical Assistant to handle a delegated follow up on a Test Result Delivery Interview whose in-completion triggered a Retrieval Alert in accordance with the present disclosure.

FIG. 24 illustrates a Delegation screen 2400 which may be used for allowing a Medical Assistant to respond to a test Retrieval Alert in accordance with instructions sent via the System from a Medical Service Provider. The illustrated screen 2400 concerns a Retrieval Alert that was raised by the System because of an Interview delivery failure for a lipid test that showed elevated cholesterol levels. This screen 2400 is presented to the Medical Assistant when that MA selects the corresponding summary row in table 1041 in FIG. 10A. Most of the elements of the screen (2400) outside of the Update and Disposition section 2401 and Next Alert button 2419 have been described above and thus do not need to be detailed again.

In the Delegated Disposition section 2402 there is an indication of the date the handling of this Alert was delegated to the Medical Assistant. The Requested Action area 2403 holds table 2404 that indicates the actions the Medical Provider requested be done for this alert, namely in this example, for the MA to inform the Patient of the result and set up an office visit for the Patient. Section 2405, entitled Disposition holds a table 2406 which provides a mechanism by way of which the Medical Assistant can indicate to the System whether and which of the requested actions were completed. In this case the Patient was contacted and informed of the results and an office visit was scheduled. Below Disposition section 2405 there are provided check boxes 2408 and 2409 where the Medical Assistant may choose to keep this Alert in table 1041 (2407) or delete it from table 1041 (2409). If the latter action is chosen as indicated in 2409 a drop down box may be accessed to provide an audit trail for the disposition of the Alert as is indicated for example in area 2411. Button 2412 allows for the information added on this screen to be recorded and the System's Database updated.

In one embodiment, Medical Assistants are blocked from being able to delete an altered (handled) Interview Alert without a Medical Provider's review of the handling of the Interview. Activating button 2419 brings up on the display of FIG. 24 information for the next Alert in table 1041.

Figure 25:
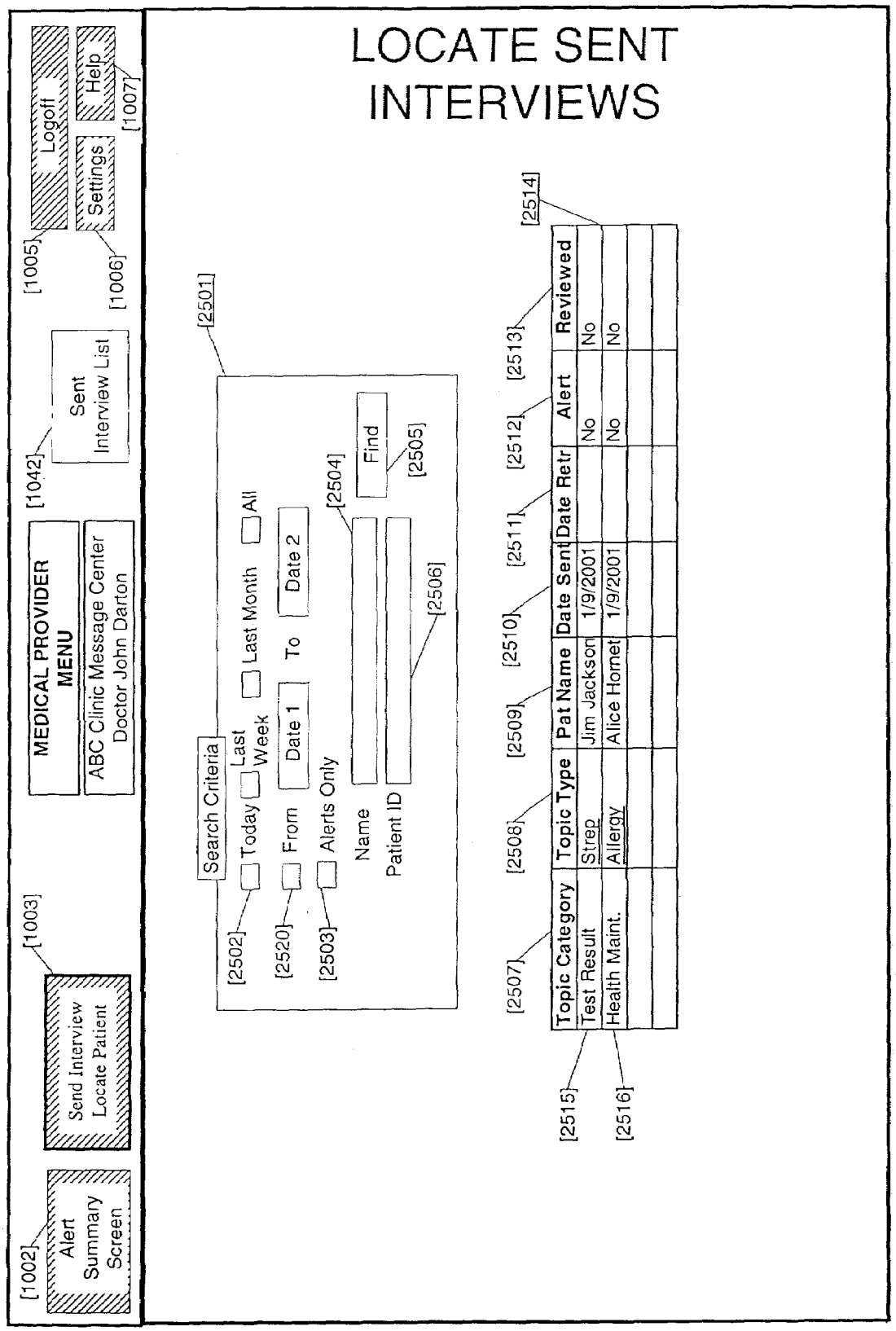
FIG. 25 illustrates an Interviews finding screen which may be used by a Medical Service Provider to locate for review and/or editing, sent Interviews whose delivery has been initiated within a System in accordance with the present disclosure.

FIG. 25 illustrates a Sent Interviews Finding screen 2500 which may be used to identify and/or locate sent Interviews within an embodiment of the current disclosure. The illustrated screen 2500 is one that Medical Service Providers may view upon selecting button 1042 of any of FIGS. 10A–24. The area of mouse-activatable button 1042 is highlighted in FIG. 25 to indicate that this screen has been selected. The Interviews Finding screen 2500 comprises a search criteria section 2501 which may be used for defining the search criteria to be used for automatically locating sent Interviews of the System. The Interviews Finding screen 2500 may further comprise a search-results table 2514 that shows the Sent Interviews that have been found by the System to fulfill the criteria established in section 2501.

In one embodiment, the search criteria section 2501 contains a first row of temporal option choices 2502 which allow a Medical Provider to either search for Interviews sent today, last week, last month or at anytime ("All"). The latter choice is, of course limited to the time period for which sent Interviews are kept on the System Database. The second row provides another temporal option choice 2520 which allows a search for Interviews sent during a user-specified time range. Search-restricting box 2503 allows the Medical Provider to restrict the searching to only a particular kind of sent Interviews such as those that have been alerted. Search-qualifying box 2504 allows the Medical Provider to enter a name of a Patient and to thereby confine the list produced to only Interviews relating to that Patient. The other, illustrated search-qualifying box 2506 provides for a similar narrowing of the search results using the Patient's ID. In one embodiment, there is a further field (not shown) in which a Medical Provider can enter a group designation in order to find the sent Interviews to members of that group.

Table 2514 presents information about the Interviews that have been found by the System in response to the given search criteria. Table 2514 has columns with headings giving the following information for each Interview illustrated: Topic Category 2507, Topic Type 2508, Patient's Name 2509, Date Sent 2510 which gives the date at which the Interview was sent, Date Retrieved 2511 which gives the date at which the Interviews were retrieved, Alert 2512 which indicates if the Interview was alerted, and Reviewed 2513 which indicates if the Interviews were reviewed and, if so, shows the name of the reviewer. The illustrated example of table 2514 holds two Interviews that were sent on Jan. 9, 2001 but not retrieved by either Patient; neither Interview was alerted.

Figure 26:
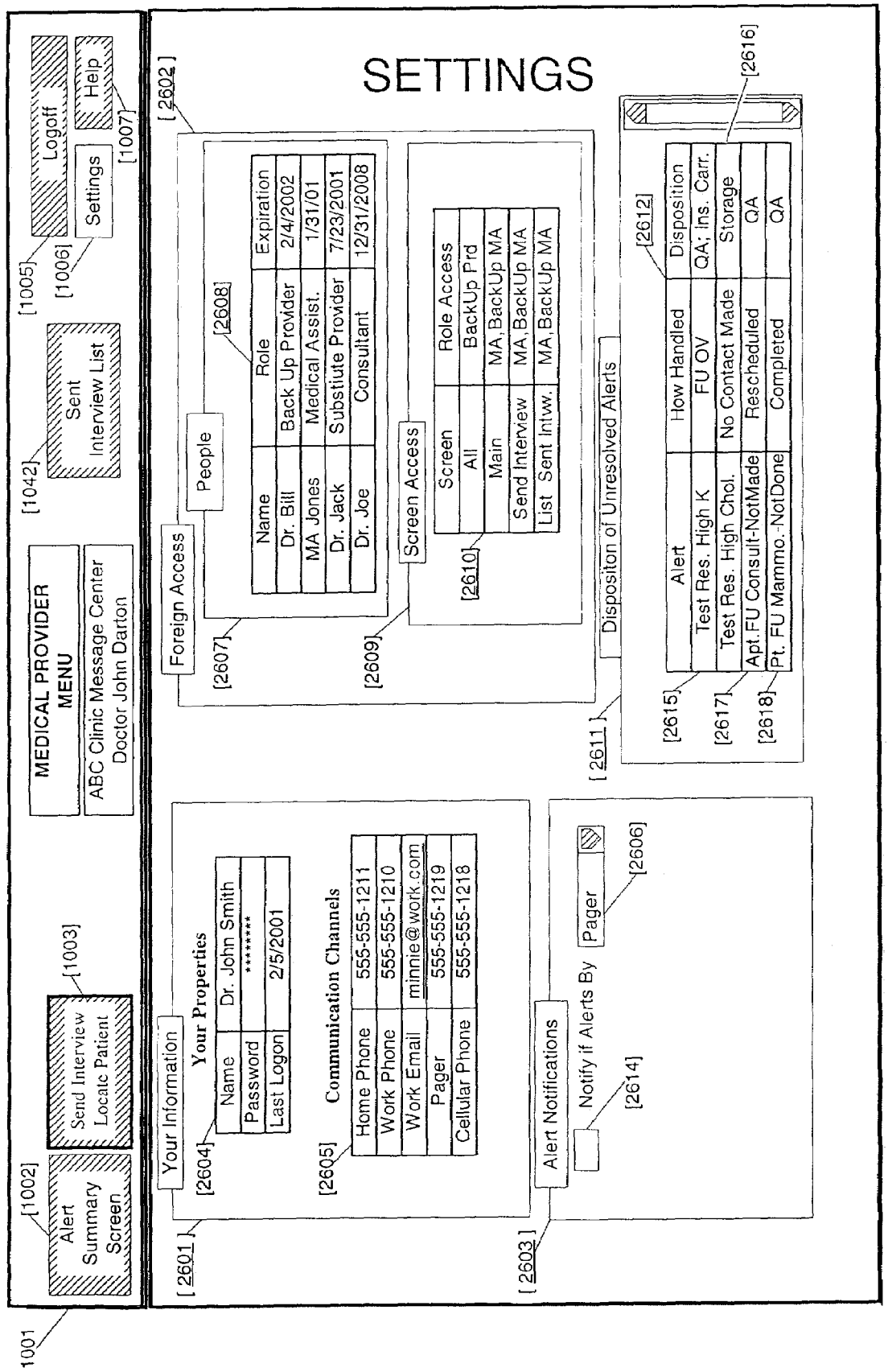
FIG. 26 illustrates an Account Settings reviews screen which may be used by a Medical Service Provider to review and/or change settings in his or her Account within a System in accordance with the present disclosure.

FIG. 26 illustrates an Account settings screen 2600 which may be used to adjust MSP account settings in an embodiment of the current disclosure. Most of the elements in the header bar have been previously described. Settings tab 1006 is highlighted indicating that this button has been selected by the Medical Provider to show this screen.

Screen section 2601 holds "Your Information" which shows information relating to the Medical Provider who is the Account Owner. This includes table 2604 "Your Properties" which holds the name of the Account Owner, the password, the last login date and time, and other Attributes. Also included is table 2605 "Communication Channels"

which holds addresses and contact numbers for various communication channels to reach the Account Owner. These may include home phone, work phone, work email, pager, and cellular phone numbers.

Section 2603 entitled "Alert Notifications" holds a drop down text box 2606. If the Account Owner indicates a desire to be notified of Alerts by means other than just the System screens by checking box 2614, drop down box 2606 indicates an ordered list of other channels to use for this purpose. The electable, other channels may include one or more of wireless pager(s), cell phone(s), PDA(s), email address(es) and so forth.

Section 2602 "Foreign Access" holds information regarding other people who may access this Account Owner's account. The Foreign Access section may also be used to designate which screens may be used by the correspondingly identified Foreign Persons. As seen, the Foreign Access section 2602 contains a "People" table 2608 in section 2607 which lists the names, roles and/or privilege expiration dates of the foreign persons who are to have such account access privileges. Thus in exemplary table 2608, Dr. Bill is given the privileges of a "Back Up Medical Provider" until Feb. 4, 2002, MA Jones is given the privileges of serving as a Medical Assistant until Jan. 31, 2001, Dr. Jack is given the privileges of serving in the Role of Substitute Medical Provider until Jul. 23, 2001, and Dr. Joe is given the privileges of serving in the Role of Consultant until Dec. 31, 2008.

The illustrated section 2609 entitled "Screen Access" holds table 2610 with columns entitled "Screen" and "Role Access." This table indicates which screens in the Account are to be given access to by which Roles. Thus, in accordance with the illustrated example, a Backup Medical Provider can access all screens. On the other hand, only the Main, Send Interview, and List Sent Interview screens can be accessed by the Medical Assistant and the Back Up Medical Assistants.

In an embodiment, section 2611 entitled "Disposition of Unresolved Alerts" holds table 2612 with columns entitled Alert, How Handled, and Disposition. The first column describes an Alert type and associated Topic category, the second column indicates how this situation was handled so far, and the third column indicates the follow up disposition for purposes of quality assurance and review after it is deleted from the System. Thus in row 2615 the clinic's quality assurance group and also the mal-practice insurance carrier are to further review the Retrieval Alert for a high potassium test abnormality handled by a follow up office visit. A Retrieval Alert 2616 for a high cholesterol value for which no successful subsequent contact was made is to be merely stored rather than reviewed by further QA entities. In row 2617 the quality assurance group is to review a consultation appointment follow up that was not made and was rescheduled. In row 2618 a follow up mammogram that was initially not done but subsequently completed is also to be subject to review by the quality assurance group.

Figure 27:
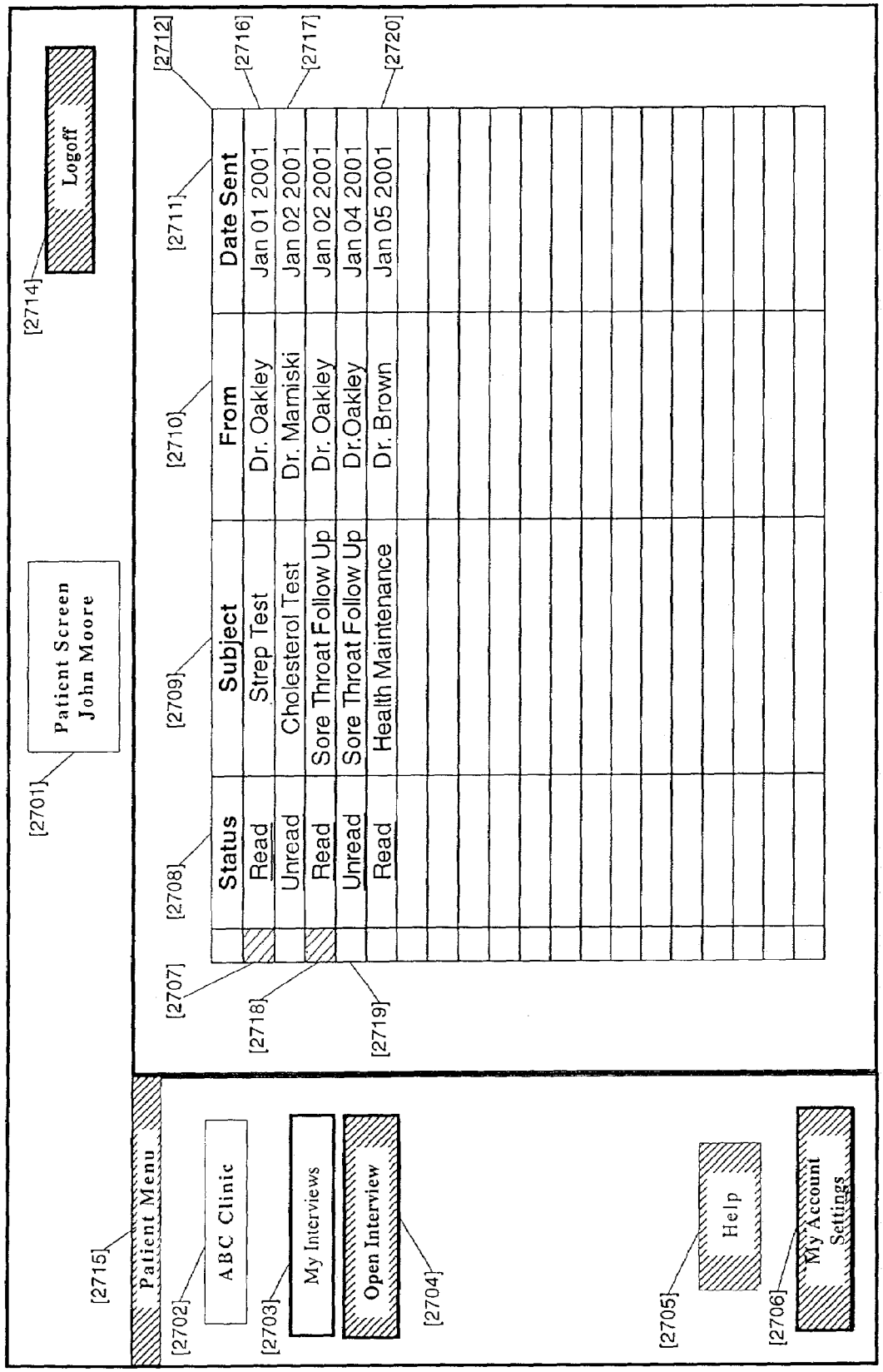
FIG. 27 illustrates an Interviews Opening screen which may be used by a Patient or another authorized Target to view, review and/or respond to Interviews he or she has received in accordance with the present disclosure.

FIG. 27 illustrates a Patient Screen 2700 that summarizes a Patient's Interviews over a period of time and for a given clinic (ABC Clinic) in accordance with the present disclosure. The title bar has a heading 2701 that indicates that this screen is for the Patient and gives the Patient's name and a logoff button 2714. The Patient Menu 2715 holds section 2702 that shows the name of the medical clinic and application that this screen is a part of, a button 2703 for selecting a table of all Patient Interviews in the given period, an Open button 2704 for presenting a screen that details the contents of a selected Interview, a help button 2705, and a Settings button 2706 to present a screen for the Patient to see his or her screen and account settings.

In one embodiment, each Patient is given the ability to access and edit portions of the information held on the corresponding Patient Screen. The My Interviews button 2703 is highlighted to indicate the Patient wishes to see his Interviews. Table 2712 illustrates the Patient's Interviews and has the following columns: 2707 which, if highlighted, indicates that the Interview on the corresponding row has a Retrieval Alert, "Status" 2708 which indicates if the Interview has been read or not by the Patient, "Subject" 2709 which gives the title of the Topic of the Interview, "From" 2710 which indicates the source of the Interview, and "Date Sent" 2711 which indicates the date that the Interview Dialog referred to on the row was first sent to the Patient.

In the illustrated example, row 2716 holds an Interview with a potential Retrieval Alert that has been read by the Patient and reports a Strep test result. Dr. Oakley sent this Interview on Jan. 1, 2001. Row 2717 holds an unread Interview reporting on cholesterol test results sent by Dr. Marniski on Jan. 2, 2001; it does not have a potential Retrieval Alert. Row 2718 refers to a Interview Dialog in a Sore Throat Follow Up Interview subsequent to an office visit. The Patient has previously accessed and read this Interview; Dr. Oakley sent the Interview on Jan. 2, 2001. Row 2719 illustrates a second, unread Interview Dialog for Sore Throat Follow Up subsequent to an office visit from Dr. Oakley sent on Jan. 4, 2001; this Interview Dialog does not have a potential Retrieval Alert. Row 2720 is a Health Maintenance Interview sent by Dr. Brown on Jan. 5, 2001 which does not have a potential Retrieval Alert.

Figure 28A:
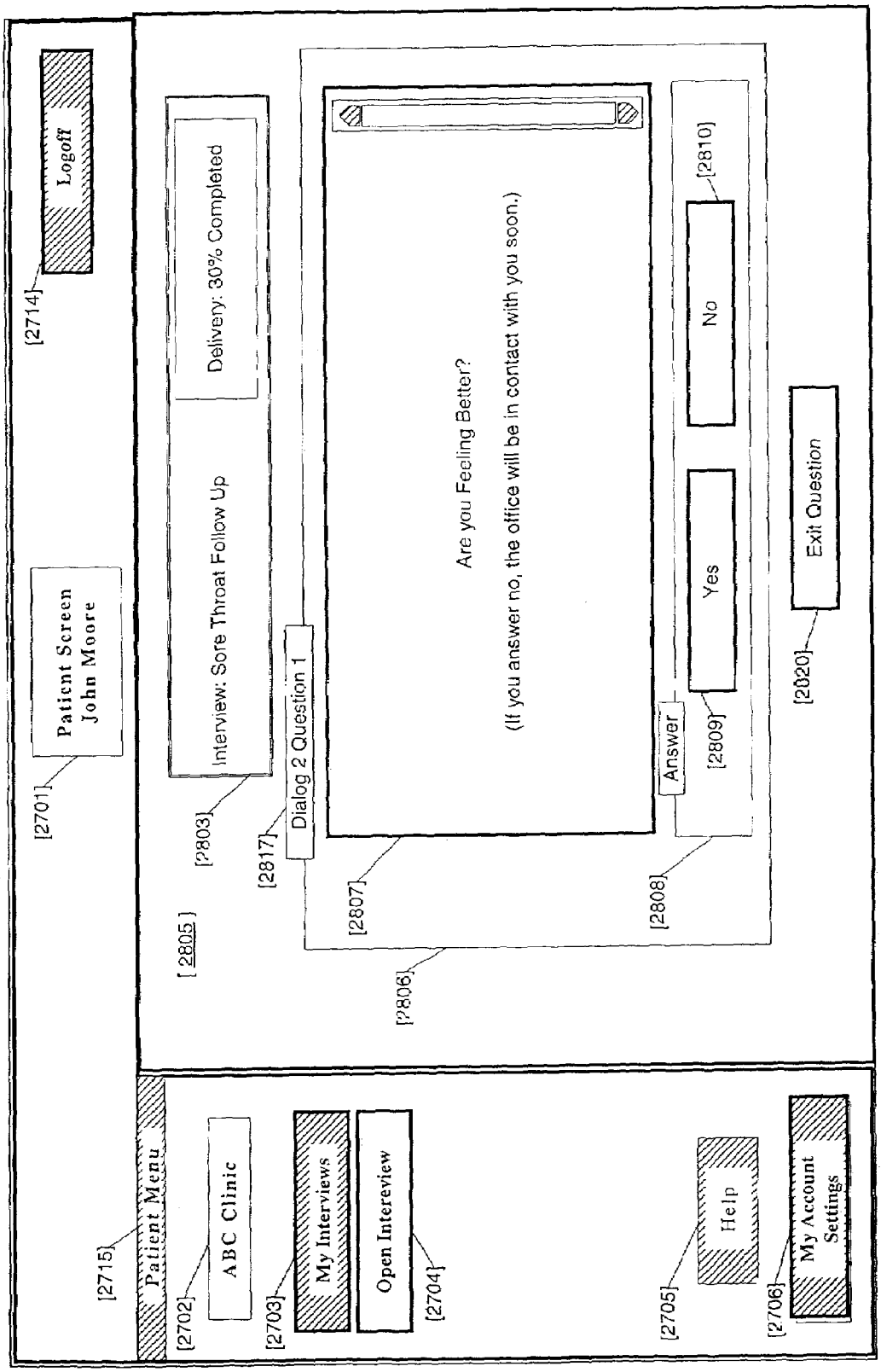
FIG. 28A illustrates a first Opened Interview screen which may be used by a Patient or another authorized Target to view, review and/or respond to an Interview for an Office Visit Follow Up for a Sore Throat which is being delivered in accordance with the present disclosure.

FIG. 28A illustrates an example of Patient screen 2800 which may be delivered to the identified Patient during the carrying out of an Acute Illness Monitor Interview, in accordance with the present disclosure. Most of the elements of the header bar and side bar of the screen (2800) have been described above. Button 2704 (Open Interview) is highlighted indicating that the Patient has chosen to view this Interview. This screen may be accessed by the Patient selecting the Interview in table 2712 of FIG. 27 and selecting button 2704 or by double clicking on this Interview in table 2712.

Section 2805 holds box 2803 that includes the Interview Topic title, "Sore Throat Follow Up," a statement "Delivery: 30% Completed," and progress box that indicates how much of the Interview Dialogs have been delivered to the Target (Patient) to date.

Section 2806 contains in the title line 2817 the Interview Dialog number and question of the Interview. The question is illustrated in 2807 with associated informative information. Section 2808 "Answer" holds buttons for the Patient to indicate his or her answer: For example, 2809 for "Yes" and 2810 for "No." The Patient may exit this question screen by selecting either 2809 or 2810 or the "Exit Question" button 2820.

Figure 28B:
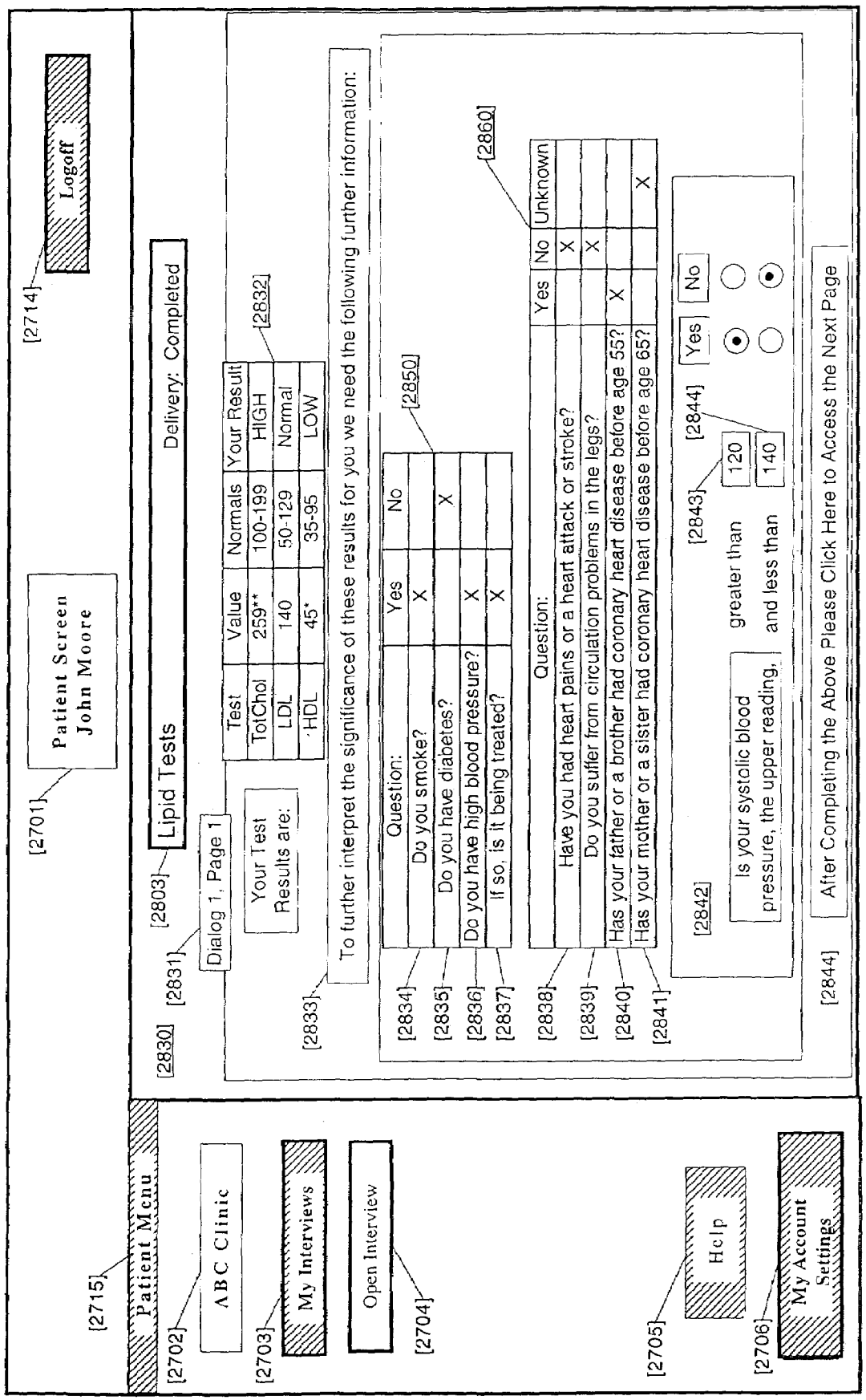
FIG. 28B illustrates a second Opened Interview screen which may be used by a Patient or another authorized Target to view, review and/or respond to an Interview concerning Lipid Test Results which is being delivered in accordance with the present disclosure.

FIG. 28B illustrates a delivery of a more complicated Interview to a Patient. Here the MSP desires to communicate a lipid panel test result to the Patient and advise the Patient of recommendations and information based on these results, the Patient's medical information or Attributes—some of which are known to the System and some of which need to be obtained from the Patient at the time of Interview delivery, and current guidelines of an educational authority such as the National Cholesterol Education Program (Journal of the American Medical Association, May 16, 2001, p. 2486–2497.)

In the illustrated example, the authority guidelines call for three categories of messages based on the lipid results as follows:

(1) The lipid test results are fine in relationship to the Patient's Attributes and no interventions are called for;
(2) The lipid tests in relationship to the Patient's Attributes call for recommendations for changes in the life style of the Patient—e.g., certain diet, exercise, or weight changes;
(3) The lipid tests are in a range where medications are indicated if life style changes can not or have not improved the results.

The System-generated decision as to which of these messages will be delivered to the Patient may be made to depend on the test results and processing of these results in terms of Patient Attributes by code, for example, either on the System's server if the Patient is accessing the information on a personal page behind the System's firewall or in a cookie delivered by the System to the Patient's own secured web page. If algorithm-requested information such as certain Patient Attributes is already known to the System (it's in the Database), the executing code may omit presenting the requests for this already-known information.

An exemplary part of the National Cholesterol Education guidelines recommend three LDL goal levels in accord with the Patient's risk of developing coronary artery disease (CAD) as follows:

(I) If the Patient has CAD or what is considered an equivalent such as diabetes mellitus or peripheral arterial disease, an accepted recommendation is to consider drug therapy if the LDL is above 100 mg/dL.

In such a situation, if the System's Patient Attributes include information indicative of this and the LDL is above 100 mg/dL, no Patient questions need to be presented by the System and a recommendation compatible with guideline option (3) above, is presented. Alternatively, the same action results if this information is not already available and the Patient affirms question 2838 or 2839. On the other hand, if the Patient has a combination of risk factors that confer a 10-year risk for CHD of more than 20% by the Framingham Heart Study parameters (See e.g., Framingham Heart Study Bibliography, www.nhlbi.nih.gov/about/Framingham), this recommendation also applies. The System accesses this 10-year risk as discussed below.

(II) If the Patient has two or more major risk factors exclusive of LDL and the calculated 10-year Framingham CAD risk is 10% to 20%, a level of LDL above 130 calls for consideration of drug therapy. If the Framingham calculated risk is less than 10% for a Patient with two or more risk factors, the drug determining LDL level is 160 mg/dL.

In such a case, major risk factors that may be considered can include cigarette smoking, high blood pressure, age, and aspects of family history. These, if not already known to the System as Patient Attributes, are asked of the Patient in questions 2834, 2836, 2840 and 2841. If the Patient passes the criteria in guideline (I) above and the Patient's LDL level is sufficiently elevated, the System may next process the information of these questions to see if this LDL level criteria applies. This may be done in conjunction with the calculation of the Framingham risk as discussed below.

(III) If the Patient has less than two major risk factors exclusive of LDL as listed above, the LDL level above which drug therapy is considered is 190 mg/dL. Thus information of questions 2834, 2836, 2840, and 2841 in conjunction with the reported LDL level determines if the Patient falls into this category and which recommendation is presented.

Figure 28C:
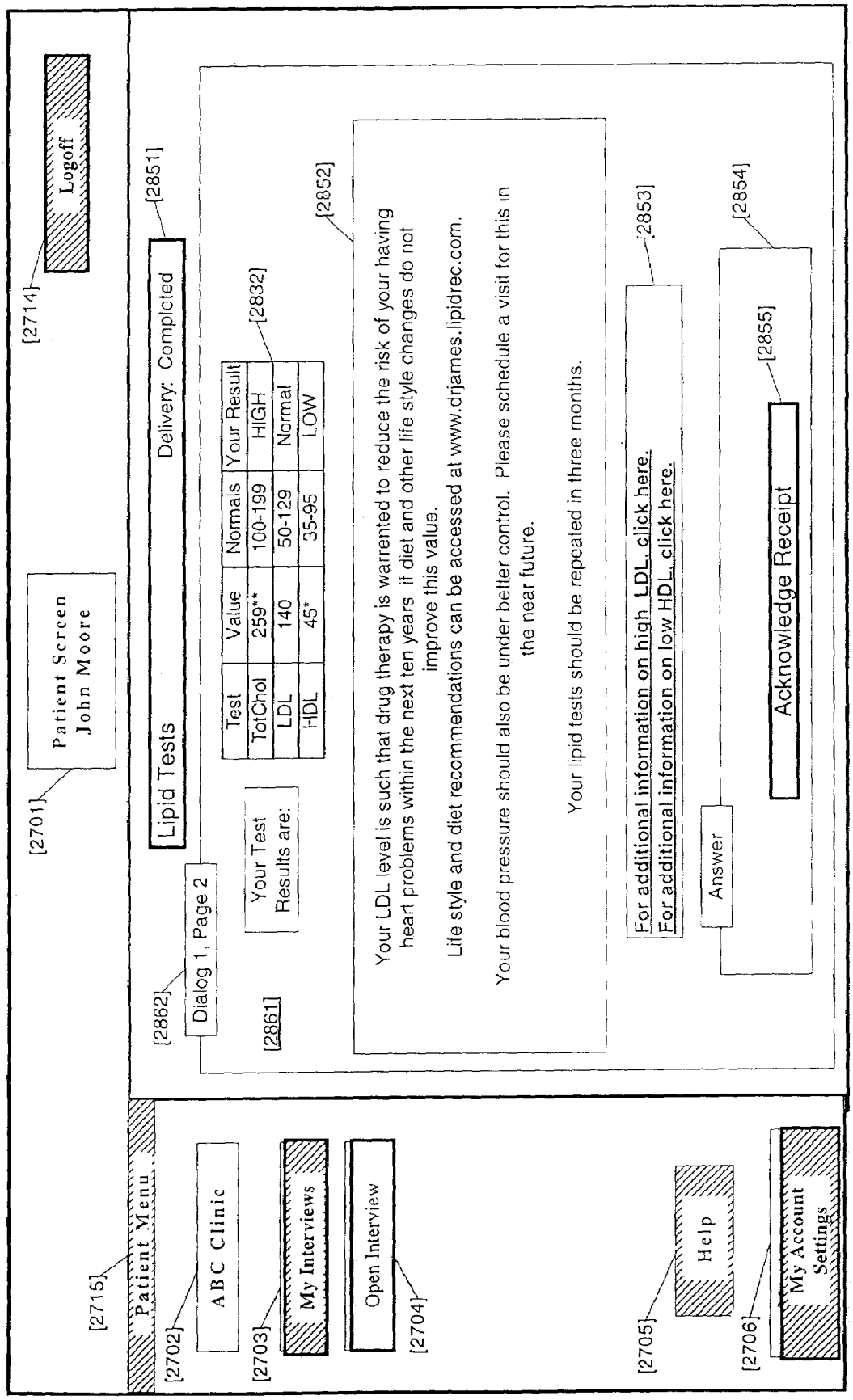
FIG. 28C illustrates a third Opened Interview screen which may be used by a Patient or another authorized Target to view, review and/or acknowledge an Interview concerning Lipid Test Results that has been delivered in accordance with the present disclosure.

In the above case, calculation of the 10-year risk for CAD with the Framingham Data may use a point system based on the following variables: sex, age, total cholesterol, smoker or not, HDL level, if the patient is under treatment for hypertension, and the systolic blood pressure. Except for the systolic pressure, the System should obtain values for all these variables from the data in tables 2832, 2850, and 2860 or Database-known Patient Attributes. The System's code can calculate the Framingham point total exclusive of this factor and then determine the lower and (if needed) the higher limits of systolic pressure that would respectively add sufficient points to produce a 10-year risk of CAD above 10% and above 20%. The System may then enter these systolic pressure limits into box 2843 and box 2844 respectively. Upon the patient answering the question in box 2842 the System may then complete the calculation of the 10-year risk of CAD and use this value with rules based on the above considerations to present the appropriate message to the Patient on the next screen (e.g., FIG. 28C).

As an example of such calculations, consider the following: A 58 year old woman who smokes, is under treatment for hypertension, and has a cholesterol of 259, HDL of 45, and an LDL of 140. Since she smokes and is older than 55, she has at least two major risk factors.

Her Framingham Points are therefore:

| | |
|---|---|
| Age 58 | 8 |
| Total Chol. 259 | 5 |
| Smoker | 4 |
| HDL 45 | 1 |

These sum to 18, without consideration of her blood pressure.

A portion of the Framingham point scheme that may be used for systolic blood pressure under treatment is as follows:

| Systolic Pressure | Points |
|---|---|
| <120 | 0 |
| 120–129 | 3 |
| 130–139 | 4 |
| 140–159 | 5 |
| >160 | 6 |

A portion of the Framingham Point Total versus percent of 10-year risk that may be used for coronary artery disease is as follows:

| Point Total | 10 year risk for CAD |
|---|---|
| 18 | 6% |
| 19 | 8% |
| 20 | 11% |
| 21 | 14% |
| 22 | 17% |
| 23 | 22% |

Given the above, if her (the Patient's) blood pressure is less than 120 systolic no points would be added and her total of 18 points would correspond to a 10 year CAD risk of 6%. Thus her LDL level of 140 would not call for drug therapy. (The LDL level would have to be above 160 for this type of recommendation.) The recommendation would change if she obtained 5 more points from her blood pressure being above 140, if life style changes did not lower the LDL. In an embodiment, if the patient indicates he or she does not know the answer to a question, the System automatically presents to the patient, alternative results based on the various, high-probability possibilities for the unknown answer.

Figure 28D:
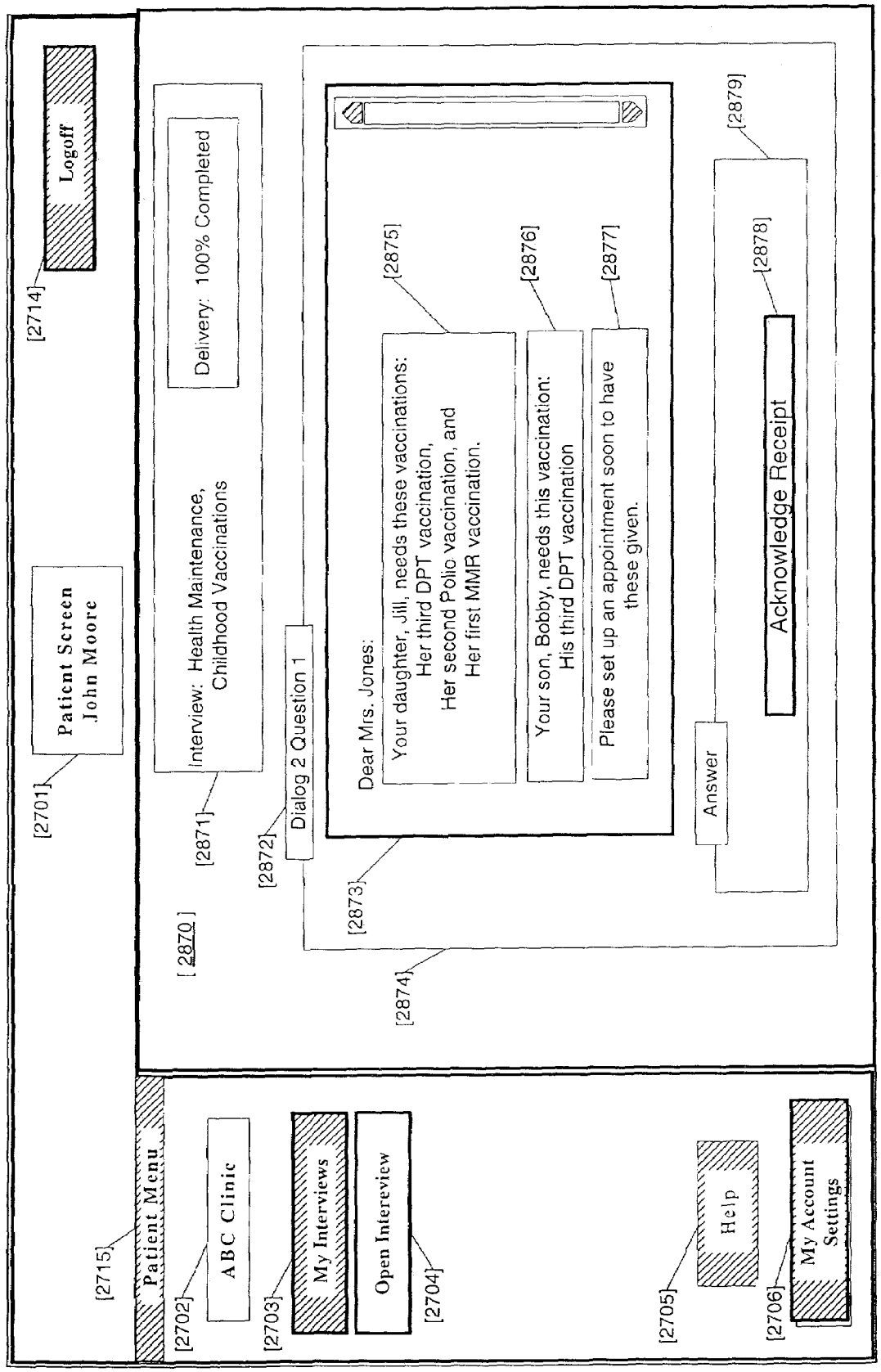
FIG. 28D illustrates another Opened Interview screen which may be used by a Patient or another authorized Target to view, review and/or acknowledge an Interview concerning Health Maintenance issues (e.g., vaccinations scheduling) that has been delivered in accordance with the present disclosure.

FIG. 28D illustrates a patient screen 2896 that may result in an embodiment of this disclosure from the execution of a System Health Maintenance paradigm for childhood vaccinations. In this case the birthdates, names, and dates of vaccinations of children are kept in the Database. Also there may be a field included for each vaccination which can indicate if a vaccination is indicated or not. This field can be changed to indicate the given vaccination should not be administered to a child in response to other fields being checked. These other fields, again specific for each vaccination, may comprise a field to indicate a severe reaction to a prior dose of the vaccine, a contra-indication to the vaccine such as egg-allergy, that the vaccine is not needed—e.g., the patient has already had the illness prevented by the vaccine and is already immune, or that the vaccine should be held for a period, indicated in an associated field, in response to medication use by that the child—e.g., a recent dose of gamma globulin.

Rules responsive to the U.S. Center for Disease Control and/or to other appropriate, authoritative guidelines for childhood vaccinations may be incorporated into the System. Examples of such rules are as follows:

VACCINATION RULES and VARIABLES FOR DaPT, DT, MMR, VARICELLA, PREVNAR, HIB1, POLIO (IP), HEPB and PPD SKIN TESTS: . . .
(i) Hepatitis B (HepB)
(1) If 6 wks<Age<19 years, and date of HepB__1 (i.e., Hepatitis B vaccination no. 1). Is null then add Need-_HepB__1 prompt
(2) If 4 months<Age<19 years,
and date of HepB__1 not null,
and date of HepB__2 is null,
and [Now-(Date of HepB__1)]>4wks then add Need-_HepB__2 prompt
(3) If 9 months<Age<19 years,
and date of HepB__1 not null,
and date of HepB__2 is not null,
and date of HepB__3 is null,
and [Now-(Date of HepB__2)]>8wks
and [Now-(Date of HepB__1)]>16wks then add Need-_HepB__3 prompt
A. Hib (*Hemophilus Influenza* Type b vaccination) immunization initiated at 7 to 11 months of age:
(1) If 7 months<(Age at which Hib1 given)<11 months
And date of Hib__2 null
And Age<15 months
And [Now-(date of Hib__1)]>8 wk then add Need_Hib2 prompt
(2) If 7 months<(Age at which Hib1 given)<11 months
And 12 months<Age<18 months
And date of Hib__2 not null
And date of Hib__3 null
And [Now-(date of Hib__2)]>8 wk then add Need_Hib3 prompt B. Hib immunization initiated at 12 to 14 months of age
(1) If 12 months<(Age at which Hib1 given)<14 months
And Age<59 months
And date Hib__2 null
And [Now-(date of Hib__1)]>8 wk Then add Need_Hib2 prompt When children in the System-supported medical practice receive vaccinations, the date of vaccination and other details such as lot number may be recorded into the System Database as Patient Attributes. The System should have a paradigm responsive to a Patient's age to search this portion of the Database periodically and apply the above rules. Children who are significantly behind on their vaccinations may be automatically selected out with data regarding their parents and contact channels and an Interview such as illustrated in FIG. 28D may be automatically instantiated and sent. Note that the System's "packing" function as described above allows appropriate Interviews for several children in a same household (e.g., same family) to be combined in one communication.

Figure 29:
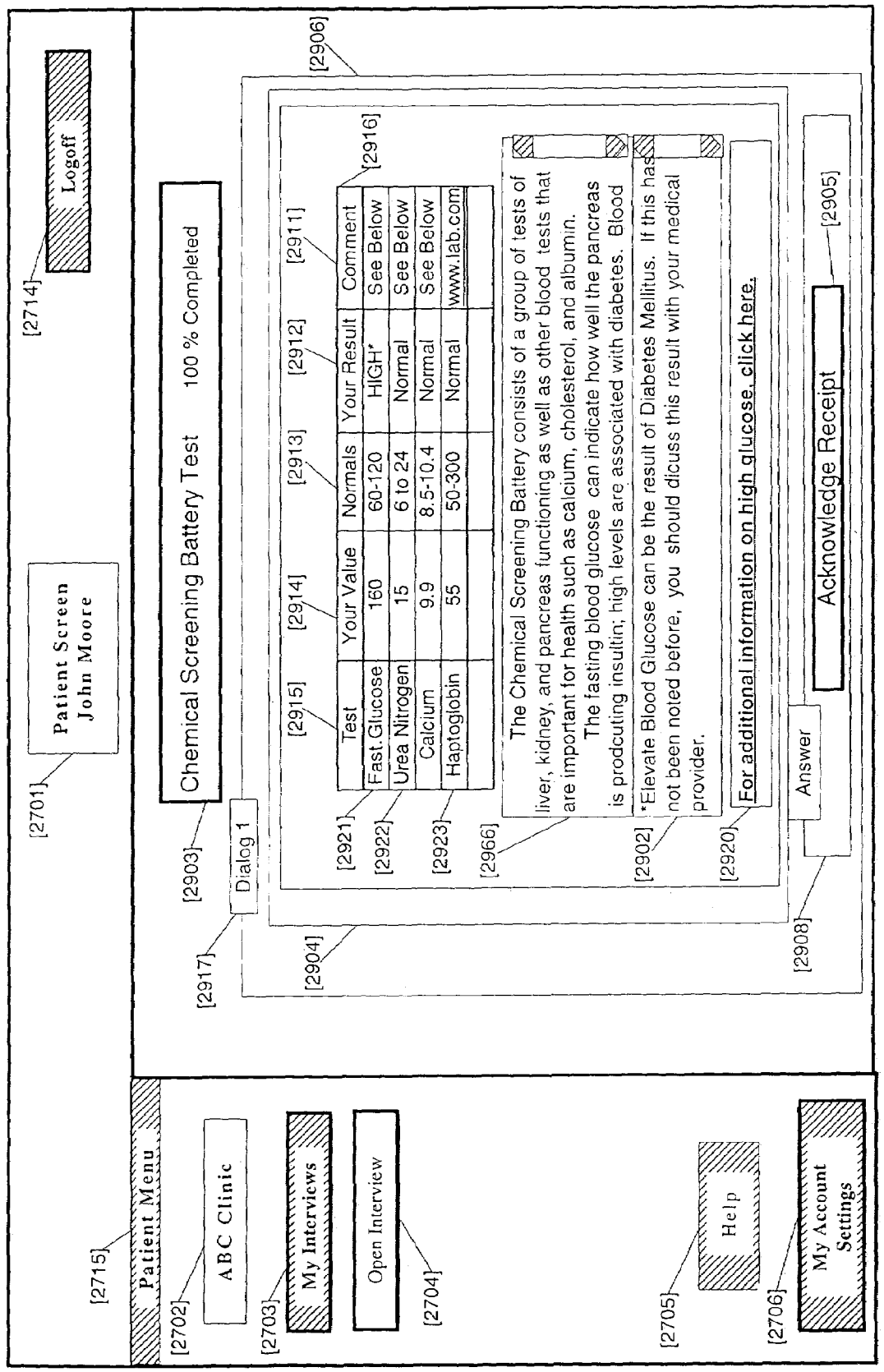
FIG. 29 illustrates a further Opened Interview screen which may be used by a Patient or another authorized Target to view, review and/or acknowledge an Interview concerning results of a chemical screening battery test that has been delivered in accordance with the present disclosure.

FIG. 29 illustrates a Patient-accessible screen 2900 which may be used by a Patient for viewing and/or responding to a Test Result Delivery Interview in accordance with the present disclosure. The exemplary delivery of a test-reporting Interview relates to a chemical screening battery. Most of the elements of the header bar and side bar of the screen have been described above. Button 2704 (Open Interview) is highlighted indicating that the Patient has chosen to view this Interview in detail.

Section 2903 indicates the Interview Topic title as being, "Chemical Screening BatteryTest," and includes a statement "Delivery: 100% Completed," where the latter is within a progress box that indicates that the Interview has been delivered (see again 2803 of FIG. 28A).

Title 2917 indicates that this is Dialog-1 of the Opened Interview. This section 2906 of the screen contains a section 2904 which has information relating to the test results and a section 2908 which has a button 2905 for allowing the Patient to acknowledge to the System, the Patient's receipt of the Interview Dialog. Section 2904 comprises of Table 2916 which lists the test results and partial explanations of these results in 2966 and 2902 as well as providing hyperlinks to additional relevant information via area 2920. Table 2916 lists the test names in column 2915, the Patient's value of the indicated test in 2914, the normal range for the test in 2913, an indication of the Patient's value relative to these normals in 2912, and a reference and/or hyperlink for further information in 2911. Row 2921 is for a "Fasting Glucose" test with reported value of "160" and normal range of "60–120." Column 2912 indicates this is a "HIGH" value and Comment section 2911 shows that further relevant information is below. Row 2922 shows the value for "Urea Nitrogen" test is "15" relative to a normal range of "6 to 24" so that this is a "Normal" result. The Patient is referred to an explanation below. Row 2923 is for a "Haptoglobin" test with value "55" that is within the normal limits of "50–300" and has a hyperlink reference in the Comment column 2911 to www.lab.com (a fictitious example of a laboratory informational page).

Box 2966 holds a statement describing for the Patient the chemical screening battery and meanings of the component tests. Box 2902 holds a statement inserted in response to the glucose test being elevated. Box 2920 gives a web link for further information regarding the abnormal glucose test.

Figure 30:
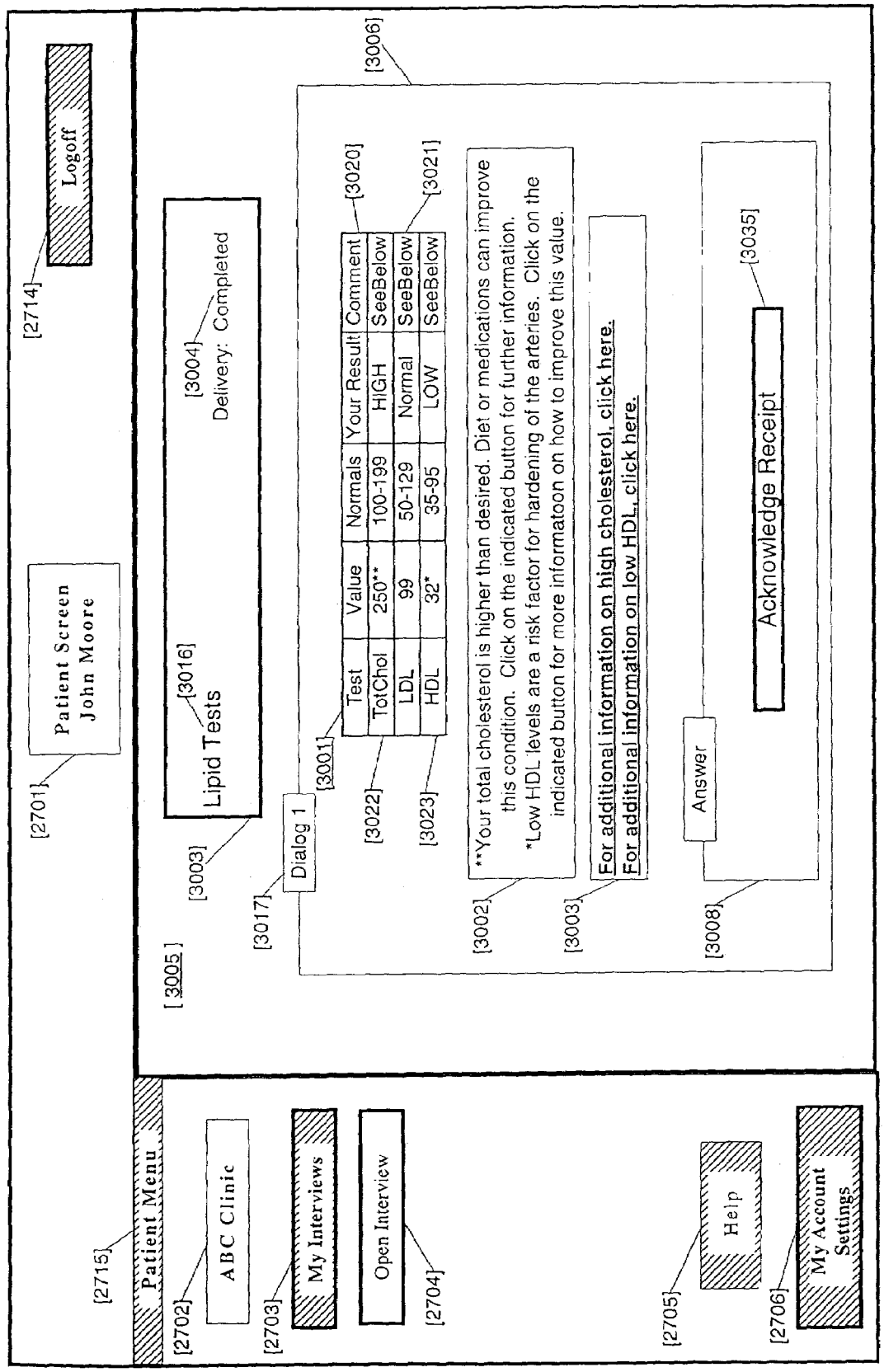
FIG. 30 illustrates another Opened Interview screen which may be used by a Patient or another authorized Target to view, review and/or acknowledge an Interview concerning results of a lipid panel test that has been formulated and delivered in accordance with the present disclosure.

FIG. 30 illustrates a Patient-accessible screen 3000 which may be used by the corresponding Patient for viewing and/or responding to a Test Result Delivery Interview for "Lipid Tests" in an embodiment of the current disclosure. Most of the elements of the header bar and side bar of the screen have been described above. Button 2704 (Open Interview) is highlighted indicating that the Patient has chosen to view this Interview in detail. In an highlighting the Test Delivery Interview in the table of FIG. 27 and selecting button 2704 or in response to the Patient double clicking the highlighted Interview. Box 3003 shows the Interview Topic title 3016, "Lipid Tests," and indicates that the Interview delivery is complete in 3004. Title 3017 indicates that this is Dialog 1 of the delivered Interview Dialog. Section 3006 holds test result information in 3001 and section 3008 holds button 3035 for the Patient to acknowledge receipt to the System of the delivered Interview Dialog.

Table 3001 in section 3006 holds the test results and partial explanations of these as well as references to additional relevant information. Table 3001 column headings in row 3020 are: the test name, the Patient's value, the normal range for the test, an indication of the Patient's value relative to these normals, and a reference for further information that is responsive to the Patient's value.

Row 3022 is for the "Total Cholesterol" value for which Patient's value is "250" versus a normal range of 100–199. The table indicates this is "HIGH" and refers the Patient to comments below (in 3003) for further information. Row 3021 is for "LDL" cholesterol and shows a value of "99" which is within normal limits. The "Your Result" column informs the Patient of this and the "Comment" column refers the Patient below for further information. Row 3023 is for "HDL" cholesterol which has a value "32" versus normal ranges of 35 to 95; this is "LOW."

Section 3002 holds information relative to high cholesterol values and low HDL values. Section 3003 has hyperlinks for obtaining further information on these subjects. Section 3008 allows for a Patient "Answer" by selecting the "Acknowledge Receipt" button 3005.

Figure 31:
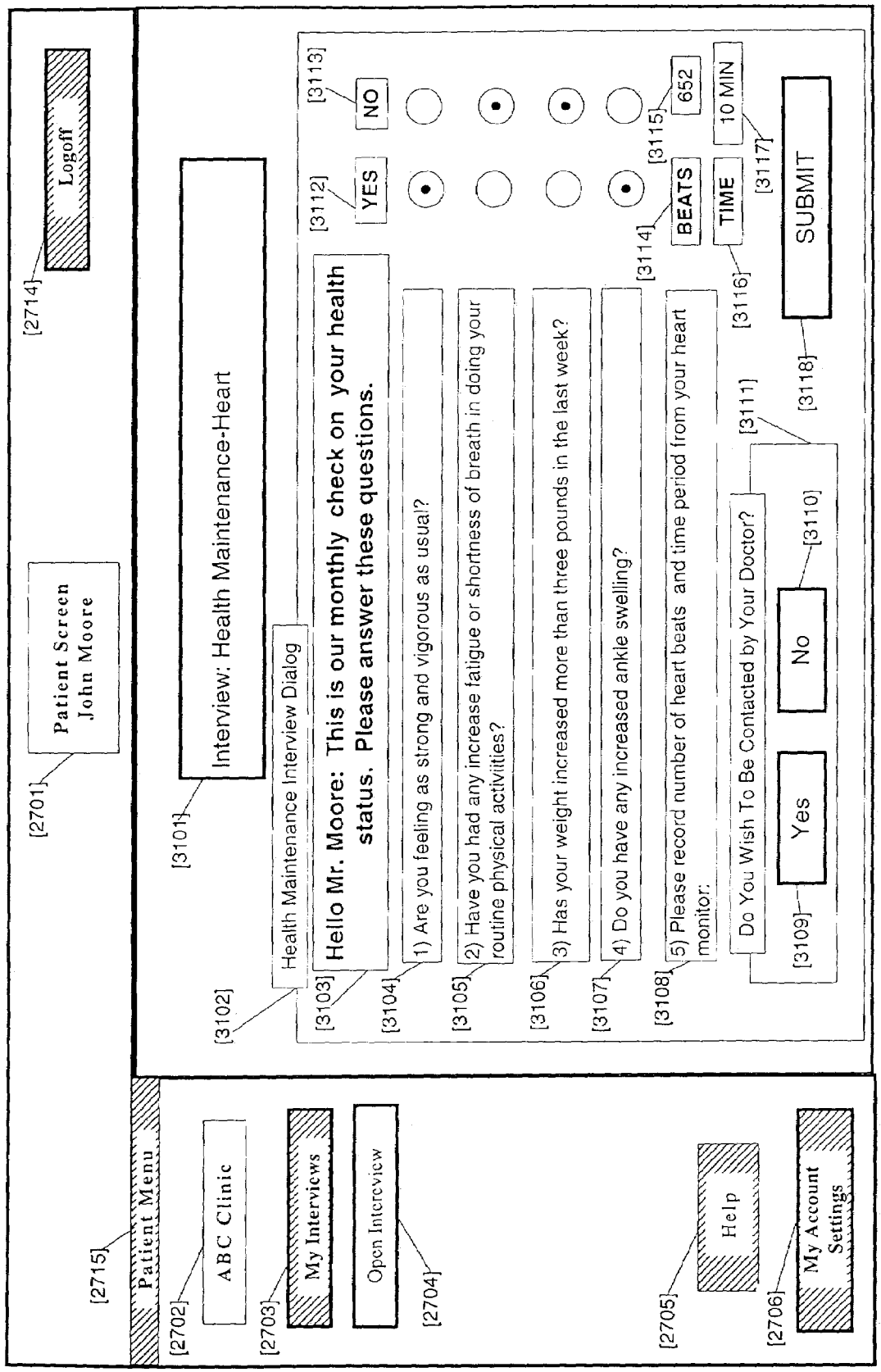
FIG. 31 illustrates a further, Opened Interview screen which may be used by a Patient or another authorized Target to view, review and/or respond to a Health Maintenance Follow Up Interview concerning a previously-detected congestive heart failure, where the Health Maintenance Follow Up Interview is being conducted in accordance with the present disclosure.

FIG. 31 illustrates one embodiment for a Patient-accessible screen 3100 which may be used for carrying out a Health Maintenance Interview Dialog concerning follow up for congestive heart failure. Most of the elements of the header bar and side bar of the screen have been described above. Button 2704 (Open Interview) is highlighted indicating that the Patient has chosen to view this Interview in detail.

Box 3101 holds the title of the Health Maintenance Topic and section 3102 holds the Health Maintenance Interview comprising of:
  i. A greeting to the patient that states that this is a monthly follow up for his heart condition—3103;
  ii. The health inquiries—3104, 3105, 3106, 3107, and 3108;
  iii. A box 3111 asking if he or she desires to be contacted by a doctor together with a button 3109 to select for a "Yes" answer and a button 3110 for a "No" answer; and,
  iv. A button 3118 for submitting the information entered.

The health inquiries in the exemplary Health Maintenance Interview comprise four questions 3104, 3105, 3106, and 3107 that have "Yes" or "No" answers that can be indicated by selections in either of the two columns of buttons 3112 for "Yes" and 3113 for "No" and a question 3108 which requests the Patient record the number of heart beats over a specified time period by entering a number of heart beats in box 3115 opposite the title "BEATS" 3114 and the time period in which these beats occurred in box 3117 opposite the title "TIME" 3116. In an embodiment, the Patient is supplied with a manually-operate-able or computer interoperable device (e.g., a Holter monitor, not shown), that can record and count instances of heartbeats. These should be monitored under standard conditions, such as in a resting basal state for a known period of time. The number of heartbeats for this time period under basal conditions can reflect heart function and can be compared over time (automatically by the System) as a index of health. In an embodiment, a Topic Dialog can contain a rule which may be used by the System for monitoring health where the rule involves the relative percent change of the pulse rate under different, standardized exercise loads. Information for this can also be recorded and used by the System as an indirect monitor of cardiac health overtime. Thus, if a Patient exercised at a set treadmill speed and slope with an average pulse rate of P1, and by increasing the rate and or slope to another set of standard values had an increase in pulse to an average steady state rate of P2, the measure reported for the index of health status could be automatically evaluated by the System with a status defining rule of the form:

$$\text{Status at a given time} = (\text{Constant}) \times (P2 - P1)/Pav$$

where $Pav = (P2 + P1)/2$.

Such a rule could automatically produce various actions by the System, such as setting of various alert(s) and changing of one or more Delivery Strategies, based on pre-specified ranges. As another embodiment of this concept, the Patient may be asked by an Interview to report the relative variability of the pulse rate, dP, at different pulse rates, P, or dP/P, as an index for monitoring heart status.

Figure 32:
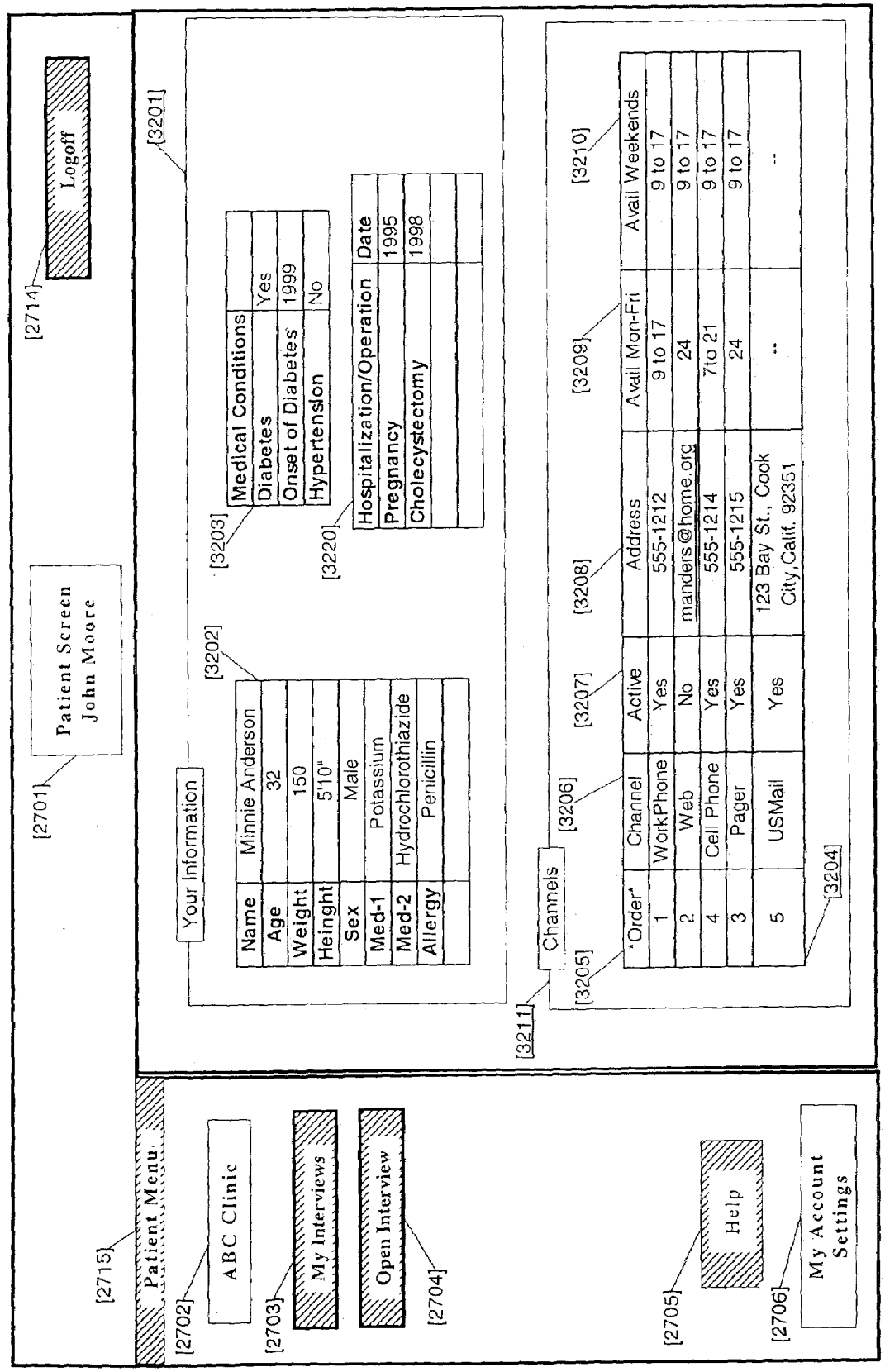
FIG. 32 illustrates a Patient's Account Settings screen which may be used by a Patient or another authorized Target to view, review and/or modify the Patient's Account settings within a System in accordance with the present disclosure.

FIG. 32 illustrates a Patient-accessible screen 3200 which may be used for allowing the corresponding Patient to edit and/or review personal-data settings associated with Patient. Most of the elements of the header bar and side bar of the screen have been described above. Button 2706 (My Account Setting) is highlighted indicating that the Patient has chosen to view his or her account settings.

Section 3201 holds Patient information in tables 3202, 3203, and 3220. Table 3202 holds the Patient's name and other personal and medical information as indicated. Table 3203 holds information regarding the presence or absence of medical conditions and table 3220 holds information regarding past hospitalizations and operations. In an embodiment, this information may be entered into the System Database by medical personnel and/or by allowing the Patient to have full or partial interaction with an electronic medical record.

Section 3211 holds first information 3204 regarding various communication channels by which the Patient may be reached in the form of a table. Column 3205 indicates the Patient's preferred order of use of the listed channels, 3206 indicates the name of the channel, 3207 indicates whether or not the channel is currently active (currently usable), 3208 indicates the channel address, 3209 indicates the probable availability times of the channel during the week, and 3210 indicates the believed availability times of the channel during weekends.

Figure 33:
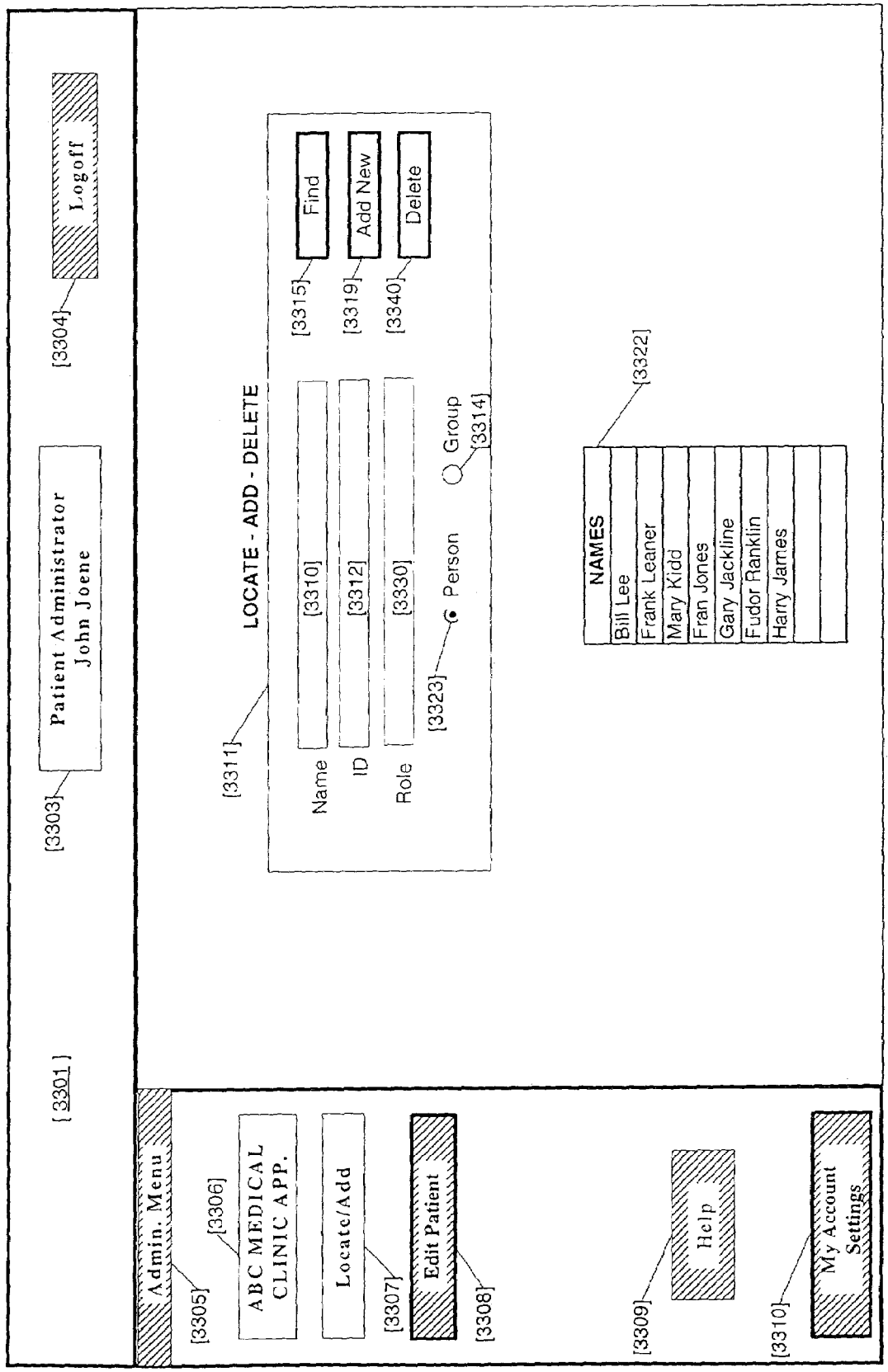
FIG. 33 illustrates an Administrator's Locate/Add screen which may be used by a System Administrator to locate and/or add and/or delete Patient Records to a System in accordance with the present disclosure.

FIG. 33 illustrates an Administrator-accessible screen 3300 which may be used by an Administrator to locate and add Patients to a System in accordance with the present disclosure. The header bar 3301 holds a first section 3303 identifying the Administrator and a logoff button 3304. The side bar holds a title area 3305 indicating that it is the Administrator's Menu and has a section 3306 indicating that this is an "ABC Medical Clinic Application." Button 3307 may be used to locate or add Patients, button 3308 to Edit Patient Attributes, button 3309 to obtain help in the use of the System, and button 3310 to access Account Settings. Button 3307 (Locate/Add) is highlighted to indicate this screen is for respectively locating or adding a Patient in/to the System Database.

Section 3311 holds a text box 3310 for entering the name of a Patient (or a query for a name, e.g. Bill L?e*) and text box 3312 for entering the ID (or a query for such an ID, e.g. ABC-P-L?e*) of the Patient. The Administrator may enter the Role of the searched for/added Person in text box 3330 if desired. If pick area 3323 is highlighted the System will search for a person with the identifiers placed in the above text boxes; if pick area 3314 is highlighted the System will search for a group using these identifiers. The Administrator initiates the search by pressing the Find button 3315. Result-Listing box 3322 lists names of people that come closest to satisfying the search criteria entered in the text boxes. If a group search is sought by picking 3314, list box 3322 changes to show group names that come closest to the entered search criteria. If the Administrator is inputting a new person or group, the Administrator selects button 3319 to add the name and/or identifier listed. The Delete button 3340 allows deletion of groups or Persons. In an embodiment the Administrator may use the Find and Add New buttons with the Name list 3322 to form new groups.

Figure 34:
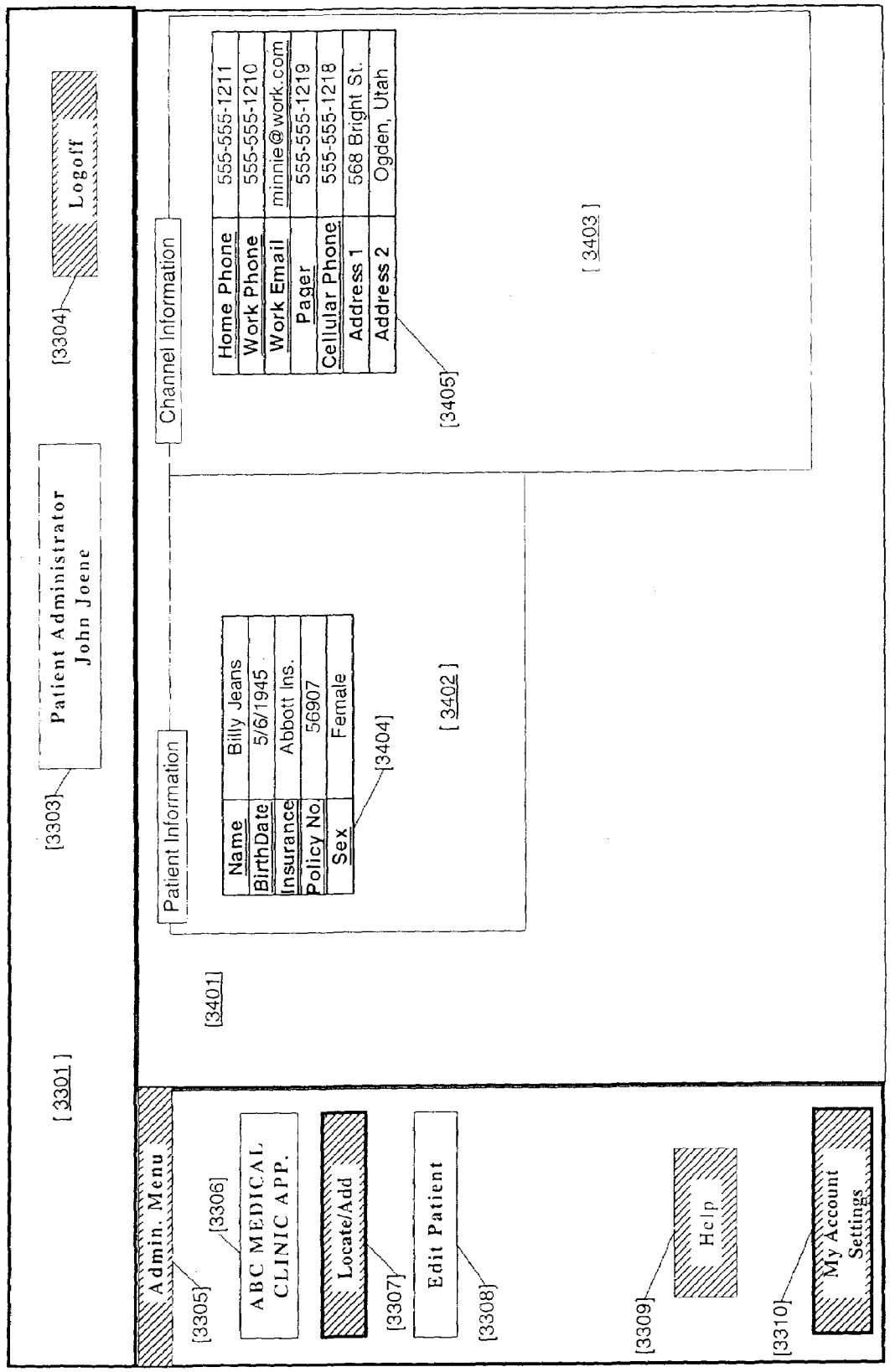
FIG. 34 illustrates an Administrator's Patient-Record Editing screen which may be used by a System Administrator to view and/or edit Patient Information and/or Patient Channel Information within a System in accordance with the present disclosure.

FIG. 34 illustrates another Administrator-accessible screen 3400 which may be used by an authorized Administrator to edit Patient data in the Database of System in accordance with the present disclosure. Most of the elements in the header bar 3301 and side bar 3305 have already been described. Button 3308 is highlighted to indicate that the Administrator has selected it to view and edit Patient information.

Section 3401 comprises a first section 3402 which allows for editing of Patient Information and a second section 3403 which allows for editing of Channel Information. The Patient Information section holds a table 3404 listing Patient data such as name, birth date, and insurance information. Section 3403 holds access and address data for various communication channels which may be used to make Interview delivery attempts to the Patient. The Administrator can use the screen 3400 to modify, add to, or delete from, the Patient and Channel data held by the System Database as may be appropriate.

Figure 35:
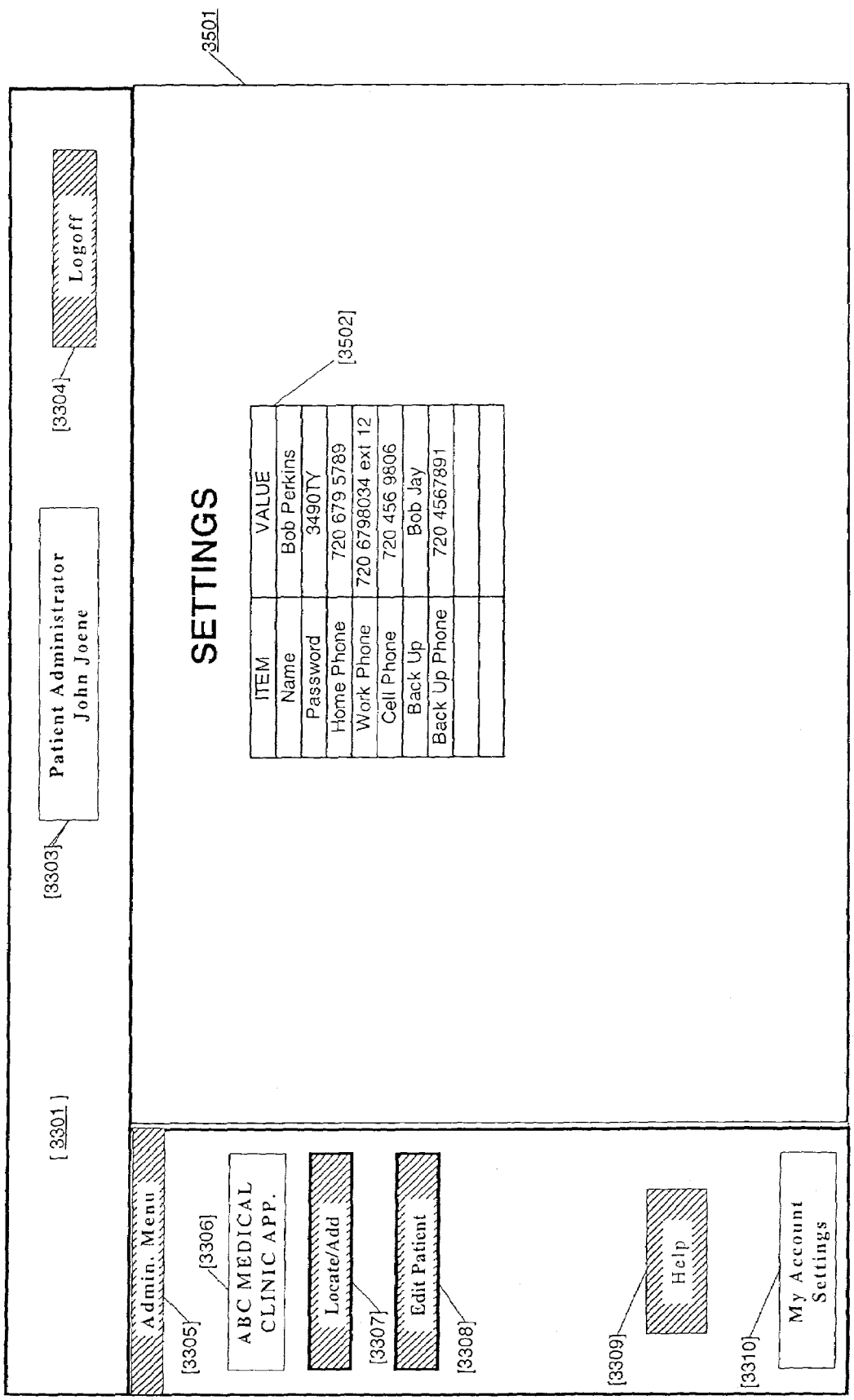
FIG. 35 illustrates an Administrator's Account Settings screen which may be used by a System Administrator to review and/or change his or her Account Settings within a System in accordance with the present disclosure.

FIG. 35 illustrates an Account Settings screen 3500 which may be used by a so-authorized Administrator to edit the System account settings of another Administrator and/or of his or her information settings in an embodiment of the current disclosure. Most of the elements in the header bar 3301 and the side bar 3305 have already been described. Area 3501 holds table 3502 that lists Attributes pertaining to the target Administrator's account. These may include name, password, phone numbers, name of back up administrator and means of contacting this target person.

Figure 36:
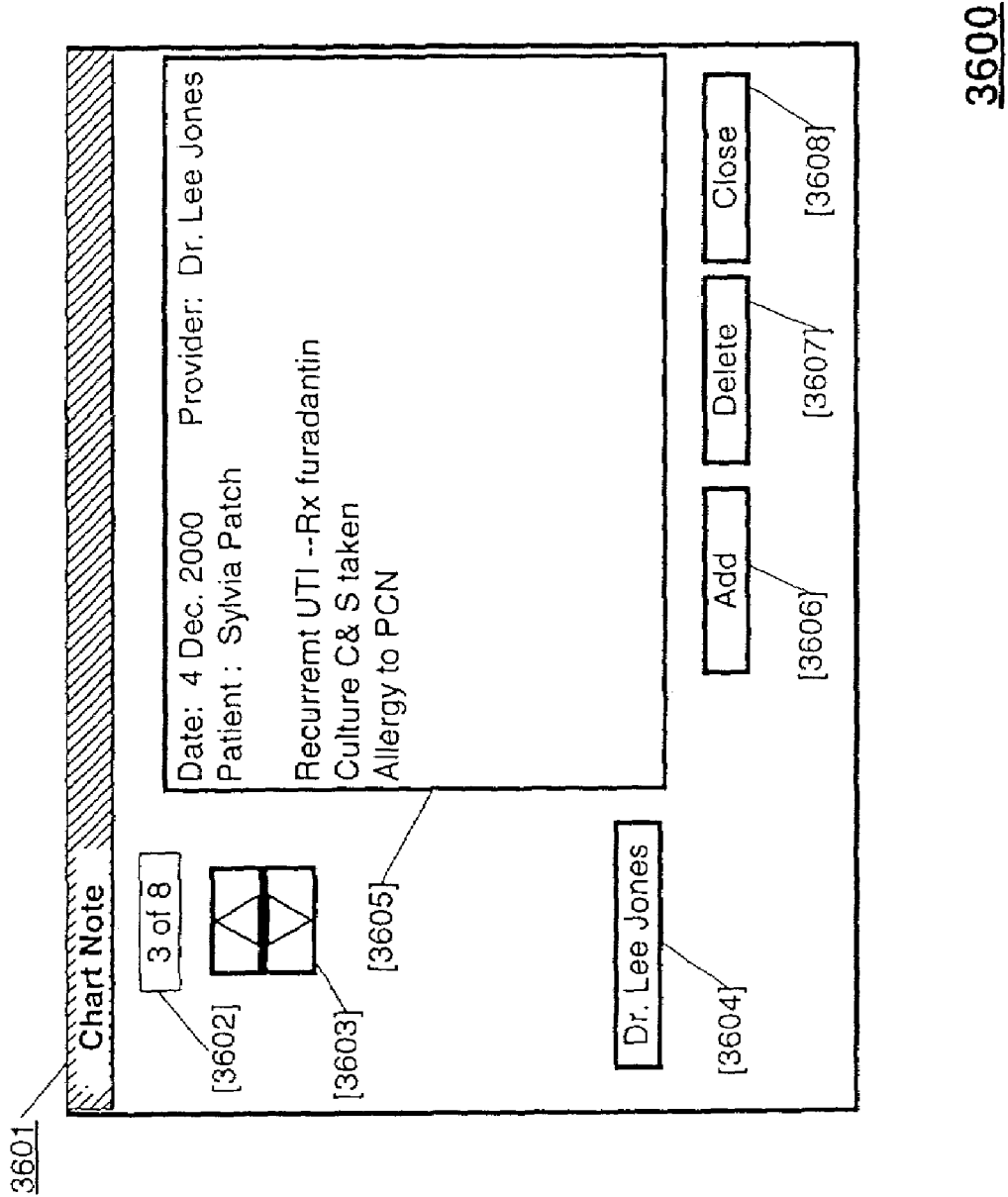
FIG. 36 illustrates a displayed Chart Note for a given Patient whose records are kept within a System in accordance with the present disclosure.

FIG. 36 illustrates a Chart Note window 3600 which may be displayed and/or used in an embodiment of the current disclosure for viewing and/or editing chart note data. When a user of the System selects a Chart Note-activating box such as 1204 in FIG. 20, the correspondingly stored Chart Notes for the identified Patient may be presented as illustrated in FIG. 36. The title bar 3601 indicates that the information shown is a Chart Note. Buttons 3603 allow the user to scroll through the Chart Notes that are stored on the System Database for the Patient being considered. Box 3602 indicates which Chart Note is being viewed and total number of Chart Notes present in the System for the identified Patient. The user's account name is indicated in box 3604.

An example of a Chart Note is illustrated in area 3605. In the instance illustrated, the Chart Note is for the Patient Sylvia Patch and was placed into the System Database on Dec. 4, 2000 by Dr. Lee Jones. Dr. Jones noted that the Patient was diagnosed as having recurrent urinary tract infections and was treated with furadantin. He also indicated that she is allergic to penicillin and that a culture is pending.

Button 3606 (Add) allows the user to add a new Chart Note; button 3607 (Delete) allows the user to delete a Chart Note; and button 3608 (Close) allows the user to close the given Chart Note window 3600 and return to working on the previously displayed screen.

FIG. 37 illustrates a Patient Information window 3700 which may be displayed when a System user selects a Patient Information box, 1202 for example in FIG. 12. The title bar 3701 indicates the information illustrated is information regarding the Patient. Table 3702 holds basic identifying and medical information for the Patient such as name, height, weight, medications and medication allergies. Table 3703 holds information regarding the medical illnesses or conditions the patient has or does not have. Button 3705 allows information regarding hospitalizations of the Patient to be obtained from the System Database and displayed. Button 3706 allows information regarding prior surgeries of the Patient to be obtained from the System Database and displayed. Button 3704 allows information regarding prior office visits of the Patient to be obtained from the System Database and displayed. In an embodiment, information in the above categories may be obtained at remote workstations using wired or wireless links to the System Database and/or to external Databases, if any.

FIG. 38 illustrates a Communication Channel window 3800 which may be displayed when a System user selects, for example, a Communication Channels box such as 1203 in FIG. 12. The title bar 3801 indicates that this is Communication Channel information that indicates the various communication channels by which the Target (e.g., a Patient) may be reached. Table 3808 has the following column headings: Column 3802 indicates the Target's (e.g., Patient's) preferred order of use of the listed channels, 3803 indicates the name of the channel, 3804 indicates whether or not the channel is currently active (currently useful for reaching the Target person), 3805 the channel address, 3806 the availability times of the channel during the week, and 3807 the availability times of the channel during weekends.

The present disclosure is to be taken as illustrative rather than as limiting the scope, nature, or spirit of the subject matter claimed below. Numerous modifications and variations will become apparent to those skilled in the art after studying the disclosure, including use of equivalent functional and/or structural substitutes for elements described herein, use of equivalent functional couplings for couplings described herein, and/or use of equivalent functional steps for steps described herein. Such insubstantial variations are to be considered within the scope of what is contemplated here. Moreover, if plural examples are given for specific means, or steps, and extrapolation between and/or beyond such given examples is obvious in view of the present disclosure, then the disclosure is to be deemed as effectively disclosing and thus covering at least such extrapolations.

By way of a first example, although the information presentation and/or exchange interfaces shown in FIGS. 8A–38 are presented in the form of visual windows or screens that are suitable for transmission over the Internet or a like link and for display on a desktop or portable computer, other visual and/or non-visual, information transmissions, presentations and/or exchanges via appropriate interfaces are within the contemplation of the present disclosure. For example, small-screen communication devices such as third-generation (3G) cell phones, PDA's (personal digital assistants), pagers and the like may call for terser visual presentations in view of their limited display and/or user-input capabilities. The System Database may store data for each kind of channel indicating the limitations of that channel's transmission capabilities and further data for each kind of communication device (e.g., cell phone, PDA, etc.) indicating the limitations of that device's user interfaces. The Target user's familiarity with using each particular kind of communication device may further be stored and adaptively used for communicating with the target. For example, an elderly Patient may own a 3G cellular telephone but may not know how to use the more advanced visual and/or keyboard and/or pointer/pen devices of such a communications device. Instead, the communications Target Person (e.g., Patient) may only know-how/be-able to use a voice-only interface, or voice for such user-centric preferences and provide its Interviews, Alerts and/or other communication exchanges accordingly.

Additionally, as has already been indicated in the context of FIG. 1A, at given times and/or locations (e.g., a physician driving to the hospital in heavy traffic) the communications Target may not be disposed to receiving and/or responding to complicated transmissions of information. The System may adaptively compensate for such user-centric limitations by giving only short Advisements of pending Alerts or other such delivery attempts and the System may schedule a series of reminder Advisements as may be appropriate. (E.g., the System may be aware that the Medical Service Provider is on the ski slope with only a pager available for receiving advisements. If the medical situation is an urgent one, the System may automatically decide to beep the pager every 5 minutes until responded to and may also make similar contact attempts to a back-up physician listed in the System Database.)

To recapitulate some of what was initially introduced in FIG. 1A and then further elaborated on in other discussions herein, effective communications within a medical practice can be blocked by many obstacles (e.g., 98 of FIG. 1A), and such obstacles may be overcome by (or at least recognized by and appropriately reacted to) machine-implemented methods and automated systems that provide, but are not limited to, the functions of: (1) finding a communications channel (cell phone, email, pager) that is not only operating at a time that a communications delivery is to be attempted, but is also conveniently useable by the targeted recipient (e.g., Patient, physician, lab tech) for the kind of exchange that is to be carried out (e.g., simple advisement or alert versus a long and complicated Interview); (2) adaptively conforming the message content to the limitations of the chosen communications channel and the current disposition of the targeted recipient (e.g., Patient is distressed, physician is driving a car, etc.); (3) adaptively finding the targeted recipient, particularly if that person tends to be highly mobile and/or travel patterns or communications-channel preferences change over time; (4) verifying that the targeted recipient actually received the delivery-attempt within an applicable time limit, if any (e.g., Patient activates acknowledgment means such as 2905 of FIG. 29; physician disposes of or delegates an Alert via the Alert Summarizing Screen of FIG. 10A or via a substitute visual or nonvisual interface means); (5) automatically recognizing that an urgent or non-urgent message delivery-attempt was not timely completed (e.g., in-completion feedback path 95 of FIG. 1A) and adaptively alerting responsible entities of the in-completion based on urgency of the in-completion (e.g., physician may be automatically bypassed and follow up can be automatically delegated to an MA if a routine test result was not picked up with acknowledgment by a Patient); (6) automatically recognizing that an urgent or non-urgent action item task was not timely completed (e.g., in-completion feedback path 95 of FIG. 1A) and adaptively alerting responsible entities of the task in-completion based on urgency of the in-completion (e.g., physician may be automatically bypassed and follow up can be automatically delegated to an MA if a routine Health Maintenance test was missed by a Patient); (7) automatically recognizing that an urgent action item task was completed (e.g., passing alerted test result 65 of FIG. 1A through filter 87) and adaptively alerting responsible entities of the task completion based on urgency of the completion (e.g., alerting MD 20 via Alert Summary of FIG. 10A to review 26 the alerted result condition); (8) automatically recognizing that an urgent change or non-change of condition has occurred by virtue of information gathered during an automated or manually-assisted Interview (e.g., if Patient responds NO 2810 in FIG. 28A during automated or manually-conducted Interview where physician expected positive progress prior to Interview) and adaptively alerting responsible entities of the changed or unchanged condition based on the urgency of the change or non-change (e.g., alerting MD 20 via Alert Summary of FIG. 10A, i.e. row 1024, to review 26 the alerted condition); (9) adaptively altering Interviews in response to information obtained from earlier Dialogs or from other sources; (10) adaptively adjusting the timing of deliveries of further Dialogs in response to information obtained from previous Dialogs; (11) adaptively delivering Interview Dialogs in an order and/or timing defined by system-changeable priority settings and/or according to available channel bandwidth and/or according to permitted times for delivery; and (12) when delivering a first message through a given channel, if the channel-use rules permit, "packing" other Dialog messages that are to be delivered via that channel to a given patient or household so that all such packed Dialogs can be simultaneously delivered if the connection attempt is successful.

Figure 39A:
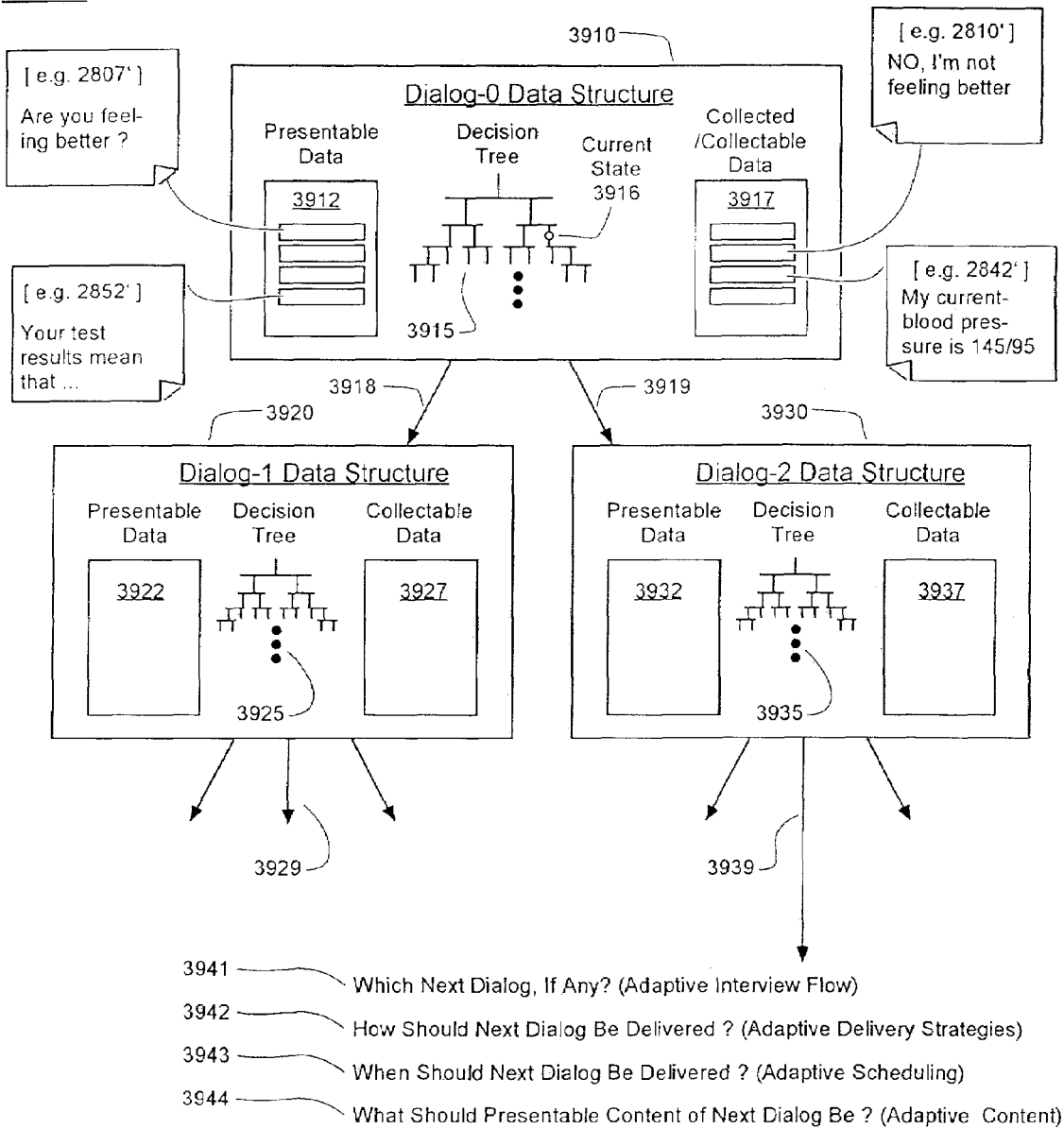
FIG. 39A illustrates an Interview Data Structure which may be generated and/or transmitted as a signal within a System in accordance with the present disclosure.

Referring to FIG. 39A, there is illustrated an Interview Data Structure 3900 that may be developed, recorded and/or transmitted as a set of one or more data signals within one embodiment of a System which is provided in accordance with the present disclosure. The Interview Data Structure 3900 may be comprised of one or more Dialog Data Structures such as the three shown for purposes of example at 3910, 3920 and 3930. Referring to Dialog-0, it may be seen that such a Dialog Data Structure (3910) may be comprised at least of a Decision Tree structure 3915 as well as at least one if not both of a Presentable-Data structure 3912 and a Collected/Collectible-Data structure 3917. While a particular dialog (communication) is being conducted with a corresponding recipient (Target), the current state of the respective, Dialog Data Structure (e.g., 3910) may be deemed to be moving progressively down its Decision Tree (3915) in response to various events or non-events that may take place during the attempted or successful carrying out of the dialog.

In the example shown at 3910, the current state of Dialog-0 is indicated by the hollow circle at position 3916 within the Decision Tree structure 3915. For the dialog to have gotten to this particular state 3916, it is possible that contact has already been successfully made through a particular channel (e.g., conventional telephone) with the Target and that default and/or event-selected ones of declarations and/or questions may have been posed to the Target. For example, if the Presentable Data stored at 2807' ("Are you feeling better?") was presented to the Target, the Target may have responded with an indication (e.g., spoken or touch tone) representing the Collected Data shown by example at 2810' ("NO, I'm not feeling better."). As a result of that response (2810'), the Decision Tree 3915 of Dialog-0 may have decided that it is time to soon terminate Dialog-0 (3910) and the Tree may have further generated a flow-controlling indication which indicates that one or the other of Interview flow paths 3918 and 3919 should next be taken to a respective one of next Dialogs 3920 and 3930. Each of respective Dialogs 3920 and 3930 has its own corresponding Decision Tree (e.g., 3925 or 3935) and one or both of its own respective Presentable Data storage regions (3922 and 3932) and its own respective Collectible Data storage regions (3927 and 3937).

The current state (e.g., 3916) achieved within a current Dialog Decision Tree (3915), and/or the data held in the Collected Data of region (3917) of the Dialog Data Structure 3910, and/or the lack of all or a particular item of data can be used to automatically and adaptively control one or more aspects of the way that the Interview-conducting System (not shown, see for example FIG. 40A) will dispense information and/or will react to the Collected Data (e.g., 3917) or lack thereof. It is seen under Interview-flow path 3939 that the one or more adaptive behaviors of the Interview-conducting System can include the automated making of decisions regarding: (a) Which next Dialog, if any, should be sent next?—this being an example of Adaptive Interview Flow, 3941; (b) How should the next Dialog be delivered—by telephone, email and/or otherwise?—this being an example of Adaptive Delivery Strategies, 3942; (c) When should the next Dialog be delivered?—this being an example of Adaptive Scheduling, 3943; and (d) What should the Presentable Content of the next Dialog be?—this being an example of Adaptive Content, 3944. (The same kinds of machine-implemented, adaptive options may be associated with the Interview-flow path 3929 emanating from the illustrated, Dialog-1 Data Structure 3920, and paths 3918, 3919 emanating from the illustrated, Dialog-0 Data Structure 3910.).

Figure 39B:
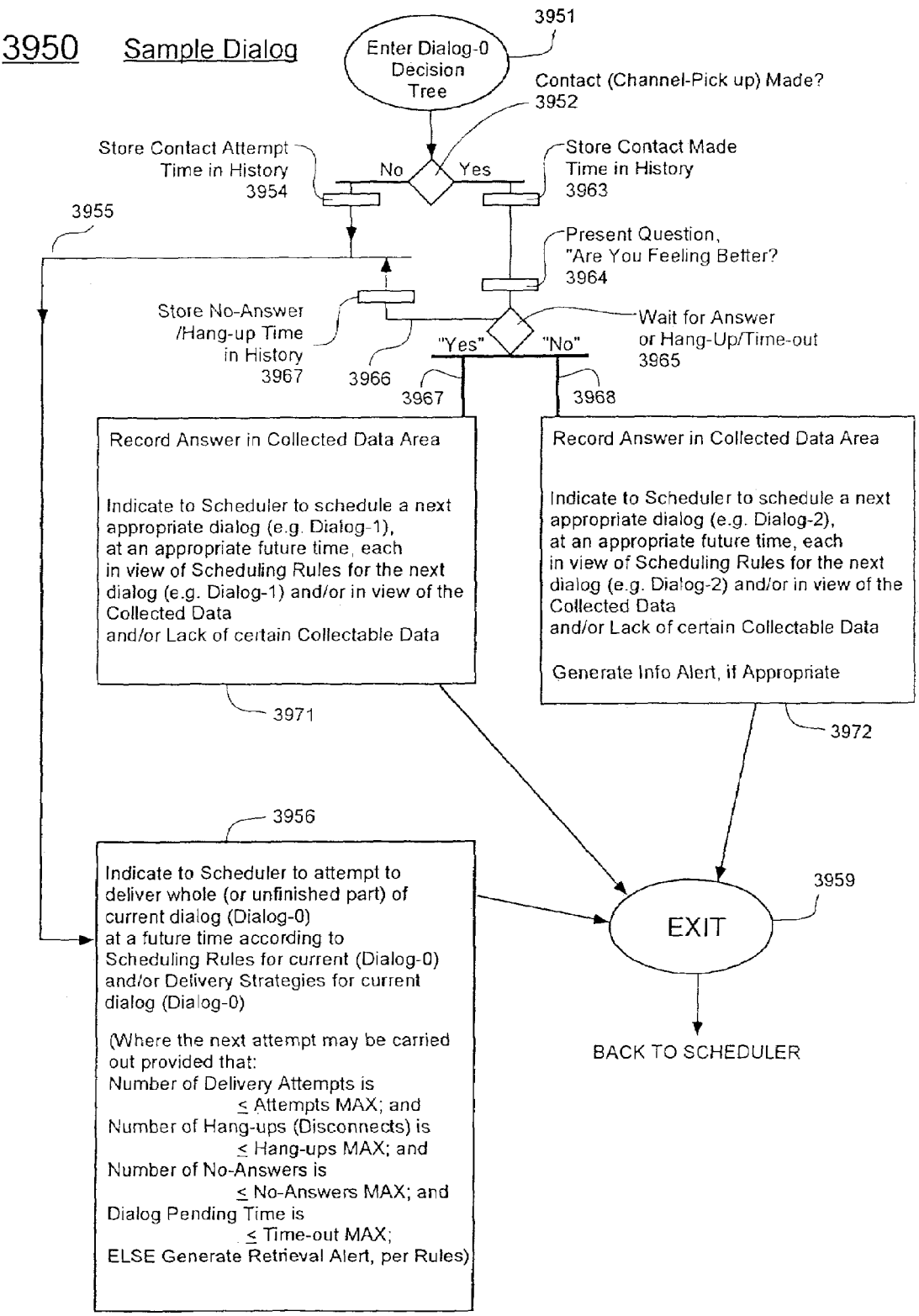
FIG. 39B illustrates details of a Dialog Data Structure which may be developed and/or transmitted as a signal within a System in accordance with the present disclosure.

Referring to FIG. 39B, there is shown an example of a simple Dialog 3950 that may be provided in one embodiment according to the present disclosure. (Other, more sophisticated representations of possible Dialogs are provided in the accompanying Exhibits 1–3.) For the illustrated Dialog 3950, entry point 3951 is taken at a time determined by a System Scheduler (not shown). Decision juncture 3952 determines whether a connection (channel-pickup) has been successfully made. If the answer is No, step 3954 stores information regarding the contact attempt time and/or the method used to try to make the contact in a history log section (e.g., 3917 of FIG. 39A) of the current Dialog Data Structure 3950 (partially shown). A Decision-Tree path 3955 is then taken to step 3956. In step 3956 an indication is produced for transmission to the Scheduler to indicate to the Scheduler that it should attempt to deliver the whole (or an unfinished part, in one embodiment) of the current Dialog (e.g., Dialog-0) at a future time, which future time will be determined according to scheduling rules for the current Dialog (Dialog-0) and/or which future time will be determined according to Delivery Strategies that have been pre-specified (in the System) for the current Dialog (Dialog-0). In one embodiment, additional provisos are provided for determining whether the next attempt may be carried out at all and these provisos (which should be set forth in the Scheduler rather than in the Dialog Data Structure 3950) may include one or more of the following: having the Scheduler determine whether the number of Delivery Attempts so far is less than or equal to a defined Attempts-Maximum value for the current Dialog or its encompassing Topic or encompassing Application; having the Scheduler determine whether the number of Hang-ups (disconnects) so far for the current Dialog is less than a prespecified Hang-ups Maximum value associated with the current dialog (Dialog-0) and/or whether the number of Hang-ups (disconnects) so far in a relevant time period exceeds a prespecified Hang-ups Frequency Maximum value associated with the current dialog; having the Scheduler determine whether the number of No-Answers thus far is less than or equal to a prespecified No-Answers Maximum value associated with the current dialog and/or whether the number of No-Answers so far in a relevant time period exceeds a prespecified No-Answers/Busy's Frequency Maximum value associated with the current dialog; and having the Scheduler determine whether the time that the current instantiated dialog (Dialog-0) has been pending within the System is less than a specified Time-out Maximum value associated with the current dialog. If one or more of these provisos is violated, the System may automatically generate a Retrieval Alert if such a Retrieval Alert is called for under the relevant System, Application and/or Topic Rules. Moreover, the automatic generating of a Retrieval Alert may be predicated on having the Scheduler determine the number of times that a telephone answering machine or a like, automated message receiving agent of the Target was reached and determining whether such number of agent-reaching times and/or the frequency of such agent-reaching events qualifies for the generation of a Retrieval Alert under maximum values and/or rules associated with the corresponding, Interview.

At next step 3959, the Dialog 3950 is exited and control is returned back to the Scheduler. The information and/or lack of information collected by the Dialog thus far and/or the state of the Dialog thus far is also returned back to the Scheduler (e.g., via a software pipe).

If the answer had instead been "Yes" at decision juncture 3952, then at the following step 3963 the time that the contact was made would be stored in the Dialog History Log. At step 3964, a Decision Tree-determined statement and/or question is presented. In this example, the presented question is, "Are you feeling better?".

At next juncture point 3965, at least one of three things may happen. The targeted recipient may fail to answer or may hang up or the connection may disconnect due to other reasons. These possibilities are represented by juncture exit path 3966. At step 3967 the no-answer and/or hang-up time and/or disconnect time is stored in the Dialog History Log. Then path 3955 is taken through step 3956 for exit at 3959.

If the answer "Yes" had been provided at junction 3965, then Dialog path 3967 would be taken to step 3971. In step 3971 the answer provided by the recipient is recorded in the Collected Data area. An indication is generated for the Scheduler to schedule a next appropriate Dialog (e.g., Dialog-1) at an appropriate future time, where each of the identify of the next appropriate Dialog and the next appropriate future time may be produced in view of the Collected Data thus far and/or the lack of certain Collectible Data and/or in view of scheduling rules that are associated in the System with the planned next Dialog. The results of step 3971 are passed through exit point 3959 for handling by the Scheduler.

If the answer at juncture point 3965 had instead been "No", then path 3968 would have been taken to step 3972. In step 3972, the obtained answer (patient information) is recorded in the Collected Data area of the Dialog. An indication is further generated for the Scheduler to schedule a next appropriate Dialog (e.g., Dialog-2) at an appropriate future time in view of the Collected Data or lack thereof and/or in view of scheduling rules provided within the System for the next planned Dialog. Also within step 3972, an indication to generate an Information Alert may be created if appropriate under the Dialog-governing rules of the System. The Decision Tree status (current state) and/or Collected Data are then returned to the Scheduler by way of exit point 3959.

Figure 40A:
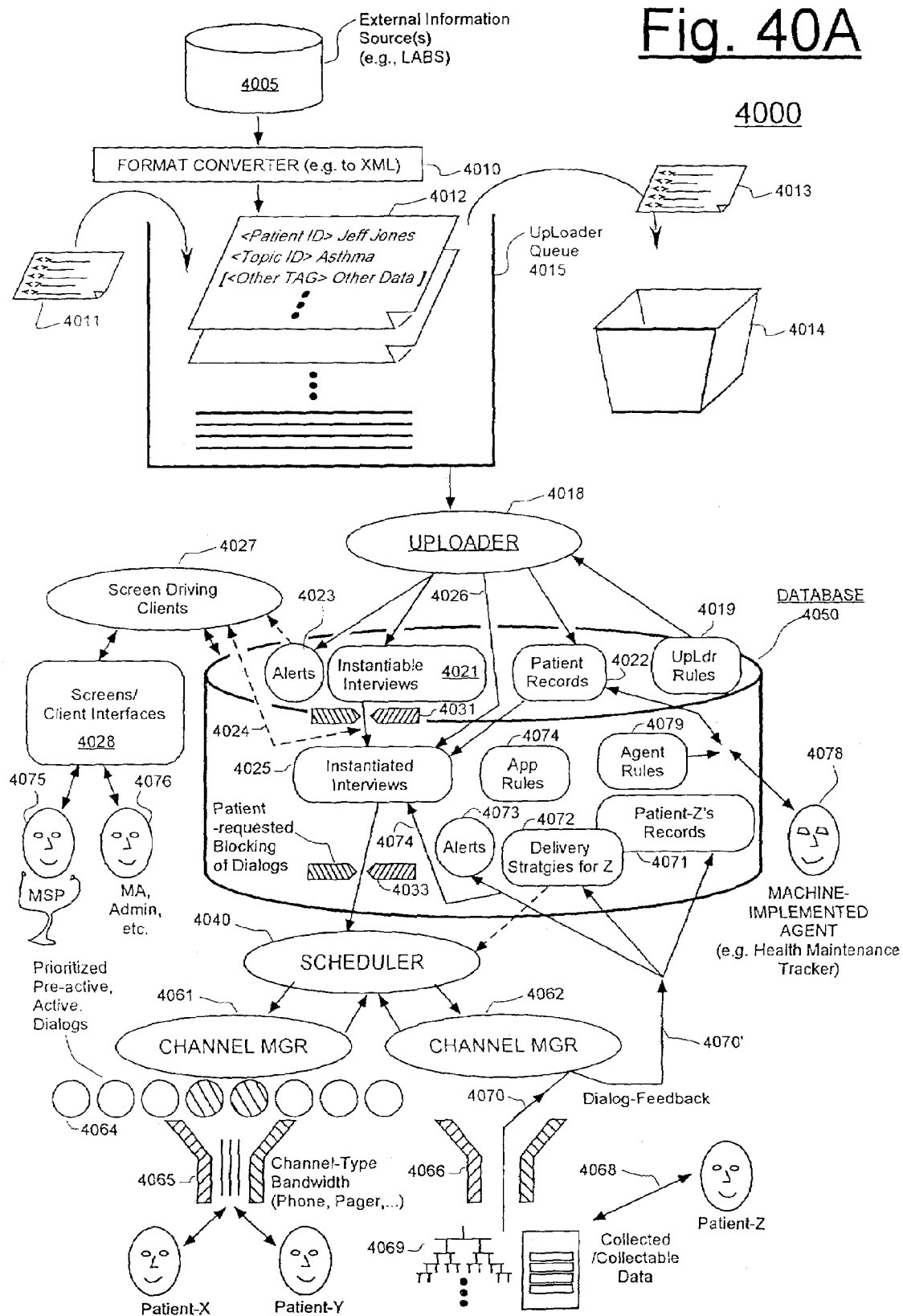
FIG. 40A is a block diagram illustrating how Dialog Data Structures may be re/formulated, instantiated, sent to targets via a scheduler and their delivery results may be returned.

FIG. 40A is a block diagram showing a structuring for an adaptive, information-dispensing and information-collecting System 4000 which may be provided in accordance with the present disclosure. External information sources such as test labs, etc. may provide test results or other information in corresponding, machine-readable formats as indicated at 4005. A format converter 4010 receives the externally-sourced transmissions, analyzes them and converts them into an appropriate System-compatible format. In one embodiment, this System-compatible format uses XML tags embedded within converter-produced, text files (e.g., .txt file extensions) where the tags identify the respective meanings of various text strings provided within the various converted forms 4012. The converted forms are stored in an UpLoader Queue 4015. In one embodiment, each converted form 4012 should have at least patient identifying information (e.g., <Patient ID>) and topic identifying information (e.g., <Topic ID>). The converted forms 4012 may include further tagged objects representing other pieces of information (not shown) that may be useful to the System 4000 such as: <MSP ID>, <Application ID>, <Action Requested>, and so forth.

A system Up-Loader 4018 repeatedly scans through the forms 4012 stored in the Up-Loader Queue 4015, looking for forms that may be currently acted upon in accordance with applicable UpLoader Rules 4019. In one embodiment, UpLoader Rules 4019 are Topic-driven, meaning that each Topic of each Application can have its own unique UpLoader Rules. The actions that may currently be taken by the Up-Loader 4018 may include converting one or more of the queued forms (4012) into instantiable interviews 4021 or new patient records 4022 or making modifications to pre-existing patient records. The applicable UpLoader Rules 4019 may define which UpLoad-generated Interview is to have its NeedsReview flag set to true rather than false. UpLoad-generated Interviews which have their Needs Review flag set true are UpLoaded into region 4021 because they are deemed to need human intervention (4024) while others of the UpLoad-generated Interviews may be routed without intervention into region 4025 (no human intervention needed). Some or all of the queued forms (4012) within the Up-Loader Queue 4015 may be stored therein from System-internal sources 4011 (e.g., created by the System Administrator in System-compatible format). Certain ones of the queued forms (4012) may remain in the Up-Loader Queue for relatively long periods of time (e.g., months) and may be repeatedly acted upon by the Up-Loader 4018 as various events occur (e.g., a new group of persons reach age 65). Other ones of the queued forms (e.g., 4013) may be discarded into a waste bin 4014 after having been acted upon just once by the Up-Loader 4018 or even if they had not been acted upon at all by the Up-Loader 4018 (e.g., the System Administrator decides to discard them).

Aside from being able to generate instantiable interviews 4021 and new or modified Patient Records 4022, the Up-Loader 4018 can also directly generate (4026) Instantiated Interviews 4025 directly from forms 4012 in the Up-Loader Queue if such forms provide all the necessary information for completing an instantiated interview. In one embodiment, an instantiated interview (4025) is defined as having all the information fields therein completed, where such completed information fields are the ones necessary for appropriately scheduling and conducting an interview. Examples have already been given herein for cases where human intervention 4024 is called for in order to complete an instantiable interview 4021 and thereby convert it into an instantiated interview 4025. The case of FIG. 12, for example, can represent a situation where a System-external laboratory (4005) has electronically sent its lab results through converter 4010 into queue 4015 and the Up-Loader 4018 has generated both an instantiable interview 4021 and a corresponding alert 4023, where the latter lets the doctor know that human-intervention 4024 is being called for. When the doctor 4075 checks an alerts-summarizing mechanism (e.g., the screen shown in FIG. 10A or another alert-reporting mechanism), he or she can respond to the generated alert (4023) by filling in the necessary information or by delegating the task to an assistant (4076). The interventions 4024 for converting instantiable-interviews (4021) into instantiated ones (4025) may take place through the interactions of the MSP, MA and/or other Persons with corresponding client interfaces 4028 and screen driving clients 4027. The latter screen driving clients 4027 have access to patient records and other information within the System database 4050 for thereby filling in parts of the instantiable-interviews (4021) with default or already-obtained information as may be appropriate. It is within the contemplation of the disclosure that certain instantiable-interviews 4021 do not need human intervention 4024 and can therefore be generated automatically by the System 4000. Patient record information 4022 and/or other information that may be needed for converting an instantiable interview 4021 into an instantiated one 4025 may be provided directly from the database 4050 without human intervention.

In some instances, Dialog-blocking or interview-blocking means such as 4031 and 4033 may be established within the System for automatically preventing certain instantiated or instantiable interviews from getting through to the Scheduler 4040. For example, a given patient may request that no Health Maintenance reminders regarding his smoking habits be sent to him. Each time the System batch-produces a series of Health Maintenance reminders for sending to smokers or smoker groups, that particular patient's blocking mechanism 4033 should come into effect and act to block out the undesired interview that is directed to him. The instantiation of that particular Interview either never happens (4031), or if it does happen, the instantiation of that particular Interview is destroyed (4033).

The System Scheduler 4040 automatically scans through the Database 4050 looking for instantiated interviews 4025 that are not blocked (4033). The Scheduler 4040 prioritizes such instantiated interviews and decides which kind of Channel to try to send respective ones of the Dialogs in those interviews through and when. Each communications channel (e.g., telephone, cell phone, pager, email, etc.) may have its own specific Channel Manager. For sake of example, two such managers are shown at 4061 and 4062.

Certain ones of the System's channels may have more restricted bandwidths than others. Say, for example, that Channel Manager 4061 manages a small number of telephone lines 4065 available to the System. The Channel Manager 4061 is aware of this situation. When the Channel Manager 4061 receives a series of requests from the Scheduler 4040 for moving a current set 4064 of already-prioritized Dialogs through the limited-bandwidth channel 4065, the Channel Manager 4061 automatically makes certain decisions about which Dialogs will get through the channel 4065 and which won't. The Channel Manager 4061 may also elect to use a channel-specific "terse" mode for delivering the Dialog rather than a "verbose" mode, as may be appropriate for the channel bandwidth. In one embodiment, each Channel Manager 4061, 4062, etc.) organizes its respective set 4064 of Dialogs received from the Scheduler 4040 first according to priority of Application (e.g., an emergency room (ER) clinic application will generally have higher priority than a smoking-management clinic) and then according to Topic priority within each of the selected Applications. Attempts will then be made to contact the corresponding targets (e.g., Patient-X and Patient-Y) through the corresponding channel 4065. As time or other events occur, certain ones of the Dialogs in set 4064 may become ineligible for further delivery-attempts and new Dialogs may be added to set 4064. Thus, set 4064 can be dynamically changing over time.

It is assumed in the case of illustrated channel 4066 that successful contact 4068 has been made with Patient-Z and that Dialog 4069 was delivered to Z and completed. The completed Dialog 4069 is then returned via path 4070 through the corresponding Channel Manager 4062 for ultimate reflection (4070') into one or more parts of the database. For example, new information that Patient-Z may have provided via Dialog 4069 may be recorded into Patient-Z's records 4071 for future use by the System. Delivery-Attempts information acquired during the interaction 4068 with Patient-Z may be reflected back into the delivery strategies 4072 that are stored within the database for Patient-Z. Particular pieces of information or lack thereof may cause the System to generate Alerts 4073 in response to what happened when Dialog 4069 was delivered or attempted to be delivered to Patient-Z. The states (e.g., internal contents or decision trees) of still-pending, instantiated Interviews 4025 may even be modified (under the applicable Application Rules 4074) by the fedback data signals 4070' resulting from the delivery-attempt or conduction of Dialog 4069. Application Rules 4074 and/or Topic Rules and/or other processing rules may be used to control how the feedback information 4070' obtained from the Channel Manager 4062 is processed. For example, certain ones of Alerts 4073 may be directed to the Alert Summaries of specific medical service providers (4075) while others are directed to other real people (4076) and yet others, which can be dealt with automatically under an Application's policies, may be directed to machine-implemented agents such as 4078.

The illustrated machine-implemented Agent 4078 acts as a sort of virtual doctor or nurse that automatically scans through the database 4050 looking for prespecified patterns of information that, according to Agent Rules 4079, justify the fully-automated formulation of instantiated interviews 4025 for transmission to patients or other persons. For example, health maintenance interviews may be automatically scheduled for certain patients whose records 4022 indicate they have reached a particular age where an examination may be warranted. Agent 4078 handles these mundane tasks thereby freeing the human participants 4075 and 4076 of the System to focus their attentions on higher priority matters. In one embodiment, if human intervention is nonetheless needed under clinic policies or otherwise, the Agent 4078 completes all the work it is allowed to do and then notifies an appropriate human being for permission to send the formulated Interview with or without human-entered modifications.

Figure 40B:
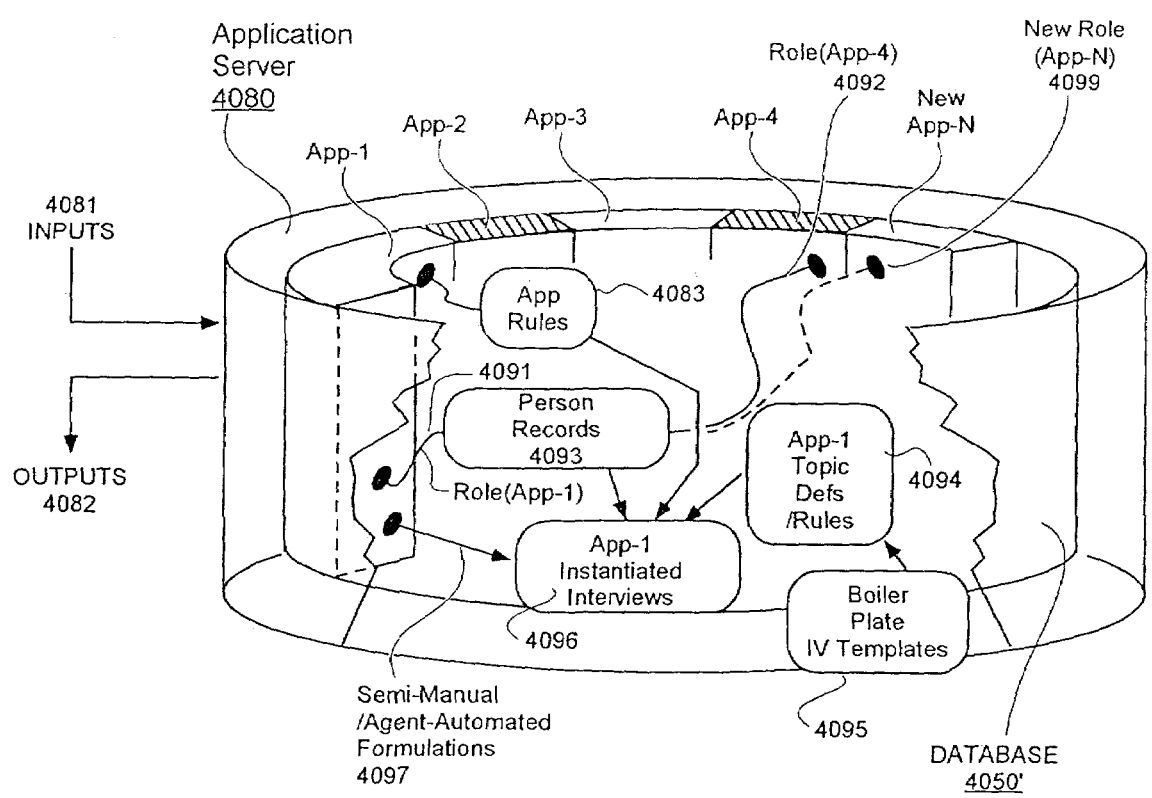
FIG. 40B is a block diagram illustrating how an Application Server may provide an I/O firewall and scalability.

Referring to FIG. 40B, one embodiment 4000B of a System in accordance with the disclosure is illustrated for purposes of explaining security and scalability. An Application Server 4080 functions to, in essence, protectively surround the Database 4050' of this embodiment 4000B and control what goes in or comes out. Substantially all data inputs 4081 and data outputs 4082 that involve sensitive information are forced to go through the Application Server firewall so as to prevent unauthorized persons from interfering with System data, or interfering with System operations or receiving information they are not supposed to receive. An interface of the Application Server 4080 routes input and/or output signals 4081/4082 along paths to/from different, System-defined Applications, such as the illustrated App-1 through App-4. Logical role assignments, such as indicated at 4091 and 4092 are made between respective Person records 4093 and the different Applications so that read or write access to data is controlled on a per-Application basis, depending on the Role of the given Person under that particular Application for which data is being communicated. In essence, appropriate ones of Person records 4093 are inherited by each respective Application under an appropriate one or more Roles relative to that Application (e.g., new Role 4099 for New Application N) so that same Person records do not have to be duplicated and duplicatively updated for each Application. Each Application may have its own specific Rules 4083 for controlling the instantiation of interviews under that Application. Each Application may have its own Topic definitions and/or Topic rules 4094 for further controlling the instantiation of interviews under respective Topics. In one embodiment, Application Rules, Topic definitions and Topic rules are not inherited into Applications but rather copied for or custom built for each new Application. Various boilerplate interview templates and Dialog templates 4095 may be provided within the System 4000B by inheritance or copying through respective Topics (4094) and may be used for facilitating the formulation of Instantiated Interviews. For the instantiation of certain Interviews, semi-manual or agent-automated formulation activities 4097 may need to take place under the rules of the respective Application. When a new Application, e.g., App-N, is to be added to the System 4000B, additional Role assignments such as 4099 can be easily made without having to generate new Person records 4093. Corresponding Application Rules 4083 and/or Topic Definitions and Topic Rules 4094 may be copied to, or custom-constructed for the new Application. Thus, a scalable and secure System 4000B may be provided for formulating and dispensing health-related information to individual patients or groups of patients; for collecting health-related information from such patients; and for taking appropriate and timely action in response to patient feedback or lack thereof.

Given that descriptions have been presented above about a variety of aspects that may be present in Service Providing Organization Supporting Systems which are structured in accordance with the present disclosure, it is now easier to complete the description of FIG. 10B, which description was started above. The signals and actions flowchart 1050 shows that a number of different events 1060 may occur within a System to lead to the creation (1070) of an Alert 1080 and a corresponding Alert Summary 1080a or the creation of other kinds of notifications, which may be treated, at least in the context of the Alert-summarizing Presentations as if they were Alerts. One of the illustrated, alert-invoking events is Message Spoilation 1061. The latter can occur when for one reason or another, a message times-out (it rots, so to speak) before the System even had a chance to carry out a delivery-attempt. The created alert that is associated with this kind of event (1061) is referred to herein as an "Unsent Alert". A possible underlying cause (1055) may be that the communication channels which were planned for making the delivery-attempts were all busy servicing more pressing messages (higher priority messages) and their bandwidths were too narrow to allow the now-spoiled message to get through. Delivery-strategies of the corresponding Application may have to be modified if too many important messages spoil in such a way.

A second of the illustrated, alert-invoking events is Message Refusal 1062. The latter can occur when for one reason or another, certain rules within the System (see items 4031 and 4033 of FIG. 40A) cause a partially instantiated or fully instantiated Interview from getting to the scheduler (4040) for subsequent attempt of delivery. An underlying reason may be an uncooperative Patient who has asked that the respective message be "blocked" from annoying him or her. The created alert that is associated with this kind of event (1062) is referred to herein as a "Blocked Alert".

A third of the illustrated, alert-invoking events is Message NonRetrival 1063. The created alert that is associated with this kind of event (1063) is referred to herein as a "Retrieval Alert". A Message NonRetrieval event 1063 can occur due to any of a number of possibilities. The telephone answering-machine of the message Target (e.g., Patient) may be overfilled or broken. The Patient may be too sick to respond. System-kept histories of what has happened in the past may be helpful in determining what the more likely underlying cause is. The Primary Care Provider may nonetheless be held ultimately responsible and thus may want to be alerted to the Message NonRetrieval event 1063.

A fourth of the illustrated, alert-invoking events is a Collected Information Triggering event 1064. The created alert that is associated with this kind of event (1064) is referred to herein as an "Info Alert". A Collected Information Triggering event 1064 can occur due to any of a number of possibilities. New, abnormal test results may have come in from a laboratory. The Patient may have reported new symptoms in the course of responding to a delivered Interview. The Patient may have reported that he/she is doing worse or not doing better at some time point in the follow up concerning a condition known to the System.

Item 1069 indicates that there can be other events which are reported to the Alert/Notification Creating mechanism 1070 of FIG. 10B. The Alert/Notification Creating mechanism 1070 can rely on the identity of the alert invoking event 1060 and/or on various Target-centric rules (discussed above) and/or Application-centric rules and/or MSP-preference rules and/or Topic-centric rules to determine whether or not to generate a corresponding Alert 1080, and if so, what Alert-summarizing Note 1094 should be used, and/or what Alert-Handling Action 1088 is to be requested of one or more of the Alert recipients and/or and if priority is to be set (1082), what base priority to establish. Referring to momentarily FIG. 10A, it may be seen from the illustrated example that the primary-responsibility table 1040 can be viewed as having been divided into 3 general groups of priority based on the ACTION (column 1008) being requested. The SEND action requested in row 1017 belongs to the highest general priority group because it is alerting/notifying the MSP of a new medical condition the MSP was probably not aware of yet, namely, that a positive strep throat culture has just been reported by the lab for the Patient named Steve Winton.

(Prior to this, the physician could not have been certain that the Patient had this new medical condition.) The REVIEW actions requested in rows 1018, 1020, 1019 belong to a next lower, general priority group because they are alerting/notifying the MSP of situations that his/her office was at least partially aware of, namely for example, that Patient Alice Holes has asthma, even though the office may not have been aware of the latest change in condition, namely that Patient Holes' peak flow is abnormally low (see column 1014). The BLANK (unnamed) actions implied in rows 1021, 1023, 1024 belong to a yet next lower, general priority group because they refer to situations the MS P has already reviewed, but for one reason or another, has decided to "keep" on his/her Alerts-Summarizing List (see button 1706 in FIG. 19). Therefore it may be seen from the example of table 1040 in FIG. 10A that the Alerts/Notices sorting rules for that particular MSP are sorting primarily based on ACTION field 1008, and then secondarily perhaps, on Alert-types of field 1016 (Info Alert versus Retrieval Alert), and then thirdly perhaps, on Alert-Notes of field 1014 (e.g., PeakFlow Low takes precedence over No-Appointment Made). The sort strategy used in the MA's list of delegated Actions, on the other hand, may be based primary on the Alert-summarizing Notes field 1014. Thus each Summaries-receiving recipient may see a differently sorted presentation of Alert/Notification summaries based on the role and/or other attributes of the recipient. Moreover, as will be seen shortly, each Summaries-receiving recipient may receive a different set of summaries for presentation on his/her, personal Alerts/Notifications Summary List. So the specific summaries that are presented by the System to each Person may different on a person-by-person basis. For example, one Medical Assistant may service the practices of several physicians in a given clinic. Each such physician may be limited by the System to receiving presentations of Alert/Notification Summaries involving only the Patients of that specific physician. The MA, on the other hand, may receive the delegated summaries from all those physicians. It may be noted in passing that although a particular approach to sorting presented-alert-summaries is shown in the example of FIG. 10A, other embodiments may use different sorting schemes for presented-alert-summaries or no sorts at all.

The created Alert or Notification 1080 and/or its corresponding summary 1080a should include some identifier of, or pointer to (1081) the underlying message (e.g., 1065) which provoked the Alert or Notification creation step 1070a. Such an identifier/pointer 1081 allows the System to fetch detailed information about the underlying cause of the Alert/Notification creation 1070a as may be appropriate. In addition to, or as an alternative to the provision of the identifier 1081 of the underlying message (e.g., 1065), the created Alert or Notification 1080 and/or its corresponding summary 1080a may include an identification 1091 of the Target (e.g., Patient) associated with the Alert/Notification creation 1070a as may be appropriate. (In an alternate or varied embodiment, a list of latest communications sent to each Target may be kept in chronological or other appropriate order and may be used by the System for fetching more detailed information about the underlying cause(s) of the Alert/Notification creation 1070a.

For purposes of providing a useful summary to the recipient (e.g., MSP) of the Alerts Summary presentation (e.g., FIG. 10A), the created, summary data structure 1080a should include an Alert-summarizing Note section 1094 that is filled upon creation to contain an Alert-summarizing Note as discussed above or a pointer to (identifier of) such a Note. The other item which the recipient (e.g., MSP) of the Alerts Summary presentation would probably want to be informed of by way of summary is the Patient name (Target ID 1091, see also column 1011 of FIG. 10A). Dashed line 1083 represents, for one class of embodiments, a dividing line between what might be deemed essential in certain Applications for providing a useful Alerts Summary presentation (above line 1083) and what might be desirable but not as vital (below line 1083).

Another part of the summary data structure 1080a that may be relatively valuable, is a field 1088 indicating the Alert-Handling Action being Requested. This corresponds to column 1008 of FIG. 10A, and as indicated above, the contents of the Alert-Handling Action Requested field 1088 may be used in machine-implemented step 1072 for adjusting priority for purposes of subsequent sorting 1073 and/or for other purposes. The base, and/or thereafter adjusted priority value(s) may be kept in field 1082 of the summary data structure 1080a.

Yet another part of the summary data structure 1080a that may be relatively valuable for purpose of presenting a summary of an Alerted/Notified situation, is a field 1096 indicating the Alert-Causation Type. This corresponds to column 1016 of FIG. 10A (Alert Type). As indicated above, the contents of the Alert-Causation Type field 1096 may be used in machine-implemented step 1072 for adjusting priority for purposes of subsequent sorting 1073 and/or for other purposes. The summary data structure 1080a may have yet other fields (represented by box 1089) which may be useful for providing summarized information about the underlying Alert 1080 and/or its corresponding message 1065. The summary data structure 1080a may be contained in, or point to its corresponding, and usually more detailed, Alert data structure 1080. The main Alert data structure 1080 may contain data and/or logic for generating the zoom-in-on-details presentations such as was exemplified above by FIGS. 12–24.

Each created summary data structure 1080a (and in one less-efficient embodiment, also its corresponding main Alert data structure 1080) should be replicated (instantiated) a number of times according to the number of persons who are initially to have the summary included on their respective Alerts/Notifications Summary List. Each such instantiated Alerts/Notifications Summary data structure 1080a (and in one less-efficient embodiment, also its correspondingly, replicated main Alert data structure 1080) may then be optionally processed through a corresponding, recipient-centric, priority adjusting means (1072, 1072', etc.) and/or a corresponding, recipient-centric, summaries sorting mechanism (1073, 1073', etc.) so that the newly instantiated Alerts/Notifications Summary data structure 1080a may be appropriately presented (e.g., 1074) to the summary recipient on a recipient-centric basis.

As has already been explained, each Summary-recipient (e.g., Primary Care Provider, Medical Assistant, etc.) may be empowered to zoom-in 1075 on details of the main body Alert/Notification 1080 that underlies the summarized Alert/Notification depending on System-assigned privileges. At least one System-authorized Person (e.g., the PCP) should be empowered to delegate (1076) the responsibility for responding to a pending Alert to another Person (e.g., the Medical Assistant). Such a delegation is represented in FIG. 10B by the flow 1068 of a corresponding Alert/Notification Summary data structure 1080a through optional function box 1067 and into routing structure 1071 for routing to the delegee (e.g., the MA). The delegation function should report its activities to an Audit Trail recording mechanism 1079 so that the System has a traceable record of how the summarized Alert/Notification was disposed of. The optional, priority-override function box 1067 represents the privileges-empowered option that may allow a PCP or other such trusted person to change the base priority value stored in section 1082 before the summarized Alert/Notification is routed through structure 1071 to the delegee. The delegee's (e.g., MA's) priority-adjusting mechanism may then further process this override-generated, priority value (1082) as may be appropriate.

Yet another option that at least one System-authorized Person (e.g., the PCP) may have, is to delete (1077) the summarized Alert/Notification from his/her personal Alerts/Notifications Summary List. The summary-delete function should report its activities to the Audit Trail recording mechanism 1079 so that the System has a traceable record of how the summarized Alert/Notification was disposed of. Deletion of a summarized Alert/Notification from a corresponding Person's Alerts/Notifications Summary List does not necessarily include full deletion of the corresponding, main body Alert/Notification 1080 from the System. As should now be apparent, the Audit Trail recording mechanism 1079 may still point to the main body Alert/Notification 1080 even though one Person has deleted the respective summary from his/her, personal Alerts/Notifications Summary List (if empowered by the System to so do). Also, the routed Alert/Notification Summary data structures (1080a, only one shown) of other persons may still point (reference) the corresponding, main body Alert/Notification 1080.

If a so-empowered, recipient (e.g., the Primary Care Provider) of an Alert/Notification Summary decides to "handle" the underlying Alert/Notification 1080 by, for example, formulating and/or sending an Interview that addresses concerns raised by the underlying Alert/Notification 1080, then a control path such as illustrated at 1057 may be taken. The Alert/Notification handling person (e.g., the PCP) formulates one or more follow up Interviews. The handling function(s) 1078 should report its/their activities to the Audit Trail recording mechanism 1079 so that the System has a traceable record of how the summarized Alert/Notification and/or the underlying Alert/Notification 1080 were responded to. Under one optional, handling approach (1059), when the Alert/Notification handling person (e.g., the PCP) instantiates the formulated response (e.g., by activating the SEND button), the corresponding Alert/Notification Summary data structure 1080a is automatically removed from his/her, personal Alerts/Notifications Summary List. The System is handed the responsibility of seeing to it that the instantiated follow up Interview(s) are delivered in timely fashion or that, otherwise a responsible person is alerted of the failed delivery attempt (1063) or of spoilation (1061) of the follow up Interview(s).

Under a second optional, handling approach (1058), when the Alert/Notification handling person (e.g., the PCP) instantiates the formulated response (e.g., by activating the SEND button), the corresponding Alert/Notification Summary data structure 1080a is automatically modified (e.g., by changing the contents of its Alert-Handling Action Requested field 1088, for example to BLANK as in the example of row 1024 of FIG. 10A and/or by changing its current priority value (1082) as may be appropriate, for example by reducing that value 1082) and the so-modified Alert/Notification Summary data structure 1080a is kept on his/her, personal Alerts/Notifications Summary List for optional later referral to. The System is still handed the responsibility of seeing to it that the instantiated follow up Interview(s) are delivered in timely fashion or that, otherwise a responsible person is alerted of the failed delivery attempt (1063) or of spoilation (1061) of the follow up Interview(s). Accordingly, responsibility is maintained by at least one of the System and a responsible Person for seeing to it that each urgent Alert and/or Notification is taken care of, or that a recorded audit trail (1079, see also item 1814 of FIG. 18) is generated to show why the Alert and/or Notification was not taken care of.

It is possible to have situations in which one or more Alerts and/or Notifications are not taken care of for an excessively long time (where that excess is defined by the respective Application) even though the corresponding summary was presented in the Alerts/Notifications Summary Lists of one or more persons. (One possibility is that the situation was handled outside the auspices of the System and no one took the trouble to properly inform the machine-implemented System of that off-System disposition. Accordingly, an automated garbage collecting mechanism 1099 may be provided for periodically scanning through the System Database and erasing excessively old Alerts (spoiled Alerts). The garbage collecting mechanism 1099 may also automatically erase sufficiently old ones (where the value for what constitutes sufficiently old is defined by the respective Application) of the main body Alert/Notifications 1080 that are marked as having been "deleted" (in the 1077 sense, and/or in the FIG. 18 sense) by actions of an appropriately responsible person (e.g., the PCP).

Given that machine-implemented and automated handling of the above situations is contemplated herein, it is to be further understood that computer-readable mediums (e.g., 88 of FIG. 1A) or another form of a software product or machine-instructing means (including but not limited to, a hard disk, a compact disk, a flash memory stick, a downloading of manufactured instructing signals over a network (e.g., 89 of FIG. 1A) and/or like software products) may be used for instructing an instructable machine (e.g., 80 of FIG. 1A) to carry out such medical-communications facilitating activities (e.g., 95 of FIG. 1A) and/or medical-action facilitating activities (e.g., 65/26 of FIG. 1A) in accordance with the disclosure provided herein. As such, it is within the scope of the disclosure to have a one or more instructable machines (e.g., server and client computers, PDA's, 3G cell phones, etc.) automatically carry out one or more of the disclosed methods, and/or it is within the scope of the disclosure to provide one or more software products adapted for causing such instructable machines to carry out Various features that may be included in Systems in accordance with the present disclosure are as follows:

1. A single alert screen (or other summarized-alerts reporting mechanism) may be provided that displays (or otherwise reports) one or more of: test result delivery alerts, health maintenance alerts, specialist referral alerts, test referral alerts, custom message alerts, failure to keep appointment alerts, and test result alerts, in a summarizing manner that allows a Medical Service Provider to easily monitor and thereby be kept aware of present time situations that are worthy of keeping a watch over, such as one or more critical clinical situations developing under his/her practice. Using such a summarized-alerts reporting mechanism the MSP can select a given one of the summarized alerts and receive further details regarding it and/or the MSP can be further empowered to issue responses via the System for handling the detailed alert-situation, such as initiating an Interview with the Patient or another Person (e.g., a consultant) or delegating the handling of the situation, with inclusion of MSP-provided instructions, to a Back-up physician, a Medical Assistant or another such Person.

2. A single screen (or other summarized-risks reporting mechanism) may be provided that displays (or otherwise reports) about one or more clinical situations which a Medical Service Provider has enhanced legal- and/or -financial liability risks for under in his/her medical practice so that the at-risk MSP can easily monitor and thereby be kept aware of present time, risk-laden situations that are worthy of keeping a watch over, such as one or more high-exposure clinical situations developing under his/her practice.

3. Means are provided for a Medical Assistant and/or another trusted and medically-trained Person to access the same single alert screen (or other summarized-alerts reporting mechanism) with selectively assignable privileges being given to that other trusted and medically-trained Person to interact with and respond to alerted situations.

4. Means are provided for facilitating the generation of situation-appropriate, timed and automated Patient follow-up Dialogs or Interviews for medical conditions indicated by the alert-detailing reports where content within the facilitated, Dialogs or Interviews is adaptively pre-defined in accordance with Patient Attributes known to the System and/or in accordance with present medical conditions indicated by relatively recent Dialogs or Interviews to be developing in a present time. Further means may be provided to adjust presentable content of current and/or future Dialogs in response to current patient's responses—in other words, adaptive prompting.

5. An automated means is provided to adjust a paradigm of usable delivery strategies on a Target-by-Target basis in response to personal attributes of the communication Target (e.g., Patient Attributes), in response to Interview answers or lack of answers provided by the communication Target (e.g., the responses that a Patient provides with regard to an Interview concerning an illness, and/or in regard to the course of the Patient's illness and/or treatment progress). Also, Adaptive Message assigning means are provided for adaptively assigning different content to Dialog flow trees based on one or more of the personal attributes of the communication Target (e.g., Patient Attributes) and the Interview answers or lack of answers provided by the communication Target.

6. The System can include Delivery strategies that are Rule-based and that determine routing of Instantiated Dialogs among different communication channels in accordance with corresponding Delivery strategy Rules for the respective Dialogs. The Delivery strategy Rules can provide automated routing decisions which are responsive to preferences of one or more of Service Providers, Patients, or Medical Facilities; the nature of the message being sent; the content of the message being sent; and Patient, Provider, and Medical Facility Attributes.

7. The System can use the Interviews which it generates, delivers and/or manages to gather information about respective communication Targets (e.g., Patients) over a time period. The System includes Alert Generating means to automatically Alert a responsible Service Provider of automatically-detected problems concerning: delivery or non-delivery of various, note-worthy Dialogs, and/or information obtained over said time period by the carrying out of Interviews or Dialogs, where the automatic detection of problems can be based on Service-Organization defined standard rules and/or personal attribute values of the communication Target.

8. The System can include coordinated, multi-media means to use multiple media types to deliver messages wherein receipt of message in one media type cancels message delivery attempts in other media types. This coordinated approach to using different communication channels can reduce annoying repetitions of message deliveries that communication Targets may experience in non-unified, uncoordinated systems which rely on automated content delivery.

9. The System can include automatic delivery-failure notification means to notify a Service Provider, in near real-time, of a failure of System-attempted communications to adequately follow up on the state and/or progress of medical conditions of specific Patients.

10. The System can include automatic content selection means for forming the content of messages based on a Patient or other Target's personal health or other Attributes, where the content selection can be further responsive to the means chosen for delivery or presentation of content information.

11. Means for enabling a Medical Service Provider to easily (e.g., one-click) add Addendum phrases to boiler-plate message templates that are automatically pre-filled with Target-specific data.

12. Audit-trail creating means for assisting a Medical Service Provider or Medical Assistant to add selectable or customizable Deletion-justification phrases to [standard] message histories to indicate how an Alerted message was handled prior to, or around the time of its deletion from an Alerted messages list.

13. Responsibility Delegation Means for allowing a Medical Service Provider to delegate through the System, responsibility for reacting to one or more alerted messages to Medical Assistants and to indicate, through the System, how the MSP desires the alerted situation to be handled by the delegated-to MA.

14. Means to pack and deliver several messages to a given Target in a single contact with said messages ordered by Priority responsive to their respective message content, Topic priority or Application priority, Target Attributes, and/or prior delivery attempts and results of such attempts.

15. Means to pack and deliver several messages to a given Target in a single contact where said messages may originate from different senders.

16. Automated instantiation of Health Maintenance Interviews and of their respective delivery schedules in response to Patient Attributes and/or Provider Attributes currently stored in the System Database.

17. Means for "Guest/Backup Service Providers" to use a Primary Service Provider's Account with limits of time and access to certain capabilities and screens.

18. Means to deliver several messages to a given Target using a set of delivery channels and providing a selected number of messages to each channel proportional to that channel's ability (bandwidth and availability) to deliver said messages in a timely manner so as not to impede promptness of subsequent message deliveries via such communication channels.

19. The Service Provider is given a clarification-supporting means for delivering further information regarding the content of a boiler-plate Dialog by way of automated delivery of a subsequent Custom Dialog that is delivered with the boiler-plate Dialog.

20. Means responsive to Rules of advising a Patient that Alerted (note-worthy) Interview Dialogs are awaiting his or her access.

21. Means of assigning appropriate health maintenance monitoring interviews responsive to Patient's Attributes and other Attributes.

22. Delivery strategies that are responsive to Successive Content Ordering Rules (e.g., Progression Requirements) regarding Dialogs or Interviews that should be delivered in a particular, preferential sequence.

23. InterDialog Time Gap and Interview Dialog Delivery Rules which automatically provide for proper minimum spacing between deliveries of successive Dialogs of a given follow up Interview.

24. Interview has a NeedsReview property that can be set True or False by rules responsive to Dialog content or Medical Facility or Provider Attributes.

25. System can generate and store the definition of an Interview Target Group whose members may be selected based on one or more Person Attributes and the System can then instantiate Interviews for each member of formed Group.

26. The System can be expanded to add new Applications (e.g., new Service-Providing Organizations or subsets thereof) without having to generate new Person records for each added Application. Roles of Persons can be changed under each Application as persons change roles with respect to such Service-Providing Organizations (e.g., clinics, hospitals, etc.).

27. The System can sift off Patient-centric, "normal" test and/or Interview results for respective Patients who are doing well and thereby leave behind for human intervention only those situations where for the given Patient (Patient-centric sifting), the obtained test and/or Interview results are worthy of human intervention such as being looked at and/or reacted to by a care-concerned service provider such as a doctor, nurse or other trained member of the Service-Providing Organization that is providing health or medical care related services to the Patient.

Other: Essentially all tests can be reported in a practice due to System's efficiency-hence, operating policy can be if patient does not hear re test, then patient should contact office as something is amiss.

In view of the above, the present disclosure is to be taken as illustrative rather than as limiting the scope, nature, or spirit of the subject matter claimed below. Numerous further modifications and variations may become apparent to those skilled in the art after studying the disclosure, including use of equivalent functional and/or structural substitutes for elements described herein, use of equivalent functional couplings for couplings described herein, and/or use of equivalent functional steps for steps described herein. Such insubstantial variations are to be considered within the scope of what is contemplated here. Moreover, if plural examples are given herein for specific means, or steps, and extrapolation between and/or beyond such given examples is obvious in view of the present disclosure, then the disclosure is to be deemed as effectively disclosing and thus covering at least such extrapolations.

Given the above disclosure of general concepts and specific embodiments, the scope of protection sought is to be defined by the claims appended hereto.

What is claimed is:

1. A machine-implemented method for notifying at least one care-concerned person to a health or medical care-related situation constituted by at least one of the following notification-worthy situations:

(0.1) completion of a care-related task where said task completion calls for relatively prompt attention thereto;

(0.2) in-completion of a care-related communication delivery-attempt where said in-completion of the delivery-attempt calls for relatively prompt attention thereto;

(0.3) in-completion of a care-related task where said in-completion of the care-related task calls for relatively prompt attention thereto;

(0.4) an unexpected change or a lack of expected change in a medical condition of a given patient where said unexpected change or lack of expected change calls for relatively prompt attention thereto; and (0.5) an apparent failure to notify a primary medical service provider, or a primary medical assistant as may be appropriate, of one of the above notification-worthy situations;

where said machine-implemented alerting method comprises:

(a) monitoring communications related to progress or lack of progress in timely completion of pre-scheduled, care-related tasks and related to timely completion of pre-scheduled, care-related communication delivery-attempts and related to medical conditions of respective ones of plural patients;

(b) identifying among the monitored communications those which are indicative of at least one of said care-related situations that call for relatively prompt attention thereto by a care-concerned person where criteria for determining whether or not a given situation is one that calls for relatively prompt attention thereto are machine-defined and where timeliness of pre-scheduled ones of said care-related tasks and care-related communication delivery-attempts are machine-defined; and (c) for an identified one of the monitored communications which is indicative of at least one of said care-related situations that call for relatively prompt attention thereto, initiating a delivery-attempt for delivering to at least one targeted recipient in a group comprised of a medical service provider and a medical assistant an alert signal for notifying the targeted recipient of the monitored and identified communication.

2. The machine-implemented notifying method of claim 1 wherein said at least one care-concerned person includes a member of the group comprising a medical service provider and a medical assistant.

3. The machine-implemented notifying method of claim 1 wherein said at least one notification-worthy situations definitively include:

(0.2) said in-completion of a care-related communication delivery-attempt where said in-completion of the delivery-attempt calls for relatively prompt attention thereto; and (0.3) said in-completion of a care-related task where said in-completion of the care-related task calls for relatively prompt attention thereto.

4. An alerting mechanism for summarily alerting a care-concerned person to a care-related situation constituted by at least one of the following situations:

(0.1) completion of a care-related task where said task completion calls for relatively prompt attention thereto;

(0.2) in-completion of a care-related communication delivery-attempt where said in-completion of the delivery-attempt calls for relatively prompt attention thereto;

(0.3) in-completion of a care-related task where said in-completion of the care-related task calls for relatively prompt attention thereto; and (0.4) an unexpected change or a lack of expected change in a medical condition of a given patient where said unexpected change or lack of expected change calls for relatively prompt attention thereto;

where said alerting mechanism comprises:

(a) action requesting means for advising the care-concerned person of an attention-giving action that is to be provided by the care-concerned person or delegated to another care-concerned person in response to an alerted situation;

(b) topic defining means for advising the care-concerned person of the medical concern that is addressed by the alerted situation;

(c) patient identifying means for advising the care-concerned person of the identity of one or more patients associated with a corresponding attention-giving action and a corresponding medical concern that is addressed by the alerted situation; and (d) situation identifying means for advising the care-concerned person of a situation type to which the alerted situation belongs.

5. The alerting mechanism of claim 4 wherein:

(a.1) said action requesting means includes means for advising the care-concerned person to at least provide an attention-giving action selected from the attention-giving group consisting of:

(a.1a) initiating a sending of test results to a tested patient to at least thereby let the tested patient know that the results have been received by the care-concerned person;

(a.1b) reviewing contents of an automated or semi-automated interview conducted with a corresponding patient; and (a.1c) becoming aware of a failed attempt to deliver a communication relating to a corresponding patient;

(b.1) said topic defining means includes means for advising the care-concerned person of at least one of the medical concerns in a topic group consisting of:

(b.1a) an identifier of a blood component that is of concern;

(b.1b) an identifier of a chronic disease that is of concern;

(b.1c) an identifier of an on-setting disease that is of concern;

(b.1d) an identifier of a body part or body system that is of concern; and (b.1e) an identifier of a type of test or other medical procedure that is of concern; and (d.1) said situation identifying means includes means for advising the care-concerned person of at least one of the situation types in a situation type group consisting of:

(d.1a) a retrieval failure situation in which a corresponding communication delivery attempt was not timely or fully completed; and (d.1b) an information-triggered situation in which information gathered during a corresponding communication delivery attempt triggered the alerted situation.

6. The alerting mechanism of claim 4 and further comprising:

(e) topic category defining means for advising the care-concerned person of a system-supported category encompassing the medical concern that is addressed by the alerted situation.

7. The alerting mechanism of claim 4 and further comprising:

(e) privilege controlling means for controlling alert-disposing privileges of pre-specified ones of care-concerned persons to certain classes or specific ones of attention-giving actions.

8. The machine-implemented notifying method of claim 4 wherein said at least one care-concerned person includes a member of the group comprising a medical service provider and a medical assistant.

9. In a machine-implemented, communications managing and delivering system having at least one of:
  (0.1) filtering means for automatically identifying intervention-worthy communications which are worthy of being reviewed by a human intervener; and
  (0.2) task in-completion detecting means for automatically detecting note-worthy failures to complete attempted communications and/or note-worthy failures to complete scheduled action items;
where the communications managing and delivering system further includes an alert generating means for generating alert reports indicative of at least one category of said intervention-worthy communications, note-worthy failures to complete attempted communications, and note-worthy failures to complete scheduled action items;
  an alerts summarizing mechanism comprising:
    (a) prioritizing means for prioritizing alert reports according to their comparative intervention-worthinesses or note-worthinesses, where said comparative worthiness characteristics are machine-defined; and
    (b) target-person identifying means for identifying a target-person to whom one of said intervention-worthy communications is to be sent, or on whose behalf a note-worthy failure to complete an attempted communication occurred, or on whose behalf a note-worthy failure to complete a scheduled action item occurred.

10. The alerts summarizing mechanism of claim 9 and further comprising:
    (c) summarized alerts reporting means for reporting summarizations of the prioritized alert reports to at least one person responsible for reacting to the alert reports; and
    (d) details providing means for providing more details about an alert report summarized by one of the reported summarizations in response to the at least one responsible person selecting one of the reported summarizations.

11. The alerts summarizing mechanism of claim 10 and further comprising:
    (e) delegation means for allowing said at least one responsible person to delegate to at least a second responsible person with instructed actions and by way of said communications managing and delivering system, the responsibility of reacting to a selected one or more of the alert reports.

12. The alerts summarizing mechanism of claim 10 and further comprising:
    (f) delegation tracking means for allowing said at least one responsible person to track the carrying out of respective ones of said instructed actions by the at least second responsible person to whom was delegated the responsibility of reacting to respective ones of said alert reports.

13. The alerts summarizing mechanism of claim 9 and further comprising:
    (c) summarized alerts reporting means for delivering predefined summarizations of the prioritized alert reports to at least one person responsible for reacting to the alert reports.

14. An automatic and adaptive dialog conducting mechanism for use in a communications managing and delivering system where the communications managing and delivering system stores attributes describing potential target persons to whom communications may be sent; and where
  said automatic and adaptive dialog conducting mechanism comprises:
    (a) a decision tree having one or more dialog flow paths that are to be automatically followed during automated carrying out of a real-time adaptive dialog, where the one or more dialog flow paths that are followed can be selected in real time response to answers or lack of answers provided by the communication target person; and
    (b) a presentable data section for storing content-variable data that is to be automatically presented at respective nodes of the decision tree, where the content-variable data can be automatically generated in response to stored personal attributes of the communication target person.

15. The adaptive dialog conducting mechanism of claim 14 and further comprising:
    (c) a collectable data section for storing response and/or non-response data generated during the automated carrying out of the real-time adaptive dialog.

16. For use in a service providing organization, a machine-implemented method for increasing likelihood that service-related communications will be delivered to and retrieved by communications-targeted persons, said machine-implemented method comprising:
    (a) adaptively defining multi-channel delivery strategies over time for potential, communications-targeted persons based on previous delivery-attempt histories so as to increasing likelihood of delivery success to specific ones of said potential, communications-targeted persons when a next communication is targeted to one or more of such potential, communications-targeted persons;
    (b) requesting confirmation by communications-targeted persons of receipt and understanding of delivered ones of said communications; and
    (c) if failed delivery-attempts exceed predefined thresholds or communications-targeted persons fail to confirm receipt and understanding of delivered ones of said communications within predefined time limits, routing alerts to responsible persons within the service providing organization asking them to respond to the failed communications attempts.

17. An alerting mechanism for alerting a health care-concerned person to a health care-related situation constituted by at least one of the following situations:
    (0.1) completion of a care-related task where said task completion calls for relatively prompt attention thereto by the health care-concerned person or another person;
    (0.2) incompletion of a care-related communication delivery-attempt where said incompletion of the delivery-attempt calls for relatively prompt attention thereto by the health care-concerned person or another person;
    (0.3) incompletion of a care-related task where said incompletion of the care-related task calls for relatively prompt attention thereto by the health care-concerned person or another person; and
    (0.4) an unexpected change or a lack of expected change in a medical condition of a given patient where said unexpected change or lack of expected change calls for relatively prompt attention thereto by the health care-concerned person or another person;
where said alerting mechanism comprises:
    (a) action advising means for automatically advising the care-concerned person of an attention-giving action that is advised to be provided by the care-concerned person or delegated to another care-concerned person in response to an alerted situation; and (b) topic defining means for automatically advising the care-concerned person of the medical concern that is addressed by the alerted situation; and (c) patient identifying means for automatically advising the care-concerned person of the identity of one or more patients associated with a correspondingly advised attention-giving action and a corresponding medical concern that is addressed by the alerted situation.

18. The alerting mechanism of claim 17 wherein:

(a.1) said action advising means includes means for advising the care-concerned person to provide at least one attention-giving action selected from the attention-giving group consisting of:

(a.1a) initiating a sending of test results and a message to a tested patient;

(a.1b) reviewing contents of an automated or semi-automated interview conducted with a corresponding patient; and (a.1c) becoming aware of a failed attempt to deliver a communication relating to a corresponding patient.

19. The alerting mechanism of claim 17 wherein:

(b.1) said topic defining means includes means for advising the care-concerned person of at least one of medical concerns in a topic group consisting of:

(b.1a) an identifier of a blood component that is of concern;

(b.1b) an identifier of a chronic disease that is of concern;

(b.1c) an identifier of an on-setting disease that is of concern;

(b.1d) an identifier of a body part or body system that is of concern;

(b.1e) an identifier of a medical related, scheduled event that is of concern; and (b.1f) an identifier of a type of test or other medical procedure that is of concern.

20. The alerting mechanism of claim 17 wherein:

(d.1) said situation identifying means includes means for advising the care-concerned person of at least one of situation types in a situation type group consisting of:

(d.1a) a retrieval failure situation in which a corresponding communication delivery attempt was not timely or fully completed; and (d.1b) an information-triggered situation in which information gathered during a corresponding communication delivery attempt triggered the alerted situation.

21. A machine-implemented follow-up method for use in providing health care services to patients, the method comprising:

(a) defining in machine-readable storage, one or more delivery deadlines by which respective deliveries of one or more, corresponding health care services to respective patients are to be timely completed;

(b) automatically first determining whether or not each health care service having a corresponding delivery deadline has been timely and completely received by the respective patient; and (c) automatically delivering corresponding alerts to one or more persons responsible for completion of delivery of a given health care service having one of said delivery deadlines if, among other alert generating criteria, the given health care service is determined by said automatic first determining step to have been not timely and completely received by the respective patient.

22. The machine-implemented follow-up method of claim 21 wherein:

said health care services to be timely and completely delivered to respective patients include machine-conducted interview dialogs that are to be timely delivered to, and completed by respective patients; and (c.1) said automatic delivering of corresponding alerts includes automatically prioritizing alerts relating to nondelivery to, or noncompletion of interview dialogs by respective patients in accordance with predefined interview alert importance rules; and (c.2) said automatic delivering of corresponding alerts includes automatically sorting prioritized alerts so that the one or more responsible persons will be presented with interview nondelivery/noncompletion alerts having relatively high priority before being made aware, if at all, of interview nondelivery/noncompletion alerts having lower priority.

23. The machine-implemented follow-up method of claim 21 wherein:

said health care services to be timely and completely delivered to respective patients include medical test result reporting dialogs that are to be timely delivered to, and acknowledged by respective patients; and (c.1) said automatic delivering of corresponding alerts includes automatically prioritizing alerts relating to nondelivery to, or nonacknowledgement of medical test result reporting dialogs by respective patients in accordance with predefined test-result report alert importance rules; and (c.2) said automatic delivering of corresponding alerts includes automatically sorting prioritized alerts so that the one or more responsible persons will be made aware of test-result report nondelivery/nonacknowledgement alerts having relatively high priority before being made aware, if at all, of test-result report nondelivery/nonacknowledgement alerts having lower priority.

24. The machine-implemented follow-up method of claim 23 and further including:

(d) instructing patients to contact their health care providers if they do not automatically receive an expected medical test result reporting dialog.

25. The machine-implemented follow-up method of claim 21 wherein:

said health care services to be timely and completely delivered to respective patients include medical treatment result feedback dialogs that are to be timely delivered to, and responded upon by respective patients; and (c.1) said automatic delivering of corresponding alerts includes automatically prioritizing alerts relating to nondelivery to, or nonresponsiveness to medical treatment result feedback dialogs by respective patients in accordance with predefined treatment-result feedback alert importance rules; and (c.2) said automatic delivering of corresponding alerts includes automatically sorting prioritized alerts so that the one or more responsible persons will be made aware of treatment-result feedback nondelivery/nonresponsiveness alerts having relatively high priority before being made aware, if at all, of treatment-result feedback nondelivery/nonresponsiveness alerts having lower priority.

26. The machine-implemented follow-up method of claim 21 wherein:
- said health care services to be timely and completely delivered to respective patients include periodic health maintenance feedback dialogs that are to be timely delivered to, and responded upon by respective patients; and
- (c.1) said automatic delivering of corresponding alerts includes automatically prioritizing alerts relating to nondelivery to, or nonresponsiveness to periodic health maintenance feedback dialogs by respective patients in accordance with predefined periodic health maintenance alert importance rules; and
- (c.2) said automatic delivering of corresponding alerts includes automatically sorting prioritized alerts so that the one or more responsible persons will be made aware of periodic health maintenance nondelivery/nonresponsiveness alerts having relatively high priority before being made aware, if at all, of periodic health maintenance nondelivery/non-responsiveness alerts having lower priority.

27. Manufactured instructing signals for causing a correspondingly instructable machine to automatically carry out a machine-implemented method for use in providing health care services to patients, the method comprising:
- (a) defining one or more delivery deadlines by which respective deliveries of one or more, corresponding health care services to respective patients are to be timely completed;
- (b) determining whether or not each health care service having a corresponding delivery deadline has been timely and completely received by the respective patient; and
- (c) delivering corresponding alerts to one or more persons responsible for completion of delivery of a given health care service having one of said delivery deadlines if, among other alert generating criteria, the given health care service is determined by said determining step to have been not timely and completely received by the respective patient.

28. A machine-implemented method for use in providing health care services to patients, under supervision of medically-trained care providers, the method comprising:
- (a) defining in machine-readable storage, one or more representations of corresponding health care services that are planned to be respectively delivered to one or more respective patients;
- (b) automatically first determining whether or not each planned health care service needs review and/or customization by a medically-trained care provider before being delivered to a corresponding patient;
- (c) defining in machine-readable storage, one or more review deadlines by which corresponding planned health care services that are determined to need said review and/or customization are to be reviewed and/or customized by a specified one or more medically-trained care providers; and
- (d) automatically delivering corresponding need-review alerts to one or more persons responsible for completion of the review and/or customization of a given health care service having one of said review deadlines if, among other alert generating criteria, the given health care service is automatically determined to have been not timely reviewed and/or customized by one of said specified one or more medically-trained care providers.

29. An automated machine system for providing machine-implemented follow-ups on progress in providing health care services to patients, the system comprising:
- (a) machine-readable storage in which is defined, one or more delivery deadlines by which respective deliveries of one or more, corresponding health care services to respective patients are to be timely completed;
- (b) first means for automatically determining whether or not each health care service having a corresponding delivery deadline has been timely and completely received by the respective patient; and
- (c) second means for automatically delivering corresponding alerts to one or more persons responsible for completion of delivery of a given health care service having one of said delivery deadlines if, among other alert generating criteria, the given health care service is determined by said first means to have been not timely and completely received by the respective patient.

30. The automated machine system of claim 29 and further comprising:
- (d) alert sorting means for automatically sorting prioritized alerts so that the one or more responsible persons will be presented with service nondelivery/noncompletion alerts having relatively high priority before being made aware, if at all, of service nondelivery/noncompletion alerts having lower priority.

31. An automated machine system for providing machine-supported health care services to patients, under supervision of medically-trained care providers, the system comprising:
- (a) machine-readable storage having defined therein one or more representations of corresponding health care services that are planned to be respectively delivered to one or more respective patients;
- (b) first means for automatically determining whether or not each planned health care service needs review and/or customization by a medically-trained care provider before being delivered to a corresponding patient;
- (c) second means for defining in machine-readable storage, one or more review deadlines by which corresponding planned health care services that are determined to need said review and/or customization are to be reviewed and/or customized by a specified one or more medically-trained care providers; and
- (d) alert means for automatically delivering corresponding need-review alerts to one or more persons responsible for completion of the review and/or customization of a given health care service having one of said review deadlines if, among other alert generating criteria, the given health care service is automatically determined to have been not timely reviewed and/or customized by one of said specified one or more medically-trained care providers.

* * * * *